(12) United States Patent
Khvorova et al.

(10) Patent No.: US 11,753,638 B2
(45) Date of Patent: Sep. 12, 2023

(54) CONJUGATED OLIGONUCLEOTIDES

(71) Applicant: UNIVERSITY OF MASSACHUSETTS, Boston, MA (US)

(72) Inventors: Anastasia Khvorova, Westborough, MA (US); Mehran Nikan, Boston, MA (US); Matthew Hassler, Worcester, MA (US); Maire Osborn, Worcester, MA (US); Reka Haraszti, Shrewsbury, MA (US); Andrew Coles, Auburn, MA (US); Anton Turanov, Boston, MA (US); Neil Aronin, Newtonville, MA (US); Annabelle Biscans, Cambridge, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/322,212

(22) PCT Filed: Aug. 11, 2017

(86) PCT No.: PCT/US2017/046593
§ 371 (c)(1),
(2) Date: Jan. 31, 2019

(87) PCT Pub. No.: WO2018/031933
PCT Pub. Date: Feb. 15, 2018

(65) Prior Publication Data
US 2019/0185855 A1 Jun. 20, 2019

Related U.S. Application Data

(60) Provisional application No. 62/374,499, filed on Aug. 12, 2016, provisional application No. 62/461,529, filed on Feb. 21, 2017.

(51) Int. Cl.
| | |
|---|---|
| *A61K 31/7088* | (2006.01) |
| *C12N 15/113* | (2010.01) |
| *A61K 47/54* | (2017.01) |
| *C07H 21/02* | (2006.01) |
| *C07H 21/04* | (2006.01) |
| *C07H 21/00* | (2006.01) |
| *C12N 15/11* | (2006.01) |
| *A61K 47/55* | (2017.01) |
| *A61P 1/16* | (2006.01) |
| *A61P 9/00* | (2006.01) |
| *A61P 13/12* | (2006.01) |
| *A61P 1/00* | (2006.01) |
| *A61P 5/00* | (2006.01) |
| *A61P 11/00* | (2006.01) |
| *A61K 9/00* | (2006.01) |

(52) U.S. Cl.
CPC .......... *C12N 15/113* (2013.01); *A61K 9/0019* (2013.01); *A61K 31/7088* (2013.01); *A61K 47/54* (2017.08); *A61K 47/543* (2017.08); *A61K 47/549* (2017.08); *A61K 47/551* (2017.08); *A61K 47/554* (2017.08); *A61P 1/00* (2018.01); *A61P 1/16* (2018.01); *A61P 5/00* (2018.01); *A61P 9/00* (2018.01); *A61P 11/00* (2018.01); *A61P 13/12* (2018.01); *C07H 21/00* (2013.01); *C07H 21/02* (2013.01); *C07H 21/04* (2013.01); *C12N 15/111* (2013.01); *C12N 2310/14* (2013.01); *C12N 2310/312* (2013.01); *C12N 2310/315* (2013.01); *C12N 2310/346* (2013.01); *C12N 2310/351* (2013.01); *C12N 2310/3515* (2013.01); *C12N 2320/32* (2013.01)

(58) Field of Classification Search
CPC ............ C12N 15/113; C12N 2310/351; C12N 2310/14; C12N 2310/3515; A61P 13/12; A61P 1/16; A61P 5/00; A61P 9/00; A61P 11/00; A61P 1/00; A61K 47/549; A61K 47/543; A61K 47/551; A61K 47/54; A61K 9/0019
USPC .......................................................... 514/25
See application file for complete search history.

(56) References Cited

U.S. PATENT DOCUMENTS

| | | | |
|---|---|---|---|
| 4,522,811 | A | 6/1985 | Eppstein et al. |
| 5,194,596 | A | 3/1993 | Tischer et al. |
| 5,219,739 | A | 6/1993 | Tischer et al. |
| 5,240,848 | A | 8/1993 | Keck et al. |
| 5,328,470 | A | 7/1994 | Nabel et al. |
| 5,332,671 | A | 7/1994 | Ferrara et al. |
| 5,684,143 | A | 11/1997 | Gryaznov et al. |
| 5,814,014 | A | 9/1998 | Elsberry et al. |
| 5,858,988 | A | 1/1999 | Wang |
| 6,093,180 | A | 7/2000 | Elsberry |

(Continued)

FOREIGN PATENT DOCUMENTS

| | | |
|---|---|---|
| CN | 101199858 A | 6/2008 |
| CN | 101365801 A | 2/2009 |
| CN | 105194689 A | 12/2015 |
| EP | 1752536 A1 | 2/2007 |
| EP | 2407539 A1 | 1/2012 |

(Continued)

OTHER PUBLICATIONS

Frigg et al. (Int J Vitam Nutr Res. 1984;54(2-3):125-33) (abstract sent).*
Dinusha (Home / Health / Medicine / Nutrients & Drugs /; Aug. 4, 2011).*

(Continued)

*Primary Examiner* — Eric Olson
(74) *Attorney, Agent, or Firm* — LATHROP GPM LLP; James H. Velema, Esq.; Michael Spellberg, Esq.

(57) ABSTRACT

Provided herein are conjugated oligonucleotides that are characterized by efficient and specific tissue distribution.

18 Claims, 97 Drawing Sheets

Specification includes a Sequence Listing.

(56) References Cited

U.S. PATENT DOCUMENTS

| | | |
|---|---|---|
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,312,900 B1 | 11/2001 | Dean et al. |
| 6,383,814 B1 | 5/2002 | Lee et al. |
| 6,447,768 B1 | 9/2002 | Van Zonneveld et al. |
| 6,471,996 B1 | 10/2002 | Sokoll et al. |
| 6,472,375 B1 | 10/2002 | Hoon et al. |
| 6,489,464 B1 | 12/2002 | Agrawal et al. |
| 7,250,496 B2 | 7/2007 | Bentwich |
| 7,459,547 B2 | 12/2008 | Zamore et al. |
| 7,691,997 B2 | 4/2010 | Khvorova et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 7,790,867 B2 | 9/2010 | Bentwich |
| 7,834,171 B2 | 11/2010 | Leake et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,501,706 B2 | 8/2013 | Yamada et al. |
| 8,507,661 B2 | 8/2013 | Manoharan et al. |
| 8,664,189 B2 | 3/2014 | Khvorova et al. |
| 8,703,731 B2 | 4/2014 | Jimenez et al. |
| 8,796,443 B2 | 8/2014 | Khvorova et al. |
| 8,815,818 B2 | 8/2014 | Samarsky et al. |
| 8,877,439 B2 | 11/2014 | Butora et al. |
| 8,906,874 B2 | 12/2014 | Rao et al. |
| 8,993,738 B2 | 3/2015 | Prakash et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,198,981 B2 | 12/2015 | Ambati et al. |
| 9,303,259 B2 | 4/2016 | Khvorova et al. |
| 9,340,786 B2 | 5/2016 | Khvorova et al. |
| 9,493,774 B2 | 11/2016 | Kamens et al. |
| 9,745,574 B2 | 8/2017 | Woolf et al. |
| 9,796,756 B2 | 10/2017 | Hadwiger et al. |
| 9,809,817 B2 | 11/2017 | Khvorova et al. |
| 9,862,350 B2 | 1/2018 | Guerrero et al. |
| 9,862,952 B2 | 1/2018 | Khvorova et al. |
| 9,867,882 B2 | 1/2018 | Manoharan et al. |
| 10,087,210 B2 | 10/2018 | Prakash et al. |
| 10,435,688 B2 | 10/2019 | Khvorova et al. |
| 10,478,503 B2 | 11/2019 | Khvorova et al. |
| 10,479,992 B2 | 11/2019 | Woolf et al. |
| 10,519,451 B2 | 12/2019 | Khvorova et al. |
| 10,633,653 B2 | 4/2020 | Khvorova et al. |
| 10,774,327 B2 | 9/2020 | Khvorova et al. |
| 10,799,591 B2 | 10/2020 | Khvorova et al. |
| 11,230,713 B2 | 1/2022 | Khvorova et al. |
| 11,279,930 B2 | 3/2022 | Khvorova et al. |
| 11,345,917 B2 | 5/2022 | Khvorova et al. |
| 11,492,619 B2 | 11/2022 | Khvorova et al. |
| 2003/0143732 A1 | 7/2003 | Fosnaugh et al. |
| 2004/0121426 A1 | 6/2004 | Hsieh |
| 2004/0198640 A1 | 10/2004 | Leake et al. |
| 2005/0096284 A1 | 5/2005 | McSwiggen et al. |
| 2005/0220766 A1 | 10/2005 | Amalfitano et al. |
| 2006/0009409 A1 | 1/2006 | Woolf |
| 2006/0078542 A1 | 4/2006 | Mah et al. |
| 2006/0094032 A1 | 5/2006 | Fougerolles et al. |
| 2007/0004664 A1 | 1/2007 | McSwiggen et al. |
| 2007/0004665 A1 | 1/2007 | Mcswiggen et al. |
| 2007/0099860 A1 | 5/2007 | Sah et al. |
| 2007/0135372 A1 | 6/2007 | MacLachlan et al. |
| 2007/0160534 A1 | 7/2007 | Dennis et al. |
| 2007/0191273 A1 | 8/2007 | Ambati et al. |
| 2007/0259827 A1 | 11/2007 | Aronin et al. |
| 2008/0039415 A1 | 2/2008 | Stewart et al. |
| 2008/0108801 A1 | 5/2008 | Manoharan |
| 2008/0119427 A1 | 5/2008 | Bhat et al. |
| 2008/0269149 A1 | 10/2008 | Bowles et al. |
| 2009/0143322 A1 | 6/2009 | Burkoth et al. |
| 2009/0234109 A1 | 9/2009 | Han et al. |
| 2010/0015706 A1 | 1/2010 | Quay et al. |
| 2010/0093085 A1 | 4/2010 | Yamada et al. |
| 2010/0184209 A1* | 7/2010 | Vermeulen ............ C12N 15/111 435/325 |
| 2010/0186103 A1 | 7/2010 | Gao et al. |
| 2011/0039914 A1 | 2/2011 | Pavco et al. |
| 2011/0201006 A1 | 8/2011 | Roehl et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2012/0016005 A1 | 1/2012 | Samarsky et al. |
| 2012/0040459 A1 | 2/2012 | Khvorova et al. |
| 2012/0052487 A9 | 3/2012 | Khvorova et al. |
| 2012/0059046 A1 | 3/2012 | Woolf et al. |
| 2012/0065243 A1 | 3/2012 | Woolf et al. |
| 2012/0136039 A1 | 5/2012 | Aronin et al. |
| 2013/0065298 A1 | 3/2013 | Davidson et al. |
| 2013/0131141 A1 | 5/2013 | Khvorova et al. |
| 2013/0131142 A1 | 5/2013 | Libertine et al. |
| 2013/0178513 A1 | 7/2013 | Dobie et al. |
| 2013/0196434 A1 | 8/2013 | Maier et al. |
| 2013/0197055 A1 | 8/2013 | Kamens et al. |
| 2014/0113950 A1 | 4/2014 | Khvorova et al. |
| 2014/0288148 A1 | 9/2014 | Biegelman et al. |
| 2014/0296486 A1 | 10/2014 | Gao et al. |
| 2014/0315974 A1 | 10/2014 | Khvorova et al. |
| 2014/0364482 A1 | 12/2014 | Khvorova et al. |
| 2015/0025122 A1 | 1/2015 | Smith |
| 2015/0190525 A1* | 7/2015 | Tatro ..................... C12N 15/11 424/78.22 |
| 2015/0209441 A1 | 7/2015 | Carell et al. |
| 2015/0232840 A1 | 8/2015 | Massachusetts |
| 2015/0247142 A1 | 9/2015 | Esau et al. |
| 2016/0017323 A1 | 1/2016 | Prakash et al. |
| 2016/0115482 A1 | 4/2016 | Libertine et al. |
| 2016/0115484 A1 | 4/2016 | Woolf et al. |
| 2016/0130578 A1 | 5/2016 | Khvorova et al. |
| 2016/0130583 A1 | 5/2016 | Yokota et al. |
| 2016/0244765 A1 | 8/2016 | Khvorova et al. |
| 2016/0281148 A1 | 9/2016 | Greenlee et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0037456 A1 | 2/2017 | Kokoris et al. |
| 2017/0043024 A1 | 2/2017 | Khvorova et al. |
| 2017/0043204 A1 | 2/2017 | James |
| 2017/0051283 A1 | 2/2017 | Khvorova |
| 2017/0051286 A1 | 2/2017 | Smith |
| 2017/0067056 A1 | 3/2017 | Khvorova et al. |
| 2017/0189541 A1 | 7/2017 | Foster |
| 2017/0281795 A1 | 10/2017 | Geall |
| 2017/0312367 A1 | 11/2017 | Khvorova et al. |
| 2017/0327524 A1 | 11/2017 | Nanna et al. |
| 2017/0369882 A1 | 12/2017 | Khvorova et al. |
| 2018/0094263 A1 | 4/2018 | Khvorova et al. |
| 2018/0179546 A1 | 6/2018 | Khvorova et al. |
| 2018/0251764 A1 | 9/2018 | Albaek et al. |
| 2019/0002880 A1 | 1/2019 | Woolf et al. |
| 2019/0185855 A1 | 6/2019 | Khvorova et al. |
| 2019/0225965 A1 | 7/2019 | Khvorova et al. |
| 2019/0247507 A1 | 8/2019 | Khvorova et al. |
| 2020/0087663 A1 | 3/2020 | Aronin |
| 2020/0095580 A1 | 3/2020 | Hauptmann et al. |
| 2020/0123543 A1 | 4/2020 | Khvorova et al. |
| 2020/0165618 A1 | 5/2020 | Khvorova et al. |
| 2020/0270605 A1 | 8/2020 | Khvorova et al. |
| 2020/0308584 A1 | 10/2020 | Khvorova et al. |
| 2020/0339983 A1 | 10/2020 | Khvorova et al. |
| 2020/0385740 A1 | 12/2020 | Khvorova et al. |
| 2021/0024926 A1 | 1/2021 | Khvorova et al. |
| 2021/0071117 A9 | 3/2021 | Khvorova et al. |
| 2021/0085793 A1 | 3/2021 | Khvorova et al. |

(56) References Cited

U.S. PATENT DOCUMENTS

| | | |
|---|---|---|
| 2021/0115442 A1 | 4/2021 | Khvorova et al. |
| 2021/0139901 A1 | 5/2021 | Khvorova et al. |
| 2022/0010309 A1 | 1/2022 | Khvorova et al. |
| 2022/0228141 A1 | 7/2022 | Khvorova et al. |
| 2022/0251554 A1 | 8/2022 | Khvorova et al. |
| 2022/0364100 A1 | 11/2022 | Khvorova et al. |

FOREIGN PATENT DOCUMENTS

| | | | |
|---|---|---|---|
| EP | | 2601204 A2 | 6/2013 |
| EP | | 2853597 A1 | 4/2015 |
| EP | | 3277811 A1 | 2/2018 |
| EP | | 3277814 A1 | 2/2018 |
| EP | | 3277815 A1 | 2/2018 |
| EP | | 3408391 A1 | 12/2018 |
| EP | | 3642341 A1 | 4/2020 |
| EP | | 3929293 A2 | 12/2021 |
| JP | | 2009-504782 A | 2/2009 |
| JP | | 2012-502657 A | 2/2012 |
| JP | | 2013-049714 A | 3/2013 |
| JP | | 2016-171815 A | 9/2016 |
| WO | | 2003/029459 A2 | 4/2003 |
| WO | WO | 2003/029459 A2 | 4/2003 |
| WO | | 2004/008946 A2 | 1/2004 |
| WO | | 2004/044136 A2 | 5/2004 |
| WO | WO | 2004/044136 A2 | 5/2004 |
| WO | | 2006/019430 A2 | 2/2006 |
| WO | WO | 2007/022470 A2 | 2/2007 |
| WO | | 2007/051045 A2 | 5/2007 |
| WO | WO | 2007/051045 A2 | 5/2007 |
| WO | | 2007/094218 A1 | 8/2007 |
| WO | | 2007/112414 A2 | 10/2007 |
| WO | | 2008/154482 A2 | 12/2008 |
| WO | WO | 2008/154482 A3 | 12/2008 |
| WO | | 2009/054551 A2 | 4/2009 |
| WO | | 2009/099991 A2 | 8/2009 |
| WO | | 2009/102427 A1 | 8/2009 |
| WO | | 2010/008582 A2 | 1/2010 |
| WO | | 2010/011346 A1 | 1/2010 |
| WO | | 2010/033246 A1 | 3/2010 |
| WO | | 2010/033247 A2 | 3/2010 |
| WO | | 2010/033248 A2 | 3/2010 |
| WO | WO | 2010/033247 A2 | 3/2010 |
| WO | | 2010/059226 A2 | 5/2010 |
| WO | WO | 2010/059226 A2 | 5/2010 |
| WO | | 2010/078536 A1 | 7/2010 |
| WO | | 2010/090762 A1 | 8/2010 |
| WO | | 2011/109698 A1 | 9/2011 |
| WO | | 2011/119852 A1 | 9/2011 |
| WO | | 2011/119871 A1 | 9/2011 |
| WO | | 2011/119887 A1 | 9/2011 |
| WO | WO | 2011/109698 A1 | 9/2011 |
| WO | WO | 2011/119871 A1 | 9/2011 |
| WO | WO | 2011/119887 A1 | 9/2011 |
| WO | | 2012/005898 A2 | 1/2012 |
| WO | WO | 2012/005898 A2 | 1/2012 |
| WO | WO | 2012/037254 A1 | 3/2012 |
| WO | WO | 2012/078637 A2 | 6/2012 |
| WO | | 2012/118911 A1 | 9/2012 |
| WO | WO | 2012/177906 A1 | 12/2012 |
| WO | | 2013/165816 A2 | 11/2013 |
| WO | WO | 2014/009429 A1 | 1/2014 |
| WO | WO | 2014/043544 A1 | 3/2014 |
| WO | | 2014/076195 A1 | 5/2014 |
| WO | WO | 2014/076195 A1 | 5/2014 |
| WO | WO | 2014/089313 A1 | 6/2014 |
| WO | WO | 2015/025122 A1 | 2/2015 |
| WO | WO | 2015/057847 A1 | 4/2015 |
| WO | | 2015/161184 A1 | 10/2015 |
| WO | WO | 2015/200078 A1 | 12/2015 |
| WO | WO | 2016/028649 A1 | 2/2016 |
| WO | | 2016/161374 A1 | 10/2016 |
| WO | WO | 2016/161374 A1 | 10/2016 |
| WO | WO | 2016/161378 A1 | 10/2016 |
| WO | WO | 2016/161388 A1 | 10/2016 |
| WO | WO | 2016/164866 A1 | 10/2016 |
| WO | WO | 2016/205410 A2 | 12/2016 |
| WO | | 2017/015555 A1 | 1/2017 |
| WO | WO | 2017/015555 A1 | 1/2017 |
| WO | WO | 2017/024239 A1 | 2/2017 |
| WO | WO | 2017/030973 A1 | 2/2017 |
| WO | WO | 2017/062862 A2 | 4/2017 |
| WO | WO | 2018/031933 A2 | 2/2018 |
| WO | WO | 2018/237245 A1 | 12/2018 |
| WO | WO | 2020/033899 A1 | 2/2020 |
| WO | WO | 2020/150636 A1 | 7/2020 |

OTHER PUBLICATIONS

Yu et al. (Aug. 31, 2012) "Single-stranded RNAs use RNAi to potently and allele-selectively inhibit mutant huntingtin expression," Cell. 150(5):895-908.

Zeng et al. (2002) "Both natural and designed micro RNAs can inhibit the expression of cognate mRNAs when expressed in human cells," Mol. Cell. 9(6):1327-1333.

Zeng et al. (2003) "Sequence requirements for micro RNA processing and function in human cells," RNA. 9 (1):112-123.

International Search Report with Written Opinion corresponding to International Patent Application No. PCT/US2016/025722, dated Aug. 12, 2016.

International Search Report with Written Opinion corresponding to International Patent Application No. PCT/US2016/025731, dated Sep. 9, 2016.

International Search Report with Written Opinion corresponding to International Patent Application No. PCT/US2016/025753, dated Sep. 14, 2016.

Raouane et al. (2012) "Lipid Conjugated Oligonucleotides: A Useful Strategy for Delivery," Bioconjugate Chemistry, 23:1091-1104.

Nikan et al. (2016) "Docosahexaenoic Acid 1-20 Conjugation Enhances Distribution and Safety of siRNA upon Local Administration in Mouse Brain—Supplementary Figures and Table S1," Molecular Therapy—Nucleic Acids, 5(1):e344.

International Search Report with Written Opinion corresponding to International Patent Application No. PCT/US2016/046810, dated Nov. 29, 2016.

Pubchem Database [Online] (2005) "SCHEMBL867745," PubChem Accession No. 12454428. National Institute for Biotechnology Information. Accessible on the Internet at URL: https://pubchem.ncbi.nlm.nih.gov/compound/12454428. [Last Accessed Aug. 31, 2017], 12 pgs.

Pubchem Database [Online] (2003) "AMINO-TEG-DIOL," PubChem Accession No. 22136768. National Institute for Biotechnology Information. Accessible on the Internet at URL: https://pubchem.ncbi.nlm.nih.gov/compound/2213676. [Last Accessed Aug. 31, 2017], 13 pgs.

Nishina et al. (2008) "Efficient In Vivo Delivery of siRNA to the Liver by Conjugation of a-Tocopherol," Mol. Ther. 16 (4):734-740.

Boutla et al. (2001) "Short 5'-phosphorylated double-stranded RNAs induce RNA interference in *Drosophila*," Current Biology, vol. 11, No. 22, pp. 1776-1780.

Alexopoulou et al. (2001) "Recognition of double-stranded RNA and activation of NF-κB by Toll-like receptor 3," Nature. 413:732-738.

Allerson et al. (2005) "Fully 2'-Modified Oligonucleotide Duplexes with Improved in Vitro Potency and Stability Compared to Unmodified Small Interfering RNA," J. Med. Chem. 48(4):901-904.

Alterman et al. (Dec. 12, 2015) "Hydrophobically Modified siRNAs Silence Huntingtin mRNA in Primary Neurons and Mouse Brain," Mol. Ther.: Nucleic Acids. 4(12):e266. pp. 1-12.

Fattal et al. (1998) "Biodegradable polyalkylcyanoacrylate nanoparticles for the delivery of oligonucleotides," J. Control Release. 53(1-3):137-43.

Ameres et al. (2007) "Molecular basis for target RNA recognition and cleavage by human RISC," Cell. 130:101-112.

Anderson et al. (2008) "Experimental validation of the importance of seed complement frequency to siRNA specificity," RNA. 14:853-861.

(56) References Cited

OTHER PUBLICATIONS

Anderson et al. (2008) "Identifying siRNA-induced off-targets by microarray analysis," Ch.4 In; Methods in Molecular Biology. 442:45-63.
Bagella et al. (1998) "Cloning of murine CDK9/PITALRE and its tissue-specific expression in development," J. Cell. Physiol. 177:206-213.
Bartlett (2006) "Insights into the kinetics of siRNA-mediated gene silencing from live-cell and live-animal bioluminescent imaging," Nucleic Acids Research. 34:322-333.
Behlke et al. (2008) "Chemical modification of siRNAs for in vivo use," Oligonucleotides. 18:305-320.
Billy et al. (2001) "Specific interference with gene expression induced by long, double-stranded RNA in mouse embryonal teratocarcinoma cell lines," Proc Natl Acad Sci USA. 98(25):14428-14433.
Birmingham et al. (2006) "3' UTR seed matches, but not overall identity, are associated with RNAi off-targets," Nat. Methods. 3:199-204.
Birmingham et al. (2007) "A protocol for designing siRNAs with high functionality and specificity," Nature Protocols. 2:2068-2078.
Braasch et al. (2003) "RNA Interference in Mammalian Cells by Chemically-Modified RNA," Biochemistry 42:7967-7975.
Brennecke et al. (2003) "Towards a complete description of the microRNA complement of animal genomes," Genome Biol. 4(9):228.
Brummelkamp et al. (2002) "A system for stable expression of short interfering RNAs in mammalian cells," Science. 296:550-553.
Burchard et al. (2009) "MicroRNA-like off-target transcript regulation by siRNAs is species specific," RNA. 15:308-315.
Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics 29:855-864.
Calegari et al. (2002) "Tissue-specific RNA interference in postimplantation mouse embryos with endoribonuclease-prepared short interfering RNA," Proc. Natl. Acad. Sci. USA. 99(22):14236-14240.
Charrier et al. (May 3, 2012) "Inhibition of SRGAP2 function by its human-specific paralogs induces neoteny during spine maturation," Cell. 149(4):923-935.
Cho et al. (Feb. 13, 2012) "Vascular endothelial growth factor receptor 1 morpholino decreases angiogenesis in a murine corneal suture model," Invest. Opthamol. Visual Sci. 53(2):685-692.
Choe et al. (2005) "Crystal structure of human toll-like receptor 3 (TLR3) ectodomain," Science. 309:581-585.
Coelho et al. (Aug. 29, 2013) "Safety and efficacy of RNAi therapy for transthyretin amyloidosis," The New England Journal of Medicine. 369:819-829.
Deleavey et al. (Jan. 5, 2013) "The 5' binding MID domain of human Argonaute2 tolerates chemically modified nucleotide analogues" Nucleic Acid Therapeutics. 23:81-87.
Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.
Felber et al. (Sep. 2012) "The interactions of amphiphilic antisense oligonucleotides with serum proteins and their effects on in vitro silencing activity," Biomaterials. 33(25):5955-5965.
Eckstein (2000) "Phosphorothioate Oligodeoxynucleotides: What Is Their Origin and What Is Unique About Them?" Antisense Nucleic Acid Drug Dev. 10(2):117-121.
Elmen et al. (2005) "Locked nucleic acid (LNA) mediated improvements in siRNA stability and functionality," Nucleic Acids Res. 33(1):439-447.
Fan et al. (Oct. 20, 2014) "Endometrial VEGF induces placental sFLT1 and leads to pregnancy complications," J. Clin. Inves. 124(11):4941-4952.
Federov et al. (2006) "Off-target effects by siRNA can induce toxic phenotype," RNA. 12:1188-1196.
Frazier (Nov. 9, 2015) "Antisense Oligonucleotide Therapies: The Promise and the Challenges from a Toxicologic Pathologist's Perspective," Toxicologic Pathology. 43:78-89.
Gaglione et al. (2010) "Recent progress in chemically modified siRNAs," Mini Rev. Med. Chem. 10(7):578-595.
Godard et al. (1995) "Antisense Effects of Cholesterol-Oligodeoxynucleotide Conjugates Associated with Poly (alkylcyanoacrylate) Nanoparticles," Eur. J. Biochem. 232(2):404-410.
Grad et al. (2003) "Computational and experimental identification of C. elegans microRNAs," Mol. Cell. 11 (5):1253-1263.
Griffiths-Jones (2004) "The microRNA Registry," Nuc. Acids Res. 32(Database Issue):D109-D111.
Grimm et al. (2006) "Fatality in mice due to oversaturation of cellular microRNA/short hairpin RNA pathways," Nature. 441:537-541.
Herdewijn (2000) "Heterocyclic modifications of oligonucleotides and antisense technology," Antisense Nucleic Acid Drug Dev. 10(4):297-310.
Heydarian et al. (2009) "Novel splice variants of sFlt1 are upregulated in preeclampsia," Placenta. 30:250-255.
Heyer et al. (Dec. 12, 2014) "An optimized kit-free method for making strand-specific deep sequencing libraries from RNA fragments," Nucleic Acids Res. 43(1):e2. pp. 1-14.
International Search Report with Written Opinion corresponding to International Patent Application No. PCT/US2017/015633, dated May 11, 2017.
Jackson et al. (2006) "Position-specific chemical modification of siRNAs reduces 'off-target' transcript silencing," RNA. 12:1197-1205.
Jackson et al. (2010) "Recognizing and avoiding siRNA off-target effects for target identification and therapeutic application," Nature Reviews in Drug Discovery. 9:57-67.
Jacque et al. (2002) "Modulation of HIV-1 replication by RNA interference," Nature. 418:435-438.
Judge et al. (2006) "Design of Noninflammatory Synthetic siRNA Mediating Potent Gene Silencing in Vivo," Molecular Therapy. 13:494-505.
Kenski et al. (2012) "siRNA-optimized Modifications for Enhanced In Vivo Activity," Mol. Ther. Nucleic Acids. 1:e5. pp. 1-8.
Khvorova et al. (2003) "Functional siRNAs and miRNAs Exhibit Strand Bias," Cell. 115:209-216.
Khvorova et al. (Mar. 15, 2016) "Abstract IA27: Advances in oligonucleotide chemistry for the treatment of neurodegenerative disorders and brain tumors," Cancer Res. 76(6) Abstract No. IA27.
Lagos-Quintana et al. (2001) "Identification of novel genes coding for small expressed RNAs," Science. 294 (5543):853-858.
Lai et al. (2003) "Computational identification of *Drosophila* microRNA genes," Genome Biol. 4(7):R42. pp. 1-20.
Lau et al. (2001) "An abundant class of tiny RNAs with probable regulatory roles in Caenorhabditis elegans," Science. 294(5543):858-862.
Lau et al. (2006) "Characterization of the piRNA complex from rat testes," Science. 313(5785):363-367.
Lee et al. (2001) "An extensive class of small RNAs in Caenorhabditis elegans," Science. 294(5543):862-864.
Lee et al. (2002) "Expression of small interfering RNAs targeted against HIV-1 rev transcripts in human cells," Nat. Biotechnol. 20:500-505.
Lim et al. (2003) "The microRNAs of Caenorhabditis elegans," Genes Dev. 17(8):991-1008.
Lim et al. (2003) "Vertebrate microRNA genes," Science. 299(5612):1540.
Lima et al. (Aug. 31, 2012) "Single-stranded siRNAs activate RNAi in animals," Cell. 150:883-894.
Lorenz et al. (2004) "Steroid and lipid conjugates of siRNAs to enhance cellular uptake and gene silencing in liver cells," Bioorg. Med. Chem. Lett. 14:4975-4977.
Luo et al. (Jun. 18, 2013) "Photoreceptor avascular privilege is shielded by soluble VEGF receptor-1," eLife. 6: e19456. pp. 1-22.
McCaffrey et al. (2002) "RNA interference in adult mice," Nature. 418(6893):38-39.

(56) References Cited

OTHER PUBLICATIONS

McManus et al. (2002) "Gene silencing using micro-RNA designed hairpins," RNA. 8:842-850.
Miyagishi et al. (2002) "U6 promoter-driven siRNAs with four uridine 3' overhangs efficiently suppress targeted gene expression in mammalian cells," Nat. Biotechnol. 20:497-500.
Molitoris et al. (2009) "siRNA Targeted to p53 Attenuates Ischemic and Cisplatin-Induced Acute Kidney Injury," Journal of the American Society of Nephrology. 20:1754-1764.
Lambert et al. (2001) "Nanoparticulate systems for the delivery of antisense oligonucleotides," Adv. Drug Deliv. Rev. 47(1):99-112.
Nair et al. (Dec. 10, 2014) "Multivalent N-Acetylgalactosamine-Conjugated siRNA Localizes in Hepatocytes and Elicits Robust RNAi-Mediated Gene Silencing," J. Am. Chem. Soc. 136(49):16958-16961.
Nielsen et al. (2001) "Sequence-selective recognition of DNA by strand displacement with a thymine-substituted polyamide," Science. 254:1497-1500.
Nikan et al. (Aug. 9, 2016) "Docosahexaenoic Acid Conjugation Enhances Distribution and Safety of siRNA upon Local Administration in Mouse Brain," Mol. Ther. Nucleic Acids. 5(8):e344. pp. 1-11.
Owen et al. (Mar. 15, 2012) "Morpholino-mediated increase in soluble Flt-1 expression results in decreased ocular and tumor neovascularization," PloS One. 7(3):e33576. pp. 1-9.
Paddison et al. (2002) "Short hairpin RNAs (shRNAs) induce sequence-specific silencing in mammalian cells," Gene Dev. 16:948-958.
Pasquinelli et al. (2000) "Conservation of the sequence and temporal expression of let-7 heterochronic regulatory RNA," Nature. 408(6808):86-89.
Paul et al. (2002) "Effective expression of small interfering RNA in human cells," Nature Biotechnol. 20:505-508.
Peel et al. (Feb. 12, 2015) "Conjugation and Evaluation of Small Hydrophobic Molecules to Triazole-Linked siRNAs," ACS Med. Chem. Lett. 6(2):117-122.
Petersen et al. (2003) "LNA: a versatile tool for therapeutics and genomics," Trends Biotechnol 21:74-81.
Putnam (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rigo et al. (Apr. 20, 2014) "Pharmacology of a central nervous system delivered 2'-O-methoxyethyl-modified survival of motor neuron splicing oligonucleotide in mice and nonhuman primates," The Journal of Pharmacology and Experimental Therapeutics. 350:46-55.
Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5 (Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.
Stalder et al. (Mar. 19, 2013) "The rough endoplasmatic reticulum is a central nucleation site of siRNA-mediated RNA silencing," EMBO J. 32:1115-1127.
Stein (2001) "Inhibition of Vesivirus infections in mammalian tissue culture with antisense morpholino oligomers," Antisense Nucleic Acid Drug Dev. 11(5):317-25.
Stokman et al. (2010) "Application of siRNA in targeting protein expression in kidney disease," Advanced Drug Delivery Reviews. 62:1378-1389.
Sui et al. (2002) "A DNA vector-based RNAi technology to suppress gene expression in mammalian cells," Proc Natl Acad Sci USA. 99:5515-5520.
Tabernero et al. (Apr. 2013) "First-in-humans trial of an RNA interference therapeutic targeting VEGF and KSP in cancer patients with liver involvement," Cancer Discovery. 3:406-417.
Thomas et al. (2009) "A recently evolved novel trophoblast-enriched secreted form of fms-like tyrosine kinase-1 variant is up-regulated in hypoxia and preeclampsia," J. Clin. Endocrinol. Metabol. 94:2524-2530.
Tuschl (2002) "Expanding small RNA interference," Nat. Biotechnol. 20(5):446-448.
Tuschl et al. (May 6, 2004) "The siRNA User Guide," Accessible on the Internet at URL: http://diyhpl.us/~bryan/irc/protocol-online/protocol-cache/sima.html. [Last Accessed Aug. 11, 2016].
Vaught et al. (2004) "T7 RNA Polymerase Transcription with 5-Position Modified UTP Derivatives," J. Am. Chem. Soc. 126:11231-11237.
Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.
Watanabe et al. (2008) "Endogenous siRNAs from naturally formed dsRNAs regulate transcripts in mouse oocytes," Nature. 453(7194):539-543.
Wooddell et al. (Feb. 26, 2013) "Hepatocyte-targeted RNAi Therapeutics for the Treatment of Chronic Hepatitis B Virus Infection," Molecular Therapy. 21:973-985.
Xia et al. (2002) "siRNA-mediated gene silencing in vitro and in vivo," Nature Biotechnol. 20(10):1006-1010.
Young et al. (2010) "Pathogenesis of preeclampsia," Annual Review of Pathology. 5:173-192.
Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press, pp. 647-664.
Yu et al. (2002) "RNA interference by expression of short-interfering RNAs and hairpin RNAs in mammalian cells," Proc Natl Acad Sci USA. 99:6047-6052.
Extended search report and written opinions of EP3496758 dated Oct. 14, 2020.
Wolfrum et al., "Mechanisms and optimization of in vivo delivery of lipophilic siRNAs", Nature Biotechnology, Gale Group Inc., New York, US, vol. 25, No. 10, pp. 1149-1157, DOI: 10.1038/NBT1339. (Sep. 16, 2007).
U.S. Appl. No. 15/089,319, filed Apr. 1, 2016, 2016/0355808, Dec. 8, 2016, U.S. Pat. No. 9,809,817, Nov. 7, 2017, Anastasia Khvorova.
U.S. Appl. No. 15/697,120, filed Sep. 6, 2017, 2018-0094263, Apr. 5, 2018, Anastasia Khvorova.
U.S. Appl. No. 15/089,437, filed Apr. 1, 2016, 2016/0355826, Dec. 8, 2016, U.S. Pat. No. 9,862,952, Jan. 9, 2018, Anastasia Khvorova.
U.S. Appl. No. 15/814,350, filed Nov. 15, 2017, 2018-0179546, Jun. 28, 2018, Anastasia Khvorova.
U.S. Appl. No. 15/089,423, filed Apr. 1, 2016, 2016/0319278, Nov. 3, 2016, Anastasia Khvorova.
U.S. Appl. No. 15/691,120, filed Aug. 30, 2017, 2017/0369882, Dec. 28, 2017, Anastasia Khvorova.
U.S. Appl. No. 15/236,051, filed Aug. 12, 2016, 2017/0043024, Feb. 16, 2017, Anastasia Khvorova.
U.S. Appl. No. 15/419,593, filed Jan. 30, 2017, 2017/0312367, Nov. 2, 2017, Anastasia Khvorova.
U.S. Appl. No. 16/322,212, filed Jan. 31, 2019, Anastasia Khvorova.
U.S. Appl. No. 15/089,319, filed Apr. 1, 2026, 2016/0355808, Dec. 8, 2016, U.S. Pat. No. 9,809,817, Nov. 7, 2017, Anastasia Khvorova, Oligonucleotide Compounds for Targeting Huntingtin mRNA.
U.S. Appl. No. 15/697,120, filed Sep. 6, 2017, 2018/0094263, Apr. 5, 2018, U.S. Pat. No. 10,435,688, Oct. 8, 2019, Anastasia Khvorova, Oligonucleotide Compounds for Targeting Huntingtin mRNA.

(56) References Cited

OTHER PUBLICATIONS

U.S. Appl. No. 16/263,200, filed Jan. 31, 2019, 2019/0225965, Jul. 25, 2019, U.S. Pat. No. 10,744,327, Sep. 15, 2020, Anastasia Khvorova, Oligonucleotide Compounds for Targeting Huntingtin mRNA.
U.S. Appl. No. 16/811,580, filed Mar. 6, 2020, 2020/0308584, Oct. 1, 2020, U.S. Pat. No. 11,230,713, Jan. 5, 2022, Anastasia Khvorova, Oligonucleotide Compounds for Targeting Huntingtin mRNA.
U.S. Appl. No. 17/536,647, filed Nov. 29, 2021, 2022/0251554, Aug. 11, 2022, Anastasia Khvorova, Oligonucleotide Compounds for Targeting Huntingtin mRNA.
U.S. Appl. No. 15/089,437, filed Apr. 1, 2016, 2016/0355826, Dec. 8, 2016, U.S. Pat. No. 9,862,952, Jan. 9, 2018, Anastasia Khvorova, Oligonucleotide Compounds for Treatment of Preeclampsia and Other Angiogenic Disorders.
U.S. Appl. No. 15/814,350, filed Nov. 15, 2017, 2018/0179546, Jun. 28, 2018, U.S. Pat. No. 10,519,451, Dec. 31, 2019, Anastasia Khvorova, Oligonucleotide Compounds for Treatment of Preeclampsia and Other Angiogenic Disorders.
U.S. Appl. No. 16/675,369, filed Nov. 6, 2019, 2020/0165618, May 28, 2020, U.S. Pat. No. 11,345,917, May 11, 2022, Anastasia Khvorova, Oligonucleotide Compounds for Treatment of Preeclampsia and Other Angiogenic Disorders.
U.S. Appl. No. 17/718,918, filed Apr. 12, 2022, 2022/0364100, Nov. 17, 2022, Anastasia Khvorova, Oligonucleotide Compounds for Treatment of Preeclampsia and Other Angiogenic Disorders.
U.S. Appl. No. 15/089,423, filed Apr. 1, 2016, 2016/0319278, Nov. 3, 2016, Anastasia Khvorova, Fully Stabilized Asymmetric Sirna.
U.S. Appl. No. 15/691,120, filed Aug. 30, 2017, 2017/0369882, Dec. 28, 2017, Anastasia Khvorova, Fully Stabilized Asymmetric Sirna.
U.S. Appl. No. 16/927,543, filed Jul. 13, 2020, 2021/0024926, Jan. 28, 2021, Anastasia Khvorov, Fully Stabilized Asymmetric Sirna.
U.S. Appl. No. 15/236,051, filed Aug. 12, 2016, 2017/0043024, Feb. 16, 2017, U.S. Pat. No. 10,633,653, Apr. 28, 2020, Anastasia Khvorova, Bioactive Congjugates for Oligonucleotide Delivery.
U.S. Appl. No. 16/812,714, filed Mar. 9, 2020, 2020/0339983, Oct. 29, 2020, Anastasia Khvorova, Bioactive Congjugates for Oligonucleotide Delivery.
U.S. Appl. No. 15/419,593, filed Jan. 30, 2017, 2017/0312367, Nov. 2, 2017, U.S. Pat. No. 10,478,503, Nov. 19, 2019, Anastasia Khvorova, Branched Oligonucleotides.
U.S. Appl. No. 16/390,712, filed Apr. 22, 2019, 2019/0247507, Aug. 15, 2019, U.S. Pat. No. 10,799,591, Oct. 13, 2020, Anastasia Khvorova, Branched Oligonuleotides.
U.S. Appl. No. 17/012,787, filed Sep. 4, 2020, 2021/0085793, Mar. 25, 2021, Anastasia Khvorova, Branched Oligonucleotides.
U.S. Appl. No. 16/322,212, filed Jan. 31, 2019, 2019/0185855, Jun. 20, 2019, Anastasia Khvorova, Conjugated Oligonucleotides.
U.S. Appl. No. 16/015,440, filed Jun. 22, 2018, 2019/0024082, Jan. 24, 2019, U.S. Pat. No. 10,844,377, Nov. 24, 2020, Anastasia Khvorova, Two-Tailed Self-Delivering Sirna.
U.S. Appl. No. 17/071,473, filed Oct. 15, 2020, 2021/0139901, May 13, 2021, Anastasia Khvorova, Two-Tailed Self-Delivering Sirna.
U.S. Appl. No. 16/537,374, filed Aug. 9, 2019, 2020/0123543, Apr. 23, 2020, Anastasia Khvorova, Modified Oligonucleotides Targeting SNPs.
U.S. Appl. No. 16/988,391, filed Aug. 7, 2020, 2021/0071177, Mar. 11, 2021, Anastasia Khvorova, Modified Oligonucleotides Targeting SNPs.
U.S. Appl. No. 16/831,470, filed Mar. 26, 2020, 2020/0385740, Dec. 10, 2020, Anastasia Khvorova, Modified Oligonucleotides with Increased Stability.
U.S. Appl. No. 17/213,852, filed Mar. 26, 2021, 20220010309, Jan. 13, 2022, Anastasia Khvorova, Synthesis of Modified Oligonucleotides with Increased Stability.
U.S. Appl. No. 16/746,555, Jan. 17, 2020, 2020/0270605, Aug. 27, 2020, U.S. Pat. No. 11,492,619, Nov. 8, 2022, Anqstasia Khvorova, Dynamic Pharmacokinetic-Modifying Anchors.
U.S. Appl. No. 17/725,102, filed Apr. 20, 2022, 2022/0372476, Nov. 24, 2022, Anastasia Khvorova, Dynamic Pharmacokinetic-Modifying Anchors.
U.S. Appl. No. 16/550,076, filed Aug. 23, 2019, 2020/0087663, Mar. 19, 2020, U.S. Pat. No. 11,279,930, Mar. 22, 2022, O-Methyl Rich Fully Stabilized Oligonucleotides.
U.S. Appl. No. 16/999,759, filed Aug. 21, 2020, 2021/0115442, Apr. 22, 2021, Anastasia Khvorova, O-Methyl Rich Fully Stabilized Oligonucleotides.
U.S. Appl. No. 17/580,269, filed Jan. 20, 2022, 2022/0251555, Aug. 22, 2022, Anastasia Khvorova, O-Methyl Rich Fully Stabilized Oligonucleotides.
U.S. Appl. No. 17/022,678, filed Sep. 16, 2020, 2021/0108200, Apr. 15, 2021, Anastasia Khvorova, Branched Lipid Conjugates of siRNA for Specific Tissue Delivery.
U.S. Appl. No. 17/331,146, filed May 26, 2021, 2021/0395739, Dec. 23, 2021, Anastasia Khvorova, Synthetic Oligonucleotides Having Regions of Block and Cluster Modifications.
U.S. Appl. No. 17/377,632, filed Jul. 16, 2021, 2022/0042015, Feb. 10, 2022, Anastasia Khvorova, Conjugated Oligonucleotides for Tissue Specific Delivery.
U.S. Appl. No. 17/532,636, filed Nov. 22, 2021, 2022/0228141, Jul. 21, 2022, Anastasia Khvorova, Oligonucleotides for DGAT2 Modulation.
Amarzguioui, et al., "Tolerance for Mutations and Chemical Modifications in a siRNA", Nucleic Acids Research, Jan. 15, 2003, 31(2): 589-595.
Ambardekar et al., "The modification of siRNA with 3' cholesterol to increase nuclease protection and suppression of native mRNA by select siRNA polyplexes", Biomaterials, Elsevier, Amsterdam, NL, vol. 32, No. 5, pp. 1404-1411. (Nov. 2, 2010).
Aubuchon, et al., "Preeclampsia: Animal Models for a Human Cure", Proceedings of the National Academy of Sciences, vol. 108, No. 4, pp. 1197-1198, Jan. 25, 2011.
Avino, et al., Branched RNA: A New Architecture for RNA Interference, Journal of Nucleic Acids, Article IC586935, 7 pages, Mar. 6, 2011.
Bartlett, et al., Can Metastatic Colorectal Cancer Be Cured?, Journal Oncology, Cancer Network, vol. 26, No. 3, pp. 266-275, Mar. 15, 2012.
Boutla et al., "Short 5'-phosphorylated double-stranded RNAs induce RNA interference in *Drosophila*", Biology, 2001, 11: 1776-1780.
Burchard, et al., MicroRNA-Like Off-Target Transcript Regulation by siRNAs is Species Specific, RNA, vol. 15, No. 2, pp. 308-315, 2009.
Burke, et al., "Spiral Arterial Remodeling is not Essential for Normal Blood Pressure Regulation in Pregnant Mice", Hypertension, vol. 55, No. 3, pp. 729-737, Jan. 25, 2010.
Carter, "Handbook of Parvoviruses", ed., P. Tijsser, CRC Press, pp. 155-168, 1990.
Chang, et al., Enhanced intracellular delivery and multi-target gene silencing triggered by tripodal RNA Structure, The journal of gene Medicine, vol. 14, No. 2, pp. 138-146, Feb. 2012.
Chang, et al., Transgenic Animal Models for Study of The Pathogenesis of Huntington's Disease and Therapy, Drug design, development and therapy, vol. 9, pp. 2179-2188, Apr. 2015.
Charnock-Jones, et al., "Identification and Localization of Alternately Spliced mRNAs for Vascular Endothelial Growth Factor in Human Uterus and Estrogen Regulation in Endometrial Carcinoma Cell Lines", Biology of Reproduction, vol. 48, pp. 1120-1128, 1993
Chen et al., "Lipophilic siRNAs mediate efficient gene silencing in oligodendrocytes with direct CNC delivery", Journal Of Controlled Release, Elsevier, vol. 144, pp. 227-232. (Feb. 17, 2010).
Chen et al., "Thermoresponsive polypeptides from pegylated poly-L-glutamates", Biomacromolecules 2011, 12: 2859-2863.
Chen et al., Influence of Particle Size on the in Vivo Potency of Lipid Nanoparticle Formulations of siRNA, Journal of Controlled Release, vol. 235, pp. 236-244, Aug. 10, 2016.
Chung et al., "Reducible siRNA Dimeric Conjugates for Efficient Cellular Uptake and Gene Silencing", Bioconjugate Chem., 2011, 22(2): 299-306.

(56) References Cited

OTHER PUBLICATIONS

Cui, et al., "Role of Corin in Trophoblast Invasion and Uterine Spiral Artery Remodelling in Pregnancy", Nature, vol. 484, No. 7393, pp. 246-250, Mar. 21, 2012.

Dahlman et al., In Vivo Endothelial siRNA Delivery using Polymeric Nanoparticles with Low Molecular Weight, Nature Nanotechnology, vol. 9, No. 8, 17 Pages, Aug. 2014.

Damha et al. (1990) "An improved procedure for derivatization of controlled-pore glass beads for solid-phase oligonucleotide synthesis," Nucleic Acids Research, 18(13):3813-3821.

De Fougerolles, et al., "Interfering With Disease: a Progress Report on siRNA-based Therapeutics", Nature Reviews Drug Discovery, vol. 6, pp. 443-453, Jun. 2007.

De Marre et al., "Synthesis, characterization, and in vitro biodegradation of poly(ethylene glycol) modified poly[5N-(2-hydroxyethyl-L-glutamine]", J Bioact Compat Polym, 1996, 11: 85-99.

De Paula et al., "Hydrophobization and bioconjugation for enhanced siRNA delivery and targeting", RNA, Feb. 28, 2007, vol. 13, No. 4, pp. 431-456.

Dinusha, Differnce Between Sterol and Steroid, Home / Health / Medicine/ Nutrients & Drugs, Aug. 4, 2011.

Dyall, et al., Long-chain omega-3 fatty acids and the brain: a review ofthe independent and shared effects of EPA, DPA and DHA, Frontiers in Aging Neuroscience, vol. 7, p. 52, Apr. 21, 2015.

Eremina, et al., "Glomerular-Specific Alterations of VEGF-A Expression Lead to Distinct Congenital and Acquired Renal Diseases", Journal of Clinical Investigation, vol. 111, No. 5, pp. 707-716, Mar. 2003.

Eremina, et al., "VEGFV inhibition and Renal Thrombotic Microangiopathy", New England Journal of Medicine, vol. 358, No. 11, pp. 1129-1136, Mar. 13, 2008.

Extended European Search Report for European Patent Application No. 16837593.9, dated Mar. 20, 2019.

Extended European Search Report for European Patent Application No. 17745083.0, dated Jul. 31, 2019.

Extended European Search Report for European Patent Application No. 17840367.1, dated Oct. 14, 2020.

Extended European Search Report for European Patent Application No. 18819571.3, dated May 14, 2021.

Extended European Search Report for European Patent Application No. 20164108.1, dated Dec. 3, 2020.

Extended European Search Report for European Patent Application No. 21197881.2, dated Oct. 31, 2022.

Fan, et al., Endometrial VEGF Induces Placental sFLT1 And Leads To Pregnancy Complications, The Journal of clinical investigation, vol. 124, No. 11, pp. 4941-4952, Oct. 20, 2014.

Foster et al., "Advanced siRNA Designs Further Improve In Vivo Performance of GalNAc-siRNA Conjugates", Molecular Therapy, vol. 26, No. 3, pp. 709-717, Mar. 2018.

Franich, et al., AAV Vector-Mediated RNAi of Mutant Huntingtin Expression is Neuroprotective in a Novel Genetic Rat Model of Huntington's Disease, Molecular Therapy, vol. 16, Issue 5, pp. 947-956, Mar. 25, 2008.

Frank et al., Structural Basis for 5'-Nucleotide Base-specific Recognition of Guide RNA by Human AGO2, Nature, vol 465, pp. 818-822, Jun. 2010.

Frigg et al., Relationships between vitamin A and vitamin E in the chick, Int J Vitam Nutr Res., 1984, 54(2-3): 125-133.

Gavrilov et al. (Jun. 2012) "Therapeutic siRNA: principles, challenges, and strategies", Yale Journal of Biology and Medicine, 85:187-200.

Geary, Antisense Oligonucleotide Pharmacokinetics and Metabolism, Expert Opinion on Drug Metabolism & Toxicology, vol. 5, pp. 381-391, Apr. 1, 2009.

Genbank, Signal Recognition Particle 54 kDa protein 2 [Perkinsus marinus ATCC 50983], NCBI Reference Sequence: XP_002784438.1, Apr. 30, 2010.

Gilbert, et al., "Hypertension Produced by Reduced Uterine Perfusion in Pregnant Rats Is Associated With Increased Soluble fms-like Tyrosine Kinase-1 Expression", Hypertension, Vol. 50, No. 6, pp. 1142-1147, Oct. 8, 2007.

Godinho et al., Pharmacokinetic Profiling of Conjugated Therapeutic Oligonucleotides: A High-Throughput Method based upon Serial Blood Microsampling Coupled to Peptide Nucleic Acid Hybridization Assay, Nucleic Acid Therapeutics, vol. 27, pp. 323-334, Dec. 1, 2017.

Goodson et al., Dental Applications, Medical Applications of Controlled Release, vol. 2, pp. 115-138, 1984.

Grimm, D, Asymmetry in siRNA Design, Gene Therapy, vol. 16, No. 7, pp. 827-829, Apr. 30, 2009.

Hammerling et al., Monoclonal Antibodies and T-Cell Hybridomas, Research Monographs in Immunology, vol. 3, pp. 563-681, 1981.

Haraszsti, et al., "5'-Vinylphosphonate improves tissue accumulation and efficacy of conjugated siRNAs in vivo", Nucleic Acids Research, Jul. 27, 2017, 45(13): 7581-7592.

Harborth et al., Sequence, Chemical, and Structural Variation of Small Interfering RNAs and Short Hairpin RNAs and the Effect on Mammalian Gene Silencing, Antisense and Nucleic Acid Drug Development, vol. 13, pp. 83-105, Apr. 1, 2003.

Hassler et al., Comparison of Partially and Fully Chemically-Modified siRNA in Conjugate-Mediated Delivery in Vivo, Nucleic Acids Research, vol. 46, No. 5, pp. 2185-2196, Mar. 16, 2018.

Heyer, et al., An Optimized Kit-Free Method for Making Strand-specific Deep Sequencing Libraries from RNA Fragments, Nucleic Acids Research, vol. 43, Issue 1, pp. 1-14, Jan. 9, 2015.

Hirashima, et al., "Trophoblast Expression of Fms-like Tyrosine Kinase 1 is not Required for the Establishment of the Maternal-fetal Interface in the Mouse Placenta", Proceedings of the National Academy of Sciences of the United States of America, vol. 100, No. 26, pp. 15637-15642, Dec. 23, 2003.

Hong et al., "Reducible Dimeric Conjugates of Small Internally Segment Interfering RNA for Efficient Gene Silencing", Macromolecular Bioscience, Jun. 2016, vol. 16, No. 10, pp. 1442-1449.

Huang, Preclinical and Clinical Advances of GalNAc-Decorated Nucleic Acid Therapeutics, Molecular Therapy—Nucleic Acids, vol. 6,, pp. 116-132, Mar. 17, 2017.

Intapad, et al., "Reduced Uterine Perfusion Pressure Induces Hypertension in the Pregnant Mouse", American Journal of Physiology-Regulatory, Integrative and Comparative Physiology, vol. 307, Issue 11, pp. R1353-R1357, Dec. 2014.

International Search Report & Written Opinion Received for PCT Application No. PCT/US2019/046013, dated Jan. 9, 2020.

International Search Report & Written Opinion Received for PCT Application No. PCT/US2020/014181, dated Jun. 2, 2020.

International Search Report and Written Opinion for PCT International Patent Application No. PCT/US2019/048027 dated Nov. 15, 2019.

International Search Report and Written Opinion for PCT International Patent Application No. PCT/US2020/047492, dated Feb. 17, 2022.

International Search Report and Written Opinion in related PCT Application No. PCT/US2020/014146, dated May 22, 2020.

International Search Report and Written Opinion received for PCT Application No. PCT/US2017/015633, dated May 11, 2017.

International Search Report and Written Opinion received for PCT Application No. PCT/US2018/038952, dated Sep. 24, 2018.

International Search Report and Written Opinion received for PCT Patent Application No. PCT/US2020/045487, dated Dec. 31, 2020.

International Search Report and Written Opinion received for PCT Patent Application No. PCT/US2021/013620, dated Apr. 26, 2021.

Iriyama et al., Hypoxia-independent up-regulation of placental HIF-1α gene expression contributes to the pathogenesis of preeclampsia, Hypertension, Jun. 2015, 65(6): 1307-1315, Supplemental Data.

Iversen et al., "Optimized siRNA-PEG Conjugates for Extended Blood Circulation and Reduced Urine Excretion in Mice", Feb. 25, 2013, Theranostics 2013, vol. 3, Issue 3, pp. 201-209.

Jackson et al., Position-Specific Chemical Modification of siRNAs Reduces "Off-Target" Transcript Silencing, RNA, vol. 12, No. 7, pp. 1197-1205, May 8, 2006.

(56) References Cited

OTHER PUBLICATIONS

Jebbink et al., "Expression of Placental FLT1 Tanscript Variants Relates to Both Gestational Hypertensive Disease and Fetal Growth", Hypertension, Apr. 25, 2011, 58(1): 70-76.

Jin, et al., DARPP-32 to Quantify Intracerebral Hemorrhage-induced Neuronal Death in Basal Ganglia, Translational Stoke Research, vol. 4, No. 1, pp. 130-134, Feb. 1, 2013.

Jo, et al., Selection and Optimization of Asymmetric siRNA Targeting the Human c-MET Gene, Molecules and cells, vol. 32, No. 6, pp. 543-548, Dec. 31, 2011.

Jung et al., "Gene silencing efficiency of siRNA-PEG conjugates: Effect of PEGylation site and PEG molecular weight", Journal of Controlled Release, Mar. 4, 2010, vol. 144, No. 3, pp. 306-313.

Kamba, et al., "VEGF-dependent Plasticity of Fenestrated Capillaries in the Normal Adult Microvasculature", American Journal of Physiology-Heart and Circulatory Physiology, vol. 29, pp. H560-H576, Feb. 1, 2006.

Karaki et al., Lipid-Oligonucleotide Conjugates Improve Cellular Uptake and Efficiency of TCTP-Antisense in Castration-Resistant Prostate Cancer, Journal of Controlled Release, vol. 258, pp. 1-9, Jul. 28, 2017.

Khan et al., Silencing Myostatin using Cholesterol-Conjugated siRNAs Induces Muscle Growth, Molecular Therapy, Nucleic Acids, vol. 5, 9 Pages, Jan. 1, 2016.

Khankin, et al., "Intravital High-frequency Ultrasonography to Evaluate Cardiovascular and Uteroplacental Blood Flow in Mouse Pregnancy", Pregnancy Hypertension: An International Journal of Women's Cardiovascular Health, vol. 2, pp. 84-92, 2012.

Khvorova, Oligonucleotide Therapeutics—A New Class of Cholesterol-Lowering Drugs, The New England Journal of Medicine, vol. 376, No. 1, pp. 4-7, Jan. 5, 2017.

Kim et al., "LHRH Receptor-Mediated Delivery of siRNA Using Polyelectrolyte Complex Micelles Self-Assembled from siRNA-PEG-LHRH Conjugate and PEI", Bioconjugate Chemistry, Oct. 14, 2008, vol. 19, No. 11, pp. 2156-2162.

Kim et al., "PEG conjugated VEGF siRNA for anti-angiognic gene therapy", Journal of Controlled Release, Jun. 3, 2006, vol. 116, No. 2, pp. 123-129.

Kubo et al., "Lipid-Conjugated 27-Nucleotide Double-Stranded RNAs with Dicer-Substrate Potency enhance RNAi-Mediated Gene Silencing", Molecular Pharmaceutics, American Chemical Society, US, vol. 9, No. 5, pp. 1374-1382, DOI: 10.1021/MP2006278. (Apr. 11, 2012).

Kubo et al., "Palmitic Acid-Conjugated 21-Nucleotide siRNA Enhances Gene-Silencing Activity", Molecular Pharmaceutics, vol. 8, No. 6, pp. 2193-2203, DOI: 10.1021/mp200250f. (Oct. 10, 2011).

Kumar, et al., "Shielding of Lipid Nanoparticles for siRNA Delivery: Impact on Physicochemical Properties", Cytokine Induction, and Efficacy, Molecular Therapy-Nucleic Acids, vol. 3, e210, pp. 1-7, Nov. 18, 2014.

Landis, et al., "A Call for Transparent Reporting to Optimize the Predictive Value of Preclinical Research", Nature, vol. 490, pp. 187-191, Oct. 10, 2012.

Laufer, et al., "Selected Strategies for the Delivery of siRNA In Vitro and In Vivo", RNA Technologies and Their Applications, 2010, pp. 29-58.

Lee et al., "Current preclinical small interfering RNA (siRNA)-based conjugate systems for RNA therapeutics", Advanced Drug Delivery Reviews, Oct. 27, 2015, vol. 104, pp. 78-92.

Lee, et al., "Recent Developments In Nanoparticle-Based siRNA Delivery For Cancer Therapy", BioMed Research International, vol. 2013, Article ID 782041, 10 Pages, Jun. 2013.

Lee, et al., RNA Interference-Mediated Simultaneous Silencing of Four Genes Using Cross-Shaped RNA, Molecules and Cells, vol. 35, No. 4, pp. 320-326, Apr. 4, 2013.

Lee, et al., Small-interfering RNA (siRNA)-based functional micro- and nanostructures for efficient and selective gene silencing, Accounts of Chemical Research, vol. 45, No. 7, pp. 1014-1025, Jul. 17, 2012.

Levine, et al., "Circulating Angiogenic Factors and the Risk of Preeclampsia", The New England Journal of Medicine, vol. 350, pp. 672-683, 2004.

Li, et al., "Recombinant Vascular Endothelial Growth Factor 121 Attenuates Hypertension and Improves Kidney Damage in a Rat Model of Preeclampsia", Hypertension, vol. 50, pp. 686-692, 2007.

Li, et al., Distribution of 5-Hydroxymethylcytosine in Different Human Tissues, "SAGE—Hindawi Access to Research, Journal of Nucleic Acids, vol. 2011", pp. 1-7, 2011.

Liu et al., Snapshot PK: A Rapid Rodent in Vivo Preclinical Screening Approach, Drug Discovery Today, vol. 13, No. 7-8, pp. 360-367, Apr. 1, 2008.

Ly et al., Visualization of Self-Delivering Hydrophobically Modified siRNA Cellular Internalization, Nucleic Acids Research, vol. 45, pp. 15-25, Nov. 29, 2016

Ma et al., Structural Basis For 5'-End-Specific Recognition Of Guide RNA By The A. Fulgidus Piwi Protein, Nature, vol. 434, No. 7033, pp. 666-670, Mar. 31, 2005.

Makris, et al., "Uteroplacental Ischemia Results in Proteinuric Hypertension and Elevated sFLT-1", Kidney International, vol. 71, Issue 1, pp. 977-984, May 2, 2007.

Maltepe, et al., "The Placenta: Transcriptional, Epigenetic, and Physiological Integration During Development", The Journal of Clinical Investigation, vol. 120, No. 4, pp. 1016-1025, Apr. 1, 2010.

Mangiarini, et al., Exon 1 ofthe HD Gene with an Expanded CAG Repeat ls Sufficient to Cause a Progressive Neurological Phenotype in Transgenic Mice, Cell, vol. 87, Issue 3, pp. 493-506, Nov. 1, 1996.

Mantha, et al., Rnai-Based Therapies For Huntington's Disease: Delivery Challenges And Opportunities, Therapeutic Delivery, vol. 3, No. 9, pp. 1061-1076, Aug. 29, 2012.

Marcus, et al., FedExosomes: Engineering Therapeutic Biological Nanoparticles that Truly Deliver, Pharmaceuticals, vol. 6, No. 5, pp. 659-680, Apr. 29, 2013.

Marques, et al., A Structural Basis For Discriminating Between Self And Nonself Double-Stranded Rnas In Mammalian Cells, Nature biotechnology, vol. 23, No. 11, pp. 1399-1405, 2005.

Masotti, et al., Comparison of Different Commercially Available Cationic Liposome-DNA Lipoplexes: Parameters Influencing Toxicity And Transfection Efficiency, Colloids and Surfaces B: Biointerfaces, vol. 68, Issue 2, pp. 136-144, Feb. 1, 2009.

Matsuda et al., siRNA Conjugates Carrying Sequentially Assembled Trivalent N-Acetylgalactosamine Linked Through Nucleosides Elicit Robust Gene Silencing In Vivo in Hepatocytes, ACS Chemical Biology, vol. 10, No. 5, pp. 1181-1187, Mar. 2, 2015.

Maynard, et al., "Excess Placental Soluble fms-like Tyrosine Kinase 1 (sFltl) may Contribute to Endothelial Dysfunction", Hypertension, and Proteinuria in Preeclampsia, The Journal of Clinical Investigation, vol. 111, pp. 649-658, 2003.

McCaffrey, et al., Gene Expression: RNA Interference in Adult Mice, Nature, vol. 418, No. 6893, pp. 38-39, Jul. 4, 2002.

Miyagishi, et al., U6 promoter—driven siRNAs With Four Uridine 3' Overhangs Efficiently Suppress Targeted Gene Expression ln Mammalian Cells, Nature Biotechnology, vol. 20, No. 5, pp. 497-500, May 1, 2002.

Mok, et al., Multimeric small interfering ribonucleic acid for highly efficient sequence- specific gene silencing~, Nature Materials, vol. 9, pp. 272-278, Jan. 24, 2010.

Molitoris, et al., siRNA Targeted to p53 Attenuates Ischemic and Cisplatin-Induced Acute Kidney Injury, Journal of the American Society of Nephrology, vol. 20, Issue 8, pp. 1754-1764, Aug. 1, 2009.

Morrissey et al., "Activity of stabilized short interfering RNA in a mouse model of hepatitis B virus replication", Hepatology, 2005, 41: 1349-1356.

Mourelatos, et al., miRNPs: A Novel Class Of Ribonucleoproteins Containing Numerous microRNAs, Genes & Development, vol. 16, No. 6, pp. 720-728, 2002.

Mullen,, et al., NeuN, A Neuronal Specific Nuclear Protein In Vertebrates, Development, vol. 116, No. 1, pp. 201-211, 1992.

Myers, et al., Optimal Alignments In Linear Space, Computer Applications in the Biosciences, vol. 4, No. 1, pp. 11-17, Mar. 1988.

(56) References Cited

OTHER PUBLICATIONS

Nagamatsu, et al., "Cytotrophoblasts Up-Regulate Soluble Fms-Like Tyrosine Kinase-1 Expression under Reduced Oxygen: An Implication for the Placental Vascular Development and the Pathophysiology of Preeclampsia", Endocrinology, vol. 145, Issue 11, pp. 4838-484, Nov. 1, 2004.
Nair, et al., Multivalent N-Acetylgalactosamine-Conjugated siRNA Localizes in Hepatocytes and Elicits Robust RNAi-Mediated Gene Silencing, Journal of the American Chemical Society, vol. 136, No. 49, pp. 16958-16961, Dec. 10, 2014.
Nallagatla et al., Nucleoside Modifications Modulate Activation of the Protein Kinase PKR in an RNA Structure-Specific Manner, RNA, vol. 14, pp. 1201-1213, Jun. 1, 2008.
Nelson et al. (1992) "Oligonucleotide labeling methods 3. Direct labeling of oligonucleotides employing a novel, non-nucleosidic, 2-aminobutyl-1,3-propanediol backbone," 20(23):6253-6259.
Neufeld, et al., "Similarities and Differences Between the Vascular Endothelial Growth Factor (VEGF) Splice Variants", Cancer and Metastasis Reviews, vol. 15, pp. 153-158, Jun. 1996.
Nikan et al., Synthesis and Evaluation of Parenchymal Retention and Efficacy of a Metabolically Stable, O-Phosphocholine-N-Docosahexaenoyl-L-serine siRNA Conjugate in Mouse Brain, Bioconjugate Chemistry, vol. 28, No. 6, 21 Pages, Jun. 21, 2017.
Oberbauer et al., Renal Uptake of an 18-mer Phosphorothioate Oligonucleotide, Kidney International, vol. 48, pp. 1226-1232, 1995.
Ohnishi, et al., "Enhancement of Allele Discrimination by Introduction of Nucleotide Mismatches into siRNA in Allele-Specific Gene Silencing by RNAi", Plos One, vol. 3, Issue 5, e2248, 9 Pages, May 2008.
Osborn et al., Hydrophobicity Drives the Systemic Distribution of Lipid-Conjugated siRNAs Via Lipid Transport Pathways, Nucleic Acids Research, vol. 47, No. 3, pp. 1070-1081, Dec. 8, 2018.
Østergaard, et al., "Fluorinated Nucleotide Modifications Modulate Allele Selectivity of SNP-Targeting Antisense Oligonucleotides", Molecular Therapy Nucleic Acids, vol. 7, pp. 20-30, Jun. 2017.
Ouimet, et al., DARPP-32, A Dopamine- And Adenosine 3':5'-Monophosphate-Regulated Phosphoprotein Enriched In Dopamine-Innervated Brain Regions. III. Immunocytochemical Localization, Journal of Neuroscience, vol. 4, No. 1, pp. 111-124, Jan. 1, 1984.
Overhoff, et al., "Quantitative Detection of siRNA and Single-stranded Oligonucleotides: Relationship Between Uptake and Biological Activity of siRNA", Nucleic Acids Research, vol. 32, Issue 21, pp. 1-5, Dec. 2, 2004.
Owen, Morpholino-Mediated Increase in Soluble Flt-1 Expression Results in Decreased Ocular and Tumor Neovascularization, PLoS One, vol. 7, No. 3, pp. e33576, Mar. 15, 2012.
Paddison, et al., Short Hairpin RNAS (shRNAs) Induce Sequence-Specific Silencing In Mammalian Cells, Genes & Development, vol. 16, No. 8, pp. 948-958, 2002.
Parmar et al., 5'-(E)-Vinylphosphonate: A Stable Phosphate Mimic can Improve the RNAi Activity of siRNA-GalNAc Conjugates, ChemBioChem, vol. 17, pp. 985-989, Jun. 2, 2016.
Partial European Search Report for European Patent Application No. 202162657, dated Nov. 10, 2021.
Partial European Search Report for European Patent Application No. 21197881.2, dated Mar. 14, 2022.
Partial Supplementary European Search Report for European Patent Application No. 207418658, dated Dec. 20, 2022.
Pasquinelli, et al., Conservation of The Sequence And Temporal Expression of let-7 Heterochronic Regulatory RNA, Nature, vol. 408, No. 6808, pp. 86-89., Nov. 2, 2000.
Paul, et al., Effective Expression of Small Interfering RNA In Human Cells, Nature Biotechnology, vol. 20, No. 5, pp. 505-508, May 1, 2002.
Peel, et al., Conjugation and Evaluaticrt of Small Hydrcphobic Molecules to Triazole-Linked siRNAs, ACS medicinal chemistry letters, vol. 6, No. 2, pp. 117-122, Dec. 4, 2014.
Pei, et al., Quantitative Evaluation of siRNA Delivery in Vivo, RNA, vol. 16, No. 12, pp. 2553-2563, Oct. 12, 2010.

Petersen, et al., LNA: A Versatile Tool for Therapeutics and Genomics, Trends in Biotechnology, vol. 21, Issue 2, pp. 74-81, Feb. 2003.
Pfister, et al., "Five siRNAs Targeting Three SNPs in Huntingtin May Provide Therapy for Three-Quarters of Huntington's Disease Patients", Current Biology, vol. 19, No. 9, pp. 774-778., May 12, 2009.
Podbevsek et al., "Solution-state structure of a fully alternately 2'-F/2'-OMe modified 42-nt dimeric siRNA construct", Nucleic Acids Research, vol. 38, No. 20, pp/ 7298-7307, DOI: 10.1093/nar/gkq621. (Jul. 12, 2010).
Pokholenko et al., Lipid Oligonucleotide Conjugates as Responsive Nanomaterials for Drug Delivery, Journal of Materials Chemistry B, vol. 1, 6 Pages, 2013.
Posocco, et al., "Impact of siRNA Overhangs for Dendrimer-mediated siRNA Delivery and Gene Silencing", Molecular Pharmaceutics, Aug. 5, 2013, 10(8): 3262-3273.
Powe, et al., "Preeclampsia, a Disease of the Maternal Endothelium: the Role of Antiangiogenic Factors and Implications for Later Cardiovascular Disease", Circulation, vol. 123, No. 24, pp. 2856-2869, Jun. 11, 2011.
Prakash et al., Targeted Delivery Of Antisense Oligonucleotides To Hepatocytes Using Triantennary N-Acetyl Galactosamine Improves Potency 10-Fold In Mice, Nucleic Acids Research, vol. 42, Issue 13, pp. 8796-8807, Jul. 29, 2014.
Pubchem Database, AMINO-TEG-DIOL, National Institute or Biotechnology Information, PubChem Accession No. 22136768, 2003.
Pubchem Database, SCHEMBL867745, National Institute for Biotechnology Information, PubChem Accession No. 12454428, 12 pages, 2005.
Putnam, David A., Antisense Strategies and Therapeutic Applications, American Journal of Health System Pharmacy, vol. 53, No. 2, pp. 151-160, Jan. 15, 1996.
Rajeev et al., Hepatocyte-Specific Delivery of Sirnas Conjugated to Novel Non-Nucleosidic Trivalent N-Acetylgalactosamine Elicits Robust Gene Silencing in Vivo, ChemBioChem, vol. 16, pp. 903-908, Apr. 13, 2015.
Reed et al., Forty Mouse Strain Survey of Body Composition, Physiology & Behavior, vol. 91, No. 5, 15 Pages, Aug. 15, 2007.
Reinhart, et al., Small RNAs Correspond to Centromere Heterochromatic Repeats, Science, vol. 297, No. 5588, 1 Page, Sep. 13, 2002.
Rigo, et al., Pharmacology of a Central Nervous System Delivered 2'-O-Methoxyethyl-Modified Survival of Motor Neuron Splicing Oligonucleotide in Mice and Nonhuman Primates, Journal of Pharmacology and Experimental Therapeutics, vol. 350, Issue 1, pp. 46-55, Jul. 1, 2014.
Rodriguez-Lebron, et al., Intrastriatal rAAV-Mediated Delivery of Anti-Huntingtin shRNAs Induces Partial Reversal Of Disease Progression In R6/1 Huntington's Disease Transgenic Mice, Molecular Therapy, vol. 12, Issue 4, pp. 618-633, Oct. 2005.
Rupprecht, et al., Neuroactive Steroids: Mechanisms Of Action And Neuropsychopharmacological Properties, Psychoneuroendocrinology, vol. 28, Issue 2, pp. 139-168, Feb. 2003.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Sah, et al., bligonucleotide Therapeutic Approaches for Huntington disease, The Journal of Clinical Investigation, vol. 121, No. 2, pp. 500-507, Feb. 1, 2011.
Samuelson, Kristin W., Post-Traumatic Stress Disorder And Declarative Memory Functioning: A Review, Dialogues In Clinical Neuroscience, vol. 13, No. 3, pp. 346-351, Sep. 2011.
Sarett, et al., Lipophilic siRNA Targets Albumin in Situ and Promotes Bioavailability, tumor Penetration, and Carrier-Free Gene Silencing, Proceedings of the National Academy of Sciences, vol. 114, pp. E6490-E6497, Jul. 24, 2017.
Scherman et al., Genetic Pharmacology: Progresses in siRNA Delivery and Therapeutic Applications, Gene Therapy, vol. 24, pp. 151-156, Mar. 2017.
Schirle, et al., Structural Basis for MicroRNA Targeting, Science, vol. 346, Issue 6209, pp. 608-613, Oct. 31, 2014.

(56) References Cited

OTHER PUBLICATIONS

Schwab, et al., An Approach For New Anticancer Drugs:Oncogene-Targeted Antisense DNA, Annals of Oncology, vol. 5, Issue 4, pp. 55-58, 1994.

Schwarz et al., Asymmetry in the Assembly of the RNAi Enzyme Complex, Cell, vol. 115, Issue 2, pp. 199-208, Oct. 17, 2003.

Seq ID No. 1112 from U.S. Pat. No. 7790867. [Accessed Nov. 28, 2018, http://seqdata.uspto.govl.psipsv?pageRequest=viewSequence&DocID=7790867&seqID=1112.].

Smith et al., Reversed-Phase High Performance Liquid Chromatography of Phosphatidylcholine: A Simple Method for Determining Relative Hydrophobic Interaction of Various Molecular Species, Journal of Lipid Research, vol. 22, pp. 697-704, May 1, 1981.

Solano et al., Toxicological and Pharmacokinetic Properties of QPI-1007, a Chemically Modified Synthetic siRNA Targeting Caspase 2 mRNA, Following Intravitreal Injection, Nucleic Acid Therapeutics, vol. 24, pp. 258-266, Aug. 1, 2014.

Song, et al., Sustained Small Interfering RNA-Mediated Human Immunodeficiency Virus Type 1 Inhibition in Primary Macrophages, Journal of Virology, vol. 77, No. 13, pp. 7174-7181, 2003.

Soutschek, et al., Therapeutic Silencing of An Endogenous Gene By Systemic Administration Of Modified siRNAs, Nature, vol. 432, No. 7014, pp. 173-178, Nov. 11, 2004.

Stalder et al., The Rough Endoplasmatic Reticulum Is A Central Nucleation Site of siRNA-Mediated RNA Silencing, The EMBO Journal, vol. 32, Issue 8, pp. 1115-1127, Mar. 19, 2013.

Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.

Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.

Stokman, et al., Application of siRNA In Targeting Protein Expression In Kidney Disease, Advanced Drug Delivery Reviews, vol. 62, Issue 14, pp. 1378-1389, Nov. 30, 2010.

Sugo et al., "Development of antibody-siRNA conjugate targeted to cardiac and skeletal muscles", Journal of Controlled Release, Jun. 29, 2016, vol. 237, pp. 1-13.

Suhr et al., Efficacy and Safety of Patisiran for Familial Amyloidotic Polyneuropathy: A Phase II Multi-Dose Study, Orphanet Journal of Rare Diseases, vol. 10, pp. 1-9, Dec. 1, 2015.

Sui, et al., A DNA Vector-Based RNAi Technology To Suppress Gene Expression In Mammalian Cells, Proceedings of the National Academy of Sciences, vol. 99, No. 8, pp. 5515-5520, Apr. 16, 2002.

Tabernero, et al., First-in-Humans Trial of an RNA Interference Therapeutic Targeting VEGF and KSP in Cancer Patients with Liver Involvement, vol. 3, Issue 4, pp. 406-417, Apr. 2013.

Tang et al., "Excess Soluble Vascular Endothelial Growth Factor Receptor-1 in Amniotic Fluid Impairs Lung Growth in Rats: Linking Preeclampsia With Bronchopulmonary Dysplasia", American Journal of Physiology-Lung Cellular and Molecular Physiology, vol. 302, No. 1, pp. L36-L46, Jan. 1, 2012.

Taniguchi et al., Plasmodium Berghei ANKA Causes Intestinal Malaria Associated with Dvsbiosis, Scientific Reports, vol. 5, pp. 1-12, Oct. 27, 2015.

Tanowitz et al., Asialoglycoprotein Receptor 1 Mediates Productive Uptake of N-Acetylgalactosamine-Conjugated and Unconjugated Phosphorothioate Antisense Oligonucleotides into Liver Hepatocytes, Nucleic Acids Research, vol. 45, No. 21, pp. 12388-12400, Dec. 1, 2017.

Thadani, et al., "Pilot Study of Extracorporeal Removal of Soluble fms-like Tyrosine kinase 1 in Preeclampsia", Circulation, vol. 124, No. 8, pp. 940-950, Aug. 1, 2011.

Thomas et al. (2007) "Intronic polyadenylation signal sequences and alternate splicing generate human soluble Flt1 variants and regulate the abundance of soluble Flt1 in the placenta," The FASEB Journal, 21(14):3885-3895.

Thomas, et al., A Recently Evolved Novel Trophoblast-Enriched Secreted Form of fms-Like Tyrosine Kinase-1 Variant Is Up-Regulated in Hypoxia and Preeclampsia, The Journal of Clinical Endocrinology & Metabolism, vol. 94, Issue 7, pp. 2524-2530, Jul. 1, 2009.

Thompson et al., Toxicological and Pharmacokinetic Properties of Chemically Modified siRNAs Targeting p53 RNA Following Intravenous Administration, Nucleic Acid Therapeutics, vol. 22, No. 4, pp. 255-264, Aug. 1, 2012.

Tischer, et al., "The Human Gene for Vascular Endothelial Growth Factor. Multiple Protein Forms are Encoded Through Alternative Exon Splicing", The Journal of Biolooical Chemistry, vol. 266, pp. 11947-11954. Jun. 25, 1991.

Turanov et al., "RNAi Modulatiort at Placental sFLT1 for the Treatment of Preeclampsia", Nature Biotechnology, Nov. 19, 2018, 36: 1164-1173.

Tuschl et al. (May 6, 2004) "The siRNA User Guide," Accessible on the Internet at URL: http://diyhpl.us/~bryan/irc/protocol-online/protocol-cache/sirna.html. [Last Accessed Aug. 11, 2016].

Tuschl, et al., Expanding small RNA interference, Nature Biotechnology, vol. 20, No. 5, pp. 446-448, 2002.

Uchida, et al., "An Integrated Approach for the Systematic Identification and Characterization of Heart-enriched Genes With Unknown Functions", BMC Genomics, vol. 10, No. 100, pp. 1-12, Mar. 2009.

Ueno et al., "Synthesis and silencing properties of siRNAs possessing lipophilic groups at their 3'-termini", Nucleic Acids Symposium Series, vol. 52, Issue 1, pp. 503-504, https://doi.org/10.1093/nass/nrn255. (Sep. 2008).

Vaught, et al., T7 RNA Polymerase Transcription with 5-Position Modified UTP Derivatives, Journal of the American Chemical Society, vol. 126, No. 36, pp. 11231-11237, Aug. 19, 2004.

Videira, et al., "Preclinical Development of siRNA Therapeutics: Towards the Match Between Fundamental Science and Engineered Systems", Nanomedicine: Nanotechnology, Biology and Medicine, vol. 10, No. 4, pp. 689-702, 2014.

Vorlová, et al., "Induction of Antagonistic Soluble Decoy Receptor Tyrosine Kinases by Intronic polyA Activation", Molecular Cell, vol. 43, Issue 6, pp. 927-939. Sep. 16. 2011.

Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.

Wada et al., "Evaluation of the effects of chemically different linkers on hepatic accumulations, cell tropism and gene silencing ability of cholesterol-conjugated antisense oligonucleotides", Journal Of Controlled Release, Elsevier, vol. 226, pp. 57-65, DOI: 10.1016/J.JCONREL.2016.02.007. (Feb. 5, 2016).

Wang, et al., Nanoparticle-Based Delivery System for Application of siRNA In Vivo, Current Drug Metabolism, vol. 11, No. 2, pp. 182-196, 2010.

Wanke et al., Overgrowth of Skin-in Growth Hormone Transgenic Mice Depends on the Presence of Male Gonads, Journal of Investigative Dermatology, vol. 113, pp. 967-971, Dec. 1, 1999.

Watanabe et al., Endogenous siRNAs From Naturally Formed dsRNAs Regulate Transcripts In Mouse Oocytes, Nature, vol. 453, No. 7194, pp. 539-543, Apr. 10, 2008.

Weyer, et al., Developmental And Cell Type-Specific Expression Of The Neuronal Marker NeuN In The Murine Cerebellum, Journal of Neuroscience Research, vol. 73, Issue 3, pp. 400-409, May 23, 2003.

Whitehead et al., Degradable Lipid Nanoparticles with Predictable in Vivo siRNA Delivery Activity, Nature Communications, vol. 5, pp. 1-10, Jun. 27, 2014.

Whitehead, et al., "Knocking Down Barriers: Advances in siRNA Delivery", Nature Reviews Drug Discovery, vol. 8, No. 2, pp. 129-138, Feb. 2009.

Wolfrum et al., "Mechanisms and optimization of in vivo delivery of lipophilic siRNAs", Nature Biotechnology, Oct. 2007, 25(10): 1149-1157.

Wong, et al., Co-lnjection of a Targeted, Reversibly Masked Endosomolytic Polymer Dramatically Improves the Efficacy of Cholesterol-Conjugated Small Interfering RNAs In Vivo, Nucleic Acid Therapeutics, vol. 22, No. 6, pp. 380-390, Nov. 26, 2012.

(56) References Cited

OTHER PUBLICATIONS

Wooddell, et al., Hepatocyte-targeted RNAi Therapeutics for the Treatment of Chronic Hepatitis B Virus Infection, Molecular Therapy, vol. 21, Issue 5, pp. 973-985, May 2013.

Wright, et al., Identification Of Factors That Contribute To Recombinant AAV2 Particle Aggregation And Methods To Prevent Its Occurrence During Vector Purification And Formulation, Molecular Therapy, vol. 12, Issue 1,, pp. 171-178, Jul. 2005.

Xia, et al., siRNA-Mediated Gene Silencing in Vitro and In Vivo, Nature Biotechnology, vol. 20, No. 10, pp. 1006-1010, Sep. 16, 2002.

Young, et al., Pathogenesis of Preeclampsia, Annual Review of Pathology: Mechanisms of Disease, vol. 5, pp. 173-192, Feb. 2, 2010.

Younis, et al., Overview of the Nonclinical Development Strategies and Class-Effects of Oligonucleotide-Based Therapeutics, A Comprehensive Guide to Toxicology in Preclinical Drug Development, Chapter 26, pp. 647-664, 2013.

Yu, et al., RNA Interference by Expression Of Short-Interfering RNAs And Hairpin Rnas ln Mammalian Cells, Proceedings of the National Academy of Sciences, vol. 99, No. 9, pp. 6047-6052., Apr. 30, 2002.

Yu, et al., Single-Stranded RNAs Use RNAi to Potently and Allele-Selectively Inhibit Mutant Huntingtin Expression, Cell, vol. 150, Issue 5, pp. 895-908, Aug. 31, 2012.

Yuan, et al., Recent Advances of siRNA Delivery By Nanoparticles, Expert Opinion on Drug Delivery vol. 8, Issue 4, pp. 521-536, 2011.

Zeng, et al., Both Natural and Designed Micre RNAs Can Inhibit the Expression of Cognate mRNAs When Expressed in Human Cells, Molecular Cell, vol. 9, pp. 1327-1333, Jun. 2002.

Zeng, et al., Sequence Requirements for Micro RNA Processing and Function in Human Cells, RNA, vol. 9, pp. 112-123, 2003.

Zhang, et al., "Birth-weight-for-gestational-age Patterns by Race, Sex, and Parity in the United States Population", Obstetrics & Gynecology, vol. 86, No. 2, pp. 200-208, 1995.

Zhang, et al., "Several rAAV Vectors Efficiently Cross the Blood-brain Barrier and Transduce Neurons and Astrocytes in the Neonatal Mouse Central Nervous System", Molecular Therapy, Volume 19, Issue 8, pp. 1440-1448, Aug. 1, 2011.

Zhang, et al., Cyclohexane 1,3-Diones And Their Inhibition Of Mutant SOD1-Dependent Protein Aggregation And Toxicity ln PC12 Cells, Bioorganic & Medicinal Chemistry, vol. 20, Issue 2, pp. 1029-1045, Jan. 15, 2012.

Zhou et al., Nanoparticle-based Delivery of RNAi Therapeutics: Progress and Challenges, Pharmaceuticals, vol. 6, pp. 85-107, Jan. 2013.

Zimmermann et al., Clinical Proof of Concept for a Novel Hepatocyte-Targeting GalNAc-siRNA Conjugate, Molecular Therapy, vol. 25, Issue 1, pp. 71-78, Jan. 4, 2017.

Zou, et al., Liposome-Mediated NGF Gene Transfection Following Neuronal Injury: Potential Therapeutic Applications, Gene Therapy, vol. 6, No. 6, pp. 994-1005, Jun. 25, 1999.

Zuccato, et al., Molecular Mechanisms and Potential Therapeutical Targets in Huntington's Disease, Physiological Reviews, vol. 90, No. 3, pp. 905-981, Jul. 1, 2010.

Akinc et al., A Combinatorial Library of Lipid-like Materials for Delivery of RNAi Therapeutics, Nature Biotechnology, vol. 26, No. 5, 20 pages, May 2008.

Biscans et al., Diverse Lipid Conjugates for Functional Extra-Hepatic siRNA Delivery in Vivo, Nucleic Acids Research, vol. 47, No. 3, pp. 1082-1096, Dec. 14, 2018.

* cited by examiner

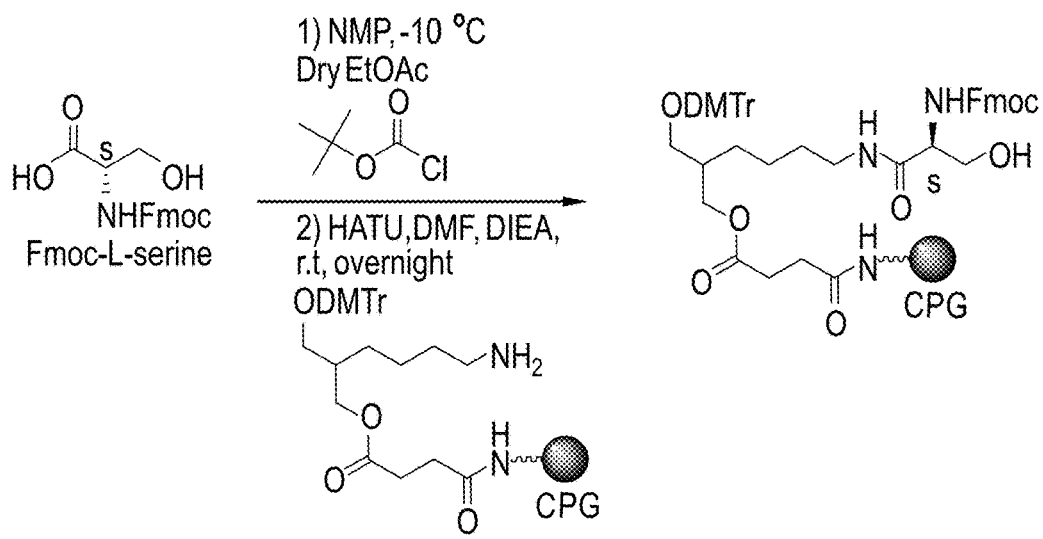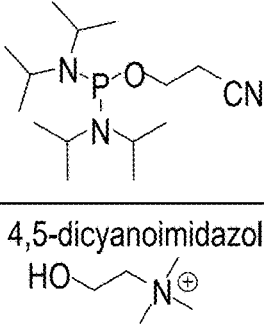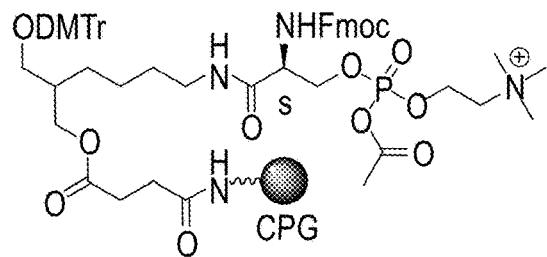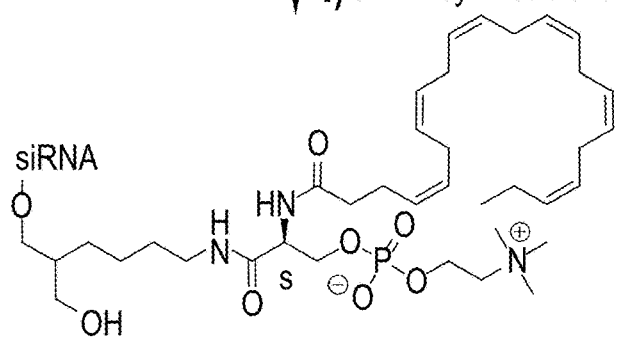
Fig. 1F

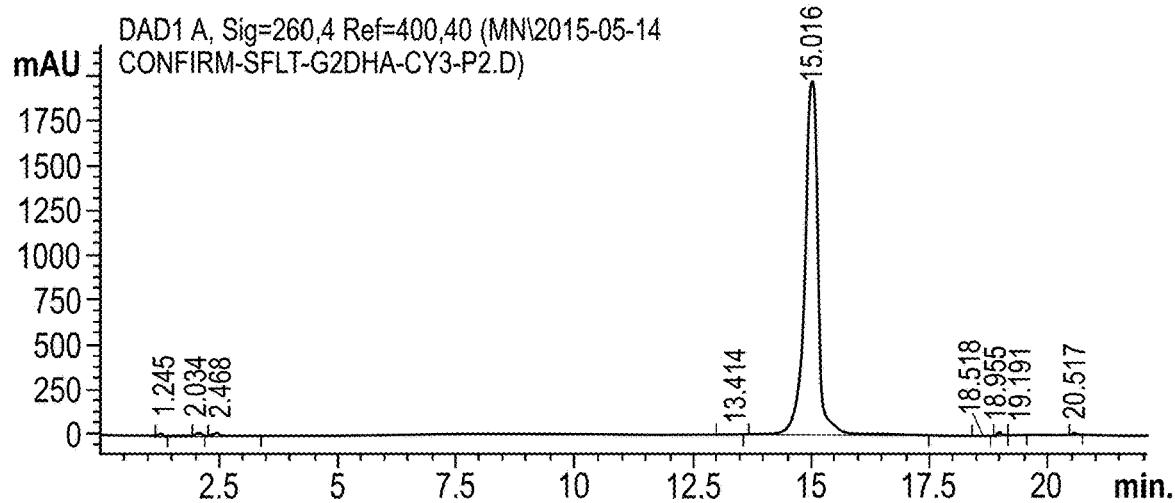
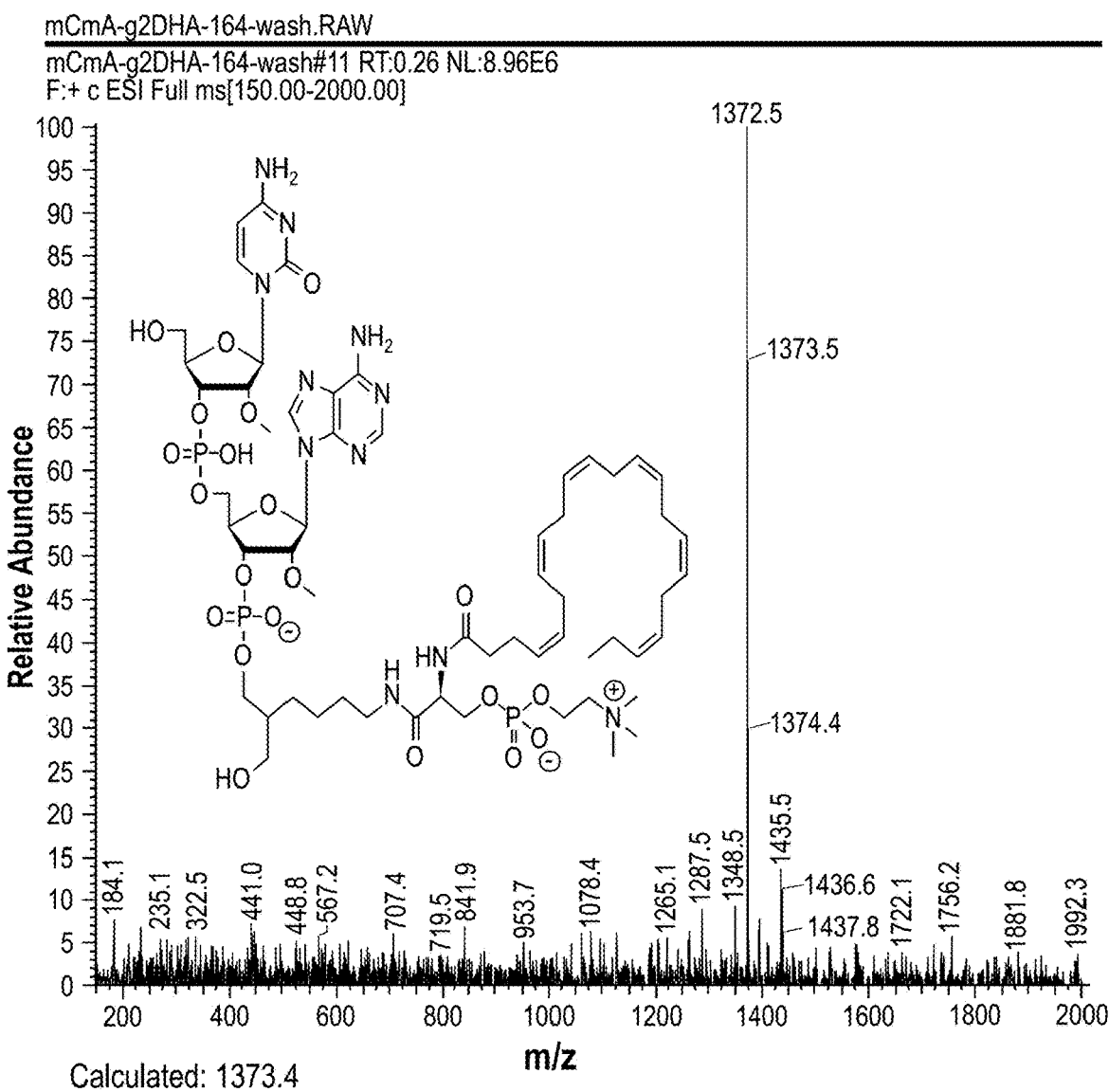
Calculated: 1373.4
Observed: 1372.5
Fig. 1J

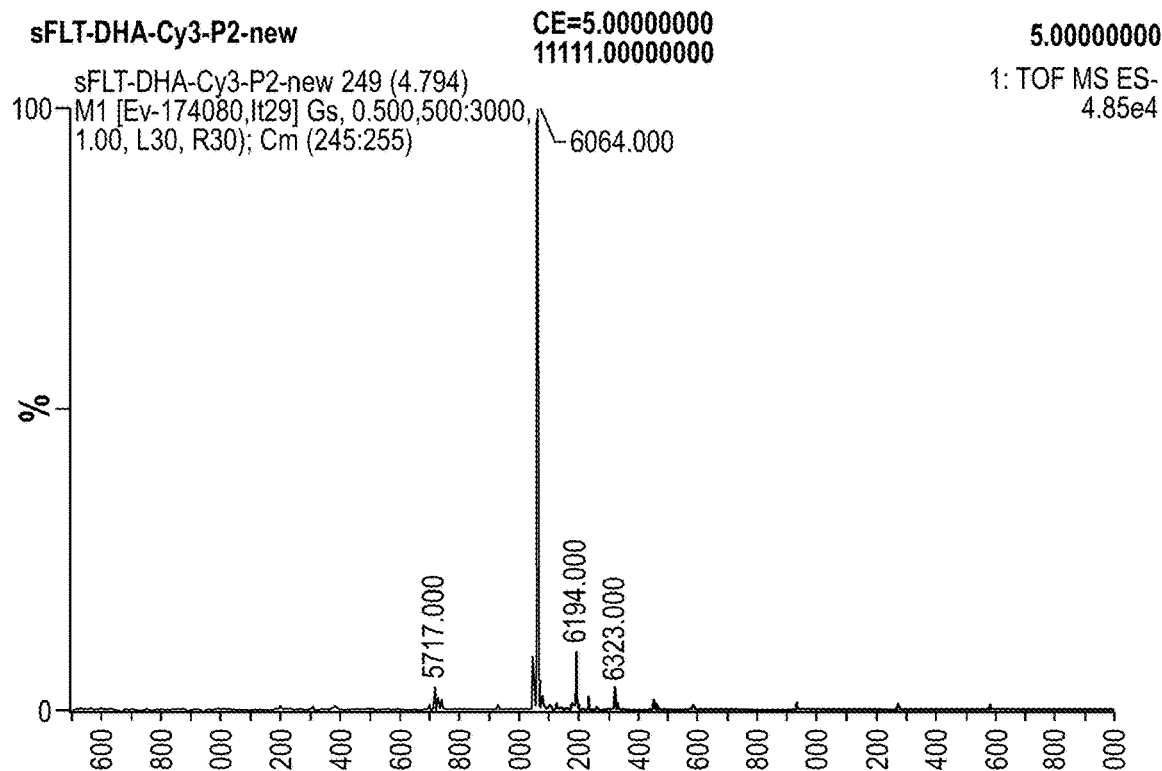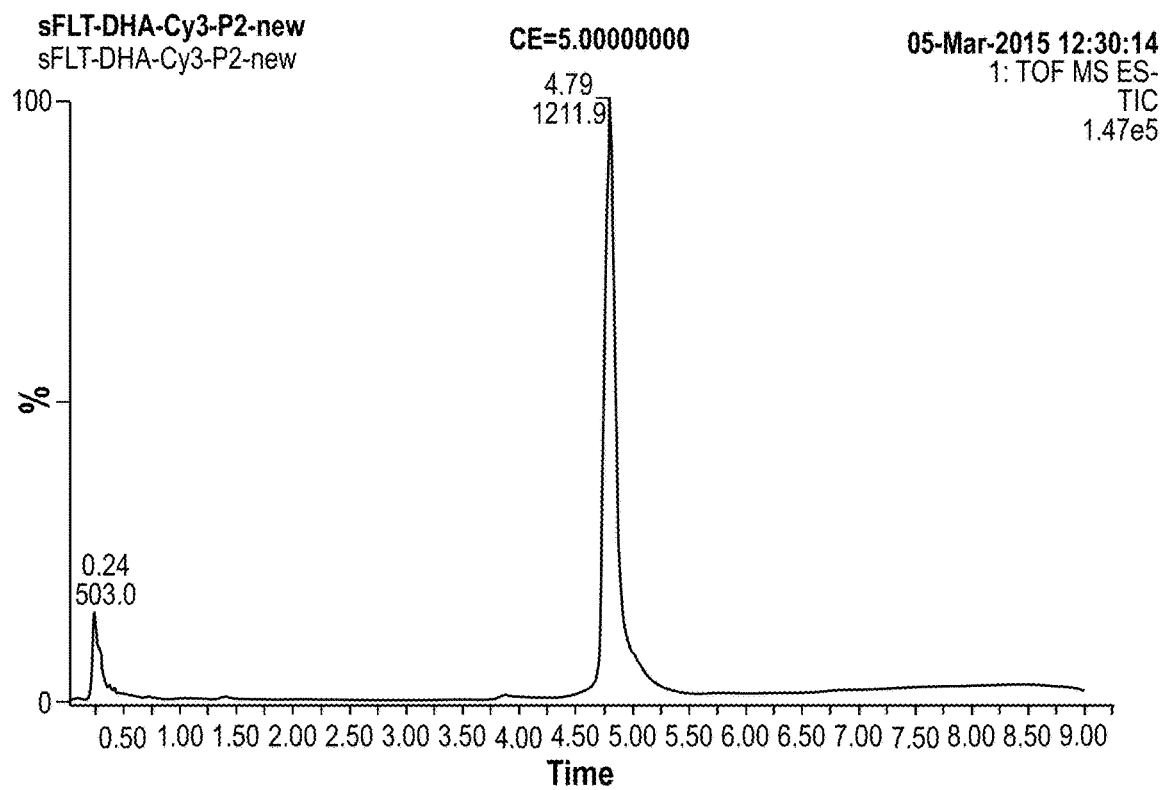
Fig. 1N

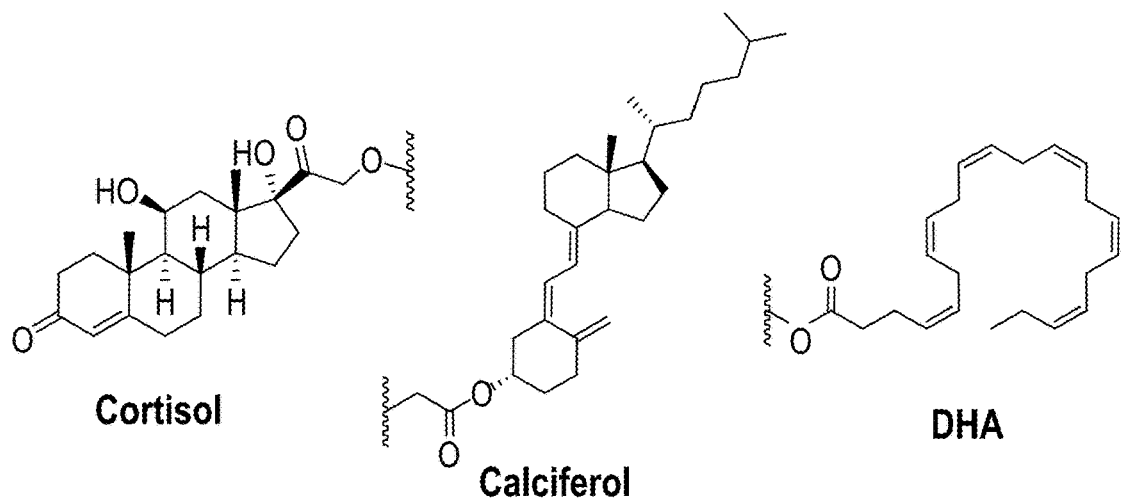
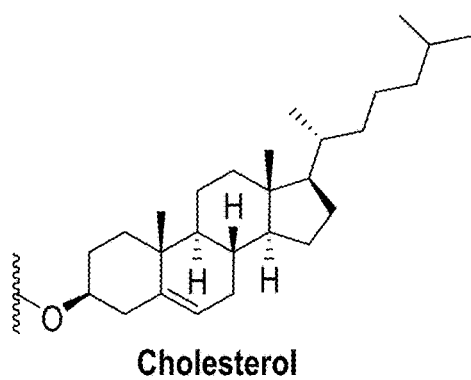
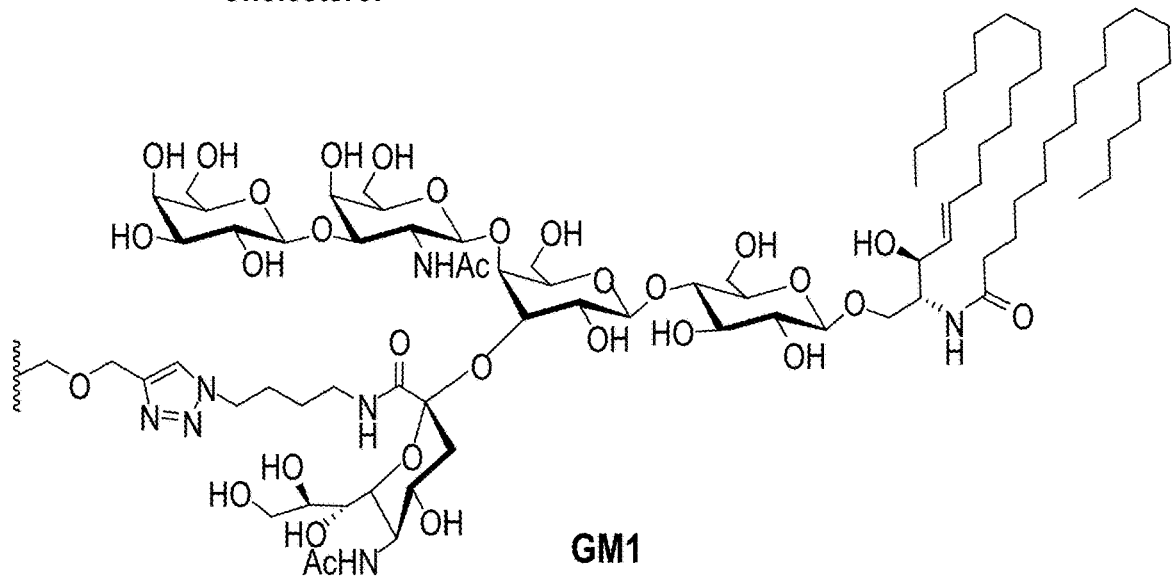
Fig. 2A

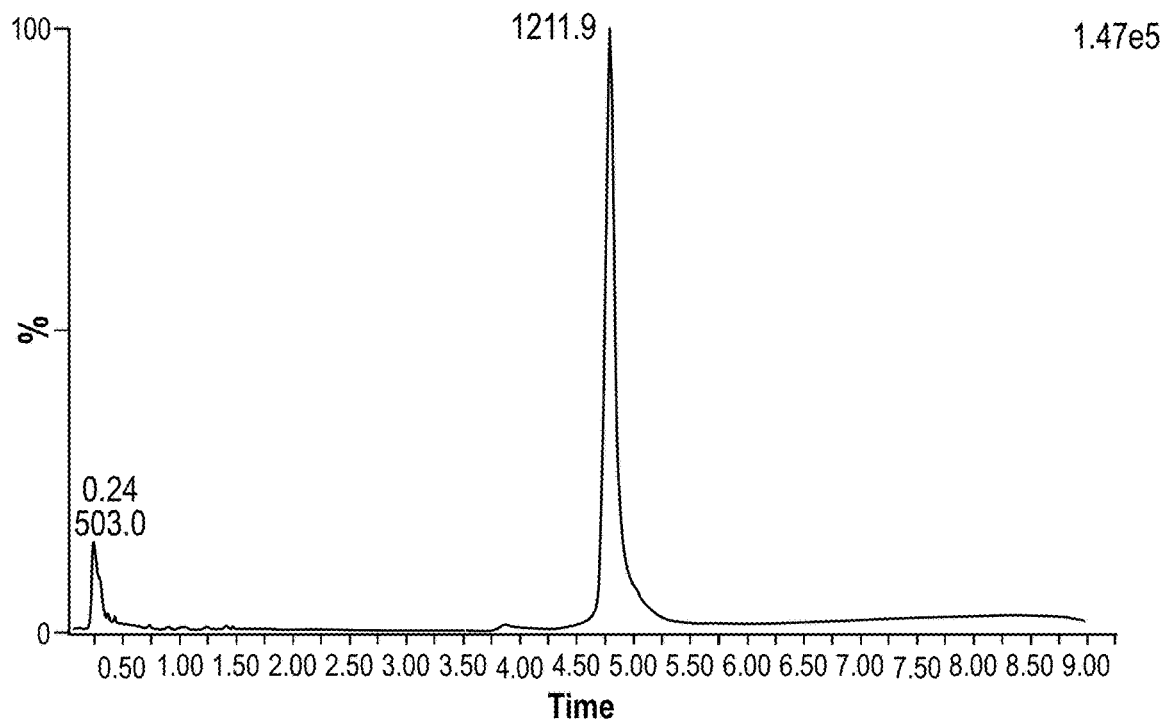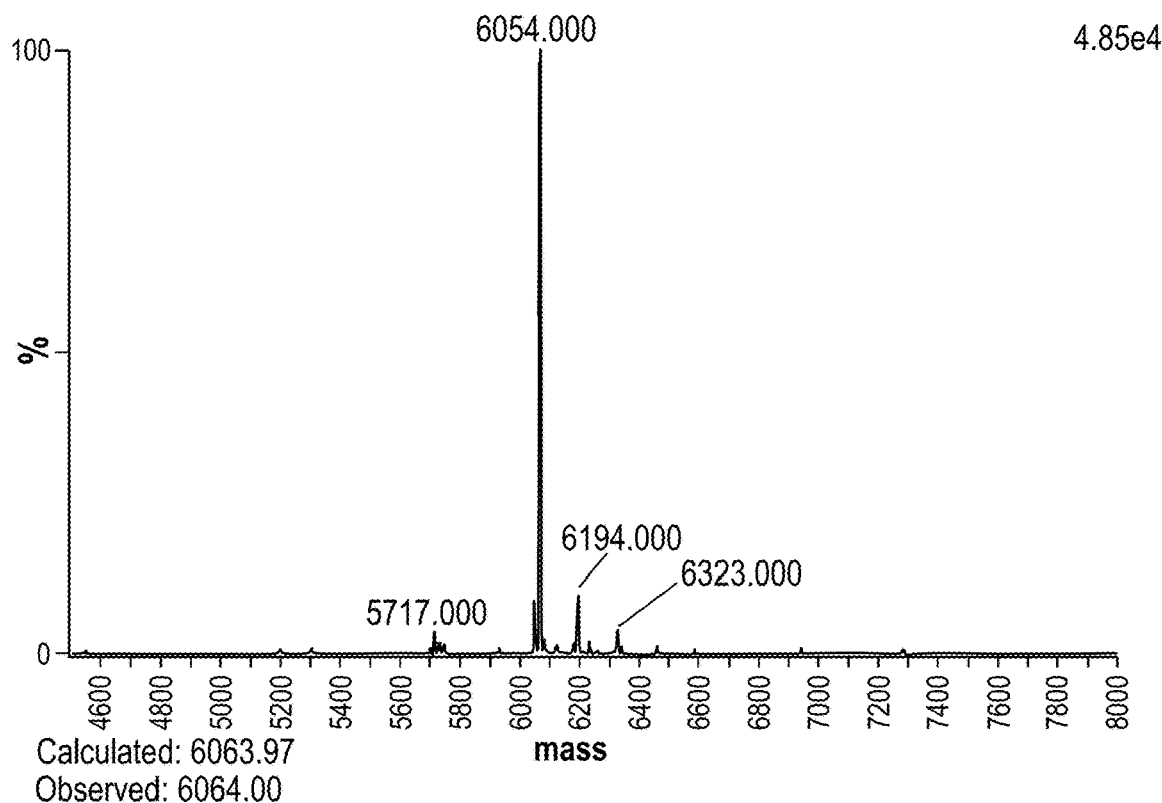
Fig. 2C

Docosanic acid (DCA)-hsiRNA

Docosahexaenoic acid (DHA)-hsiRNA

Phosphatidylcholine-DHA (g2DHA or DHAPCL)-hsiRNA

Eicosapentanoic acid (EPA)-hsiRNA

Cholesterol (Chol)-hsiRNA

Cholesterol (Chol)-hsiRNA

| | siRNA ID | Gene | Targeting Position | Strand | Sequence and chemical modification pattern | Conjugate |
|---|---|---|---|---|---|---|
| 1 | Chol-hsiRNA<sup>HTT</sup> | HTT | 10150 | S | fC#mA#fG.mU.fA.mA.fA.mG.fA.mG.fA.mG.fA.mU.fU#mA#fA | 3'-Teg-Cholesterol |
|   |   | HTT | 10150 | AS | PmU#fU#mA.fA.mU.fC.mU.fC.mU.fC.mU.fU#mA#fA.mC#fU#mG#fA#mU#fA#mU#fA#fA | |
| 2 | Cy3-Chol-hsiRNA<sup>HTT</sup> | HTT | 10150 | S | fC#mA#fG.mU.fA.mA.fA.mG.fA.mG.fA.mG.fA.mU.fU#mA#fA | 3'-Teg-Cholesterol, 5'-Cy3 |
|   |   | HTT | 10150 | AS | PmU#fU#mA.fA.mU.fC.mU.fC.mU.fC.mU.fU#mA#fA.mC#fU#mG#fA#mU#fA#mU#fA#fA | |
| 3 | DHA-hsiRNA<sup>HTT</sup> | HTT | 10150 | S | fC#mA#fG.mU.fA.mA.fA.mG.fA.mG.fA.mG.fA.mU.fU#mA#fA | 3'-C7DHA |
|   |   | HTT | 10150 | AS | PmU#fU#mA.fA.mU.fC.mU.fC.mU.fC.mU.fU#mA#fA.mC#fU#mG#fA#mU#fA#mU#fA#fA | |
| 4 | C7-DHA-hsiRNA<sup>HTT</sup> | HTT | 10150 | S | fC#mA#fG.mU.fA.mA.fA.mG.fA.mG.fA.mG.fA.mU.fU#mA#fA | 3'-C7 |
|   |   | HTT | 10150 | AS | PmU#fU#mA.fA.mU.fC.mU.fC.mU.fC.mU.fU#mA#fA.mC#fU#mG#fA#mU#fA#mU#fA#fA | |
| 5 | Cy3-DHA-hsiRNA<sup>HTT</sup> | HTT | 10150 | S | fC#mA#fG.mU.fA.mA.fA.mG.fA.mG.fA.mG.fA.mU.fU#mA#fA | 3'-C7-DHA, 5'-Cy3 |
|   |   | HTT | 10150 | AS | PmU#fU#mA.fA.mU.fC.mU.fC.mU.fC.mU.fU#mA#fA.mC#fU#mG#fA#mU#fA#mU#fA#fA | |

*Fig. 7*

| | siRNA ID | Gene | Targeting Position | Strand | Sequence and chemical modification pattern | Conjugate |
|---|---|---|---|---|---|---|
| 6 | DHA-hsiRNA*PPIB* | PPIB | 437 | S | fC#mA#fA.mA.fU.mU.fC.mC.fA.mU.fC. mG.fU#mG#fA | 3'-C7-DHA |
| | | PPIB | 437 | AS | PmU#fC#mA.fC.mG.fA.mU.fG.mG.fA.m A.fU.mU#fU#mG#fC#mU##G#mU#fU | |
| 7 | DHA-hsiRNA*PLK1* | PLK1 | 2140 | S | fG#mC#fA.mC.fA.mU.fU.mA.fA.mA.fC. mA.fG.mA.fA | 3'-C7-DHA |
| | | PLK1 | 2140 | AS | PmU#fU#mC.fU.mG.fU.mU.fA.mA.m U.fG.mU#fG#mC#fA#mU#fA#mA#fA | |
| 8 | DHA-hsiRNA*NTC* | NTC | -- | S | fU#mG#fA.mC.fA.mA.fA.mU.fA.mC.fG. mA.fU#mU#fA | 3'-C7-DHA |
| | | | -- | AS | PmU#fA#mA.fU.mC.fG.mU.fA.mU.fU.m U.fG.mU#fC#mA#fA#mU#fC#mA#fU | |

*Fig. 7*
*(Continued)*

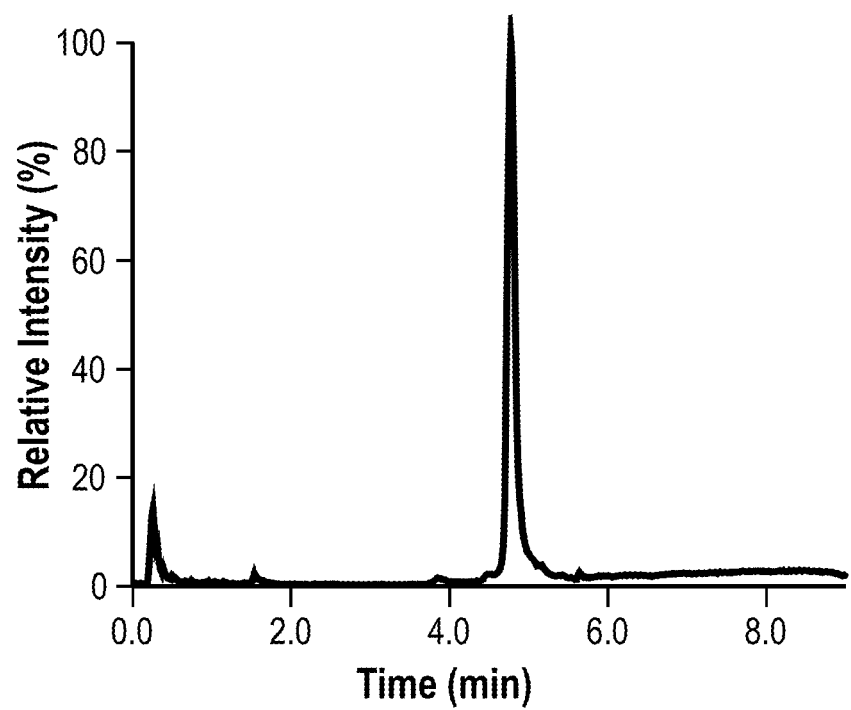
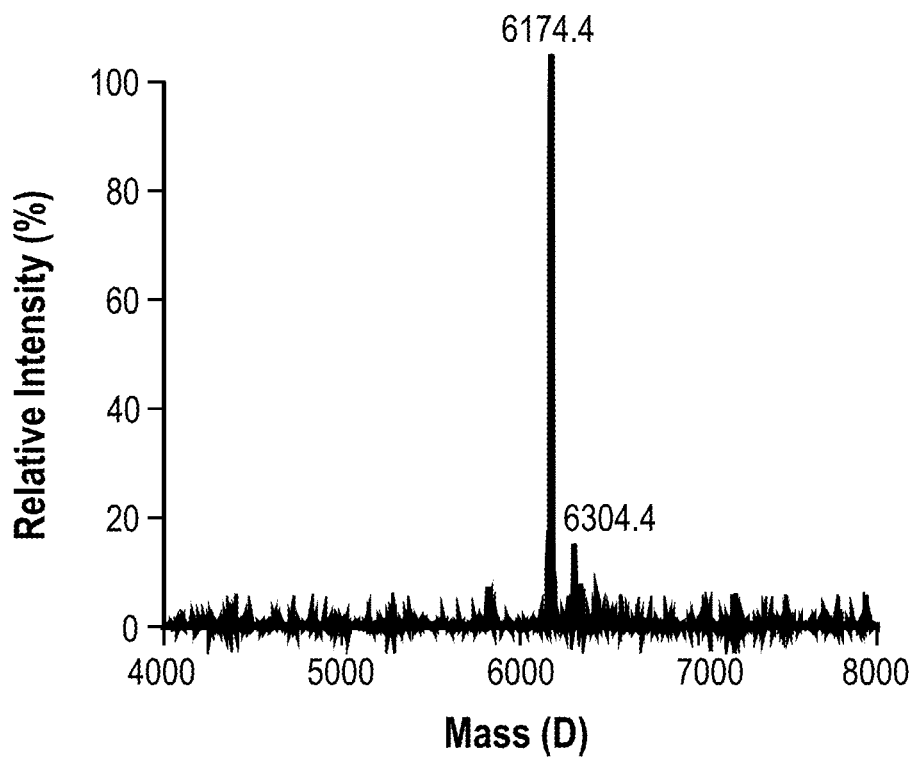
Fig. 9

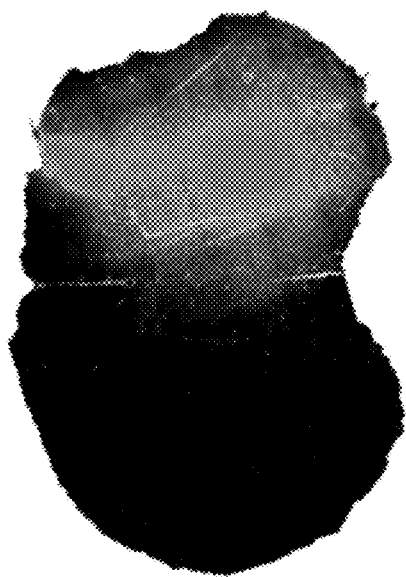
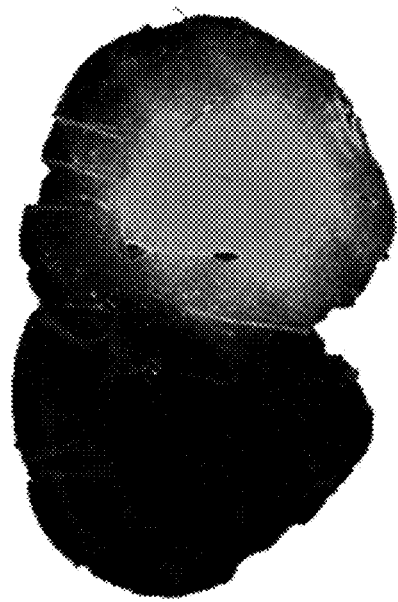
Fig. 10

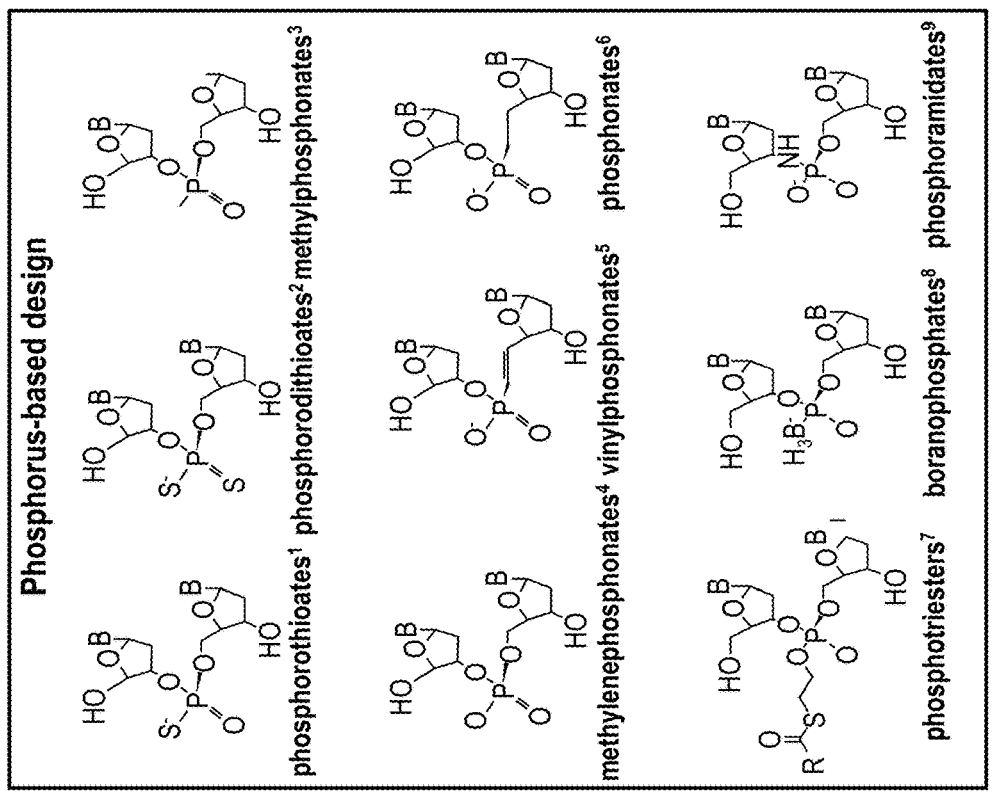
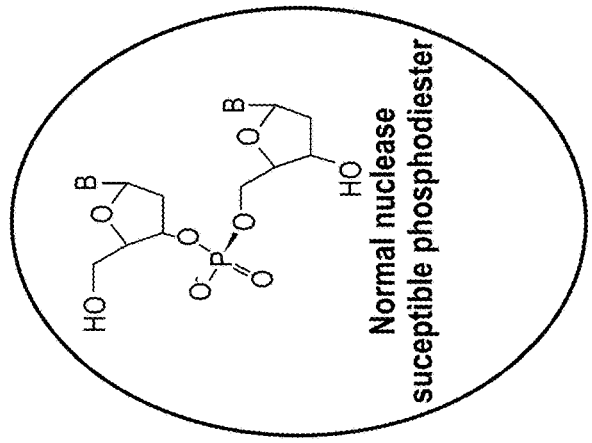
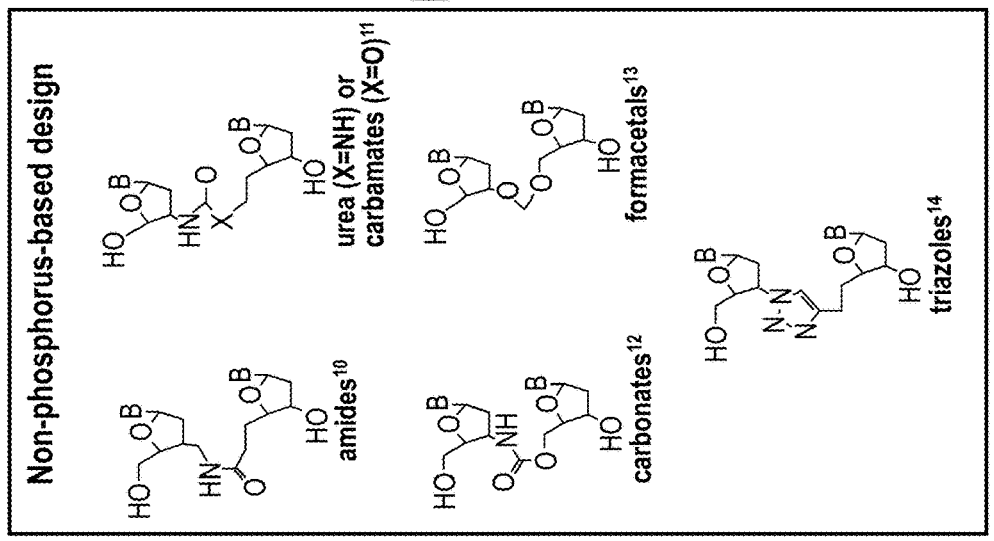
Fig. 15

|  | VLDL | IDL | LDL | HDL |
|---|---|---|---|---|
| Enriched proteins | Apo B-100 | Apo B-100 | Apo B-100 | Apo A1, Apo A2 |
| Enriched lipids | Triglycerides | Triglycerides, Phospholipids, Cholesterol | Phospholipids, Cholesterol | Cholesterol |
| Primary Receptors | LDL (Apo B-100) receptor | LDL (Apo B-100) receptor | LDL (Apo B-100) receptor | Scavenger receptor B1 (SR-B1) |
| Receptor expression patterns | Liver, Gut, Adrenal, Lung | Liver, Gut, Adrenal, Lung | Liver, Gut, Adrenal, Lung | Megalin/Cubulin SR-B1: Adrenals, Ovary, Testes, Liver Megalin/Cubulin: Kidney, Placenta |

*Fig. 29*

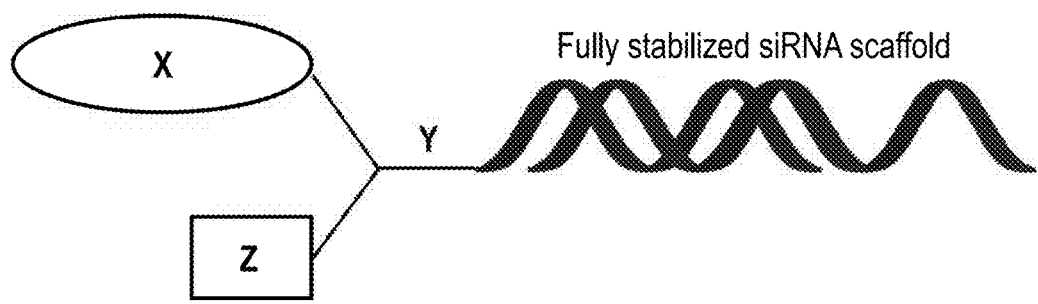
Fig. 32A
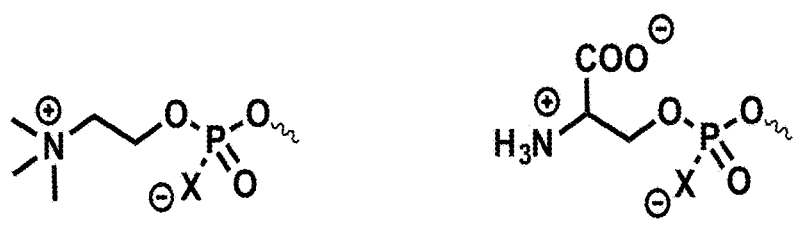
Phosphatidylcholine          Phosphatidylserine
X = O, S, BH$_3$
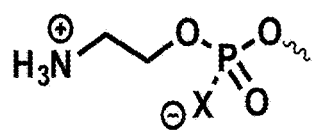 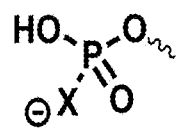
Phosphatidylamine            Phosphoric acid
Fig. 32B

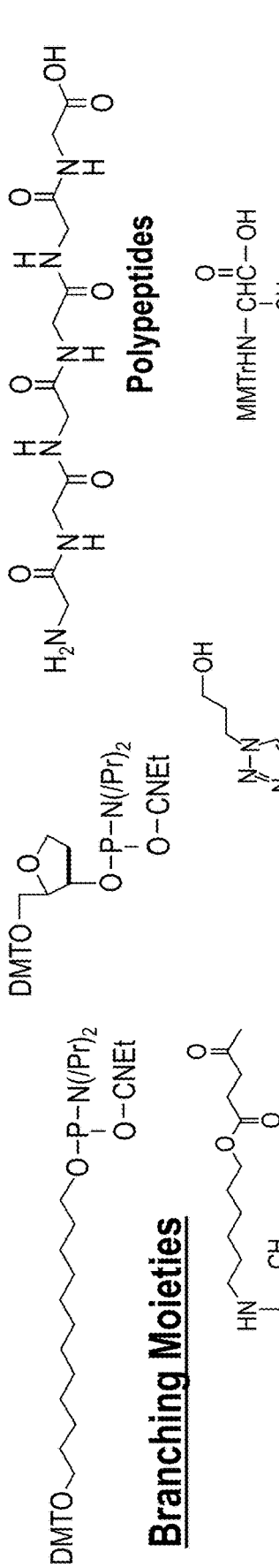
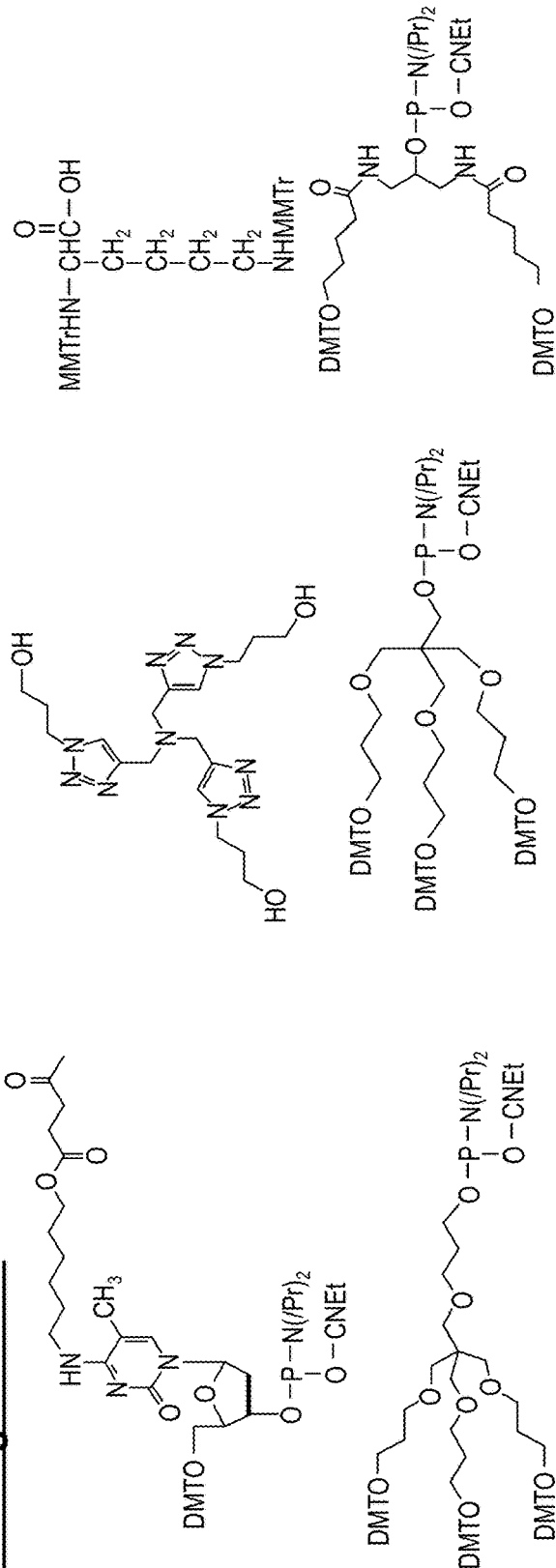
Fig. 33 hsiRNA association with different lipoprotein particles

|  | VLDL | LDL | HDL | Albumin |
|---|---|---|---|---|
| hsiRNA | 30% | | | 80% |
| PC-hsiRNA | 5-10% | | | 90-95% |
| LCA-hsiRNA | | | | 100% |
| LCA-PC-hsiRNA | | | | 100% |
| DHA-hsiRNA | 20% | | 50% | 30% |
| DHA-PC-hsiRNA | | | 70% | 30% |
| EPA-hsiRNA | 10% | | 60% | 30% |
| GM1-hsiRNA | | 100%* | | |
| DCA-hsiRNA | | 100%* | | |
| DCA-PC-hsiRNA | | 100%* | | |
| Chol-hsiRNA | | 100%* | | |

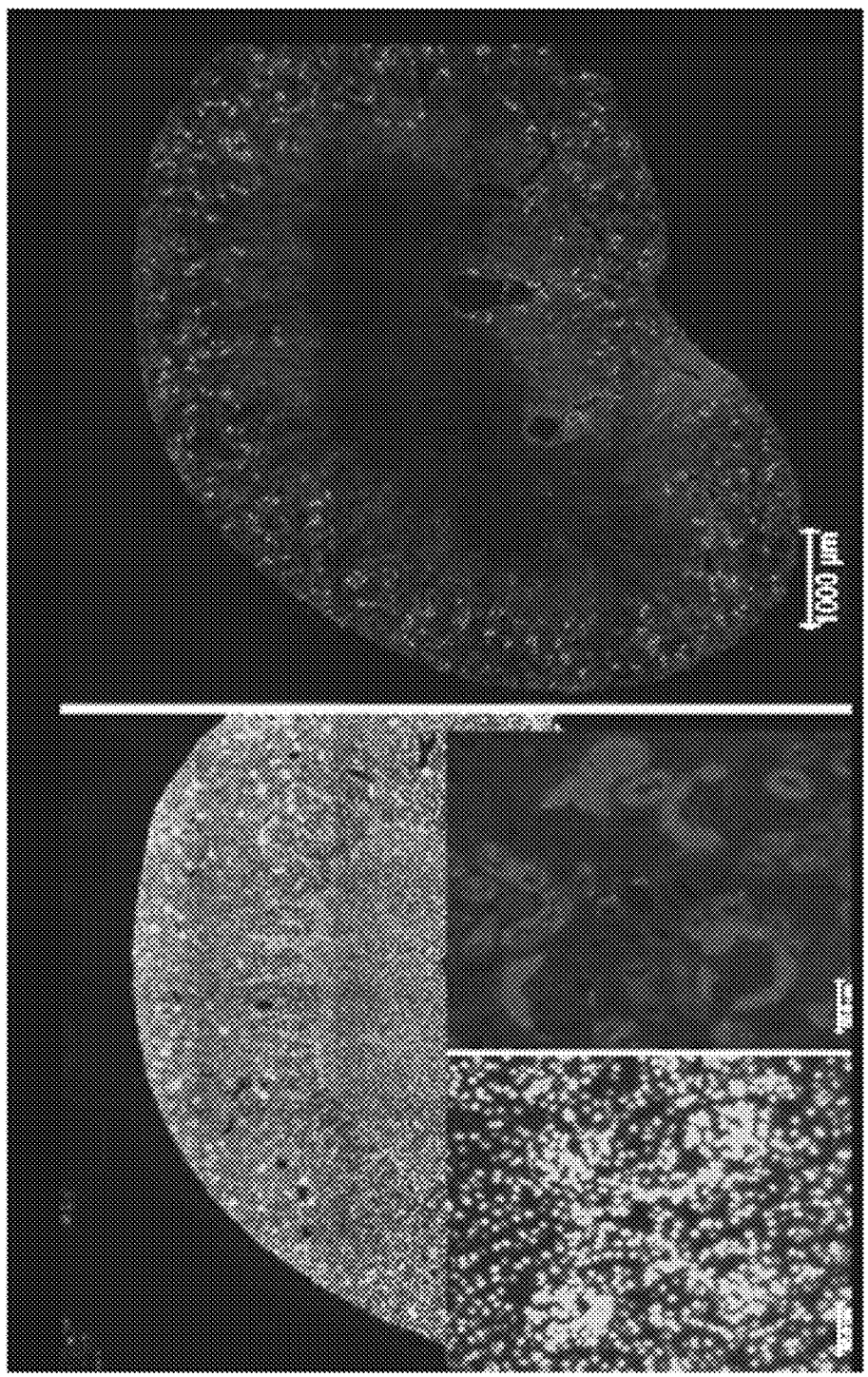

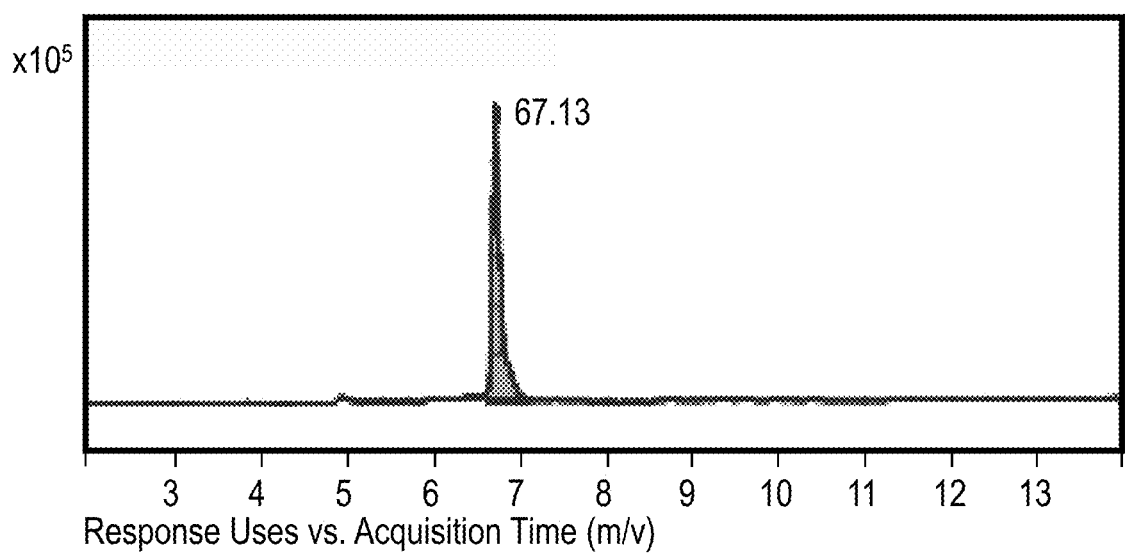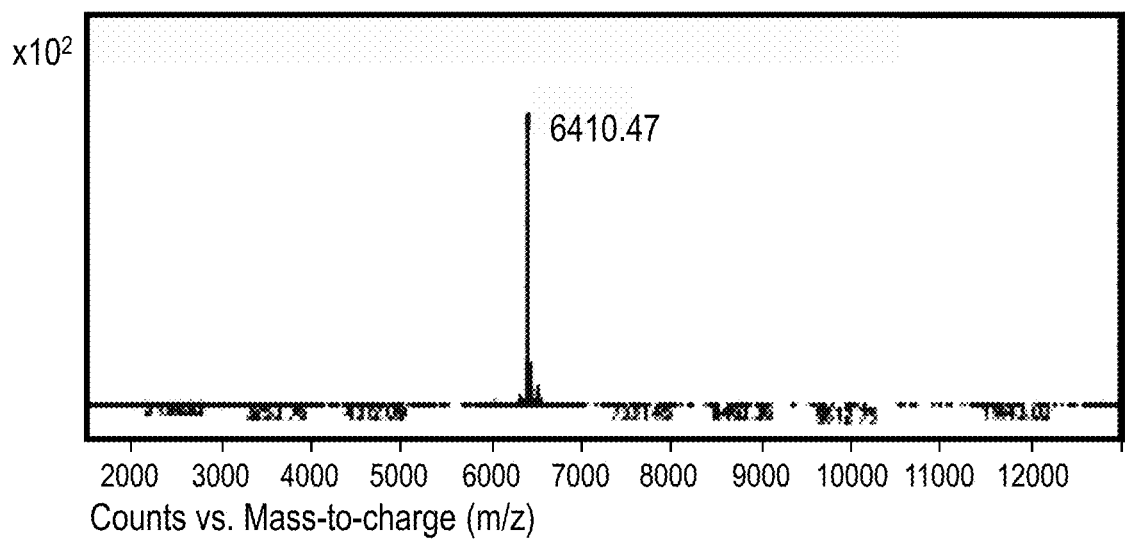
Fig. 46A

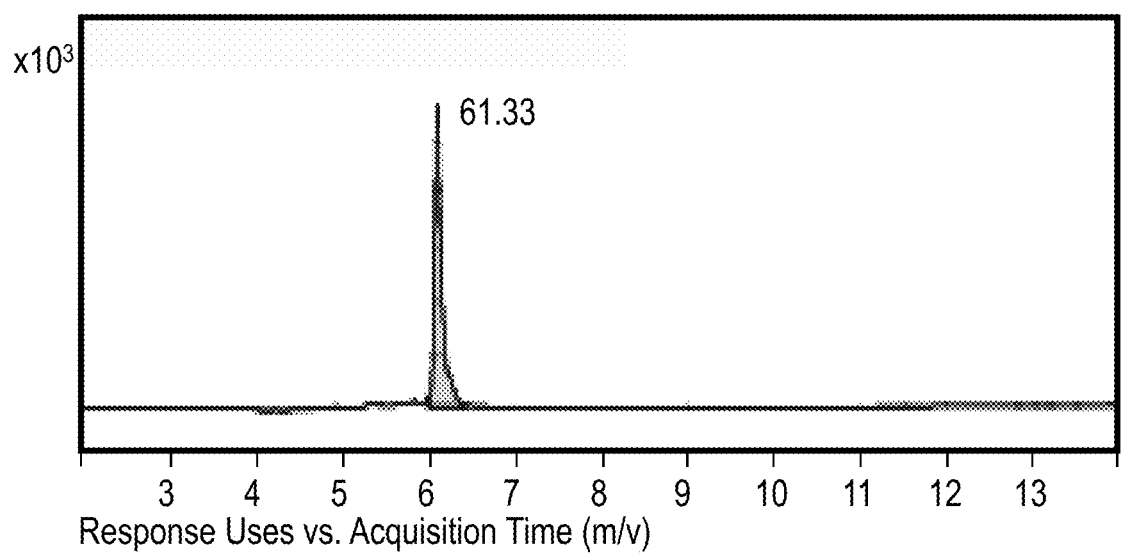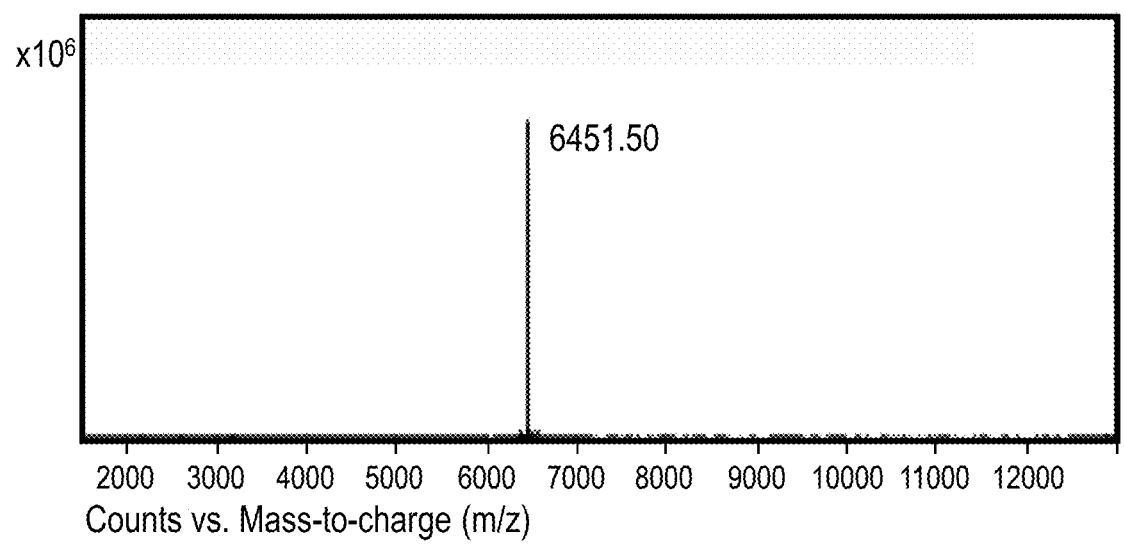
Fig. 46B

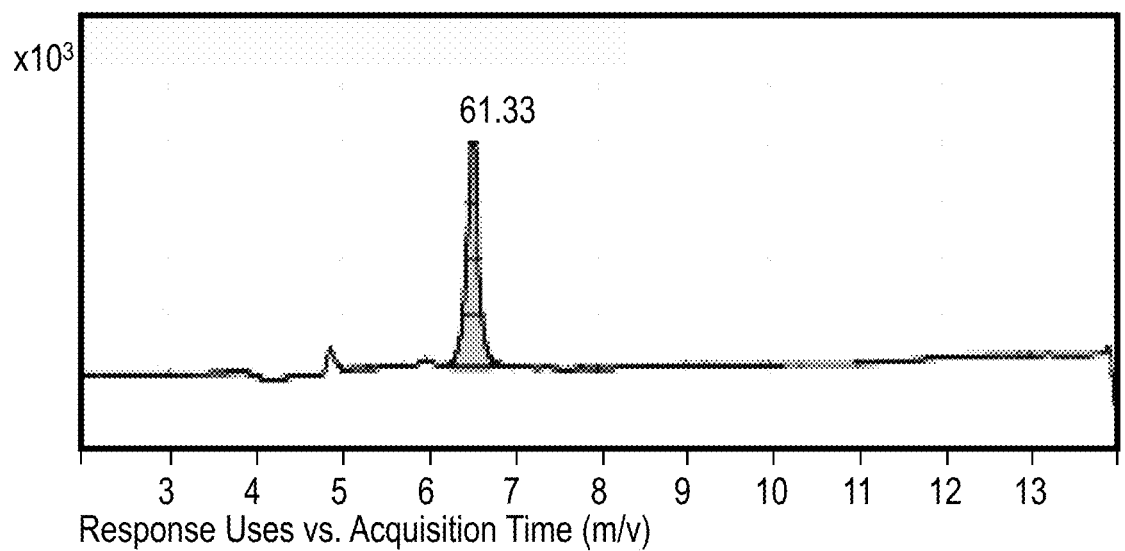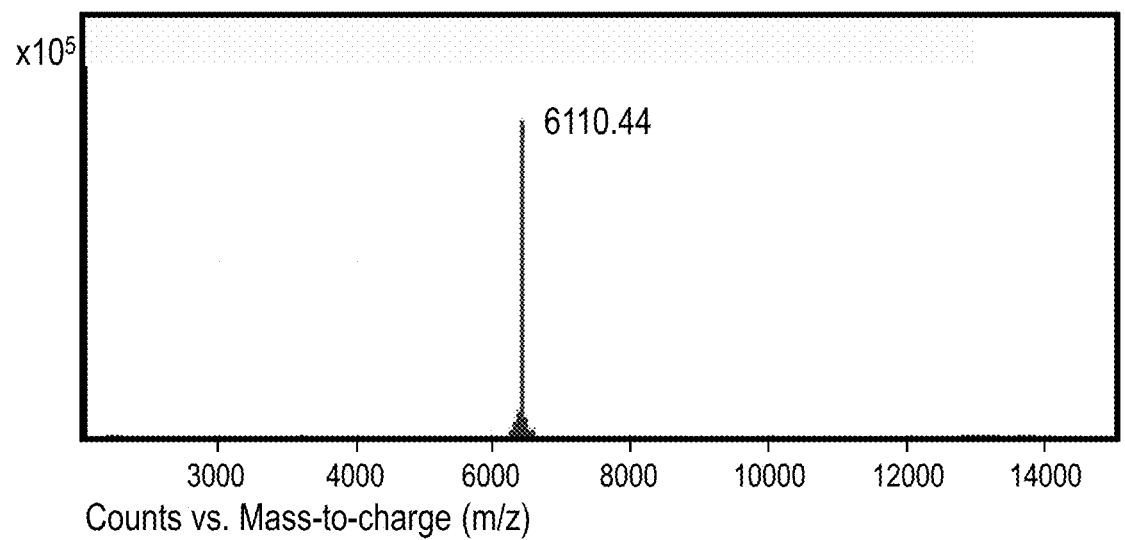
Fig. 46C

CONJUGATED OLIGONUCLEOTIDES

RELATED APPLICATIONS

This application is a 35 U.S.C. § 371 filing of International Patent Application No. PCT/US2017/046593, filed Aug. 11, 2017, which claims priority to U.S. Provisional Patent Application Ser. No. 62/461,529, filed Feb. 21, 2017, and U.S. Provisional Patent Application Ser. No. 62/374,499, filed Aug. 12, 2016, each of which is hereby incorporated herein by reference in its entirety for all purposes.

STATEMENT OF FEDERALLY SPONSORED RESEARCH

This invention was made with government support under Grant Nos. GM108803 and TR000888 awarded by the National Institutes of Health. The Government has certain rights in this invention.

TECHNICAL FIELD

This disclosure relates to novel hydrophobically-conjugated oligonucleotides. The oligonucleotide conjugates are designed to achieve unexpectedly high efficacy, uptake and tissue distribution.

BACKGROUND

RNA interference represents a simple and effective tool for inhibiting the function of genes. The promise of RNA interference as a general therapeutic strategy, however, depends on the ability to deliver small RNAs to a wide range of tissues. Currently, small therapeutic RNAs can only be delivered effectively to liver. There remains a need for self-delivering siRNA that are characterized by efficient RISC entry, minimal immune response and off-target effects, efficient cellular uptake without formulation, and efficient and specific tissue distribution.

SUMMARY

In one aspect, provided herein is a compound of formula (1):

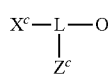

wherein:
O is a double-stranded nucleic acid comprising a first oligonucleotide and a second oligonucleotide, wherein:
 (1) the first oligonucleotide comprises at least 16 contiguous nucleotides, a 5' end, a 3' end and has complementarity to a target;
 (2) the second oligonucleotide comprises at least 15 contiguous nucleotides, a 5' end, a 3' end, and has homology with a target; and
 (3) a portion of the first oligonucleotide is complementary to a portion of the second oligonucleotide;
L is a divalent or trivalent linker;
$X^c$ is a hydrophobic moiety; and
$Z^c$ is a phosphodiester or phosphodiester derivative, or is absent.

In certain embodiments, L comprises an ethylene glycol chain, an alkyl chain, a peptide, RNA, DNA, a phosphodiester, a phosphorothioate, a phosphoramidate, an amide, a carbamate, or a combination thereof; and wherein L is attached to O via the second oligonucleotide.

In certain embodiments, Xc is selected from the group consisting of fatty acids, steroids, secosteroids, lipids, gangliosides and nucleoside analogs, endocannabinoids, and vitamins (e.g., a fatty acid selected from the group consisting of cholesterol, Lithocholic acid (LCA), Eicosapentaenoic acid (EPA), Docosahexaenoic acid (DHA) and Docosanoic acid (DCA), a vitamin selected from the group consisting of choline, vitamin A, vitamin E, and derivatives or metabolites thereof, or a vitamin selected from the group consisting of retinoic acid and alpha-tocopheryl succinate.

In certain embodiments, Xc has an affinity for low density lipoprotein and/or intermediate density lipoprotein or is a saturated or unsaturated moiety having fewer than three double bonds; has an affinity for high density lipoprotein (e.g., is a polyunsaturated moiety having three or more double bonds).

In certain embodiments, $Z^c$ is selected from the group consisting of:

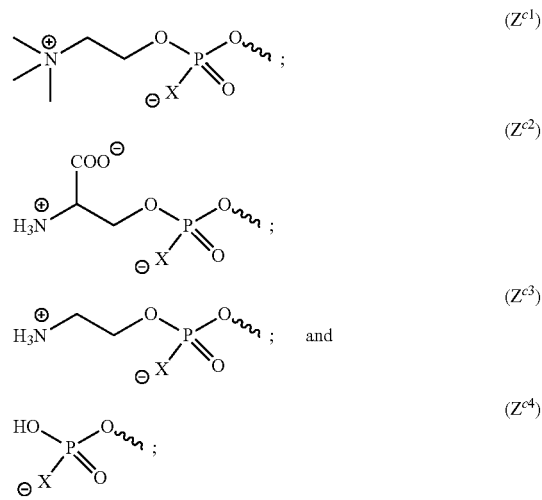

wherein X is O, S or $BH_3$. Zc may optionally be Zc1.

In certain embodiments, O comprises one or more chemically-modified nucleotides.

In certain embodiments, the first oligonucleotide comprises alternating 2'-methoxy-ribonucleotides and 2'-fluoro-ribonucleotides, the second oligonucleotide comprises alternating 2'-methoxy-ribonucleotides and 2'-fluoro-ribonucleotides and/or the nucleotides at positions 2 and 14 from the 5' end of the second oligonucleotide are 2'-methoxy-ribonucleotides.

In certain embodiments, the nucleotides of the first oligonucleotide are connected via phosphodiester or phosphorothioate linkages, the nucleotides of the second oligonucleotide are connected via phosphodiester or phosphorothioate linkages, the nucleotides at positions 1 and 2 from the 3' end of the second oligonucleotide are connected to adjacent nucleotides via phosphorothioate linkages, and/or the nucleotides at positions 1 and 2 from the 5' end of the second oligonucleotide are connected to adjacent nucleotides via phosphorothioate linkages.

In certain embodiments, the first oligonucleotide comprises alternating 2'-methoxy-ribonucleotides and 2'-fluoro-ribonucleotides, wherein each nucleotide is a 2'-methoxyribonucleotide or a 2'-fluoro-ribonucleotide; and the nucleotides at positions 2 and 14 from the 5' end of the first oligonucleotide are not 2'-methoxy-ribonucleotides; the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides; the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

In certain embodiments, the first oligonucleotide comprises a moiety X at the 5' end, wherein X is selected from the group consisting of:

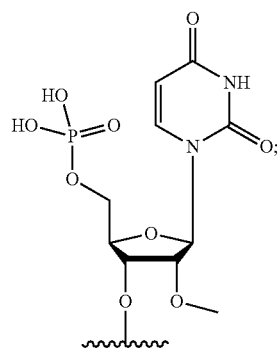

X1

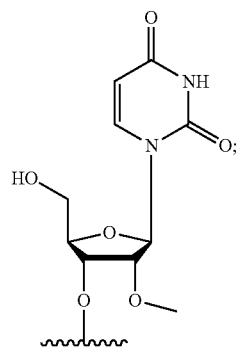

X2

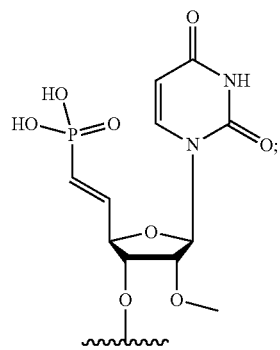

X3

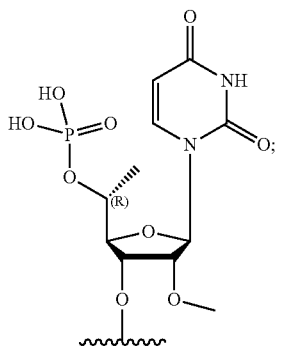

X4

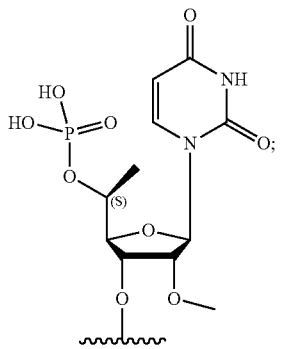

X5

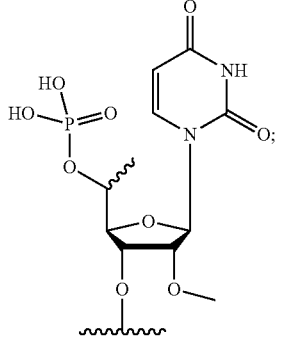

X6

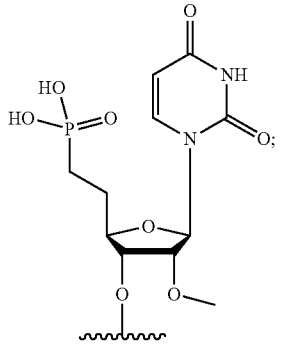

X7

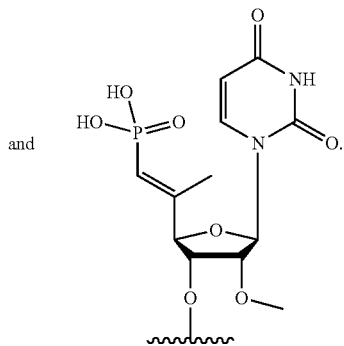
X8
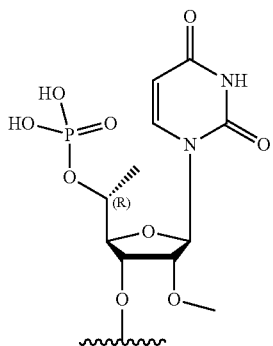
X4
and
In certain embodiments, X is X3.
In certain embodiments, the first oligonucleotide has the structure of formula (Ia):
$$X(-K-B-K-A)_j(-S-B-S-A)_r(-S-B)_t-OR \qquad (Ia)$$
wherein:
X is selected from the group consisting of:
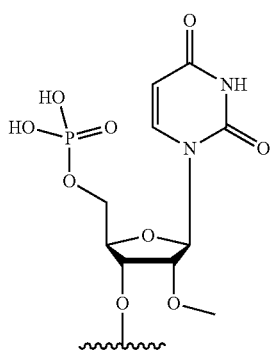
X1
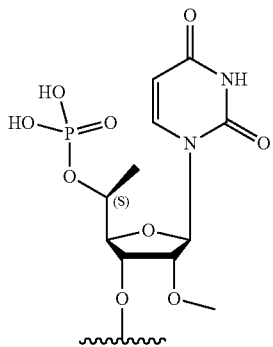
X5
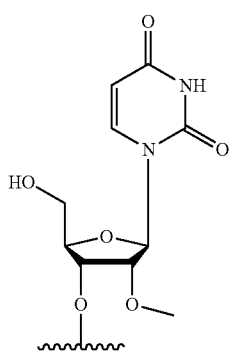
X2
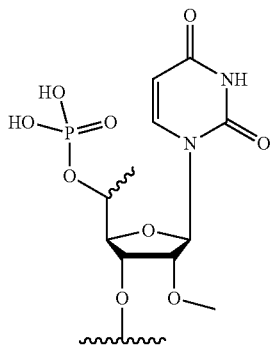
X6
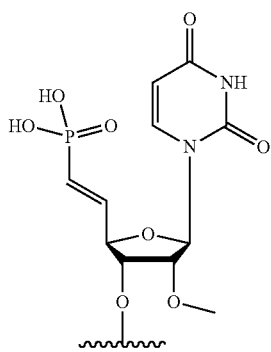
X3
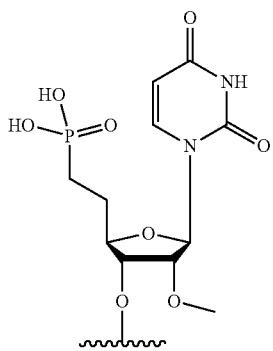
X7

-continued

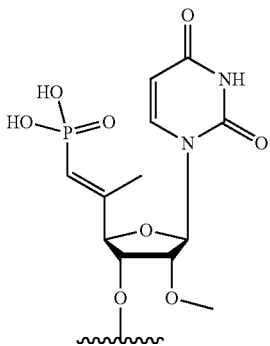

X8

A, for each occurrence, independently is a 2'-methoxy-ribonucleotide;
B, for each occurrence, independently is a 2'-fluoro-ribonucleotide;
K, for each occurrence independently is a phosphodiester or phosphorothioate linker;
S is a phosphorothioate linker;
R is hydrogen, phosphate, vinylphosphonate, or a capping group;
j is 4, 5, 6 or 7;
r is 2 or 3; and
t is 0 or 1.

In certain embodiments, the first oligonucleotide has the structure of formula (IIa):

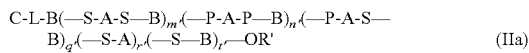

(IIa)

wherein:
C-L is:

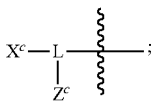

A, for each occurrence, independently is a 2'-methoxy-ribonucleotide;
B, for each occurrence, independently is a 2'-fluoro-ribonucleotide;
S is a phosphorothioate linker;
P is a phosphodiester linker;
R' is hydrogen, phosphate, vinylphosphonate, or a capping group;
m' is 0 or 1;
n' is 4, 5 or 6;
q' is 0 or 1;
r' is 0 or 1; and
t' is 0 or 1.

In certain embodiments, the first oligonucleotide has 3-7 more nucleotides than the second oligonucleotide, the sequences of the first and second oligonucleotides comprise sequences selected from the tables of FIG. 7, Xc is DHA, Zc is not Zc1, and/or Zc is Zc1 and Xc is not DHA.

In certain embodiments, the first oligonucleotide has perfect complementarity to the target, the second oligonucleotide has complete homology with the target, and/or the target is mammalian or viral mRNA (e.g., an intronic region of said mRNA).

In one aspect, a method for delivering any of the compounds described herein to an organ or tissue in a patient, comprising administering said compound to the patient, wherein the compound has a selective affinity for a serum lipoprotein is provided.

In certain embodiments, the organ is the kidney, the brain or the epidermis, and the compound has a selective affinity for high density lipoprotein versus low density lipoprotein and/or high density lipoprotein. The compound may be to the patient intravenously or subcutaneously. Xc may be a polyunsaturated moiety having three or more double bonds.

In certain embodiments, a method for treating a disease or disorder of the kidneys, brain, epidermis or liver, in a patient in need of such treatment, comprising administering to the patient a compound described herein is provided.

In certain embodiments, the disease or disorder is selected from the group consisting of glomerulonephritis, glomerulosclerosis, nephrolithiasis, Lightwood-Albright syndrome, polycystic kidney disease, acute renal failure, acute renal injury, chronic kidney disease, kidney fibrosis, diabetic nephropathy, Fabry disease, Fanconi syndrome, focal segmental glomerulosclerosis, Goodpasture syndrome, Liddle syndrome, nutcracker syndrome, peritoneal-renal syndrome, and renal cell cancer.

In certain embodiments, the disease or disorder is selected from the group consisting of: Alzheimer's disease, amyotrophic lateral sclerosis, aneurysm, attention deficit disorder, attention deficit hyperactivity disorder, autism spectrum disorder, brain cancer, concussion, coma, cerebral palsy, dementia, dyslexia, epilepsy, encephalitis, Friedreich's ataxia, Huntington's disease, migraine, multiple sclerosis, narcolepsy, Parkinson's disease, stroke, and traumatic brain injury.

In certain embodiments, the disease or disorder is selected from the group consisting of: ichthyosis, ectodermal dysplasia, psoriasis, eczema, Darier's disease, porokeratosis, acne, vitiligo, and skin cancer.

In certain embodiments, the disease or disorder is selected from the group consisting of: liver disease, cirrhosis, fatty liver, liver cancer, hemochromatosis, toxic hepatitis, viral hepatitis, Gibert's syndrome, galactosemia, cystic disease of the liver, and Alagille syndrome.

In another aspect, a method for delivering a compound described herein to an organ or tissue in a patient, comprising administering to the patient said compound, wherein the organ or tissue is selected from the group consisting of thymus, bladder, intestine, skin, bone marrow, placenta, adipose tissue, muscle, spleen, pancreas, lung, fallopian tube, adrenal gland, heart, liver and kidney, is provided.

In certain embodiments, $X^c$ is selected from the group consisting of DHA g1, DHA g2, DCA g1, DCA g2, EPA g1, EPA g2, cholesterol g1, cholesterol C7 g1, cholesterol g2, LA g1, LA g2, RA g1, RA g2, TOCO g1 and TOCO g2.

In certain embodiments, the organ is the thymus and $X^c$ is selected from the group consisting of RA g1, RA g2, DHA g1, DHA g2 and DCA g2.

In certain embodiments, the organ is the bladder and $X^c$ is selected from the group consisting of DHA g1, DHA g2, EPA g1, LA g1 and LA g2.

In certain embodiments, the organ is the intestine and $X^c$ is selected from the group consisting of EPA g1, EPA g2, RA g1, DHA g1, DHA g2 and LA g2, (e.g., selected from RA g1, EPA g1 and EPA g2).

In certain embodiments, the organ is the skin and $X^c$ is selected from the group consisting of RA g1, RA g2, EPA g1, EPA g2, DHA g1, DHA g2, DCA g1, DCA g2, LA g1, LA g2, cholesterol g1, cholesterol C7 g1 and cholesterol g2.

In certain embodiments, the tissue is bone marrow and $X^c$ is selected from the group consisting of RA g1, RA g2, TOCO g1, DHA g1, DHA g2, EPA g1, EPA g2, DCA g1, DCA g2, LA g1, LA g2, cholesterol C7 g1, cholesterol g2 and choline.

In certain embodiments, the organ is the placenta and $X^c$ is selected from the group consisting of cholesterol g1, DCA g1, DCA g2, DHA g1, DHA g2 (e.g., wherein Xc is DCA g1 or DCA g2).

In certain embodiments, the tissue is adipose tissue and $X^c$ is selected from the group consisting of RA g1, DHA g1, DHA g2, EPA g1, DCA g1, DCA g2, LA g1 and LA g2.

In certain embodiments, the tissue is muscle tissue and $X^c$ is selected from the group consisting of TOCO g1, DHA g2, EPA g1, EPA g2 and DCA g2.

In certain embodiments, the organ is spleen and $X^c$ is selected from the group consisting of RA g1, RA g2, TOCO g1, TOCO g2, DHA g1, DHA g2, EPA g1, EPA g2, DCA g1, DCA g2, LA g1, LA g2, cholesterol g1, cholesterol C7 g1 and cholesterol g2 (e.g., selected from cholesterol g1, cholesterol g2, DCA g1 and DCA g2).

In certain embodiments, the organ or tissue is pancreas and Xc is selected from the group consisting of RA g2, DHA g2, EPA g1, DCA g2 and LA g1.

In certain embodiments, the organ is lung and $X^c$ is selected from the group consisting of RA g1, RA g2, EPA g1, EPA g2, DCA g1 and DCA g2 (e.g., selected from DCA g1, DCA g2, EPA g1 and EPA g2).

In certain embodiments, the organ is the fallopian tube and $X^c$ is selected from the group consisting of RA g1, TOCO g1, EPA g2, DCA g2, LA g2 and cholesterol g2.

In certain embodiments, the organ is the adrenal gland and $X^c$ is selected from the group consisting of RA g1, RA g2, DCA g1, DCA g2, LA g1, LA g2, cholesterol g1, cholesterol C7 g1 and cholesterol g2 (e.g., selected from RA g1, DCA g1, DCA g2, cholesterol g1 and cholesterol g2).

In certain embodiments, the organ is the heart and $X^c$ is selected from the group consisting of DCA g1, DCA g2, EPA g1, EPA g2, cholesterol g1 and cholesterol g2.

In certain embodiments, the organ is the kidney and $X^c$ is selected from the group consisting of RA g1, RA g2, TOCO g1, DCA g1, DCA g2, DHA g1, DHA g2, EPA g1, EPA g2, LA g1, LA g2, cholesterol g1 and choline (e.g., selected from RA g1, EPA g1, EPA g2, DCA g2 and cholesterol g1).

In certain embodiments, the organ is the liver and $X^c$ is selected from the group consisting of RA g1, RA g2, TOCO g1, TOCO g2, DHA g1, DHA g2, EPA g1, EPA g2, DCA g1, DCA g2, LA g1, cholesterol g1, cholesterol C7 g1 and cholesterol g2 (e.g., selected from RA g1, DCA g1, DCA g2, EPA g1, EPA g2, cholesterol g1 and cholesterol g2).

In one aspect, a method for treating a disease or disorder of adipose tissue, fallopian tube, adrenal gland, spleen, pancreas, or adipose tissue, in a patient in need of such treatment, comprising administering to the patient a compound described herein, is provided.

In certain embodiments, the disease or disorder is selected from the group consisting of: obesity, diabetes, insulin resistance, lipodystrophies, Dercum's disease, adipose tissue neoplasm, general adipose tissue inflammation, cardiovascular disease, hypertension and stroke, hypercholesterolemia, hypertriglyceridemia, arthritis, asthma and cancer.

In certain embodiments, the disease or disorder is selected from the group consisting of: salpingitis, endosalpingiosis, tubal torsion, paratubal cyst, endometriosis, fallopian tube cancers, infertility, fallopian tube obstruction, and adhesions.

In certain embodiments, the disease or disorder is selected from the group consisting of: Addison's disease, adrenal tumors, adrenal insufficiency, adrenal hyperplasia, primary aldosteronism, hyperaldosteronism, hypoaldosteronism, adrenal crisis, Cushing's disease, adrenocortical hyperfunction, adrenoleukodystrophy, adrenal fatigue, and adrenal incidentaloma.

In certain embodiments, the disease or disorder is selected from the group consisting of: splenomegaly, splenic disease, Gaucher's disease, asplenia, splenic infarction, spherocytosis, wandering spleen, splenic tumors, infectious mononucleosis, splenic injury, hyaloserositis, and anemias.

In certain embodiments, the disease or disorder is selected from the group consisting of: pancreatitis, pancreatic cancer, cystic fibrosis, pseudocyst, exocrine pancreatic insufficiency, diabetes, gastrointestinal diseases, pancreas divisum, steatorrhea, and sphincter of Oddi dysfunction.

In certain embodiments, the organ or tissue is adipose tissue, Xc is choline and Zc is absent.

In certain embodiments, the organ or tissue is adipose tissue, and wherein Xc is choline and Zc is absent.

In certain embodiments, the organ or tissue is the adrenal gland, and wherein Xc is LCA and Zc is Zc1.

In certain embodiments, the organ or tissue is fallopian tube, and wherein Xc is EPA and Zc is Zc1.

In certain embodiments, the organ or tissue is muscle, and wherein Xc is LCA and Zc is absent.

In certain embodiments, the organ or tissue is the pancreas, and wherein Xc is EPA and Zc is Zc1.

In certain embodiments, the organ or tissue is the heart.

In another aspect, a compound of formula (I):

wherein:
O is an oligonucleotide;
L is a divalent or trivalent linker selected from an ethylene glycol chain, an alkyl chain, a peptide, RNA, DNA, a phosphodiester, a phosphorothioate, a phosphoramidate, an amide, a carbamate, or a combination thereof;
$X^c$ is a hydrophobic moiety; and
$Z^c$ is a phosphodiester or phosphodiester derivative, or is absent, is provided.

In another aspect, a compound of formula (I):

wherein:
O is an oligonucleotide;
L is a divalent or trivalent linker a divalent or trivalent linker selected from an ethylene glycol chain, an alkyl chain, a peptide, RNA, DNA, a phosphodiester, a phosphorothioate, a phosphoramidate, an amide, a carbamate, or a combination thereof;
$X^c$ is a hydrophobic moiety selected from fatty acids, steroids, secosteroids, lipids, gangliosides and nucleoside analogs, or endocannabinoids; and
$Z^c$ is absent, or is a phosphodiester or phosphodiester derivative selected from

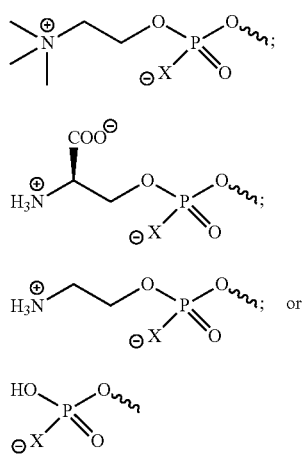

wherein X is O, S or BH₃, is provided.

In another aspect, a compound of formula (I):

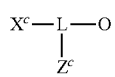
(I)

wherein:
O is an oligonucleotide;
L is a divalent or trivalent linker selected from an ethylene glycol chain, an alkyl chain, a peptide, RNA, DNA, a phosphodiester, a phosphorothioate, a phosphoramidate, an amide, a carbamate, or a combination thereof;
$X^c$ is a hydrophobic moiety selected from fatty acids, steroids, vitamins, secosteroids, lipids, gangliosides and nucleoside analogs, or endocannabinoids; and $Z^c$ is absent or is a phosphodiester or phosphodiester derivative selected from

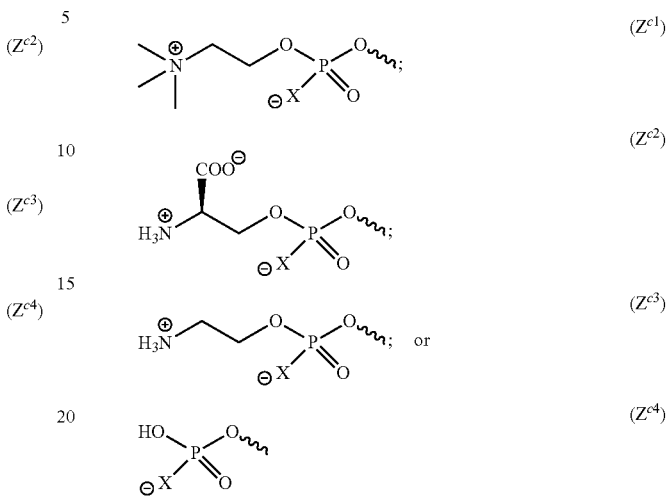

wherein X is O, S or BH₃, is provided.

In another aspect, a compound of formula (I):

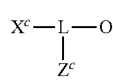
(I)

wherein:
O is an oligonucleotide;
L is a divalent or trivalent linker selected from:

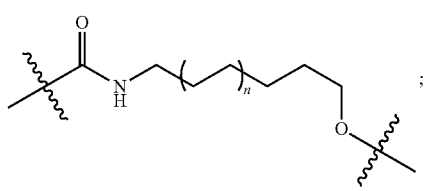

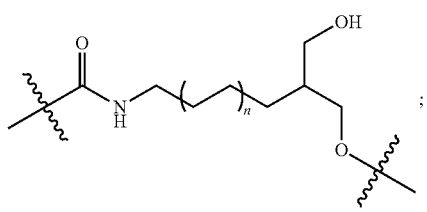

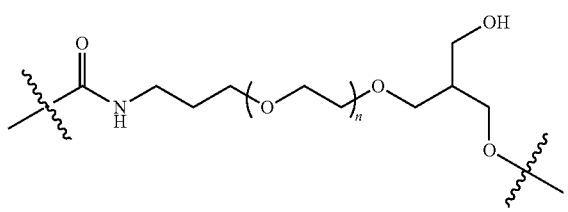

-continued

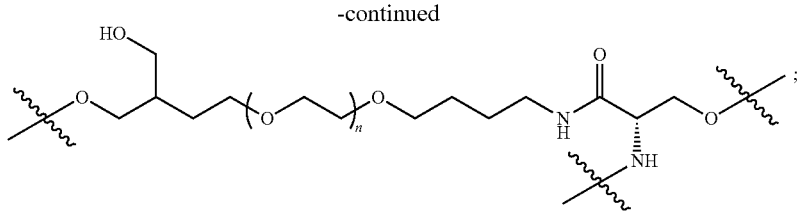

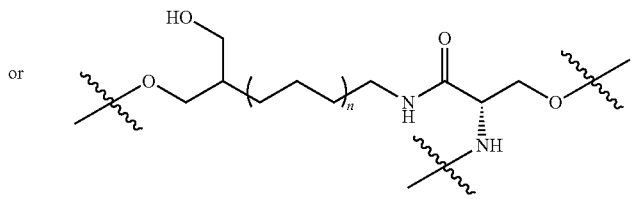

or wherein n is 1, 2, 3, 4, or 5;

$X^c$ is DHA, DCA, EPA, cholesterol, Lithocholic acid, Retinoic acid or α-tocopheryl succinate; and $Z^c$ is absent, or is a phosphodiester or phosphodiester derivative selected from

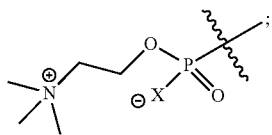

$Z^{c1}$

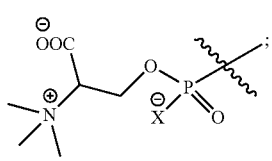

$Z^{c2}$

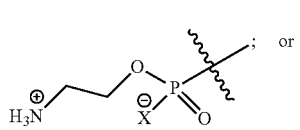

$Z^{c3}$

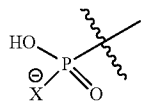

$Z^{c4}$

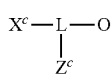

wherein X is O, S or $BH_3$, is provided.

In another aspect, a compound of formula (I):

$$X^c-L-O \atop Z^c \qquad (I)$$

wherein:

O is an oligonucleotide;

L is a linker selected from:

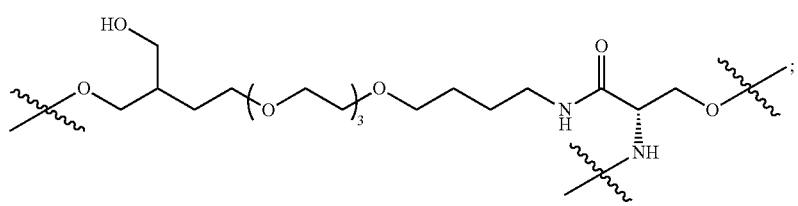

or

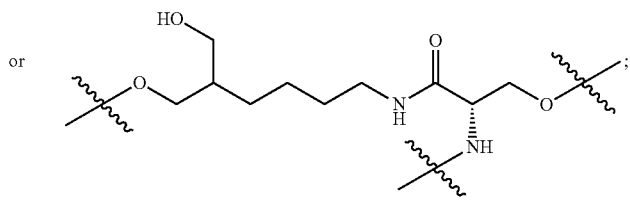

$X^c$ is a DHA, DCA, EPA, cholesterol, Lithocholic acid, Retinoic acid or α-tocopheryl succinate; and
$Z^c$ is a phosphodiester or phosphodiester derivative selected from
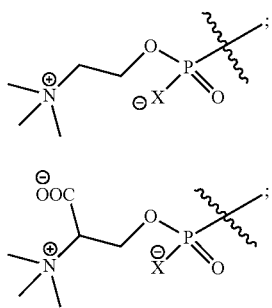
$Z^{c1}$
$Z^{c2}$
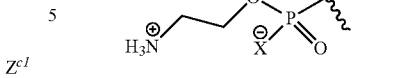
$Z^{c3}$
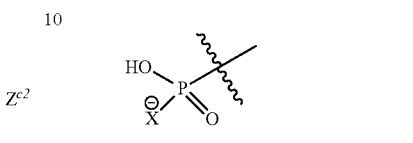
$Z^{c4}$
wherein X is O, S or $BH_3$, is provided.
In another aspect, a compound comprising a structure selected from:
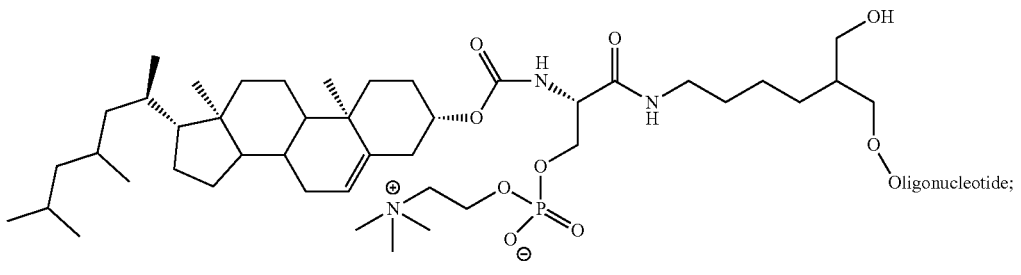
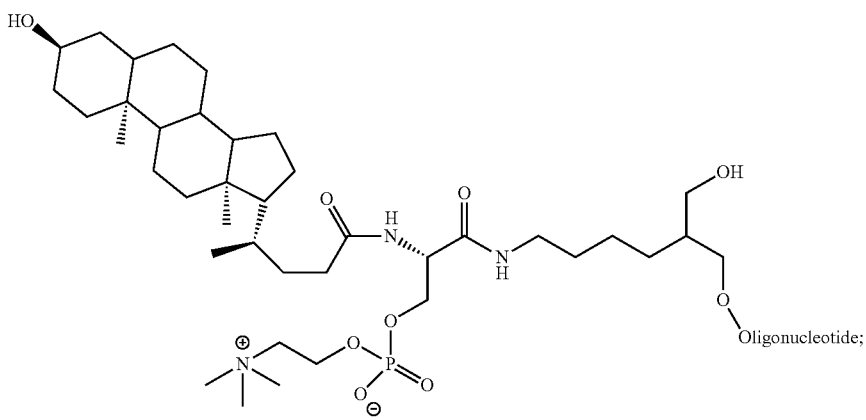
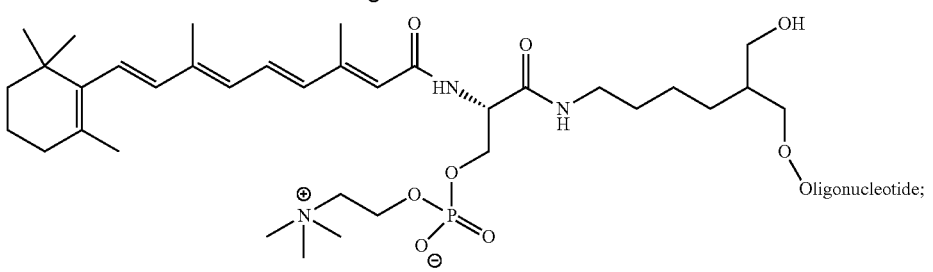
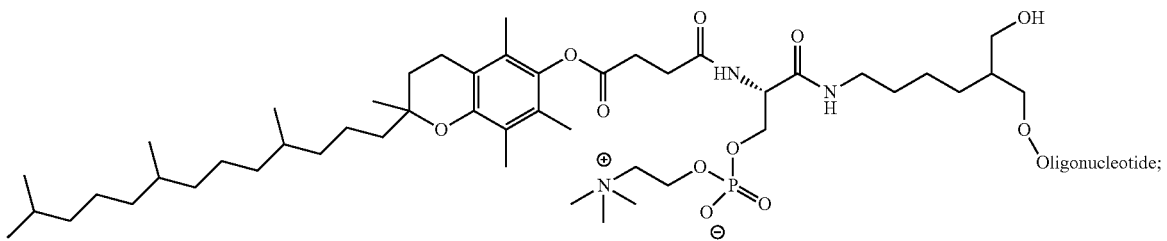

-continued

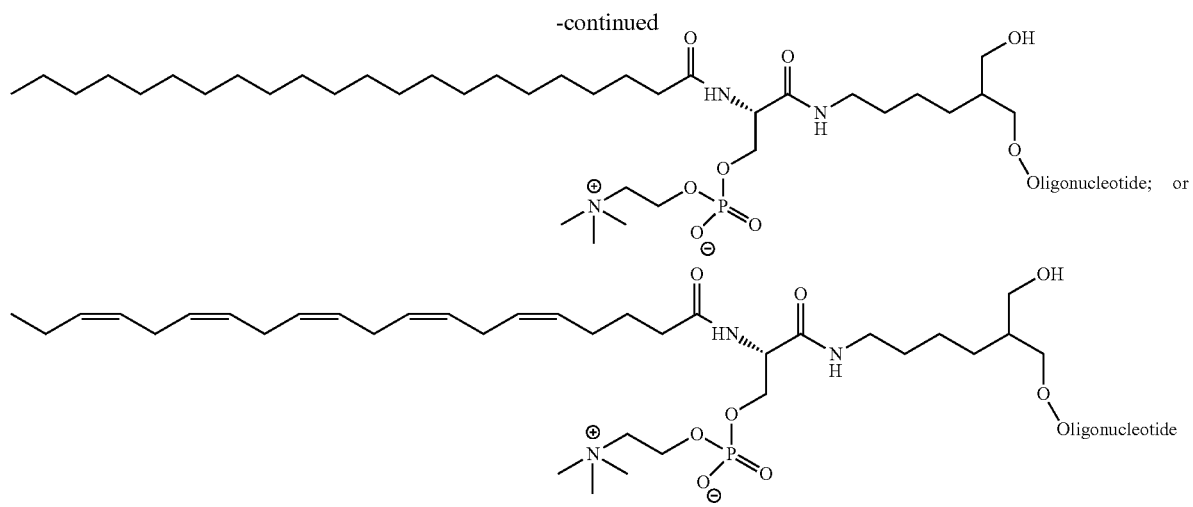

is provided.

In another aspect, a method for delivering the compound according to a compound described herein to an organ or tissue in a subject, comprising administering said compound to the subject, wherein Xc is DHA g1 or DHA g2, and wherein the organ or tissue is selected from the group consisting of thymus, bladder, intestine, skin, bone marrow, placenta, adipose, muscle, spleen, pancreas, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is DCA g1 or DCA g2, and wherein the organ or tissue is selected from the group consisting of thymus, skin, bone marrow, placenta, adipose, muscle, spleen, pancreas, lung, fallopian tube, adrenal gland, heart, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is EPA g1 or EPA g2, and wherein the organ or tissue is selected from the group consisting of thymus, bladder, intestine, skin, bone marrow, adipose, muscle, spleen, pancreas, lung, fallopian tube, heart, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is cholesterol g1, cholesterol C7 g1 or cholesterol g2, and wherein the organ or tissue is selected from the group consisting of skin, bone marrow, placenta, spleen, fallopian tube, adrenal gland, heart, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is LA g1 or LA g2, and wherein the organ or tissue is selected from the group consisting of bladder, intestine, skin, bone marrow, adipose, spleen, pancreas, fallopian tube, adrenal gland, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is RA g1 or RA g2, and wherein the organ or tissue is selected from the group consisting of thymus, intestine, skin, bone marrow, adipose, spleen, pancreas, lung, fallopian tube, adrenal gland, liver and kidney, is provided.

In certain embodiments, the compound is delivered subcutaneously or intravenously.

In another aspect, a method for delivering the compound according to a compound described herein to an organ or tissue in a subject, comprising administering said compound to the subject, wherein Xc is TOCO g1 or TOCO g2, and wherein the organ or tissue is selected from the group consisting of bone marrow, muscle, spleen, fallopian tube, liver and kidney, is provided.

In certain embodiments, the compound is delivered subcutaneously or intravenously.

In another aspect, a method for treating a disease or disorder of an organ or tissue selected from the group consisting of thymus, bladder, intestine, skin, bone marrow, adipose tissue, muscle, spleen, pancreas, lung, fallopian tube, adrenal gland, heart, liver and kidney in a patient in need of such treatment, comprising administering to the patient a compound described herein, is provided.

In certain embodiments, $X^c$ is selected from the group consisting of DHA g1, DHA g2, DCA g1, DCA g2, EPA g1, EPA g2, cholesterol g1, cholesterol C7 g1, cholesterol g2, LA g1, LA g2, RA g1, RA g2, TOCO g1 and TOCO g2.

In certain embodiments, the organ is the thymus and $X^c$ is selected from the group consisting of RA g1, RA g2, DHA g1, DHA g2 and DCA g2.

In certain embodiments, the organ is the bladder and $X^c$ is selected from the group consisting of DHA g1, DHA g2, EPA g1, LA g1 and LA g2.

In certain embodiments, the organ is the intestine and Xc is selected from the group consisting of EPA g1, EPA g2, RA g1, DHA g1, DHA g2 and LA g2 (e.g., selected from RA g1, EPA g1 and EPA g2).

In certain embodiments, the organ is the skin and $X^c$ is selected from the group consisting of RA g1, RA g2, EPA g1, EPA g2, DHA g1, DHA g2, DCA g1, DCA g2, LA g1, LA g2, cholesterol g1, cholesterol C7 g1 and cholesterol g2.

In certain embodiments, the tissue is bone marrow tissue and $X^c$ is selected from the group consisting of RA g1, RA g2, TOCO g1, DHA g1, DHA g2, EPA g1, EPA g2, DCA g1, DCA g2, LA g1, LA g2, cholesterol C7 g1, cholesterol g2 and choline.

In certain embodiments, the organ is the placenta and $X^c$ is selected from the group consisting of cholesterol g1, DCA g1, DCA g2, DHA g1 and DHA g2 (e.g., $X^c$ is DCA g1 or DCA g2).

In certain embodiments, the tissue is adipose tissue and $X^c$ is selected from the group consisting of RA g1, DHA g1, DHA g2, EPA g1, DCA g1, DCA g2, LA g1 and LA g2.

In certain embodiments, the organ or tissue is muscle and $X^c$ is selected from the group consisting of TOCO g1, DHA g2, EPA g1, EPA g2 and DCA g2.

In certain embodiments, the organ is spleen and $X^c$ is selected from the group consisting of RA g1, RA g2, TOCO g1, TOCO g2, DHA g1, DHA g2, EPA g1, EPA g2, DCA g1, DCA g2, LA g1, LA g2, cholesterol g1, cholesterol C7 g1 and cholesterol g2 (e.g., $X^c$ is selected from cholesterol g1, cholesterol g2, DCA g1 and DCA g2).

In certain embodiments, the organ is the pancreas and $X^c$ is selected from the group consisting of RA g2, DHA g2, EPA g1, DCA g2 and LA g1.

In certain embodiments, the organ is the lung and Xc is selected from the group consisting of RA g1, RA g2, EPA g1, EPA g2, DCA g1 and DCA g2 (e.g., selected from DCA g1, DCA g2, EPA g1 and EPA g2).

In certain embodiments, the organ is the fallopian tube and $X^c$ is selected from the group consisting of RA g1, TOCO g1, EPA g2, DCA g2, LA g2 and cholesterol g2.

In certain embodiments, the organ is the adrenal gland and $X^c$ is selected from the group consisting of RA g1, RA g2, DCA g1, DCA g2, LA g1, LA g2, cholesterol g1, cholesterol C7 g1 and cholesterol g2 (e.g., $X^c$ is selected from RA g1, DCA g1, DCA g2, cholesterol g1 and cholesterol g2).

In certain embodiments, the organ is the heart and $X^c$ is selected from the group consisting of DCA g1, DCA g2, EPA g1, EPA g2, cholesterol g1 and cholesterol g2.

In certain embodiments, the organ is the kidney and Xc is selected from the group consisting of RA g1, RA g2, TOCO g1, DCA g1, DCA g2, DHA g1, DHA g2, EPA g1, EPA g2, LA g1, LA g2, cholesterol g1 and choline (e.g., $X^c$ is selected from RA g1, EPA g1, EPA g2, DCA g2 and cholesterol g1).

In certain embodiments, the organ or tissue is the liver and Xc is selected from the group consisting of RA g1, RA g2, TOCO g1, TOCO g2, DHA g1, DHA g2, EPA g1, EPA g2, DCA g1, DCA g2, LA g1, cholesterol g1, cholesterol C7 g1 and cholesterol g2 (e.g., selected from RA g1, DCA g1, DCA g2, EPA g1, EPA g2, cholesterol g1 and cholesterol g2).

In certain embodiments, the organ is the thymus and the disease or disorder is selected from the group consisting of myasthenia gravis, pure red cell aplasia, hypogammaglobulinemia and cancer.

In certain embodiments, the organ is the bladder and the disease or disorder is selected from the group consisting of flaccid neurogenic bladder, spastic bladder, mixed type flaccid and spastic bladder, overflow incontinence, overflow dribbling, urinary tract infections, urinary calculi, cystitis, interstitial cystitis, bladder rupture, bladder obstruction, paruresis, cystocele, bladder fistula, bladder stones, bladder exstrophy, bladder diverticulum and cancer.

In certain embodiments, the organ is the intestine and the disease or disorder is selected from the group consisting of celiac disease, Crohn's disease, irritable bowel syndrome, ulcer (e.g., peptic ulcer), intestinal dysmobility, intestinal pseudo-obstruction, short bowel syndrome, intestinal malrotation, Meckel's diverticulum, superior mesenteric artery syndrome, necrotizing enterocolitis, duodenal artesia, enteritis, small bowel bacterial overgrowth, Yersinia enterocolitica infection, Yersinia pseudotuberculosis infection and cancer.

In certain embodiments, the organ is the skin and the disease or disorder is selected from the group consisting of ichthyosis, ectodermal dysplasia, psoriasis, eczema, Darier's disease, porokeratosis, acne, vitiligo and skin cancer.

In certain embodiments, the tissue is bone tissue and the disease or disorder is selected from the group consisting of leukemia, lymphoma, aplastic anemia, a myeloproliferative disorder and a myelodysplastic syndrome.

In certain embodiments, the organ is the placenta and the disease or disorder is selected from the group consisting of abruptio placentae, placenta accretia, placenta increta, placenta percreta, chorioamnionitis, intervillitis, TORCH infections (e.g., CMV placentitis), chronic deciduitis, circumvallate placenta, placental villous immaturity, placenta previa, vasa previa, fetal thrombic vasculopathy, hypertrophic decidual vasculopathy, chorangiosis, chorangioma, placental infarction, hydatidiform mole, choriocarcinoma and placental cancer.

In certain embodiments, the tissue is adipose tissue and the disease or disorder is selected from the group consisting of obesity, diabetes, insulin resistance, a lipodystrophy, Dercum's disease, adipose tissue neoplasm, general adipose tissue inflammation, cardiovascular disease, hypertension, stroke, hypercholesterolemia, hypertriglyceridemia, arthritis, asthma and cancer.

In certain embodiments, the tissue is muscle tissue and the disease or disorder is selected from the group consisting of myositis, myotonia congenita, paramyotonia congenita, periodic paralyses, central core disease/malignant hyperthermia susceptibility, nemaline myopathy, centronuclear myopathies, sarcopenia, mitochondrial myopathies, hypotonia, muscular dystrophy, dermatomyositis, cerebral palsy, compartment syndrome, myasthenia gravis, amyotrophic lateral sclerosis, rhabdomyolysis, polymyositis, fibromyalgia, myofascial pain syndrome, muscle cramp, muscle sprain, muscle strain and tendonitis.

In certain embodiments, the organ is the spleen and the disease or disorder is selected from the group consisting of splenomegaly, splenic disease, Gaucher's disease, asplenia, splenic infarction, spherocytosis, wandering spleen, splenic tumor, infectious mononucleosis, hyaloserositis and anemia.

In certain embodiments, the organ is the pancreas and the disease or disorder is selected from the group consisting of pancreatitis, pancreatic cancer, cystic fibrosis, pseudocyst, exocrine pancreatic insufficiency, diabetes, gastrointestinal diseases, pancreas divisum, steatorrhea and sphincter of Oddi dysfunction.

In certain embodiments, the organ is the lung and the disease or disorder is selected from the group consisting of chronic obstructive pulmonary disease, asthma, chronic bronchitis, acute bronchitis, emphysema, cystic fibrosis, pneumonia, tuberculosis, pulmonary edema, lung cancer, acute respiratory distress syndrome, pneumoconiosis, interstitial lung disease, pulmonary embolism, pulmonary hypertension, pleural effusion, pneumothorax, mesothelioma and obesity hypoventilation syndrome.

In certain embodiments, the organ is the fallopian tube and the disease or disorder is selected from the group consisting of salpingitis, endosalpingiosis, tubal torsion, paratubal cyst, endometriosis, fallopian tube cancer, infertility, fallopian tube obstruction and one or more adhesions.

In certain embodiments, the organ is the adrenal gland and the disease or disorder is selected from the group consisting of Addison's disease, adrenal tumors, adrenal insufficiency, adrenal hyperplasia, primary aldosteronism, hyperaldosteronism, hypoaldosteronism, adrenal crisis, Cushing's disease, adrenocortical hyperfunction, adrenoleukodystrophy, adrenal fatigue and adrenal incidentaloma.

In certain embodiments, the organ is the brain and the disease or disorder is selected from the group consisting of Alzheimer's disease, amyotrophic lateral sclerosis, aneurysm, attention deficit disorder, attention deficit hyperactivity disorder, autism spectrum disorder, brain cancer, concussion, coma, cerebral palsy, dementia, dyslexia, epilepsy, encephalitis, Friedreich's ataxia, Huntington's disease, migraine, multiple sclerosis, narcolepsy, Parkinson's disease, stroke, and traumatic brain injury.

In certain embodiments, the organ is the heart and the disease or disorder is selected from the group consisting of atherosclerosis, coronary artery disease, myocarditis, endocarditis, pericarditis, rheumatic heart disease, hypertensive heart disease, aneurysm, angina, myocardial infarction, cardiomyopathy, valvular heart disease, congenital heart disease, heart failure, arrhythmia, cardiac arrest, congestive heart failure, atrial fibrillation, Brugada syndrome, tachycardia, catecholaminergic polymorphic ventricular tachycardia, long QT syndrome, progressive cardiac conduction defect, stroke, peripheral artery disease, thromboembolism, high blood pressure, heart murmur, Kawasaki disease, DiGeorge syndrome, pre-eclampsia and cardiac tumor.

In certain embodiments, the organ is the kidney and the disease or disorder is selected from the group consisting of glomerulonephritis, glomerulosclerosis, nephrolithiasis, Lightwood-Albright syndrome, polycystic kidney disease, acute renal failure, acute renal injury, chronic kidney disease, kidney fibrosis, diabetic nephropathy, Fabry disease, Fanconi syndrome, focal segmental glomerulosclerosis, Goodpasture syndrome, Liddle syndrome, nutcracker syndrome, peritoneal-renal syndrome, and renal cell cancer.

In certain embodiments, the organ is the liver and the disease or disorder is selected from the group consisting of liver disease, cirrhosis, fatty liver, liver cancer, hemochromatosis, toxic hepatitis, viral hepatitis, Gibert's syndrome, galactosemia, cystic disease of the liver and Alagille syndrome.

BRIEF DESCRIPTION OF THE DRAWINGS

FIG. 1F shows a synthetic approach for lysophosphatidylcholine esterified DHA-hsiRNA conjugate (referred to as DHAPCL-hsiRNA, PC-DHA-hsiRNA, g2DHA-hsiRNA, or DHA-G2-hsiRNA).

FIG. 1J shows a representative analytical HPLC trace and an ESI-MS spectra of a synthesized hsiRNA conjugate; lysophosphatidylcholine esterified DHA-hsiRNA conjugate is shown.

FIG. 1N shows a representative LC-MS profile following purification of a synthesized hsiRNA conjugate as in FIG. 1L; Cy3-labeled sFLT-DHA conjugate (pure product) shown.

FIG. 2A depicts exemplary hydrophobic moieties.

FIG. 2C shows an exemplary LC-MS analysis of a synthesized hsiRNA conjugate; DHA-hsiRNA shown.

FIG. 7 shows modified oligonucleotide sequences. Chemical modifications are abbreviated as follows, wherein "X" represents A, U, G, or C: fX (2'-fluoro), mX (2'-O-methyl), P (5'-phosphate), Chol (Cholesterol), '#' (phosphorothioate backbone modification), (phosphodiester backbone).

FIG. 9 shows a representative LC-MS characterization of Cy3-DHA-hsiRNA$^{HTT}$; Calculated: 6174.1 for [M−H]−, found: 6174.4. Conditions: Buffer A: 15 mM Dibutylamine/ 25 mM HFIP, Buffer B: 20% A in MeOH, Column: xbidge OST C18, 2.5 um, Gradient: 0-10 min (1% B-80% B), 10-13 min (80% B-80% B), 13.1 min (80% B-1% B), 13.1-18 min (1% B-1% B).

FIG. 10 shows brain retention and distribution of g2DHA-hsiRNA.

FIG. 15 depicts exemplary internucleotide linkages.

FIG. 29 shows serum lipoprotein binding properties of lipid-conjugated siRNAs.

FIG. 32A-B show chemical structures of novel hydrophobic siRNA constructs. Polyunsaturated fatty acids are typically circulated in the bloodstream in an esterified form, meaning they are linked to glycerol, long-chain aliphatic alcohols, amides, phosphatidylcholine, phosphatidylserine, phosphoric acid, and phosphatidylethanolamine, among others. Defining the path to synthesize metabolically stable analogs of these naturally existing circulating compounds is one way to improve polyunsaturated fatty acid-siRNA tissue distribution and cellular uptake. (A) A generic hydrophobic siRNA construct where X is a hydrophobic lipid bioconjugate (e.g. polyunsaturated fatty acid, cholesterol). Y is a chemically stable trifunctional spacer or linker, which could be cleavable or not. Z is a naturally occurring ester linkage (e.g. phosphatidycholine, phosphatidylserine, phosphoric acid, see FIG. 32B)

FIG. 33 shows examples of linkers, spacer, and branching moieties. The exact chemical composition of the linker is not essential for activity as long as the branching structure can be generated

FIG. 42 shows preferential delivery to podocytes in the Bowman's capsule of the kidney with Retinoic Acid (RA)-hsiRNA.

FIG. 46A-C show data for HTT Cy3 DHAg2 conjugates (FIG. 46A), HTT Cy3 LCAg2 conjugates (FIG. 46B), and HTT Cy3 retinoic acid g2 conjugates (FIG. 46C).

DETAILED DESCRIPTION

Figure 1A:
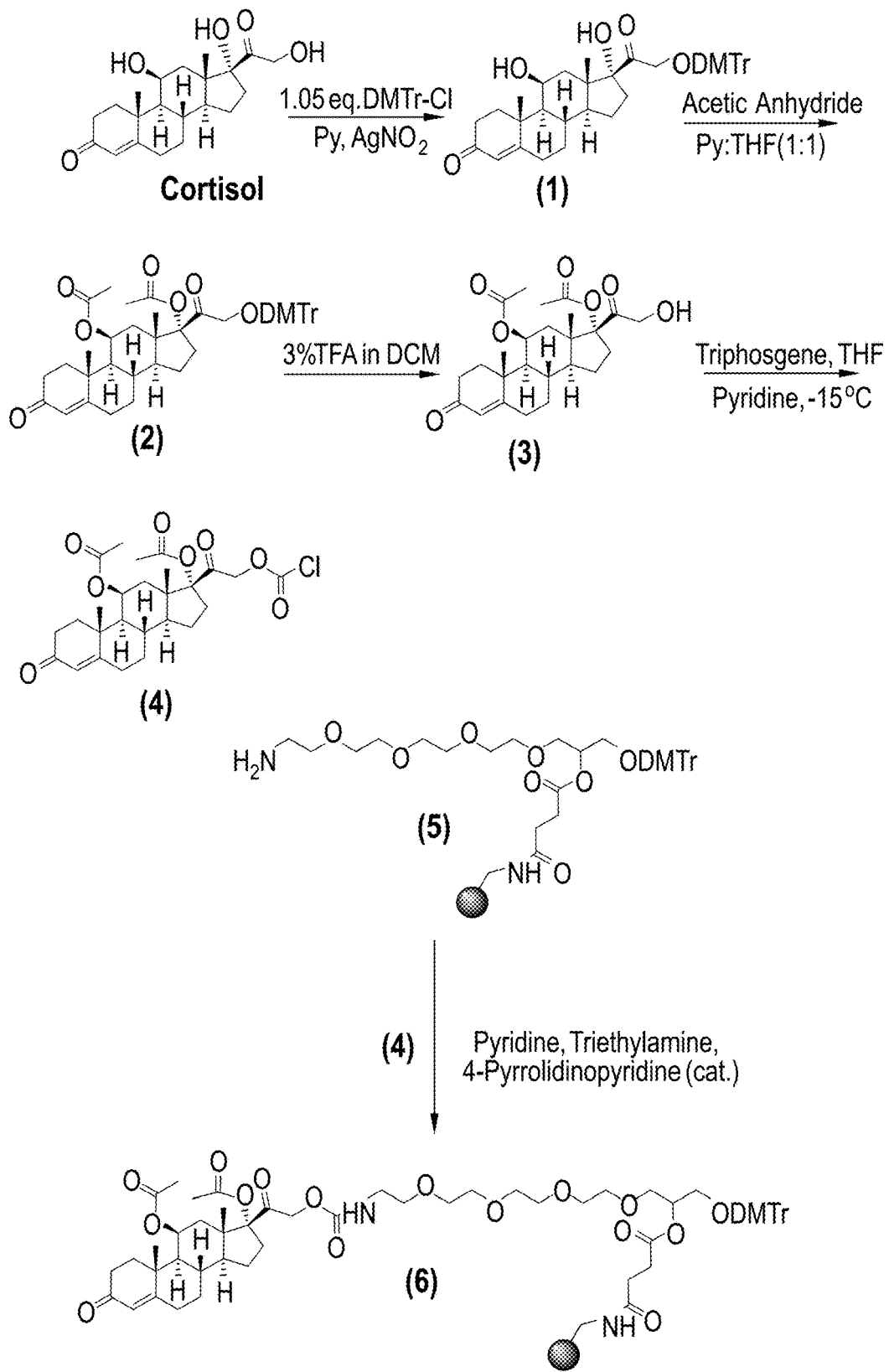
FIG. 1A shows a synthetic approach for cortisol-conjugated oligonucleotides.
Figure 1B:
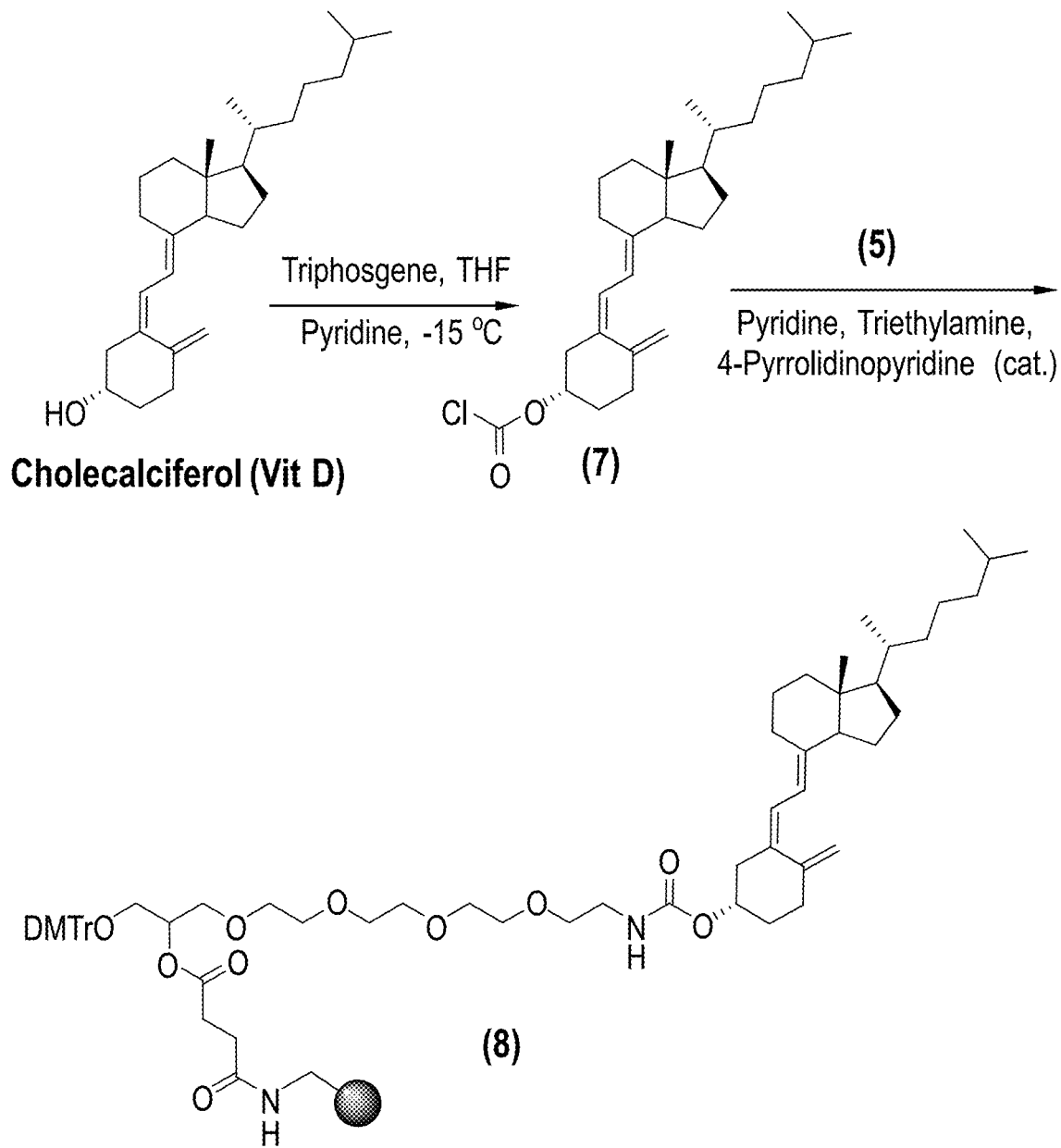
FIG. 1B shows a synthetic approach for calciferol-conjugated oligonucleotides.

The present disclosure relates to conjugated oligoinucleotides that are completely stable and fully active. To identify chemical and biological properties that drive oligonucleotide (e.g., small RNA), tissue distribution and cellular uptake, these oligonucleotides (e.g., small RNAs), were conjugated to several naturally occurring bioactive steroids, endocannabinoid-like lipids, vitamins and nucleoside analogs. The resulting conjugates selectively delivered small RNAs to a range of tissues, including thymus, bladder, intestine, skin, bone marrow, placenta, adipose tissue, muscle, spleen, pancreas, lung, fallopian tube, adrenal gland, heart, liver and kidney.

The compositions described herein promote simple, efficient, non-toxic delivery of oligonucleotides (e.g, metabolically stable siRNA), and promote potent silencing of therapeutic targets in a range of tissues in vivo. Provided herein is a chemistry platform for targeting other tissues matching the performance and clinical impact of GalNAc conjugates in the liver. Several bio-active steroids endocannabinoid-like bioactive lipid conjugates and vitamin-based conjugates were screened and identified. These compounds show unprecedented distribution, neuronal uptake, efficacy, and lack of toxicity in several tissues, including thymus, bladder, intestine, skin, bone marrow, placenta, adipose tissue, muscle, spleen, pancreas, lung, fallopian tube, adrenal gland, heart, liver and kidney.

In certain aspects, the oligonucleotide conjugates of the invention were identified through a process involving: (1) providing a fully metabolically stable scaffolds (no RNA left); (2) selecting compounds which are biologically known to internalize inside the cells and identifying the ranges of hydrophobicities which allow efficient tissue distribution; (3) conjugating these hydrophobic compounds to the metabolically stable siRNAs; and (4) screening distribution, efficacy and toxicity in vivo. The discovery of the optimal range of hydrophobicity defines the chemical scaffold ranges expected to be efficacious. It was found that low hydrophobicity (cortisol like) was not sufficient to secure good tissue retention, whereas too much hydrophobicity (e.g., cholesterol) minimized distribution from the site of injection.

In a first aspect, provided herein is a compound of formula (1):

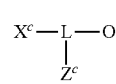

wherein:
O is a double-stranded nucleic acid comprising a first oligonucleotide and a second oligonucleotide, wherein:
(1) the first oligonucleotide comprises at least 16 contiguous nucleotides, a 5' end, a 3' end and has complementarity to a target;
(2) the second oligonucleotide comprises at least 15 contiguous nucleotides, a 5' end, a 3' end, and has homology with a target; and
(3) a portion of the first oligonucleotide is complementary to a portion of the second oligonucleotide;
L is a divalent or trivalent linker;
$X^c$ is a hydrophobic moiety; and
$Z^c$ is a phosphodiester or phosphodiester derivative, or is absent.

Variable L

In one embodiment, L comprises an ethylene glycol chain, an alkyl chain, a peptide, RNA, DNA, a phosphodiester, a phosphorothioate, a phosphoramidate, an amide, a carbamate, or a combination thereof; and wherein L is attached to O via the second oligonucleotide. In one embodiment, L is a divalent linker. In another embodiment, L is a trivalent linker. In certain embodiments, L corresponds to a linker of FIG. 33.

In a particular embodiment, L is the trivalent linker L1, also referred to herein as C7:

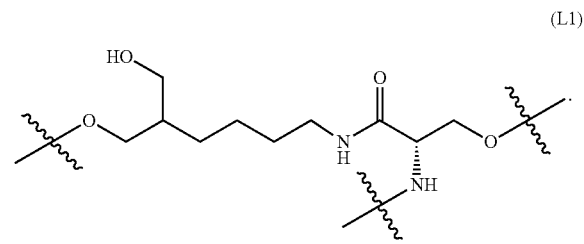

In another particular embodiment, L is the divalent linker L2:

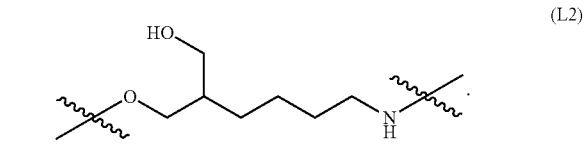 [SMILES: *NCCCCC(CO)CO*]

In another particular embodiment, L is a trivalent or bivalent linker selected from the group consisting of:

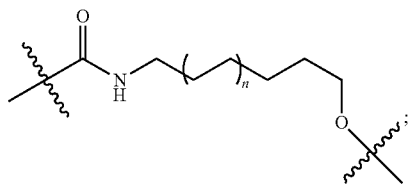

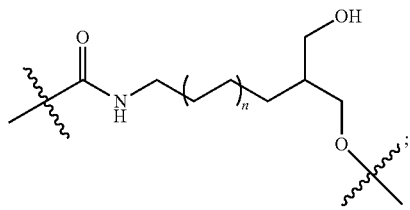

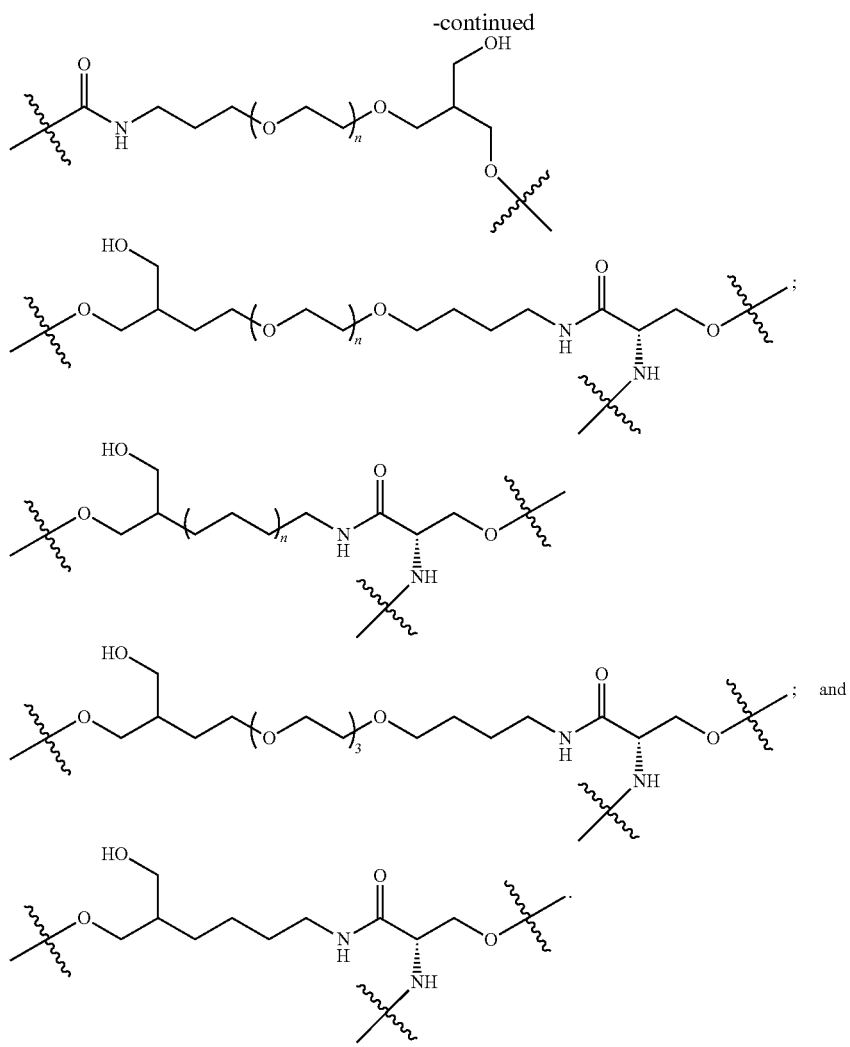

In one embodiment, an oxygen atom of L is bonded to the 3' position of the second oligonucleotide by a phosphodiester for example, as shown in FIG. 1j.

Variable $X^c$

In one embodiment, $X^c$ has an affinity for low density lipoprotein and/or intermediate density lipoprotein. In a related embodiment, $X^c$ is a saturated or unsaturated moiety having fewer than three double bonds.

In another embodiment, $X^c$ has an affinity for high density lipoprotein. In a related embodiment, $X^c$ is a polyunsaturated moiety having at three or more double bonds (e.g., having three, four, five, six, seven, eight, nine or ten double bonds). In a particular embodiment, $X^c$ is a polyunsaturated moiety having three double bonds. In a particular embodiment, $X^c$ is a polyunsaturated moiety having four double bonds. In a particular embodiment, $X^c$ is a polyunsaturated moiety having five double bonds. In a particular embodiment, $X^c$ is a polyunsaturated moiety having six double bonds.

In another embodiment, $X^c$ is selected from the group consisting of fatty acids, steroids, secosteroids, lipids, gangliosides and nucleoside analogs, and endocannabinoids.

In another embodiment, $X^c$ is a neuromodulatory lipid, e.g., an endocannabinoid. Non-limiting examples of endocannabinoids include: Anandamide, Arachidonoylethanolamine, 2-Arachidonyl glyceryl ether (noladin ether), 2-Arachidonyl glyceryl ether (noladin ether), 2-Arachidonoylglycerol, and N-Arachidonoyl dopamine.

In another embodiment, $X^c$ is an omega-3 fatty acid. Non-limiting examples of omega-3 fatty acids include: Hexadecatrienoic acid (HTA), Alpha-linolenic acid (ALA), Stearidonic acid (SDA), Eicosatrienoic acid (ETE), Eicosatetraenoic acid (ETA), Eicosapentaenoic acid (EPA, Timnodonic acid), Heneicosapentaenoic acid (HPA), Docosapentaenoic acid (DPA, Clupanodonic acid), Docosahexaenoic acid (DHA, Cervonic acid), Tetracosapentaenoic acid, and Tetracosahexaenoic acid (Nisinic acid).

In another embodiment, $X^c$ is an omega-6 fatty acid. Non-limiting examples of omega-6 fatty acids include: Linoleic acid, Gamma-linolenic acid (GLA), Eicosadienoic acid, Dihomo-gamma-linolenic acid (DGLA), Arachidonic acid (AA), Docosadienoic acid, Adrenic acid, Docosapentaenoic acid (Osbond acid), Tetracosatetraenoic acid, and Tetracosapentaenoic acid.

In another embodiment, $X^c$ is an omega-9 fatty acid. Non-limiting examples of omega-9 fatty acids include: Oleic acid, Eicosenoic acid, Mead acid, Erucic acid, and Nervonic acid.

In another embodiment, $X^c$ is a conjugated linolenic acid. Non-limiting examples of conjugated linolenic acids include: α-Calendic acid, β-Calendic acid, Jacaric acid, α-Eleostearic acid, β-Eleostearic acid, Catalpic acid, and Punicic acid.

In another embodiment, $X^c$ is a saturated fatty acid. Non-limiting examples of saturated fatty acids include: Caprylic acid, Capric acid, Docosanoic acid, Lauric acid, Myristic acid, Palmitic acid, Stearic acid, Arachidic acid, Behenic acid, Lignoceric acid, and Cerotic acid.

In another embodiment, $X^c$ is an acid selected from the group consisting of: Rumelenic acid, α-Parinaric acid, β-Parinaric acid, Bosseopentaenoic acid, Pinolenic acid, and Podocarpic acid.

In another embodiment, $X^c$ is selected from the group consisting of: docosanoic acid (DCA), docosahexaenoic acid (DHA), and eicosapentaenoic acid (EPA). In a particular embodiment, $X^c$ is docosanoic acid (DCA). In another particular embodiment, $X^c$ is DHA. In another particular embodiment, $X^c$ is EPA.

In another embodiment, $X^c$ is a secosteroid. In a particular embodiment, $X^c$ is calciferol. In another embodiment, $X^c$ is a steroid other than cholesterol.

In a particular embodiment, $X^c$ is not cholesterol.

In another embodiment, $X^c$ is an alkyl chain, a vitamin, a peptide, or a bioactive conjugate (including but not limited to: glycosphingolipids, polyunsaturated fatty acids, secosteroids, steroid hormones, sterol lipids. In other embodiments, the hydrophobic moiety comprises a moiety depicted in FIGS. 2a and 14.

In another embodiment of the oligonucleotide, $X^c$ is characterized by a clogP value in a range selected from: −10 to −9, −9 to −8, −8 to −7, −7 to −6, −6 to −5, −5 to −4, −4 to −3, −3 to −2, −2 to −1, −1 to 0, 0 to 1, 1 to 2, 2 to 3, 3 to 4, 4 to 5, 5 to 6, 6 to 7, 7 to 8, 8 to 9, and 9 to 10.

Variable $Z^c$

In one embodiment, $Z^c$ is selected from the group consisting of $Z^{c1}$, $Z^{c2}$, $Z^{c3}$ and $Z^{c4}$:

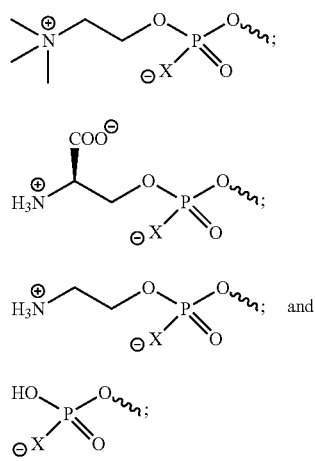

wherein X is O, S or BH$_3$.

In a particular embodiment, $Z^c$ is $Z^{c1}$. In another particular embodiment, $Z^c$ is not $Z^{c1}$, In another embodiment, $Z^c$ is selected from the group consisting of $Z^{c2}$, $Z^{c3}$ and $Z^{c4}$. In a particular embodiment, $Z^c$ is $Z^{c2}$. In a particular embodiment, $Z^c$ is $Z^{c3}$. In a particular embodiment, $Z^c$ is $Z^{c2}$. In a particular embodiment, X is O. In a particular embodiment, X is S. In a particular embodiment, X is BH$_3$.

Proviso

In a particular embodiment of compound (1), when $X^c$ is DHA, $Z^c$ is not Z. In another particular embodiment, when $Z^c$ is $Z^{c1}$, $X^c$ is not DHA.

Variable O

In an embodiment, O comprises an oligonucleotide which may optionally be chemically modified. As used herein, an oligonucleotide refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. Oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

In certain embodiments, an oligonucleotide comprises a DNA polymer, an RNA polymer or a DNA/RNA polymer hybrid. In certain exemplary embodiments, an oligonucleotide comprises an RNA silencing agent or a gene silencing agent.

Exemplary RNA silencing agents include, but are not limited to, siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

An exemplary gene silencing agent is a CRISPR-Cas9-type system that utilizes a guide RNA (gRNA) oligonucleotide agnet.

In an embodiment, O comprises compound (I): an oligonucleotide of at least 16 contiguous nucleotides, said oligonucleotide having a 5' end, a 3' end and complementarity to a target. In a particular embodiment, the target is mammalian or viral mRNA. In another particular embodiment, the target is an intronic region of said mRNA. In one embodiment, the oligonucleotide has sufficient complementarity to the target to hybridize. In certain embodiments, the complementarity is >95%, >90%, >85%, >80%, >75%, >70%, >65%, >60%, >55% or >50%. In one embodiment, compound (I) has perfect complementarity to the target.

In an embodiment, compound (I) comprises one or more chemically-modified nucleotides. In a particular embodiment, compound (I) comprises alternating 2'-methoxy-nucleotides and 2'-fluoro-nucleotides. In another particular embodiment, one or more nucleotides of compound (I) are connected to adjacent nucleotides via phosphorothioate linkages.

In an embodiment, the 5' terminus of compound (I) comprises a moiety selected from the group of:

X1
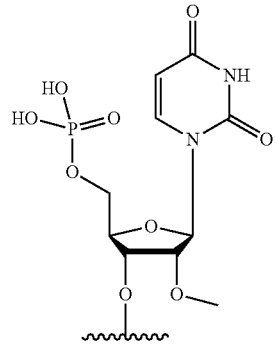

X2
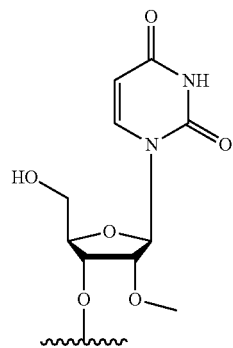

X3
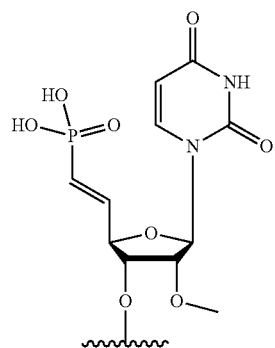

X4
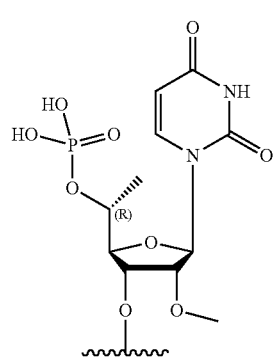

-continued

X5
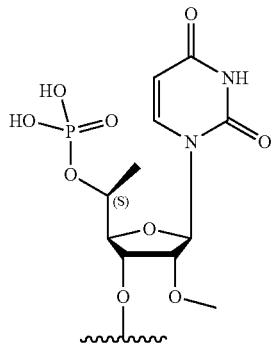

X6
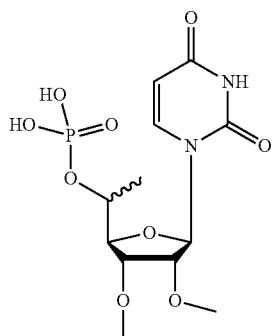

X7
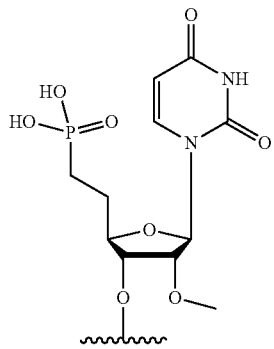

X8
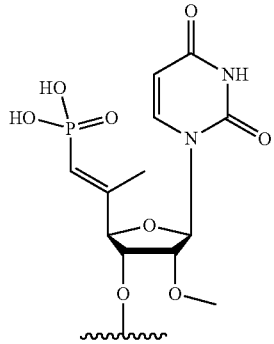

In another embodiment, 0 comprises compound (II): an oligonucleotide of at least 15 contiguous nucleotides, said oligonucleotide having a 5' end, a 3' end, and homology with a target, wherein the oligonucleotide is conjugated at the 3' end to -L(X$^c$)(Z$^c$), defined above.

In an embodiment, compound (II) has complete homology with the target. In a particular embodiment, the target is mammalian or viral mRNA. In another particular embodiment, the target is an intronic region of said mRNA.

In an embodiment, compound (II) comprises one or more chemically-modified nucleotides. In a particular embodiment, compound (II) comprises alternating 2'-methoxy-nucleotides and 2'-fluoro-nucleotides. In another particular embodiment, the nucleotides at positions 1 and 2 from the 3' end of compound (II) are connected to adjacent nucleotides via phosphorothioate linkages. In yet another particular embodiment, the nucleotides at positions 1 and 2 from the 3' end of compound (II) and the nucleotides at positions 1 and 2 from the 5' end of compound (II) are connected to adjacent nucleotides via phosphorothioate linkages.

In an embodiment, O is a double-stranded nucleic acid comprising a first oligonucleotide and a second oligonucleotide, wherein:

(1) the first oligonucleotide is compound (I), or any one of the previous embodiments thereof;

(2) the second oligonucleotide is compound (II), or any one of the previous embodiments thereof; and (3) a portion of the first oligonucleotide is complementary to a portion of the second oligonucleotide.

In one embodiment of O, the first oligonucleotide comprises at least 16 contiguous nucleotides, a 5' end, a 3' end, and has complementarity to a target, wherein:

(1) the first oligonucleotide comprises alternating 2'-methoxy-nucleotides and 2'-fluoro-nucleotides;

(2) the nucleotides at positions 2 and 14 from the 5' end are not 2'-methoxy-nucleotides;

(3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a particular embodiment of the double-stranded nucleic acid, the first oligonucleotide has perfect complementarity to the target.

In another particular embodiment of the double-stranded nucleic acid, the sequences of the first and second oligonucleotides are selected from FIG. 7.

Advanced Stabilization Pattern

In one embodiment, compound (I) has the structure of Formula (Ia):

$$X(-K-B-K-A)_j(-S-B-S-A)_r(-S-B)_t-OR \quad (Ia)$$

wherein:

X is selected from the group consisting of X1, X2, X3, X4, X5, X6, X7 and X8, defined above.

A, for each occurrence, independently is a 2'-methoxy-ribonucleotide;

B, for each occurrence, independently is a 2'-fluoro-ribonucleotide;

K, for each occurrence independently is a phosphodiester or phosphorothioate linker;

S is a phosphorothioate linker;

R is selected from hydrogen and a capping group (e.g., an acyl group such as acetyl);

j is 4, 5, 6 or 7;

r is 2 or 3; and t is 0 or 1.

In one embodiment, the oligonucleotide of Formula (Ia) has the structure of Formula (Ib):

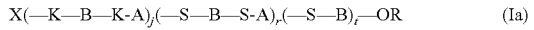

wherein:

X is as defined above;

A, for each occurrence, independently is a 2'-methoxy-ribonucleotide;

B, for each occurrence, independently is a 2'-fluoro-ribonucleotide;

S is a phosphorothioate linker;

P is a phosphodiester linker;

R is as defined above;

m is 0 or 1; n is 4, 5 or 6; q is 0 or 1; r is 2 or 3; and t is 0 or 1.

In a particular embodiment, R is hydrogen. In another particular embodiment, X is X1. In still another particular embodiment, X is X3.

In another embodiment, O is a double-stranded, chemically-modified nucleic acid comprising a first oligonucleotide and a second oligonucleotide, wherein:

(1) the first oligonucleotide is selected from the oligonucleotides of Formulas (I) and (Ia);

(2) a portion of the first oligonucleotide is complementary to a portion of the second oligonucleotide; and (3) the second oligonucleotide is selected from the oligonucleotides of Formulas (II) and (IIa):

$$C\text{-}L\text{-}B(-S\text{-}A\text{-}S-B)_{m'}(-P\text{-}A\text{-}P-B)_{n'}(-P\text{-}A\text{-}S-B)_{q'}(-S\text{-}A)_{r'}(-S-B)_{t'}-OR' \quad (IIa)$$

wherein:

C-L is:

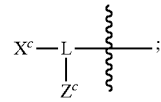

wherein

L; $X^c$; $Z^c$; A; B; S; P are defined above m' is 0 or 1; n' is 4, 5 or 6; q' is 0 or 1; r' is 0 or 1; and t' is 0 or 1.

In one embodiment of compound (1):

(1) the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides;

(2) the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides;

(3) the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages; and (4) the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

In one embodiment of O, the first oligonucleotide has 3-7 more ribonucleotides than the second oligonucleotide.

In one embodiment, O comprises 11-16 base pair duplexes, wherein the nucleotides of each base pair duplex have different chemical modifications (e.g., one nucleotide has a 2'-fluoro modification and the other nucleotide has a 2'-methoxy).

In one embodiment of 0, the first oligonucleotide has 3-7 more ribonucleotides than the second oligonucleotide. In another embodiment, each R is hydrogen.

In one embodiment, the first oligonucleotide is the antisense strand and the second oligonucleotide is the sense strand.

Pharmaceutical Compositions and Methods of Administration

In one aspect, provided herein is a pharmaceutical composition comprising a therapeutically effective amount of one or more compound, oligonucleotide, or nucleic acid as described herein, and a pharmaceutically acceptable carrier. In one embodiment, the pharmaceutical composition comprises one or more double-stranded, chemically-modified nucleic acid as described herein, and a pharmaceutically acceptable carrier. In a particular embodiment, the pharmaceutical composition comprises one double-stranded, chemically-modified nucleic acid as described herein, and a pharmaceutically acceptable carrier. In another particular embodiment, the pharmaceutical composition comprises two double-stranded, chemically-modified nucleic acids as described herein, and a pharmaceutically acceptable carrier.

A pharmaceutical composition of the invention is formulated to be compatible with its intended route of administration. Examples of routes of administration include parenteral, e.g., intravenous (IV), intradermal, subcutaneous (SC or SQ), intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

Methods of Treatment

In one aspect, provided herein is a method for delivering (e.g., selectively delivering) an oligonucleotide conjugate described herein to a target in an organ or a tissue in a subject, comprising administering said oligonucleotide conjugate to the subject. In certain embodiments, the oligonucleotide conjugate may have a selective affinity for a serum lipoprotein.

As used herein, a "target" refers to a particular nucleic acid sequence (e.g., a gene, an mRNA, a miRNA or the like) that an oligonucleotide conjugate of the invention binds to and/or otherwise effects the expression of. In certain embodiments, the target is expressed in a particular tissue, organ or tissue type. In other embodiments, a target is associated with a particular disease or disorder in a subject. Exemplary diseases and disorders are described herein.

One of ordinary skill in the art would readily appreciate that a nucleic acid sequence (e.g., an mRNA) associated with a particular tissue, organ, disease or disorder may be targeted using an oligonucleotide (e.g., an siRNA) conjugated to a hydrophobic compound described herein using the guidance provided herein and the knowledge in the art.

For example, an mRNA that is associated with a neurodegenerative disorder such as Huntington's disease (HD) and/or expressed in a particular neural tissue (e.g., brain or CNS) could be targeted for downregulation using an siRNA conjugated to a hydrophobic compound as described herein that is sufficiently complementary to a variety of well-known HTT mRNA sequences to downregulate their expression, thus treating or lessening one or more symptoms of HD in an subject. Examples of HD mRNA sequences such as, e.g., particular known HTT mRNA 3' untranslated region (UTR) sequences, are described in WO 2016/161374, incorporated herein by reference in its entirety for all purposes.

Similarly, one of ordinary skill in the art could readily target an mRNA associated with an angiogenic disorder such as pre-eclampsia (PE) and/or expressed in a particular tissue (e.g., placenta) by targeting a variety of well-known PE soluble FLT ("sFLT") mRNAs such as sFLT1-i13 short isoform, sFLT1-i13 long isoform, sFLT1415a or the like for downregulation using an siRNA conjugated to a hydrophobic compound as described herein that is sufficiently complementary to the sFLT target, thus treating or otherwise reducing one or more symptoms of PE. Suitable PE mRNA sequences for targeting are described in WO 2016/161378, incorporated herein by reference in its entirety for all purposes.

In one embodiment, the organ is the kidney and the compound has a selective affinity for high density lipoprotein versus low density lipoprotein and/or high density lipoprotein. In a particular embodiment, the organ is the kidneys and $X^c$ is a polyunsaturated moiety having at three or more double bonds (e.g., DHA).

In another embodiment, the organ is the liver and the compound has a selective affinity for low density lipoprotein and/or high density lipoprotein versus high density lipoprotein. In a particular embodiment, the organ is the liver and $X^c$ is a moiety that is saturated or has fewer than three double bonds.

In another embodiment, the organ is the brain and the compound has a selective affinity for high density lipoprotein versus low density lipoprotein and/or high density lipoprotein. In a particular embodiment, the organ is the brain and $X^c$ is a polyunsaturated moiety having three or more double bonds (e.g., DHA).

In another embodiment, the organ is the placenta and the compound has a selective affinity for high density lipoprotein versus low density lipoprotein and/or high density lipoprotein. In a particular embodiment, the organ is the placenta and $X^c$ is PC-DCA or DCA.

In another embodiment, the organ is the epidermis and the compound has a selective affinity for high density lipoprotein versus low density lipoprotein and/or high density lipoprotein. In a particular embodiment, the organ is the epidermis and $X^c$ is a polyunsaturated moiety having three or more double bonds (e.g., EPA).

In another aspect, provided herein is a method for delivering (e.g., selectively delivering) a compound of formula (1), or a disclosed embodiment thereof, to the kidneys of a patient, comprising administering said compound to the patient intravenously, wherein $X^c$ is a polyunsaturated moiety having three or more double bonds (e.g., DHA).

In another aspect, provided herein is a method for treating a disease or disorder of the kidneys in a patient in need of such treatment, comprising administering to the patient a compound of formula (1), or a disclosed embodiment thereof. Non-limiting examples of such disease or disorders include: Abderhalden-Kaufmann-Lignac syndrome; Acute kidney injury; Acute proliferative glomerulonephritis; Adenine phosphoribosyltransferase deficiency; Alport syndrome; Analgesic nephropathy; Autosomal dominant polycystic kidney disease; Autosomal recessive polycystic kidney disease; Benign nephrosclerosis; Bright's disease; Cardiorenal syndrome; CFHR5 nephropathy; Chronic kidney disease; Chronic kidney disease-mineral and bone disorder; Congenital nephrotic syndrome; Conorenal syndrome; Contrast-induced nephropathy; Cystic kidney disease; Danubian endemic familial nephropathy; Dent's disease; Diabetic nephropathy; Diffuse proliferative nephritis; Distal renal tubular acidosis; Diuresis; EAST syndrome; Epithelial-mesenchymal transition; Fanconi syndrome; Fechtner syndrome; Focal proliferative nephritis; Focal segmental glomerulosclerosis; Fraley syndrome; Galloway Mowat syndrome; Gitelman syndrome; Glomerulocystic kidney disease; Glomerulopathy; Glomerulosclerosis; Goldblatt kidney; Goodpasture syndrome; High anion gap metabolic acidosis; HIV-associated nephrapathy; Horseshoe kidney; Hydronephrosis; Hypertensive nephropathy; IgA nephropathy; Interstitial nephritis; Juvenile nephronophthisis; Kidney cancer; Lightwood-Albright syndrome; Lupus nephritis; Malarial nephropathy; Medullary cystic kidney disease; Medullary sponge kidney; Membranous glomerulonephritis; Mesoamerican nephropathy; Milk-alkali syndrome; Minimal mesangial glomerulonephritis; Multicystic dysplastic kidney; Nephritis; Nephrocalcinosis; Nephrogenic diabetes insipidus; Nephromegaly; Nephroptosis; Nephrosis; Nephrotic syndrome; Nutcracker syndrome; Papillorenal syndrome; Phosphate nephropathy; Polycystic kidney disease; Primary hyperoxaluria; Proximal renal tubular acidosis; Pyelonephritis; Pyonephrosis; Rapidly progressive glomerulonephritis; Renal agenesis; Renal angina; Renal artery stenosis; Renal cyst; Renal ischemia; Renal osteodystrophy; Renal papillary necrosis; Renal tubular acidosis; Renal vein thrombosis; Reninoma; Serpentine fibulapolycystic kidney syndrome; Shunt nephritis; Sickle cell nephropathy; Thin basement membrane disease; Transplant glomerulopathy; Tubulointerstitial nephritis and uveitis; Tubulopathy; Uremia and Wunderlich syndrome.

In another aspect, provided herein is a method for delivering (e.g., selectively delivering) such treatment, comprising administering to the patient a compound disclosed herein to the liver of a patient, comprising administering said compound to the patient intravenously, wherein $X^c$ is a moiety that is saturated or has fewer than three double bonds.

In another aspect, provided herein is a method for treating a disease or disorder of the brain in a patient in need of such treatment, comprising administering to the patient a compound of formula (1), or a disclosed embodiment thereof, Non-limiting examples of such disease or disorders include: Acute Disseminated Encephalomyelitis, Agnosia, Alpers' Disease, Angelman Syndrome, Asperger Syndrome, Alzheimer's Disease, Amyotrophic Lateral Sclerosis, Aneurysm, Attention Deficit Hyperactivity Disorder, Autism, Bell's Palsy, Batten Disease, Brain Cancer, Canavan Disease, Concussion, Coma, Cerebral Hypoxia, Cerebral Palsy, Creutzfeldt-Jakob Disease, Dementia, Dravet Syndrome, Dyslexia, Epilepsy, Encephalitis, Farber's Disease, Febrile Seizures, Friedreich's Ataxia, Gaucher Disease, Huntinton's Disease, Hypersomnia, Migraine, Multiple Sclerosis, Narcolepsy, Parkinson's Disease, Stroke, and Traumatic Brain Injury, Tremor, and Wallenberg's Syndrome.

In another aspect, provided herein is a method for treating a disease or disorder of the epidermis in a patient in need of such treatment, comprising administering to the patient a compound of formula (1), or a disclosed embodiment thereof, Non-limiting examples of such disease or disorders include: Ichthyosis, Ectodermal Dysplasia, Psoriasis, Eczema, Darier's Disease, Infantile acropustulosis, Acrokeratoelastoidosis, Pityriasis rubra pilaris, Glucagonoma Syndrome, Acrodermatitis enteropathica, Porokeratosis, Acne, Vitiligo, Skin Cancer, Grover's Disease, Alopecia, Dermatitis, Leiner's Disease, Xeroderma pigmentosum, Toxic Epidermal Necrolysis, Seborrheic Keratoses, Uticaria, Erythema Multiforme, Pemphigus Vulgaris, Bullous Pemphigoid, Scleroderma, and Lupus Erythematosus.

In another aspect, provided herein is a method for treating a disease or disorder of the liver in a patient in need of such treatment, comprising administering to the patient a compound of formula (1), or a disclosed embodiment thereof. Non-limiting examples of such disease or disorders include: liver disease; acute fatty liver of pregnancy; acute liver failure; alcoholic liver disease; alpha-1 antitrypsin deficiency; alveolar hydatid disease; bacillary peliosis; Budd-Chiari syndrome; liver cancer; chronic liver disease; cirrhosis; congenital hepatic fibrosis; congestive hepatopathy; epithelial-mesenchymal transition; fatty liver; fibrolamellar hepatocellular carcinoma; focal fatty liver; gastric antral vascular extasia; hepatic encephalopathy; hepatolithiasis; hepatopulmonary syndrome; hapatorenal syndrome; hepatosplenomegaly; Laennec's cirrhosis; liver abscess; liver failure; Lyngstadaas syndrome; non-alcoholic fatty liver disease; non-cirrhotic portal fibrosis; non-alcoholic fatty liver disease; non-cirrhotic portal fibrosis; non-alcoholic fatty liver disease; pediatric end-stage liver disease; peliosis hepatis; polycystic liver disease; primary biliary cirrhosis; progressive familial intrahepatic cholestasis; steatohepatitis; viral hepatitis; Wilson's diease; Zahn infarct; and Zieve's syndrome.

In certain aspects, the particular tissue or organ to be targeted is selected from the group consisting of thymus, bladder, intestine, skin, bone marrow, placenta, adipose tissue, muscle, spleen, pancreas, lung, fallopian tube, adrenal gland, heart, liver and kidney.

Diseases and conditions related to the thymus include but are not limited to myasthenia gravis (MG), pure red cell aplasia (PRCA), hypogammaglobulinemia and cancer.

Diseases and conditions related to the bladder include but are not limited to flaccid (hypotonic) neurogenic bladder, spastic bladder, a mix of flaccid and spastic bladder ("mixed type"), overflow incontinence, overflow dribbling, urinary tract infections, urinary calculi, cystitis, interstitial cystitis, bladder rupture, bladder obstruction (tamponade), paruresis, cystocele, bladder fistula, bladder stones, bladder exstrophy, bladder diverticulum and cancer.

Diseases and disorders related to the intestine (e.g., large and/or small intestine) include but are not limited to celiac disease, Crohn's disease, irritable bowel syndrome, ulcer (e.g., peptic ulcer), intestinal dysmobility, intestinal pseudo-obstruction, short bowel syndrome, intestinal malrotation, Meckel's diverticulum, superior mesenteric artery syndrome, necrotizing enterocolitis, duodenal artesia, enteritis, small bowel bacterial overgrowth, Yersinia enterocolitica infection, Yersinia pseudotuberculosis infection and cancer.

Diseases and disorders related to bone marrow include but are not limited to leukemia, lymphoma, aplastic anemia, myeloproliferative disorders, myelodysplastic syndromes and other cancers.

Diseases and disorders of the placenta include but are not limited to abruptio placentae, placenta accretia, placenta increta, placenta percreta, chorioamnionitis, intervillitis, TORCH infections (e.g., CMV placentitis), chronic deciduitis, circumvallate placenta, placental villous immaturity, placenta previa, vasa previa, fetal thrombic vasculopathy, hypertrophic decidual vasculopathy, chorangiosis, chorangioma, placental infarction, hydatidiform mole, choriocarcinoma and placental cancer.

Diseases and conditions related to adipose tissue include but are not limited to obesity, diabetes, insulin resistance, lipodystrophies, Dercum's disease, adipose tissue neoplasm, general adipose tissue inflammation, cardiovascular disease, hypertension and stroke, hypercholesterolemia, hypertriglyceridemia, arthritis, asthma and cancer.

Lipodystrophies include Berardinelli-Seip syndrome, Barraquer-Simons syndrome, Lawrence-Seip syndrome, Centrifugal lipodystrophy, Ferreira-Marques lipoatrophia, Familial Partial lipodystrophy, Dunnigan syndrome, Localized lipodystrophy, metabolic syndrome, and HIV-related lipodystrophy.

Adipose tissue acts as an endocrine organ, secreting proteinaceous hormones called adipokines. The action of these adipokines effects numerous cellular functions. They regulate food intake, insulin sensitivity, fatty acid oxidation rates, serum fatty acid and glucose levels, and cellular growth and differentiation. Exemplary adipokines include but are not limited to leptin, ghrelin, adiponectin, apelin, chemerin, interleukin-6 (IL-6), monocyte chemotactic protein-1 (MCP-1), plasminogen activator inhibitor-1 (PAI-1), retinol binding protein (RBP4), tumor necrosis factor-alpha (TNFα), visfatin, omentin, vaspin, and progranulin. In a further embodiment, the oligonucleotide conjugates of the present invention can be used to modulate (increase or decrease) the expression of adipokines.

Diseases and conditions related to muscle tissue include but are not limited to myositis, myotonia congenita, paramyotonia congenita, periodic paralyses, central core disease/malignant hyperthermia susceptibility, nemaline myopathy, centronuclear myopathies, sarcopenia, mitochondrial myopathies, hypotonia, muscular dystrophy, dermatomyositis, cerebral palsy, compartment syndrome, myasthenia gravis, amyotrophic lateral sclerosis (ALS), rhabdomyolysis, polymyositis, fibromyalgia, myofascial pain syndrome, muscle cramps, muscle sprains and strains, and tendonitis.

Diseases and conditions related to the spleen include but are not limited to splenomegaly, splenic disease, Gaucher's disease, asplenia, splenic infarction, spherocytosis, wandering spleen, splenic tumors, infectious mononucleosis, splenic injury, hyaloserositis, and anemias.

Diseases and conditions related to the pancreas include but are not limited to pancreatitis, pancreatic cancer, cystic fibrosis, pseudocyst, exocrine pancreatic insufficiency, diabetes, gastrointestinal diseases, pancreas divisum, steatorrhea, and sphincter of Oddi dysfunction.

Much like adipose tissue, the pancreas is a major endocrine organ. Exemplary secreted pancreatic hormones include but are not limited to glucagon, insulin, pancreatic polypeptide, preproinsulin, proglucagon, somatostatin, vasoactive intestinal peptide, growth hormone releasing hormone, gastrin, ghrelin, amylin, secretin, and cholecystokinin. In a further embodiment, the oligonucleotide conjugates of the present invention can be used to modulate (increase or decrease) the expression of pancreatic endocrine hormones.

In addition to pancreatic endocrine function, the pancreas has exocrine functions, i.e., the production of enzymes involved in digestion. Exemplary secreted pancreatic exocrine enzymes include but are not limited to trypsin, chymotrypsin, lipases, amylases, nucleases, gelatinase, and elastase. In a further embodiment, the oligonucleotide conjugates of the present invention can be used to modulate (increase or decrease) the expression of pancreatic exocrine enzymes. Diseases and disorders of the lung include but are not limited to chronic obstructive pulmonary disease, asthma, chronic bronchitis, acute bronchitis, emphysema, cystic fibrosis, pneumonia, tuberculosis, pulmonary edema, lung cancer, acute respiratory distress syndrome, pneumoconiosis, interstitial lung disease (e.g., sarcoidosis, idopathic pulmonary fibrosis, autoimmune disease), pulmonary embolism, pulmonary hypertension, pleural effusion, pneumothorax, mesothelioma and obesity hypoventilation syndrome.

Diseases and conditions related to the fallopian tube include but are not limited to salpingitis, endosalpingiosis, tubal torsion, paratubal cyst, endometriosis, fallopian tube cancers, infertility, fallopian tube obstruction, and adhesions.

Diseases and conditions related to the adrenal gland include but are not limited to Addison's disease, adrenal tumors, adrenal insufficiency, adrenal hyperplasia, primary aldosteronism, hyperaldosteronism, hypoaldosteronism, adrenal crisis, Cushing's disease, adrenocortical hyperfunction, adrenoleukodystrophy, adrenal fatigue, and adrenal incidentaloma.

The adrenal gland is another major endocrine organ. Exemplary secreted adrenal hormones include but are not limited to aldosterone, cortisol, adrenaline, noradrenaline, epinephrine, dehydroepiandrosterone, testosterone, and estrogen. In a further embodiment, the oligonucleotide conjugates of the present invention can be used to modulate (increase or decrease) the expression of adrenal gland hormones.

Diseases and conditions related to the heart include but are not limited to atherosclerosis, coronary artery disease, myocarditis, endocarditis, pericarditis, rheumatic heart disease, hypertensive heart disease, aneurysm, angina, myocardial infarction, cardiomyopathy, valvular heart disease, congential heart disease, heart failure, arrhythmia, cardiac arrest, congestive heart failure, atrial fibrillation, Brugada syndrome, tachycardia, Catecholaminergic Polymorphic Ventricular Tachycardia (CPVT), long QT syndrome, Progressive Cardiac Conduction Defect (PCCD), stroke, Peripheral Artery Disease (PAD), thromboembolisms, high blood pressure, heart murmurs, Kawasaki disease, DiGeorge syndrome, pre-eclampsia, and cardiac tumors.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for one or more target sequences within the gene, such that sequence specific interference with the gene is achieved. These methods can be performed in vitro (e.g., by culturing the cell with the agent) or, alternatively, in vivo (e.g., by administering the agent to a subject).

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain, spinal column, placenta, liver and/or kidneys) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder (e.g., Huntington's disease) or a liver-, kidney- or pregnancy-related disease or disorder (e.g., PE, postpartum PE, eclampsia and/or HELLP). In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

In one aspect, provided herein is a method of treating or managing preeclampsia, post-partum preeclampsia, eclampsia or HELLP syndrome comprising administering to a subject in need of such treatment or management a therapeutically effective amount of a compound, oligonucleotide, or nucleic acid as described herein, or a pharmaceutical composition comprising said compound, oligonucleotide, or nucleic acid.

In another aspect, provided herein is a method of treating or managing Huntington's disease comprising administering to a patient in need of such treatment or management a therapeutically effective amount of a compound, oligonucleotide, or nucleic acid as described herein, or a pharmaceutical composition comprising said compound, oligonucleotide, or nucleic acid.

Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein in the context of oligonucleotide sequences, "A" represents a nucleoside comprising the base adenine (e.g., adenosine or a chemically-modified derivative thereof), "G" represents a nucleoside comprising the base guanine (e.g., guanosine or a chemically-modified derivative thereof), "U" represents a nucleoside comprising the base uracil (e.g., uridine or a chemically-modified derivative thereof), and "C" represents a nucleoside comprising the base adenine (e.g., cytidine or a chemically-modified derivative thereof), As used herein, the terms "DHAPCL-hsiRNA," "PC-DHA-hsiRNA," "g2DHA-hsiRNA," and "DHA-G2-hsiRNA" refer to an embodiment of compound (1) wherein $X^c$ is DHA, L is L1 and O is a fully chemically modified as described herein.

As used herein, the term "capping group" refers to a chemical moiety that replaces a hydrogen atom in a functional group such as an alcohol (ROH), a carboxylic acid ($RCO_2H$), or an amine ($RNH_2$). Non-limiting examples of capping groups include: alkyl (e.g., methyl, tertiary-butyl); alkenyl (e.g., vinyl, allyl); carboxyl (e.g., acetyl, benzoyl); carbamoyl; phosphate; and phosphonate (e.g., vinylphosphonate). Other suitable capping groups are known to those of skill in the art.

By "trophoblast" is meant the mesectodermal cell layer covering the blastocyst that erodes the uterine mucosa and through which the embryo receives nourishment from the mother. Trophoblast cells contribute to the formation of the placenta.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Linkers useful in conjugated compounds of the invention include glycol chains (e.g., polyethylene glycol), alkyl chains, peptides, RNA, DNA, and combinations thereof. As used herein, the abbreviation "TEG" refers to triethylene glycol.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

In some embodiments, the compounds, oligonucleotides and nucleic acids described herein may be modified to comprise the internucleotide linkages provided in FIG. 15. In particular embodiments, the compounds, oligonucleotides and nucleic acids described herein comprise internucleotide linkages selected from phosphodiester and phosphorothioate.

It is understood that certain internucleotide linkages provided herein, including, e.g., phosphodiester and phosphorothioate, comprise a formal charge of −1 at physiological pH, and that said formal charge will be balanced by a cationic moiety, e.g., an alkali metal such as sodium or potassium, an alkali earth metal such as calcium or magnesium, or an ammonium or guanidinium ion.

Figure 16:
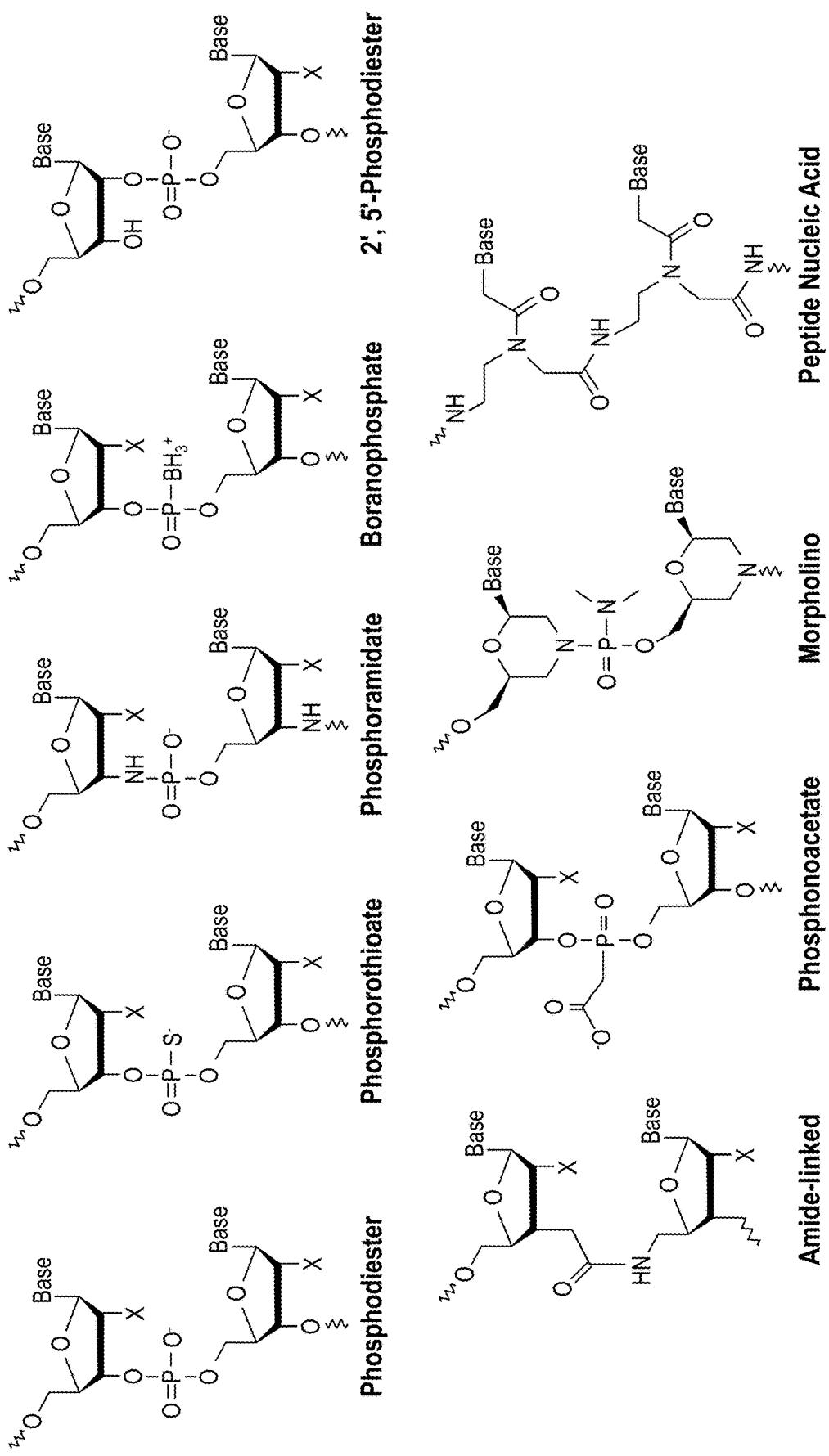
FIG. 16 depicts exemplary internucleotide backbone linkages.

Oligonucleotide backbones may comprise phosphates, phosphorothioates (a racemic mixture or stereospecific), diphosphorothioates, phosphoramidates, peptide nucleic acid, boranophosphate, 2'-5' phosphodiester, amides, phosphonoacetate, morpholino moieties, or a combination thereof. In some embodiments, the compounds, oligonucleotides and nucleic acids described herein may be modified to comprise the internucleotide backbone linkages provided in FIG. 16.

In certain embodiments, provided herein are compounds comprising a phosphate moiety (e.g., X1, X4, X5 and X6), a phosphonate moiety (e.g., X3, X7 and X8). These moieties will be partially or completely ionized as a function of the moiety's pKa and the pH of the environment. It is understood that negatively charged ions will be balanced by a cationic moiety, e.g., an alkali metal such as sodium or potassium, an alkali earth metal such as calcium or magnesium, or an ammonium or guanidinium ion.

Figure 17:
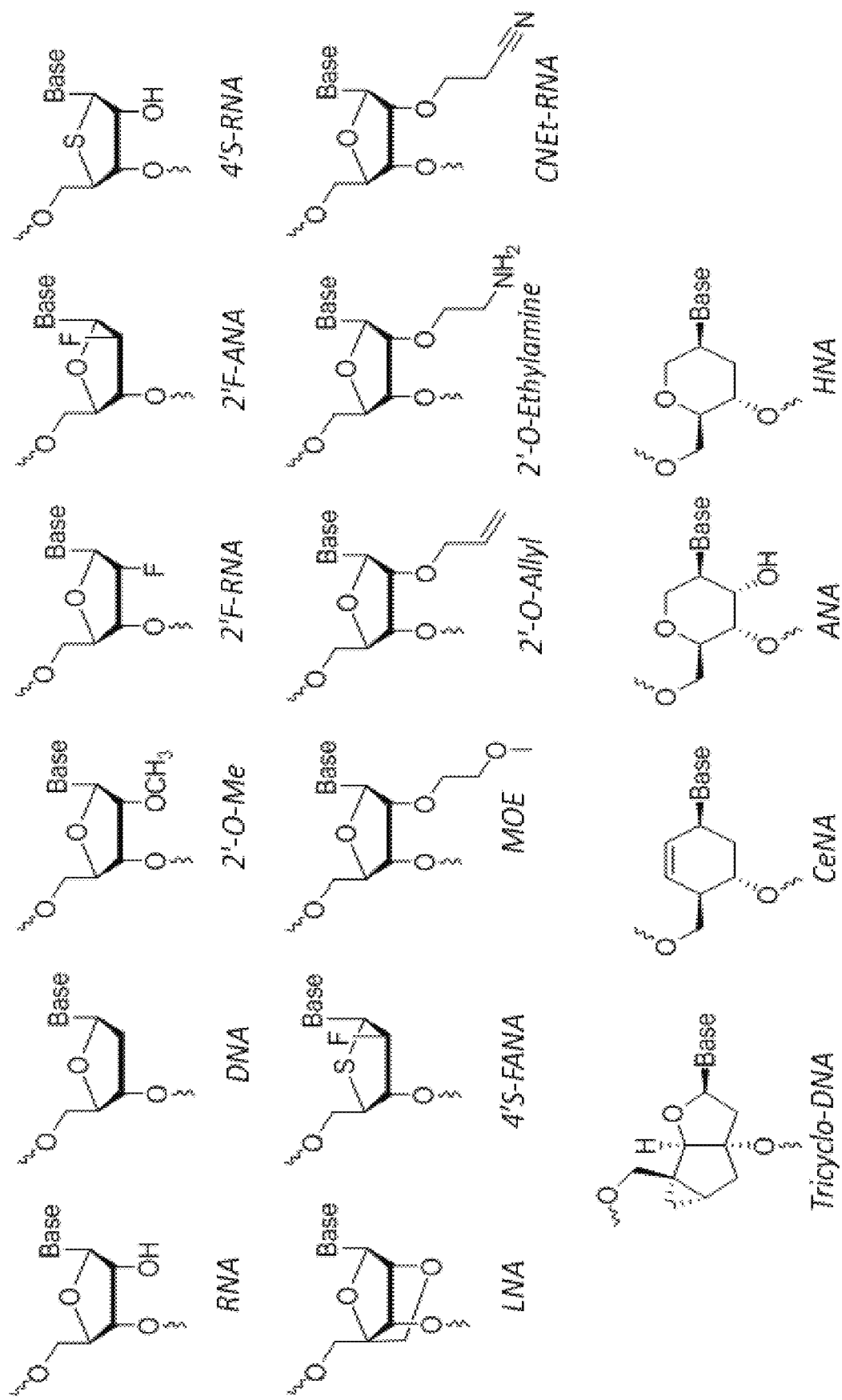
FIG. 17 depicts exemplary sugar modifications.
Figure 18A:
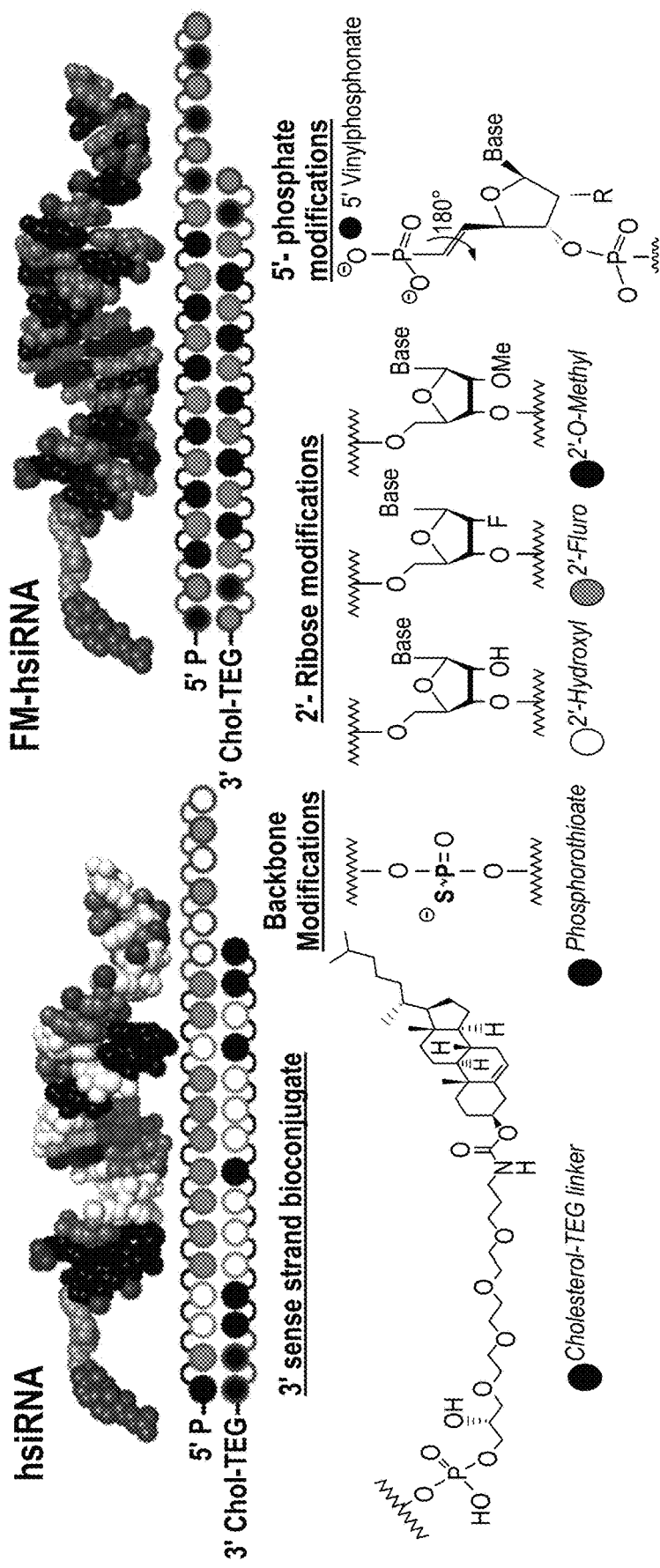
FIG. 18A-E depict fully metabolically stabilized hsiRNAs (FM-hsiRNAs). (A) Schematics of partially and fully modified hsiRNAs. (B) hsiRNA and FM-hsiRNA have equal ability to enter RISC (HeLa, 72 hours, QuantiGene®). hsiRNA-conjugate structures, sequences, and modifications are found in FIG. 5A-F. (C) FM-hsiRNA, but not naked siRNA, supports passive delivery. (D) Metabolically stable 5'-E-VP (Vinylphosphonate) is as active as 5'-P (Phosphate). The antisense strand of the hsiRNAs are capped at the 5' as follows: FM-hsiRNA-no P is capped with a 5'-OH; FM-hsiRNA is capped with a 5' phosphate; FM-hsiRNA-EVP is capped with a 5' vinyl phosphonate. (E) 5'-E-VP enables sustained delivery to distant tissues (7 days post injection, PNA assay). The antisense strand of the hsiRNAs are capped at the 5' as follows: 5'P-hsiRNA is capped with a 5' phosphate; 5VP'-hsiRNA is capped with a 5' vinyl phosphonate. The hsiRNA sequence for FIG. 33D-E is PPIB, found in FIG. 7.
Figure 18B:
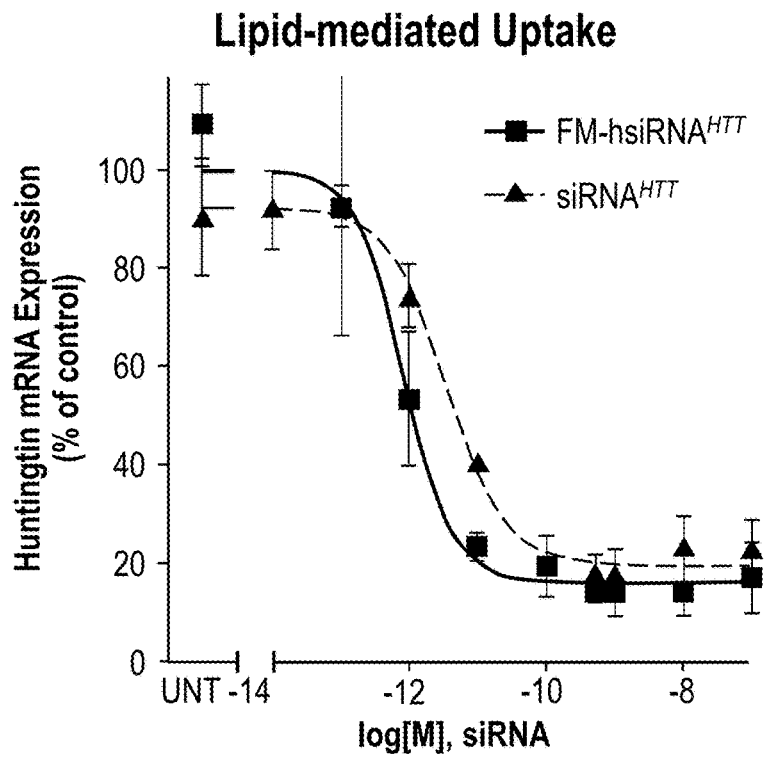
Figure 18C:
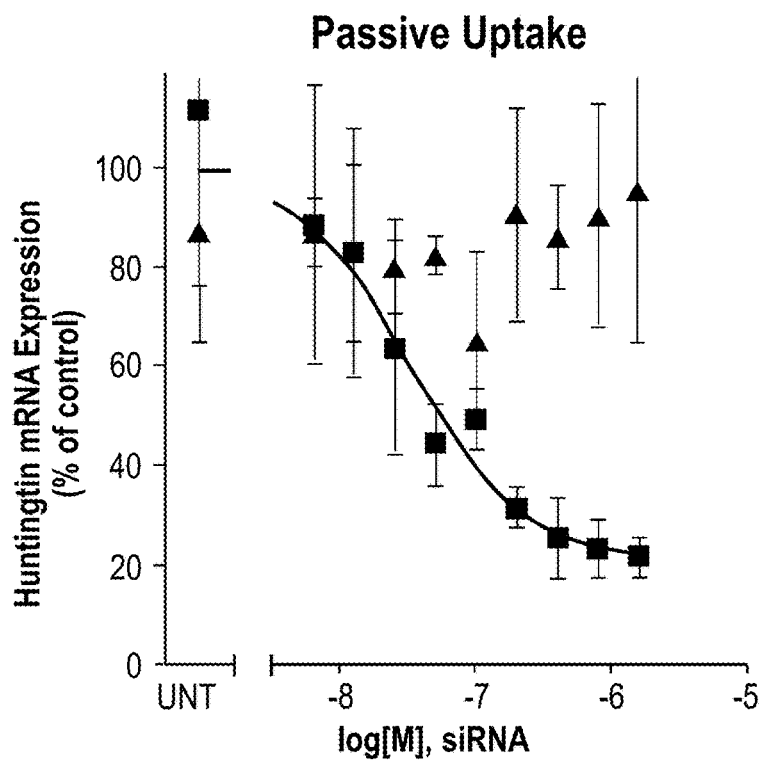
Figure 18D:
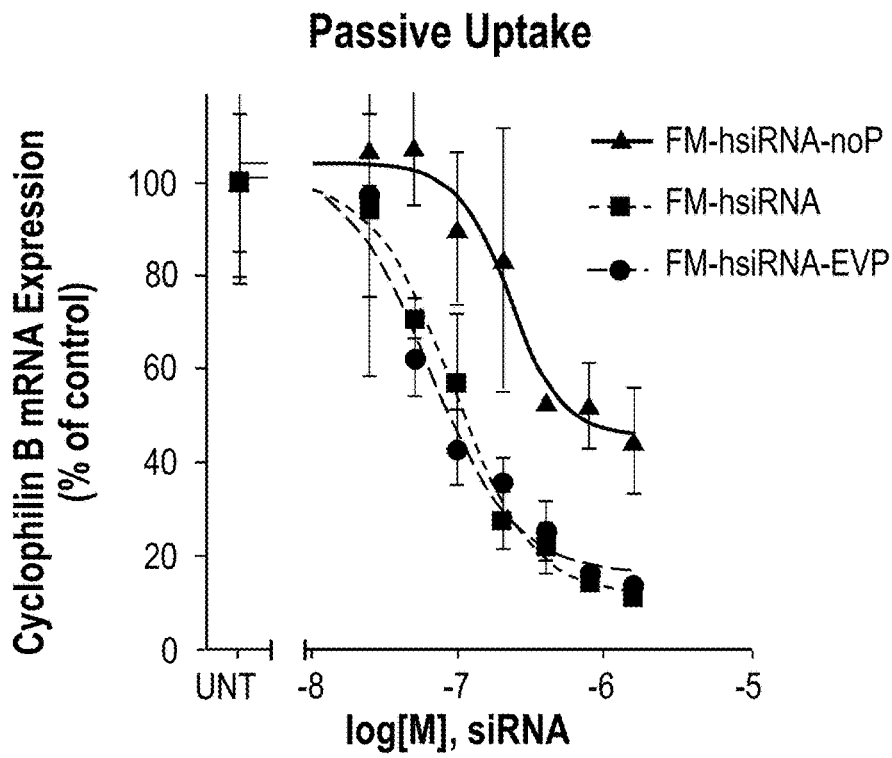
Figure 18E:
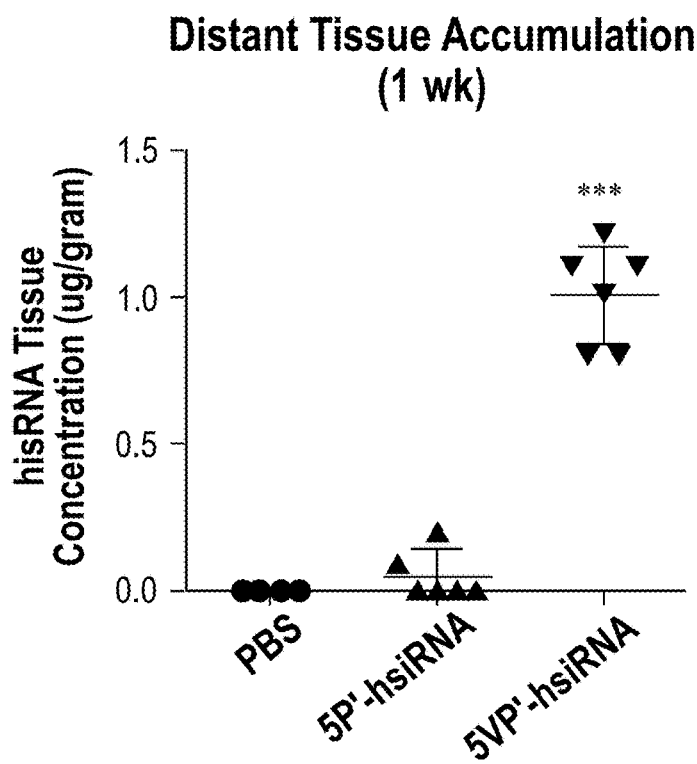

In some embodiments, the compounds, oligonucleotides and nucleic acids described herein may be modified to comprise the sugar modifications provided in FIG. 17.

Methods of Delivering Nucleic Acid

In another aspect, provided herein is a method for selectively delivering a compound or nucleic acid as described herein to a particular organ in a patient, comprising administering said nucleic acid to the patient, wherein the nucleic acid comprises a bioactive molecule having an affinity for a receptor. In one embodiment, the organ is the liver. In another embodiment, the organ is the kidneys. In another embodiment, the organ is the spleen. In another embodiment, the organ is the heart. In another embodiment, the organ is the brain.

The nature of the conjugated hydrophobic moiety (e.g., DHA and EPA) dramatically alters tissue distribution profiles. In certain embodiments, cholesterol and saturated fatty acid (e.g., DCA)-conjugated hsiRNA distributes preferentially to the liver and spleen. In other embodiments, polyunsaturated fatty acid (e.g., DHA and EPA) -conjugated hsiRNA distributes preferentially to the kidneys and heart in addition to the liver and spleen. In a particular embodiment, DHA-conjugated hsiRNA distributes preferentially to the kidneys. In another particular embodiment, the delivery of DHA-conjugated hsiRNA to the kidneys is specific to proximal tubule cells, preferentially involved in a range of kidney diseases including diabetic nephropathy, renal cancer, and lupus. DHA-conjugated hsiRNA shows robust gene modulation in the liver and kidney after a single IV injection of 15 mg/kg.

Figure 21:
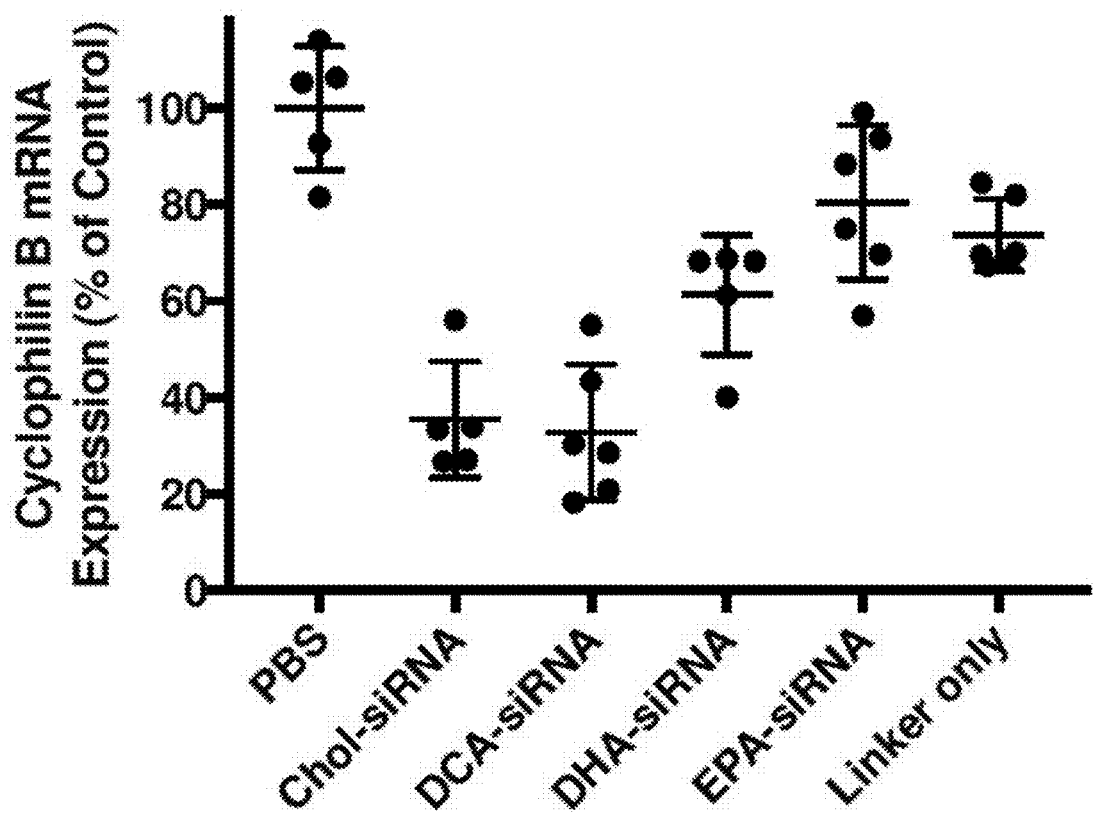
FIG. 21 shows that intravenous injection of lipid-siRNA conjugates induces differential levels of gene silencing in the liver, which is directly proportional to the degree of accumulation. Intravenous injection (20 mg/kg) of each siRNA conjugate. Animals sacrificed 7 days post-injection. Tissue punches taken from the liver tissue. mRNA was quantified using Affymetrix Quantigene 2.0 as per Coles et al. 2015. hsiRNA-conjugate structures and modifications are shown in FIGS. 5A-F and the PPIB hsiRNA sequence is shown in FIG. 7.

As shown in FIG. 21, highly hydrophobic siRNA conjugates (e.g. cholesterol, docosanoic acid) distribute primarily to the liver after systemic (intravenous or subcutaneous) delivery, with residual accumulation in the spleen. Less hydrophobic siRNA conjugates (e.g. polyunsaturated fatty acids such as docosahexaenoic acid and eicosapentaenoic acid) distribute to the kidney, liver, and heart after systemic delivery. This distribution pattern correlates with the observed efficacy of this panel of conjugates in the liver, where Chol- and DCA-siRNA are highly accumulated and show higher silencing (~70%), while DHA- and EPA-siRNA conjugate accumulation is less pronounced and therefore shows lower levels of silencing (40% and 25%, respectively). An siRNA containing the tetraethylene glycol linker only (Linker only) shows residual levels of liver silencing as well.

Figure 22A:
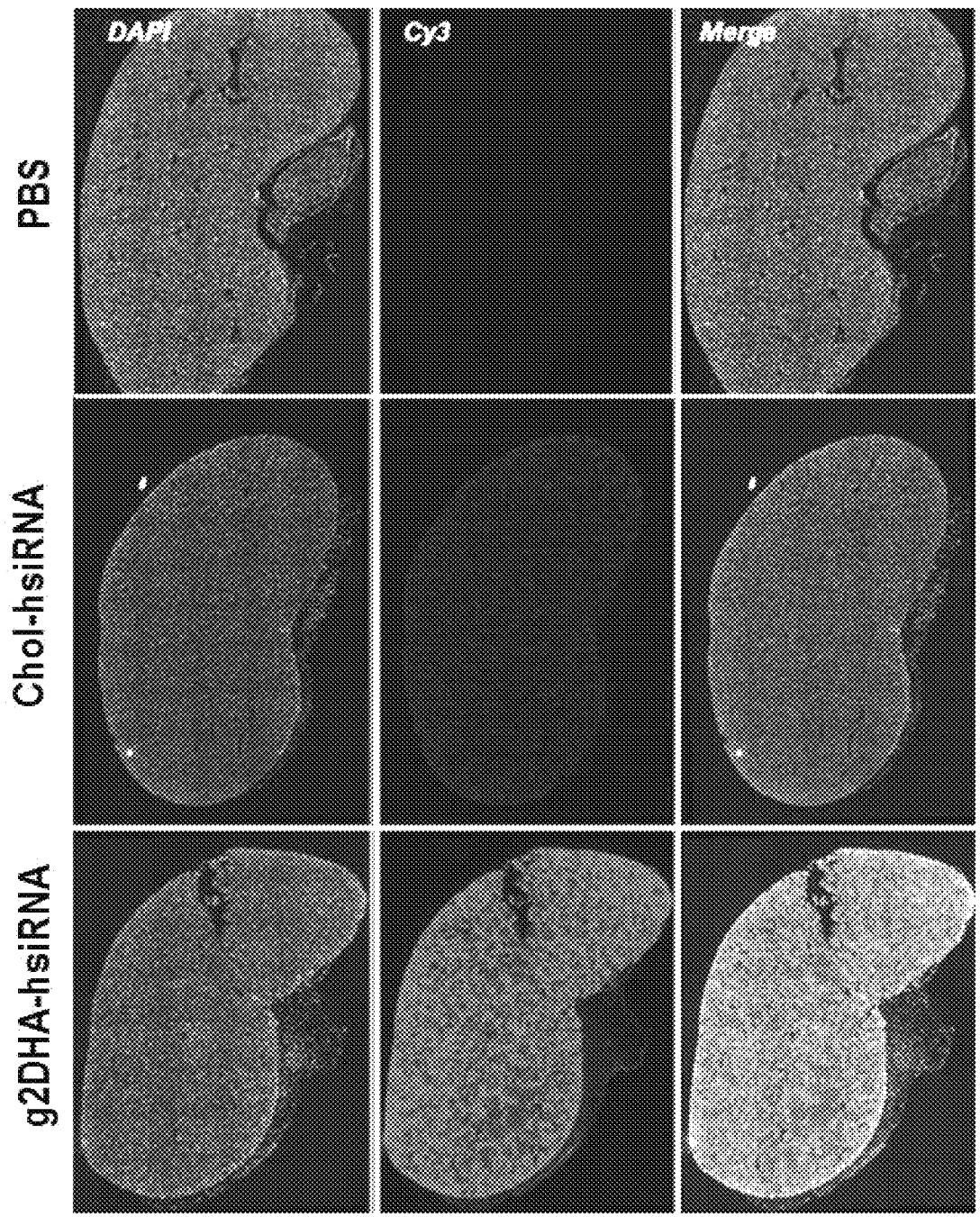
FIG. 22A-B depicts targeted kidney delivery with polyunsaturated fatty acid chemical scaffolds. (A) Intravenous injection of PBS, Chol-siRNA, or g2DHA-siRNA (20 mg/kg twice daily for two days). Animals sacrificed 7 days post-injection. 63× image of kidney sections showing Cy3-fluorescence of oligonucleotides. hsiRNA-conjugate structures and modifications are shown in FIG. 5A-F. (B) siRNA antisense strands present in liver and kidney were quantified using Cy3-labeled complimentary PNA to hybridize to the strand and HPLC to quantify ng of oligo per mg of tissue. hsiRNA-conjugate structures and modifications are shown in FIGS. 5A-F and the PPIB sequence is on FIG. 7.
Figure 22B:
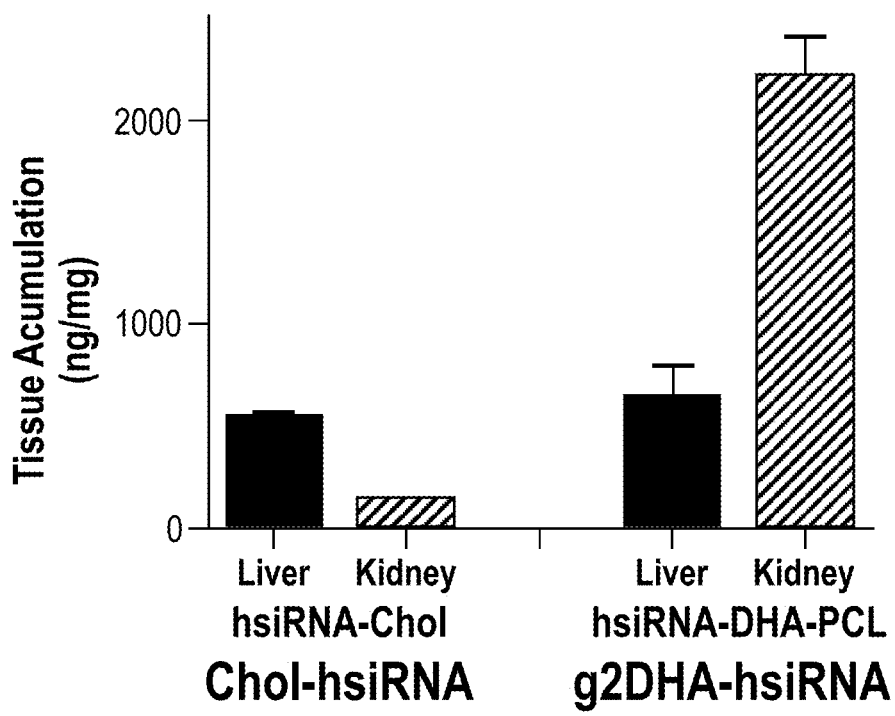
Figure 23:
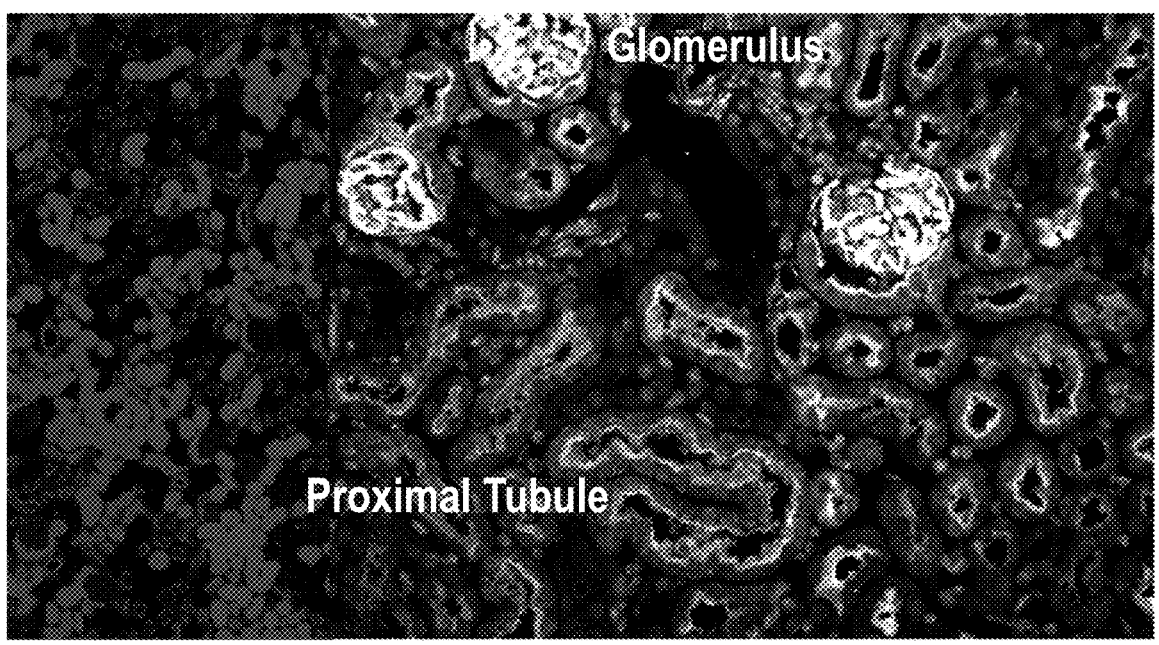
FIG. 23 shows that g2DHA-hsiRNA preferentially distributes to proximal convoluted tubule cells throughout the kidney following systemic administration (two IV injections of 20 mg/kg, 48 hours). This sharply contrasts with the predominant liver localization exhibited by most siRNA therapeutics in the clinic and opens the window to expand the clinical utility of siRNA beyond liver indications.
Figure 24:
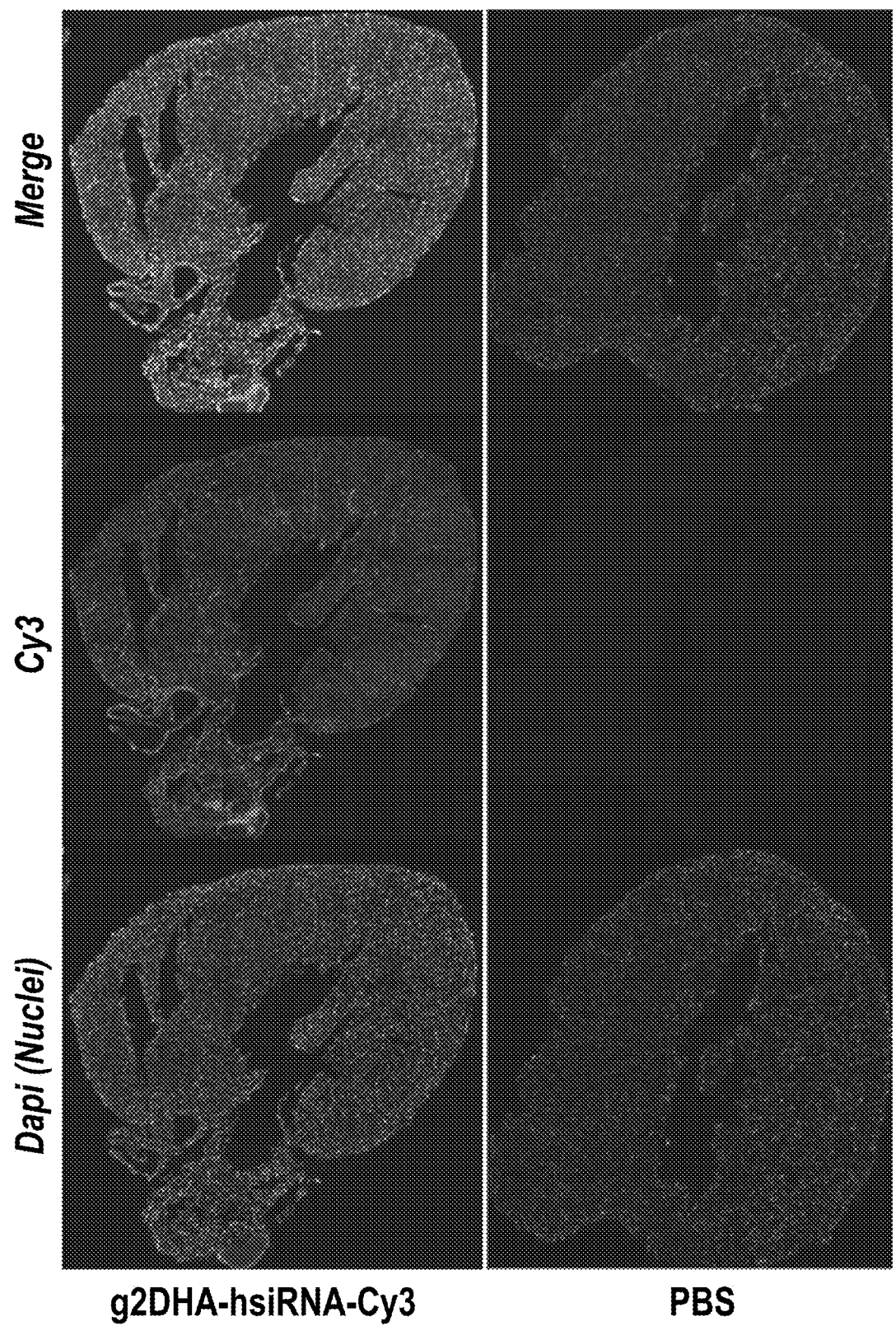
FIG. 24 shows g2DHA-hsiRNA distributed to heart tissue following systemic administration (one intravenous injection, 10 mg/kg). These tissues are not typically accessed by therapeutic siRNAs following intravenous administration.
Figure 25:
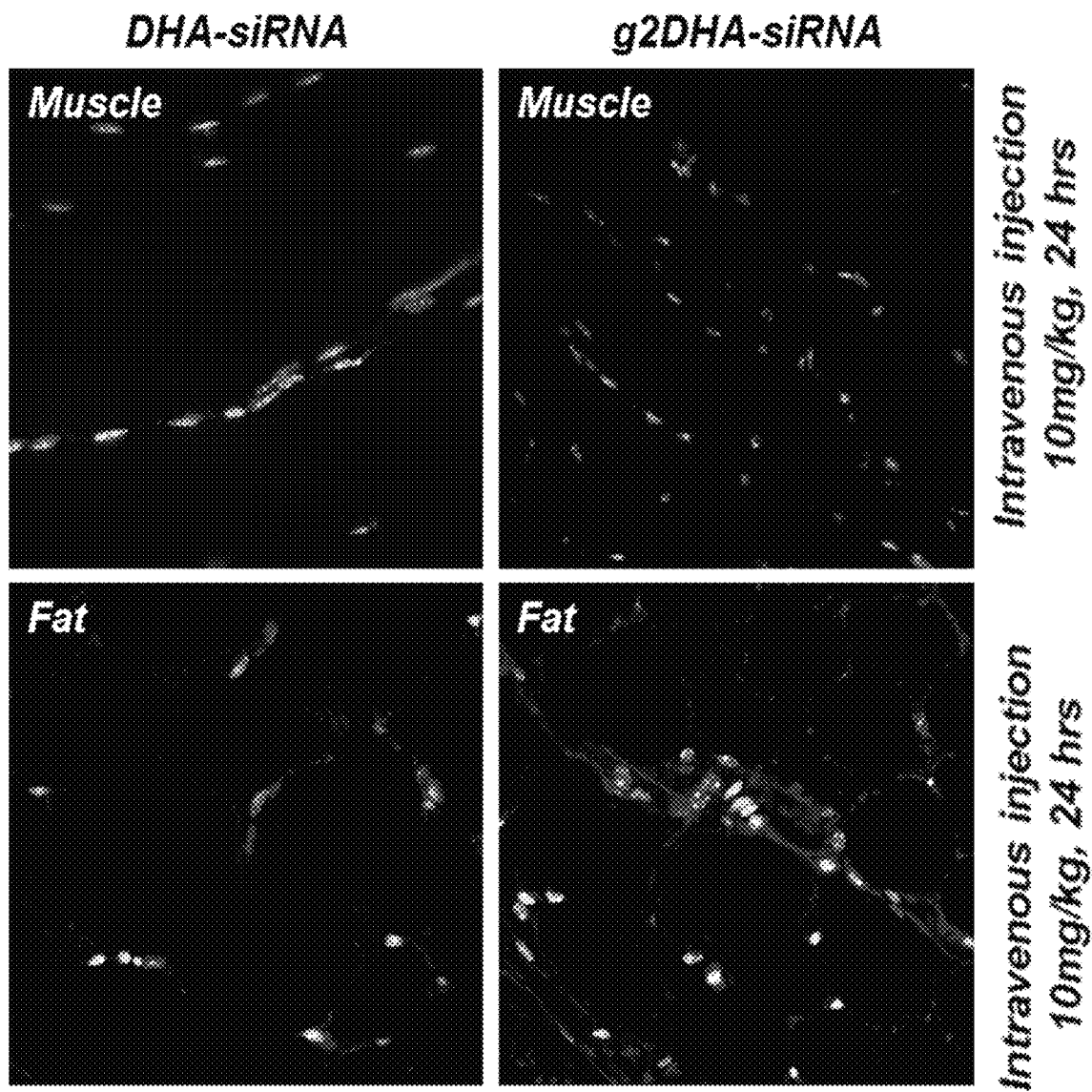
FIG. 25 shows g2DHA-hsiRNA distributed to muscle and fat tissue following systemic administration (one intravenous injection, 10 mg/kg). These tissues are not typically accessed by therapeutic siRNAs following intravenous administration. hsiRNA-conjugate structures and modifications are shown in FIG. 5A-F.
Figure 26:
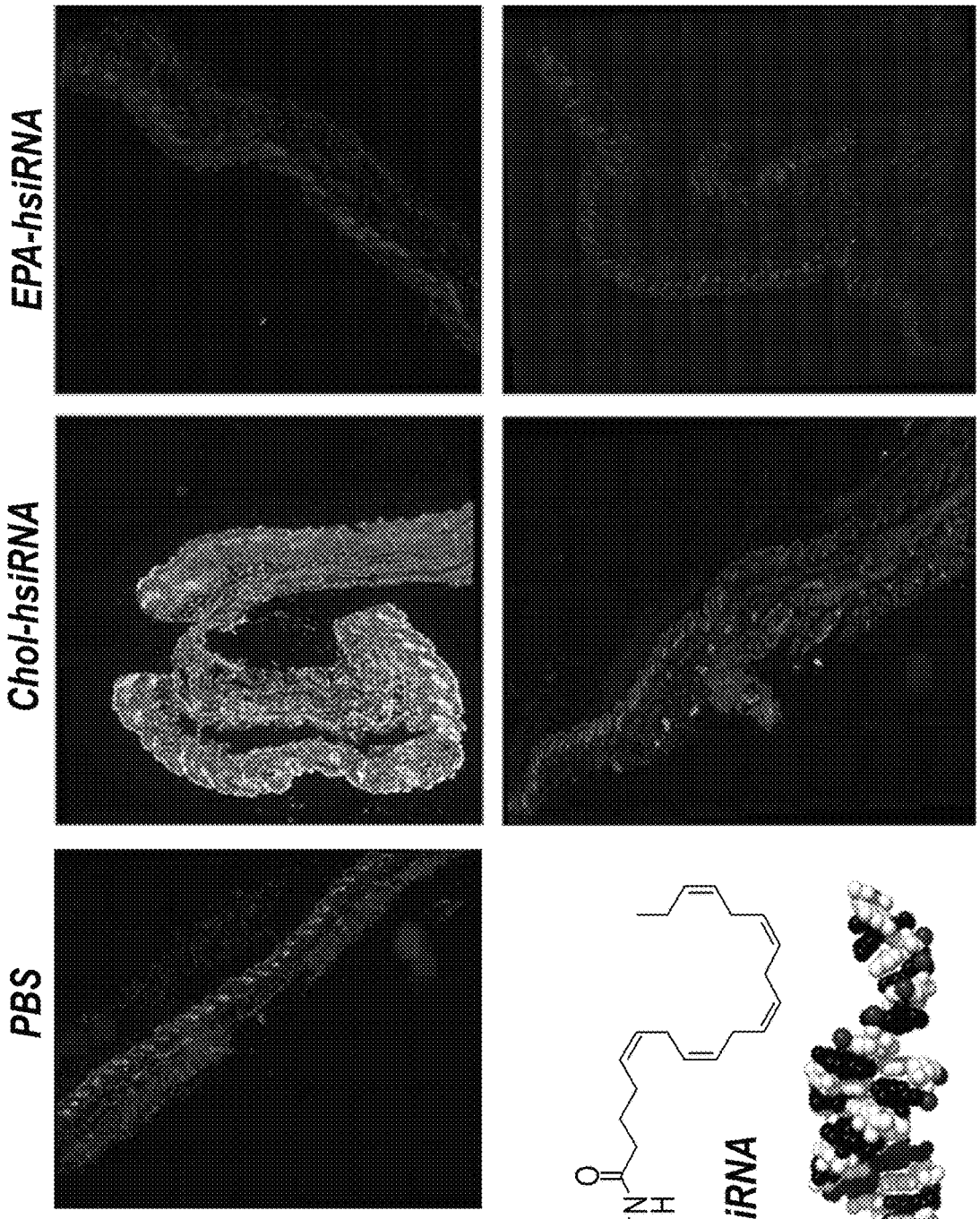
FIG. 26 shows Eicosapentanoic acid (EPA)-hsiRNA accumulation in the skin following subcutaneous injection. This can be directly compared to cholesterol-conjugated hsiRNA, which accumulates to a greater degree around the site of injection. This higher degree of accumulation may cause local toxicity and adverse effects, which is well documented for intrastriatal (CNS) administration. hsiRNA-conjugate structures and modifications are found in FIG. 5A-F.
Figure 27:
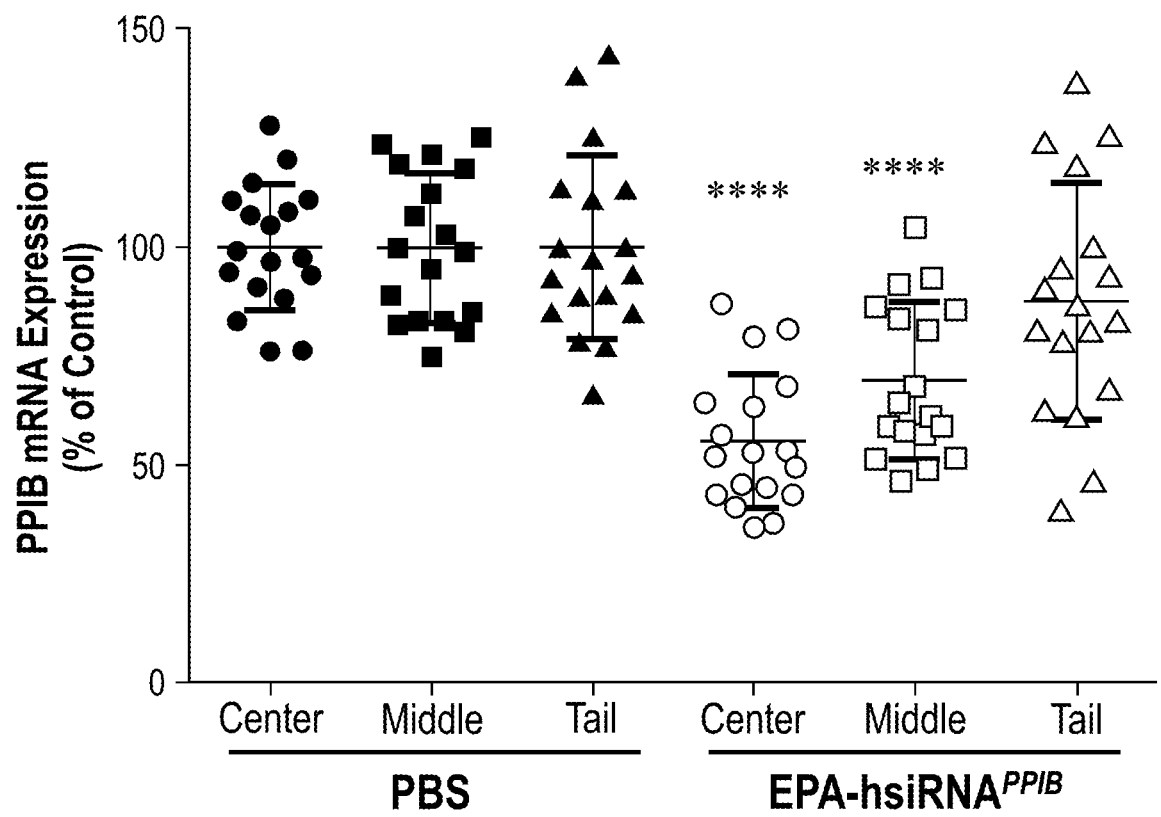
FIG. 27 shows that subcutaneous injection of EPA-hsiRNA induces gene silencing in the skin. Subcutaneous injection (40 mg/kg) EPA-siRNA. Animals sacrificed 7 days post-injection. Tissue punches taken from the center (skin from head to the center of the back), middle (skin around the midpoint of the animal), and tail skin. mRNA was quantified using Affymetrix Quantigene 2.0 as per Coles et al. 2015. hsiRNA sequence PPIB is found in FIG. 7.
Figure 28A:
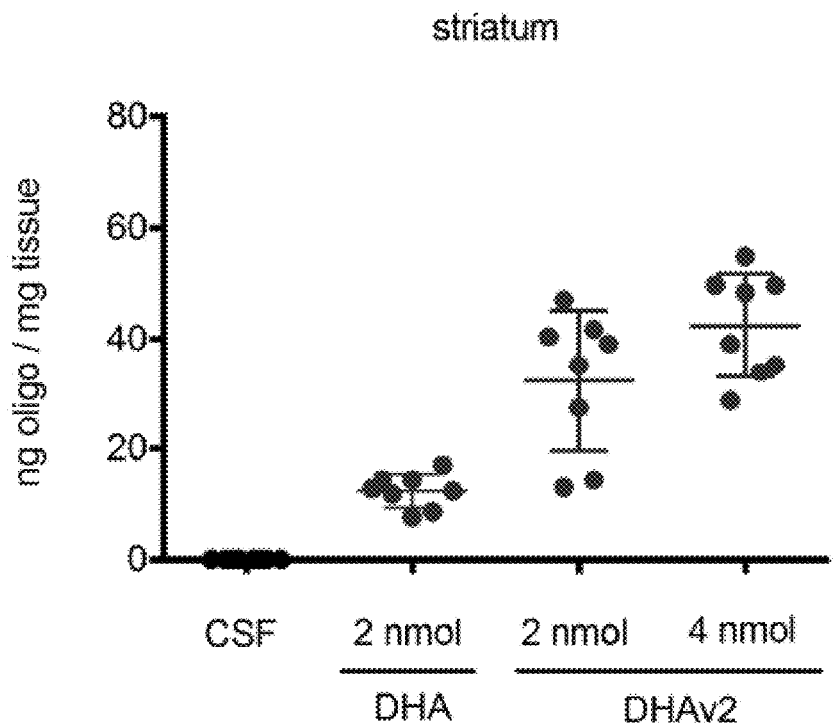
FIG. 28A-B show that a single injection of DHA- or g2DHA-siRNA is detected in both the striatum (A) and cortex (B) on the injected side. Alternative methods of injection including intracerebroventricular may also facilitate bilateral distribution with only one injection. Intrastriatal injection 2-4 nmols DHA- or g2DHA-siRNA. Animals sacrificed 7 days post-injection. Tissue punches taken from the 300 um brain slices from the striatum and cortex. siRNA antisense strands present in different brain regions were quantified using Cy3-labeled complimentary PNA to hybridize to the strand and HPLC to quantify ng of oligo per mg of tissue. aCSF—Artificial CSF. hsiRNA-conjugate structures and modifications are found in FIGS. 5A-F and the PPIB sequence is shown in FIG. 7.
Figure 28B:
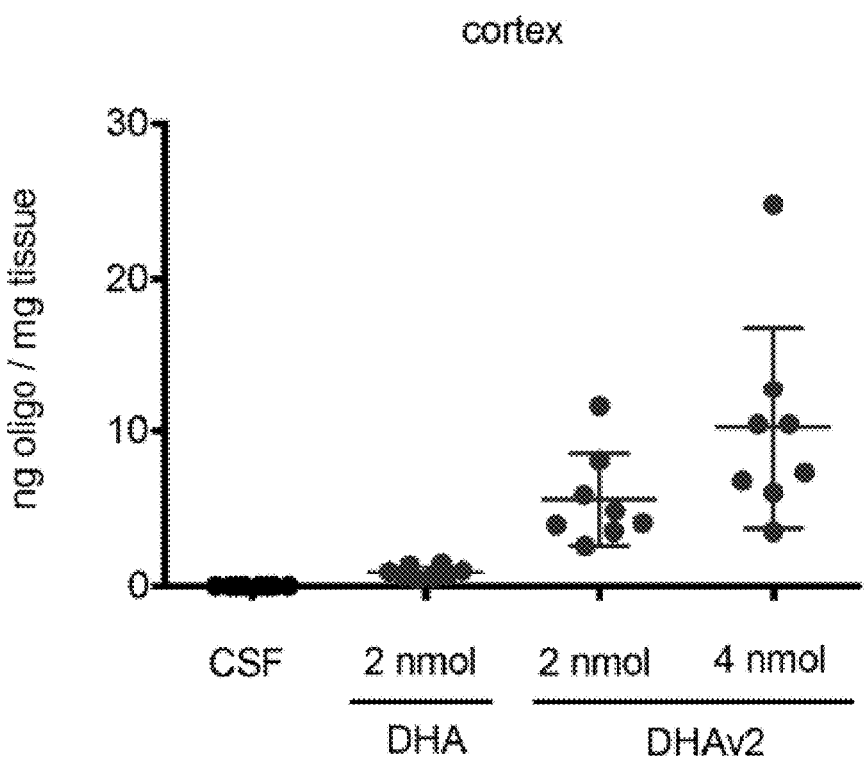

As shown in FIG. 22, g2DHA-siRNA shows preferential localization in the kidney following a single, intravenous injection, which directly contrasts the typical liver distribution observed for highly hydrophobic lipid-siRNA conjugates (e.g. cholesterol, DCA). The differences in the degree of accumulation was measured using a quantitative peptide nucleic acid hybridization assay. We observe a statistically significant increase in kidney accumulation and decrease in liver accumulation with g2DHA-siRNA compared to Chol-siRNA.

Serum lipoprotein complexes are responsible for trafficking endogenous fatty acids and lipids throughout the bloodstream. Lipid-conjugated siRNAs may avail themselves of this mechanism to achieve distribution to different tissues following intravenous administration. FIG. 29 describes the different lipid-binding and systemic distribution characteristics of each individual serum lipoprotein. Very low density lipoprotein (VLDL); Intermediate density lipoprotein (IDL); Low density lipoprotein (LDL); High density lipoprotein (HDL).

Figure 30:
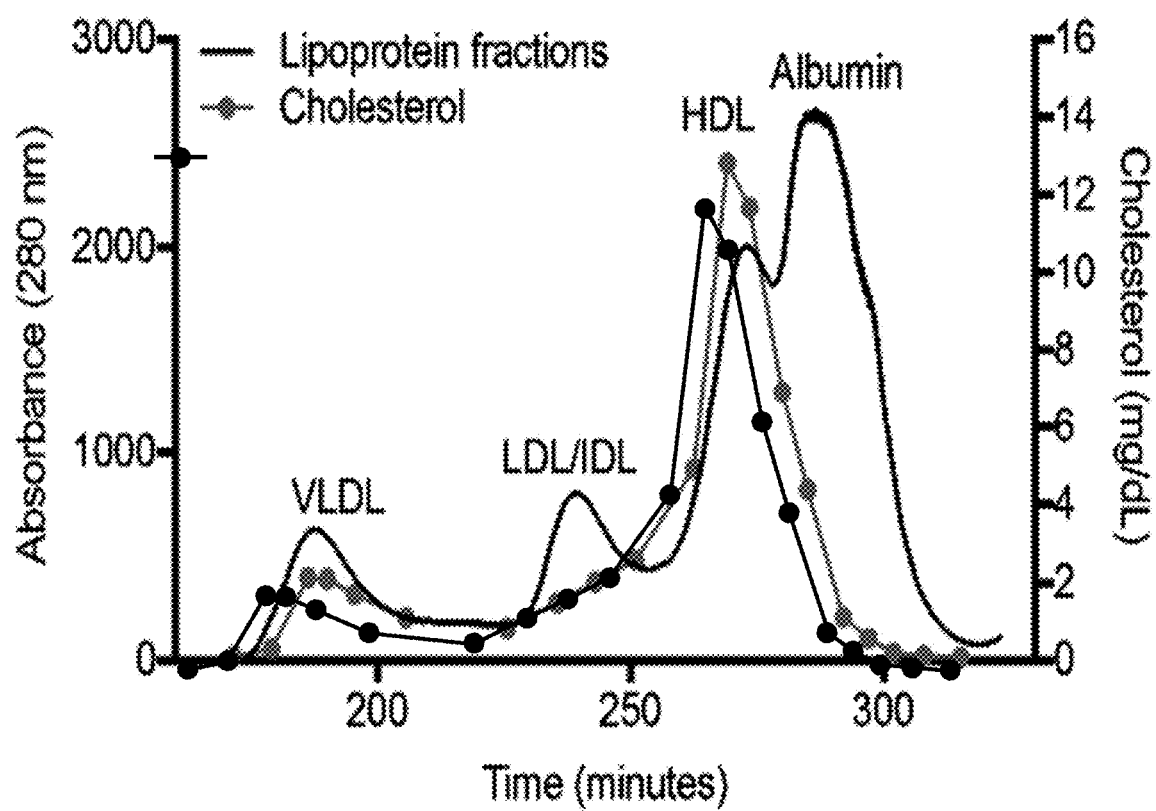
FIG. 30 shows the lipoprotein profile of FVB/NJ mice. Whole mouse blood (~500 µL) was collected in a sterile EDTA-coated tube following cardiac puncture. Samples were spun at 10,000 RPM for 10 minutes. 50 µL of serum was directly injected on Superose 360 size exclusion column. Fractions were collected over 300 minutes and analyzed for cholesterol content by the HDL/LDL Cholesterol Assay Kit (Abcam).

The different tissue distribution patterns observed in vivo for each distinct siRNA conjugate are determined by their lipoprotein binding profiles. These profiles can be determined empirically using size exclusion chromatography and monitoring the absorbance at 280 nm (protein). As shown in FIG. 30, protein peak fractions were collected and a cholesterol quantification assay was used to determine the identity of each peak in the trace. In wild-type FVB/NJ mice, cholesterol is primarily associated with HDL. From this, the albumin, HDL, LDL/IDL, and VLDL peaks were assigned.

Figure 31A:
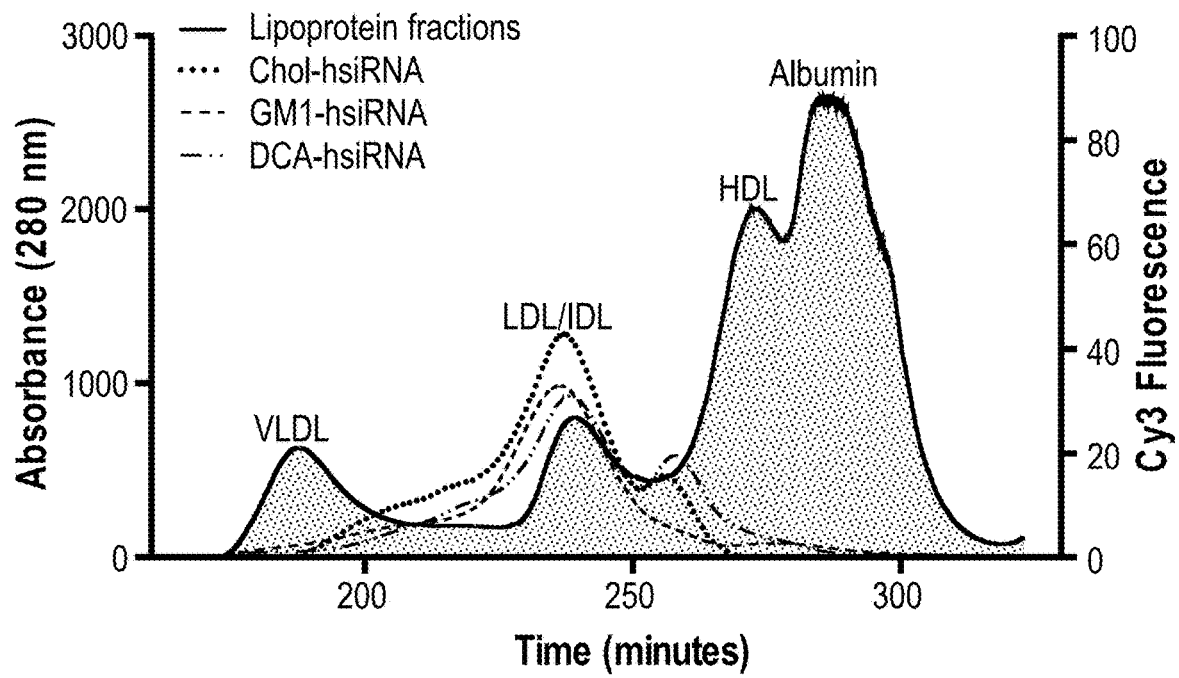
FIG. 31A-B depict serum lipoprotein profile analysis of siRNA in mouse blood. (A) cholesterol, DCA, and GM1 conjugates preferentially associate with IDL and LDL. hsiRNA-conjugate structures and modifications are found in FIG. 5A-F. (B) EPA, DHA, and DHAg2 conjugates preferentially associate with HDL. The structure of the EPA conjugate can be found in FIG. 41. hsiRNA conjugates (15 µM) were incubated in 50 µL of serum at room temperature for 30 minutes. 50 µL of serum was directly injected on Superose 360 size exclusion column. Fractions were collected over 300 minutes and analyzed for cholesterol content by the HDL/LDL Cholesterol Assay Kit (Abcam). The HTT sequence is shown in FIG. 7.
Figure 31B:
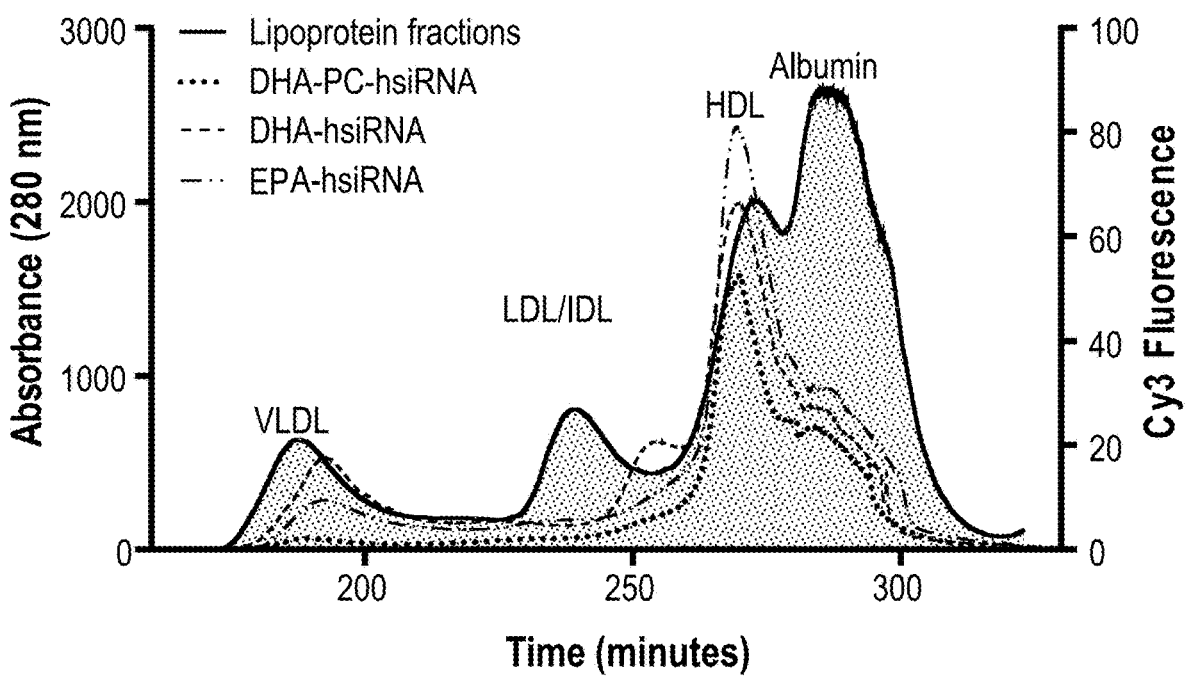
Figure 34:
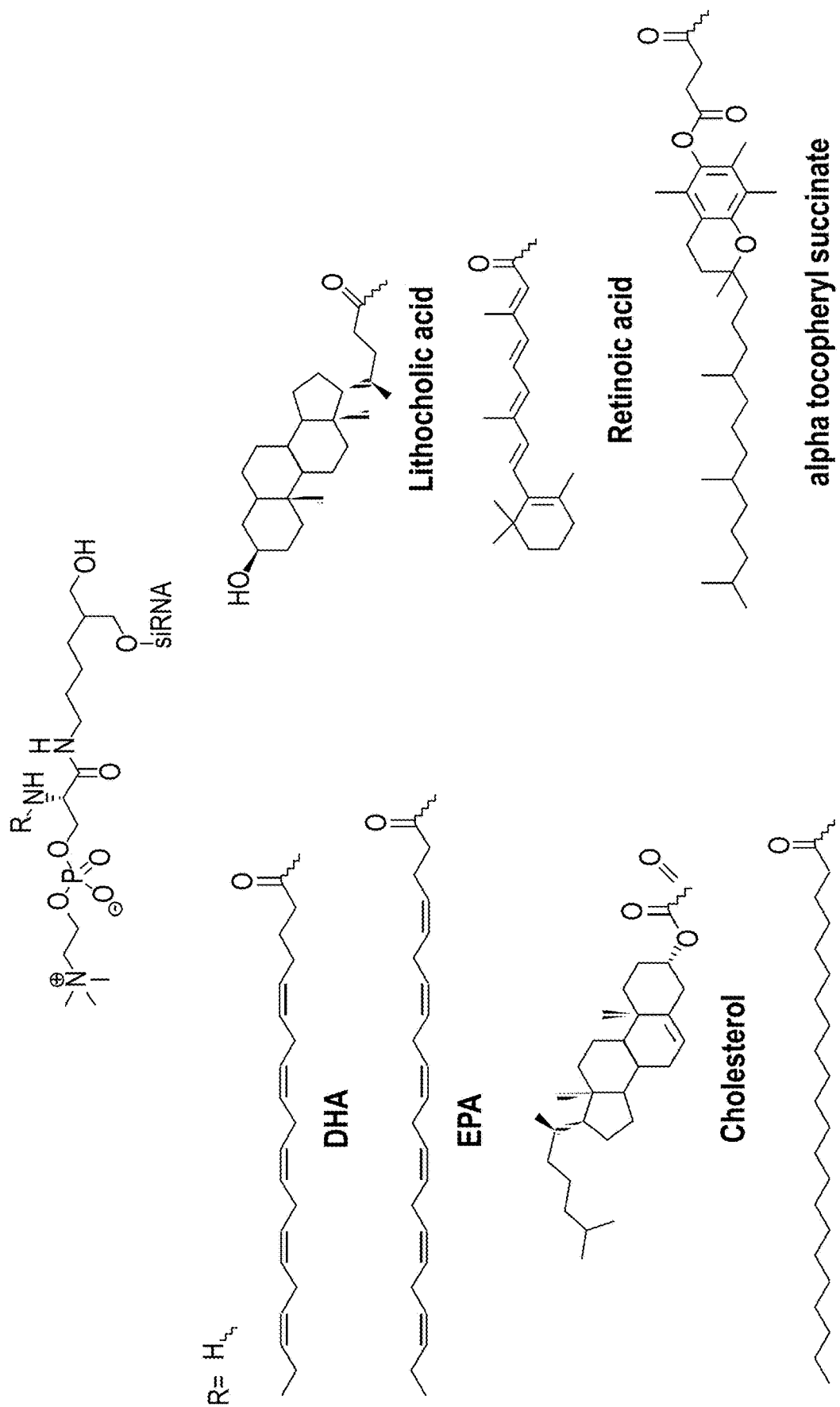
FIG. 34 shows hydrophobic siRNA conjugates with esterified phosphatidylcholine modifiers.
Figures 35A, 35B:
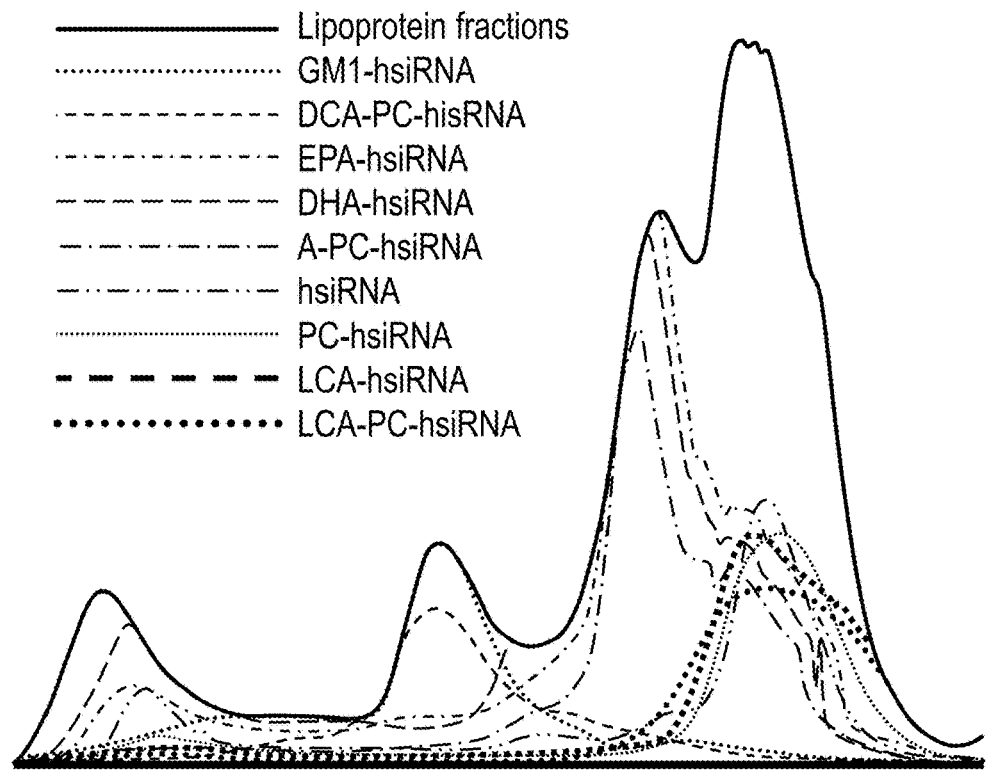
FIG. 35A-B show hsiRNA conjugates association with different lipoprotein particles.
Figure 36:
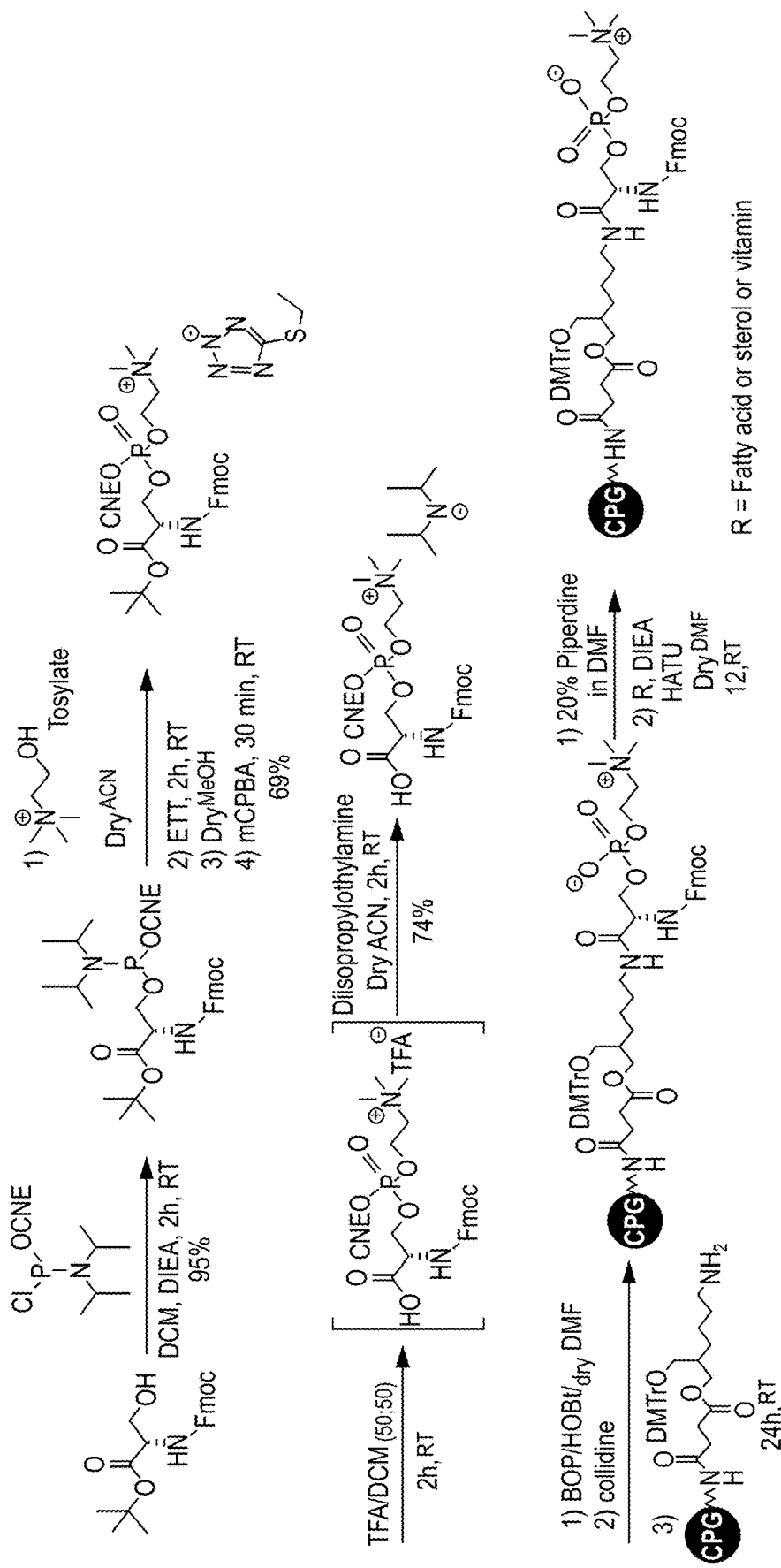
FIG. 36 shows the route of synthesis of g2 conjugated CPG.
Figure 37:
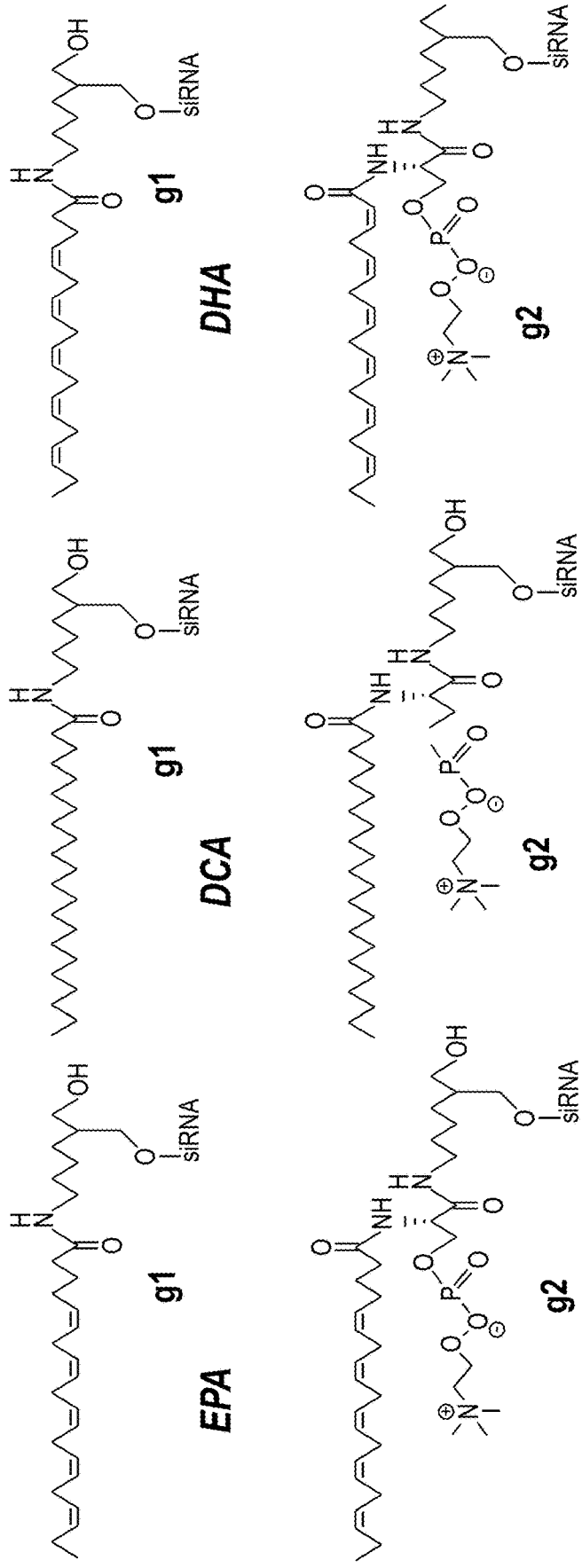
FIG. 37 shows exemplary lipophilic conjugates in both g1 (without a Zc modifier) and g2 (with a Zc modifier) forms. Shown are docosahexaenoic acid ("DHA" or "DHA g1"), DHA g2 (also referred to herein as "PC-DHA"), docosanoic acid ("DCA" or "DCA g1"), DCA g2 (also referred to herein as "PC-DCA"), eicosapentaenoic acid ("EPA" or "EPA g1"), EPA g2 (also referred to herein as "PC-EPA"), cholesterol g1, cholesterol C7 g1, cholesterol g2, lithocholic acid ("LA" or "LA g1"), LA g2 (also referred to herein as "PC-LA"), retinoic acid ("vitamin A," "RA" or "RA g1"), RA g2 (also referred to herein as "PC-RA"), a-tocopherol succinate ("vitamin E," "TOCO" or "TOCO g1"), and TOCO g2 (also referred to herein as "PC-TOCO").
Figure 37:
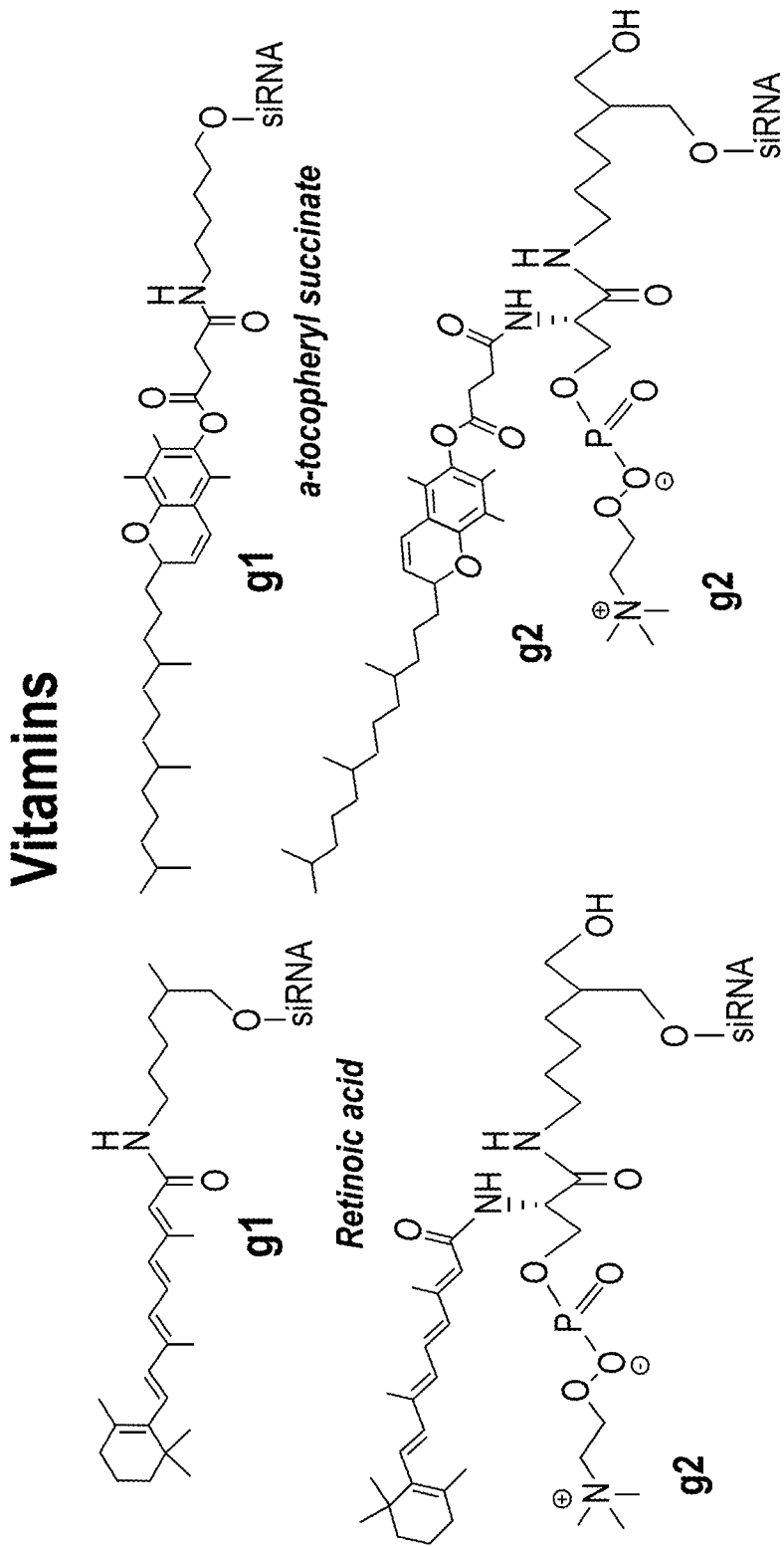
Figure 37:
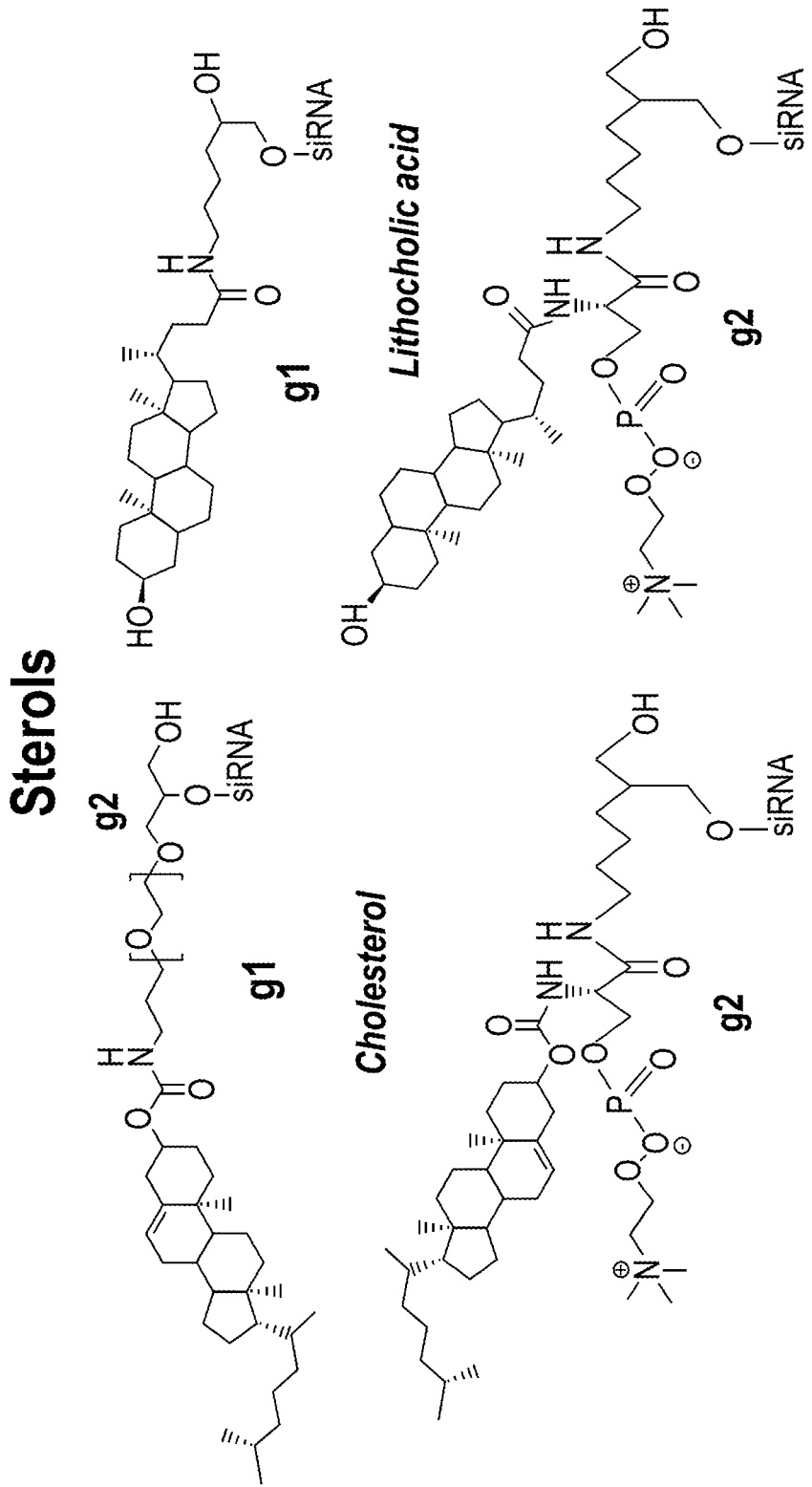
Figure 38:
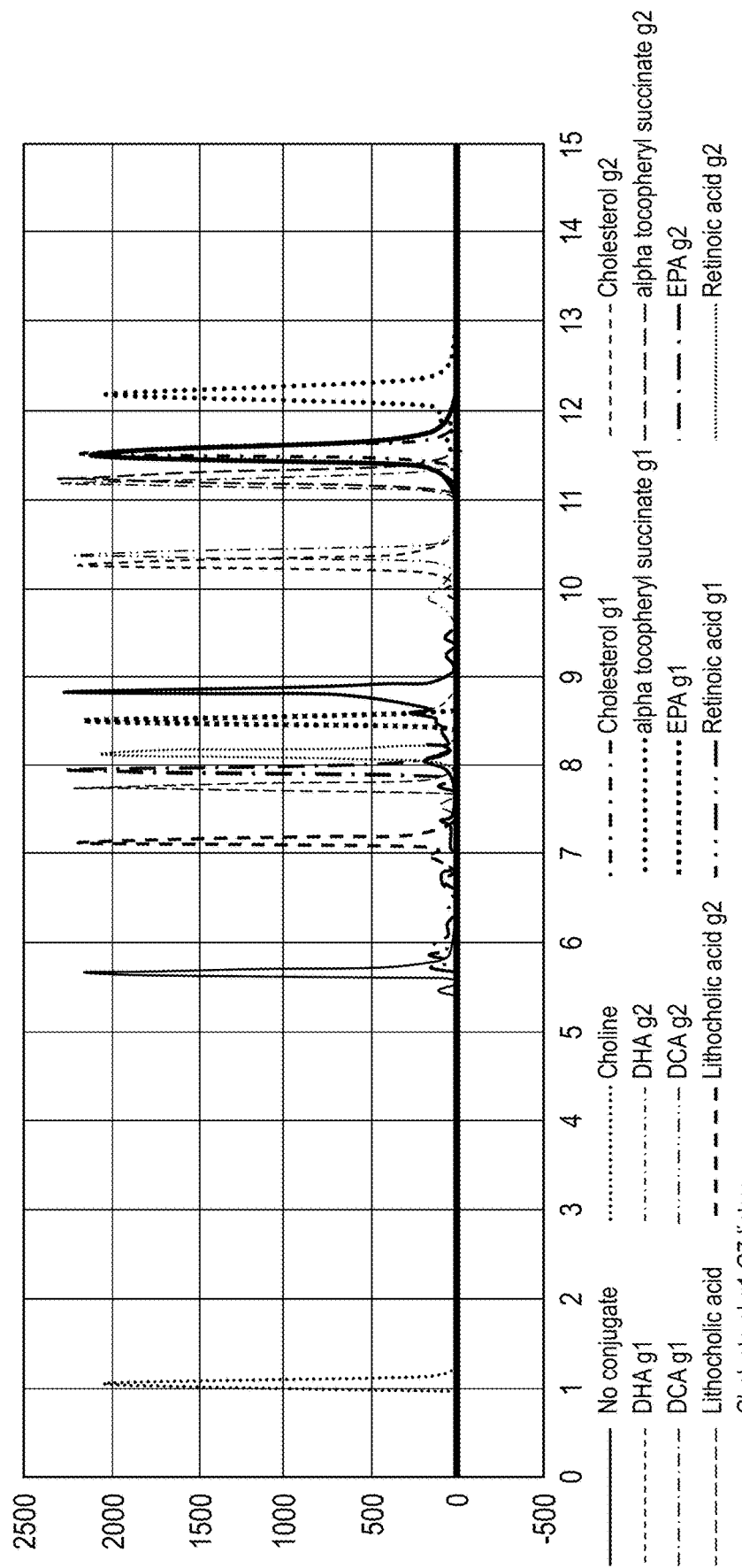
FIG. 38 shows reverse phase HPLC data of conjugated Cy3 HTT sense strand oligonucleotides with various exemplary conjugates.
Figure 39:
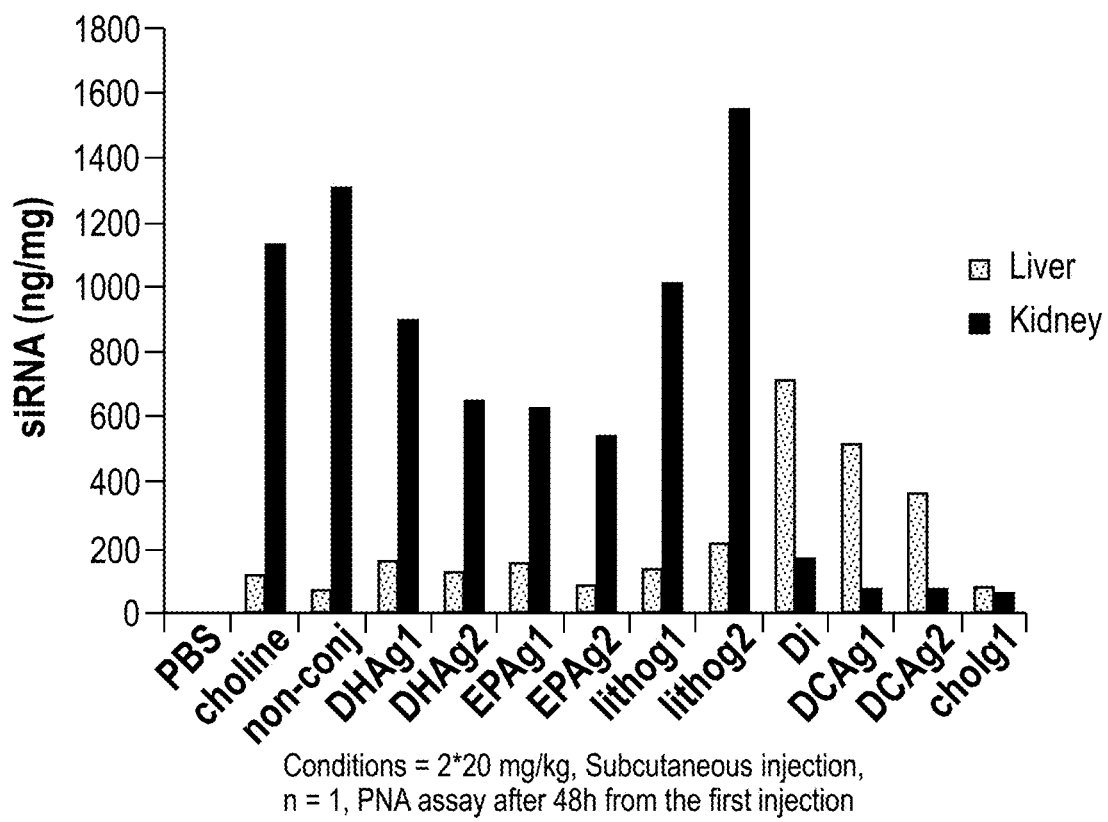
FIG. 39 shows altered liver/kidney distribution of siRNAs conjugated to various exemplary lipophilic moieties.
Figure 40:
FIG. 40 shows fluorescent images of liver/kidney distribution of various exemplary siRNA conjugates.
Figure 41:
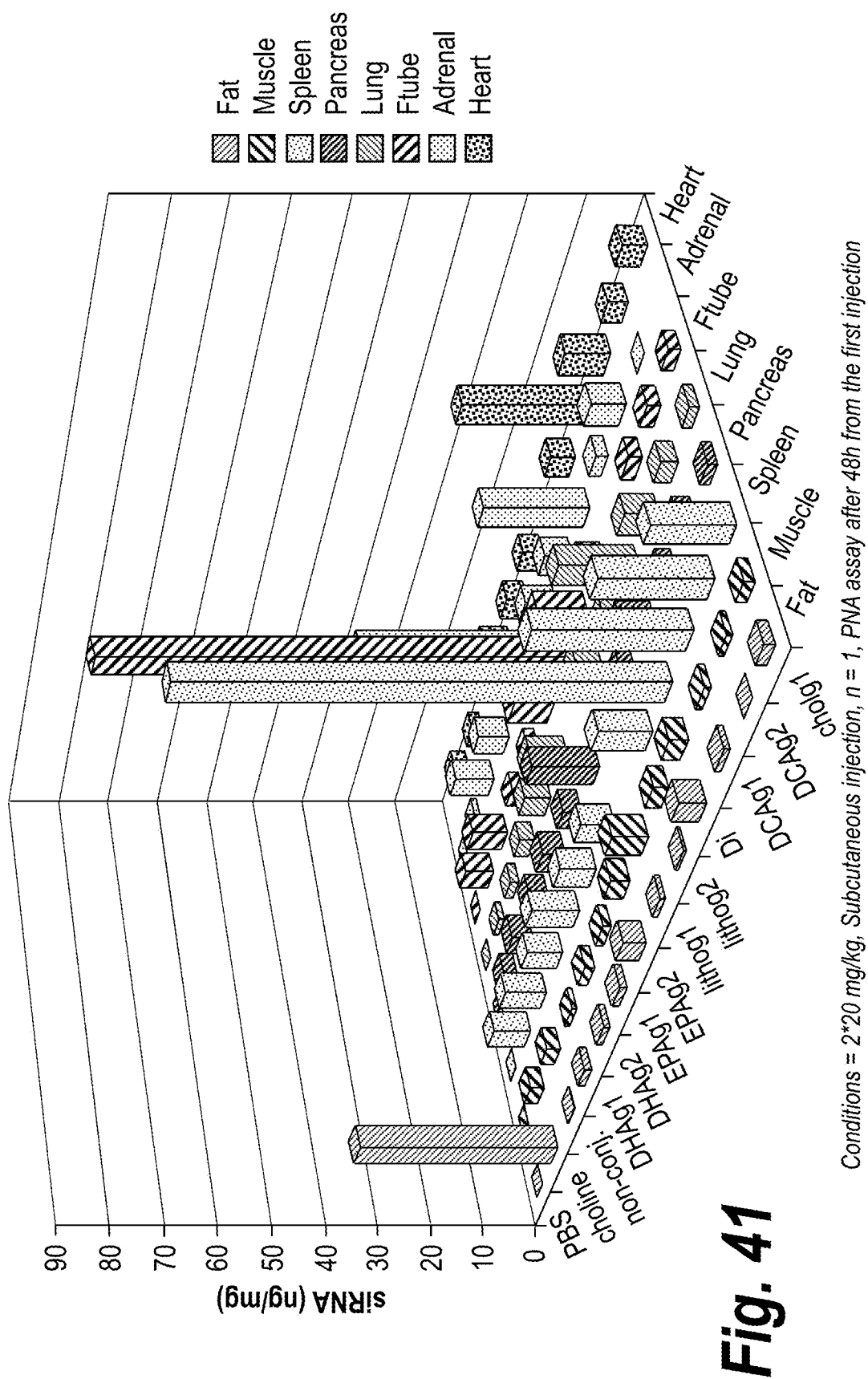
FIG. 41 shows the altered tissue distribution of siRNA conjugates.
Figure 43A:
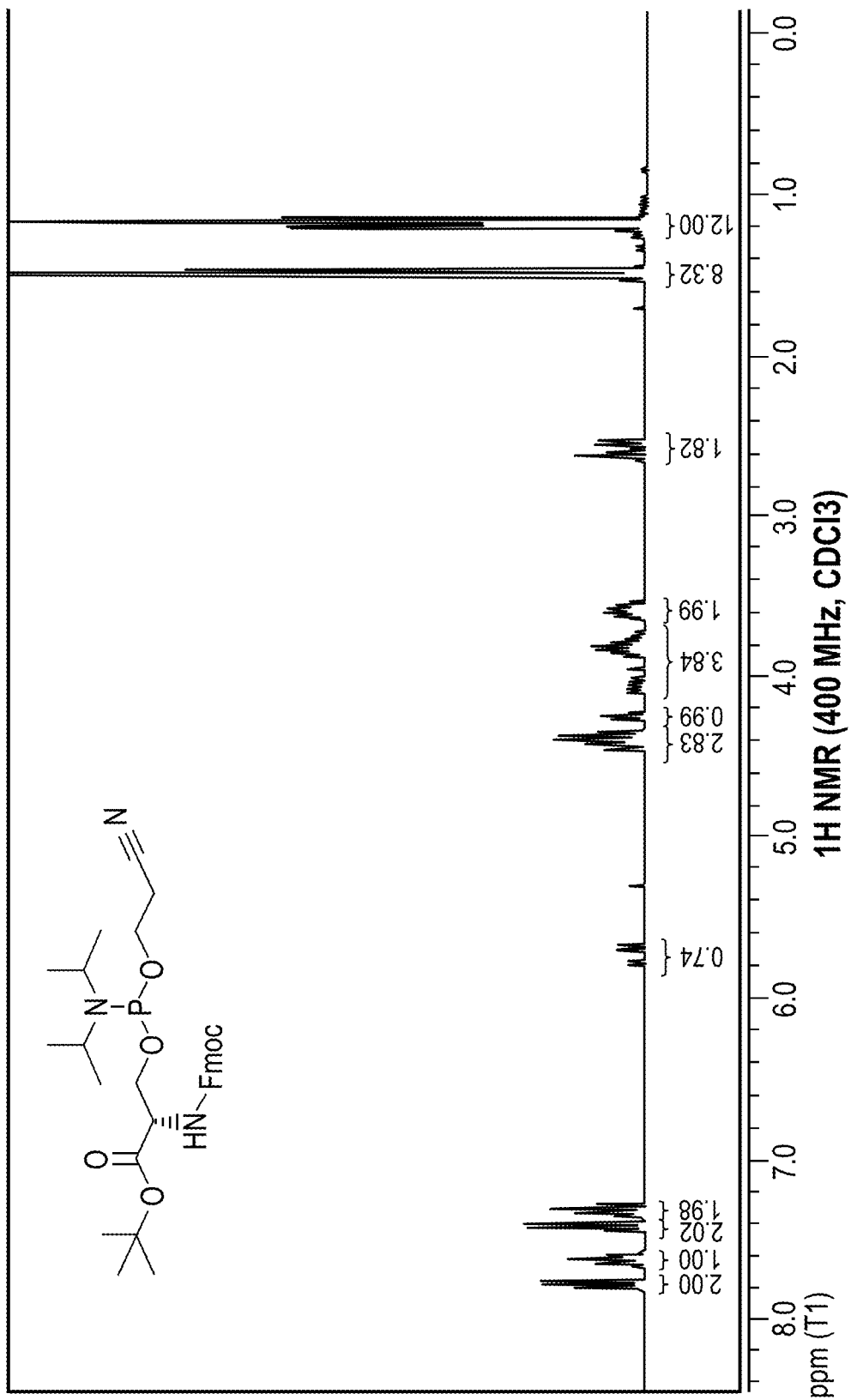
FIG. 43A-D show NMR and HRMS characterization of a synthesis intermediate shown in FIG. 36.
Figure 43B:
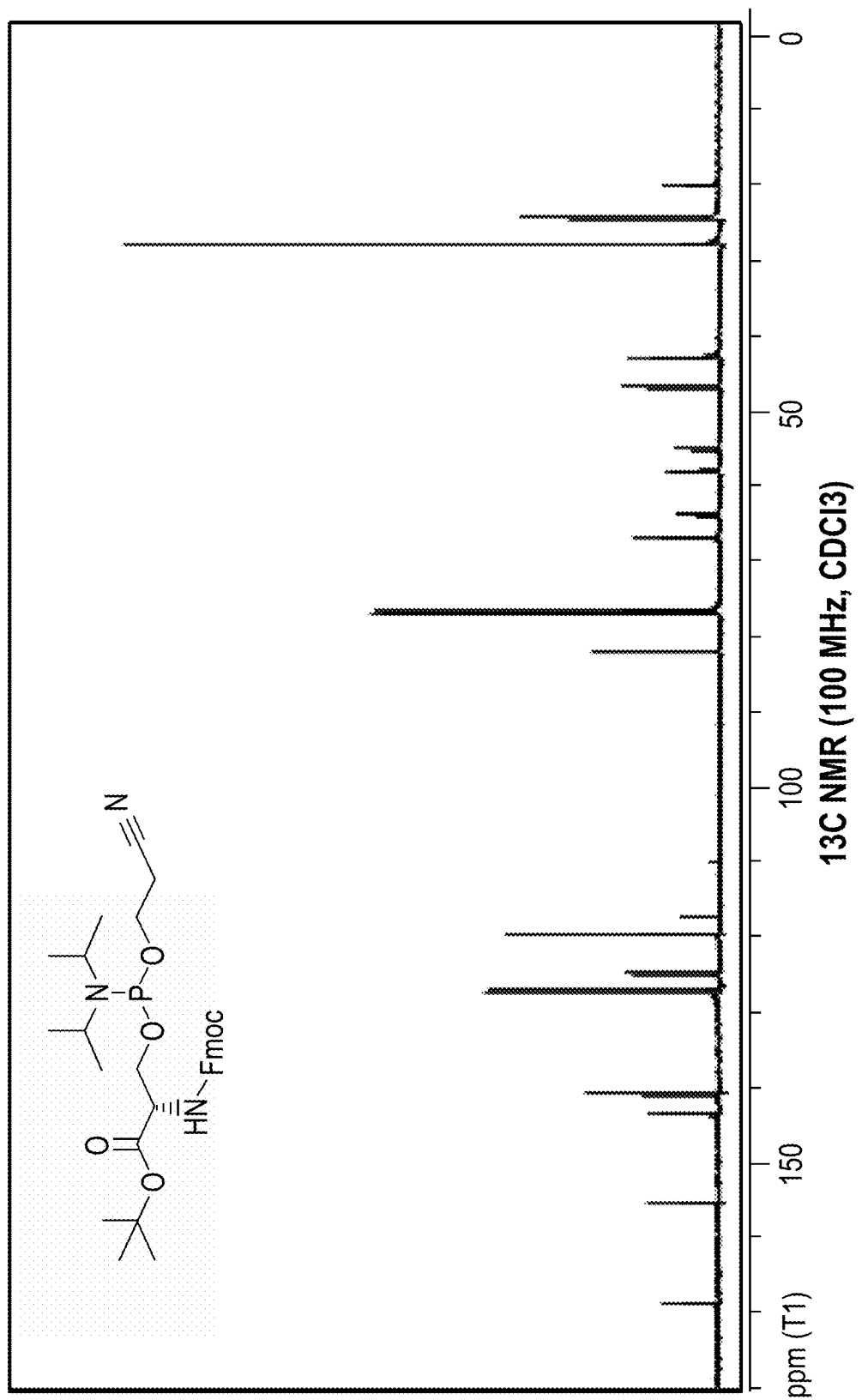
Figure 43C:
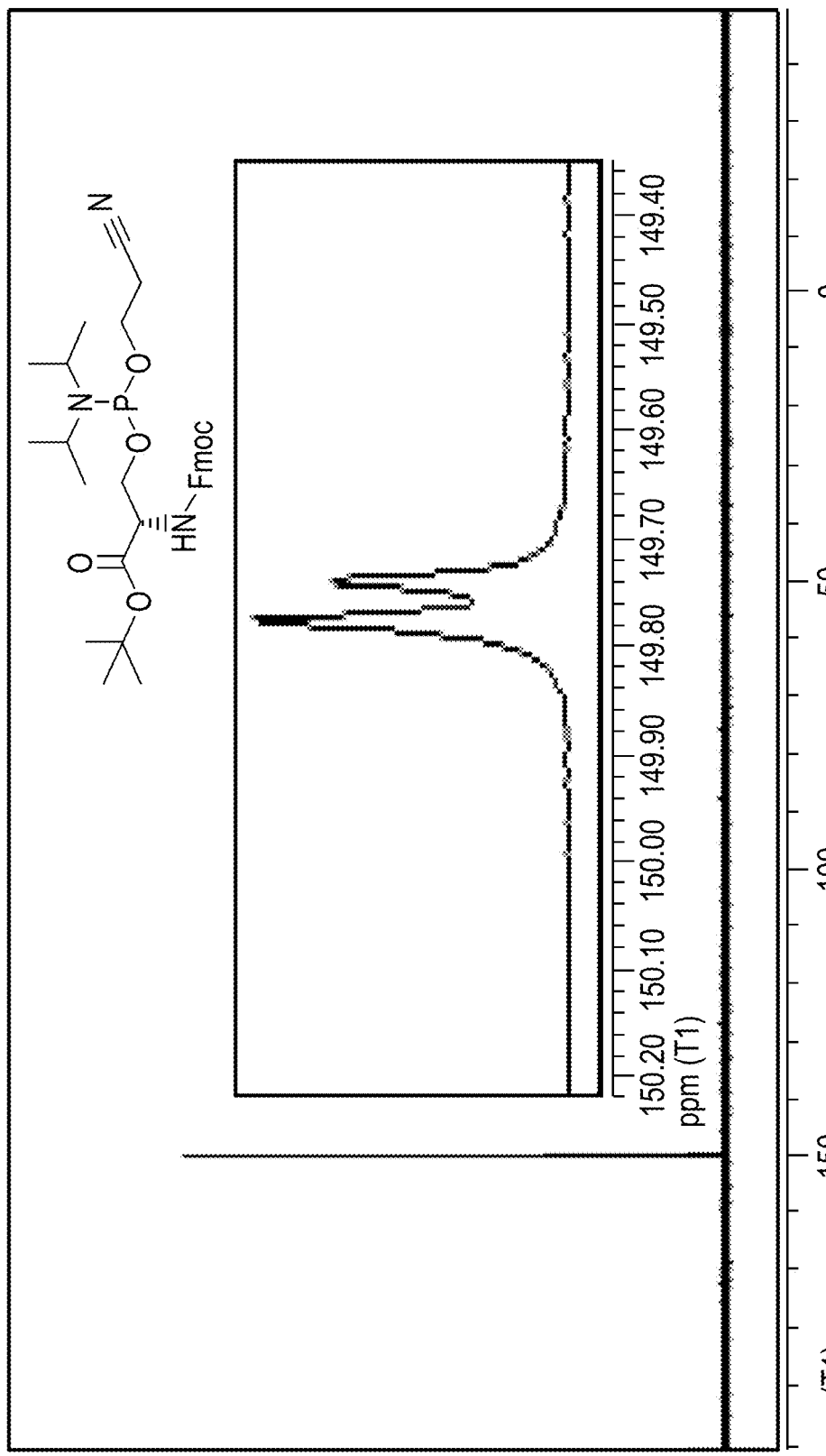
Figure 43D:
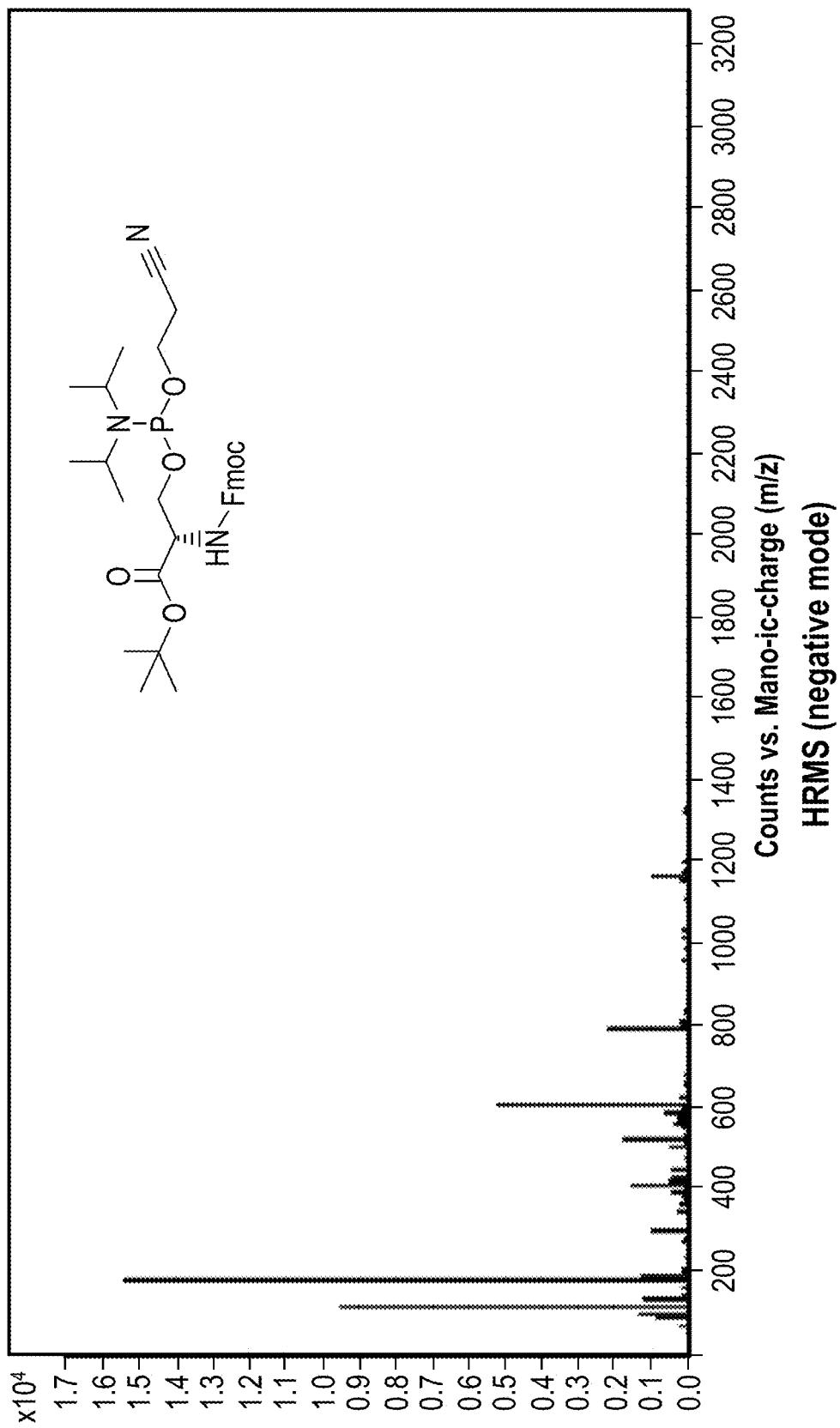
Figure 44A:
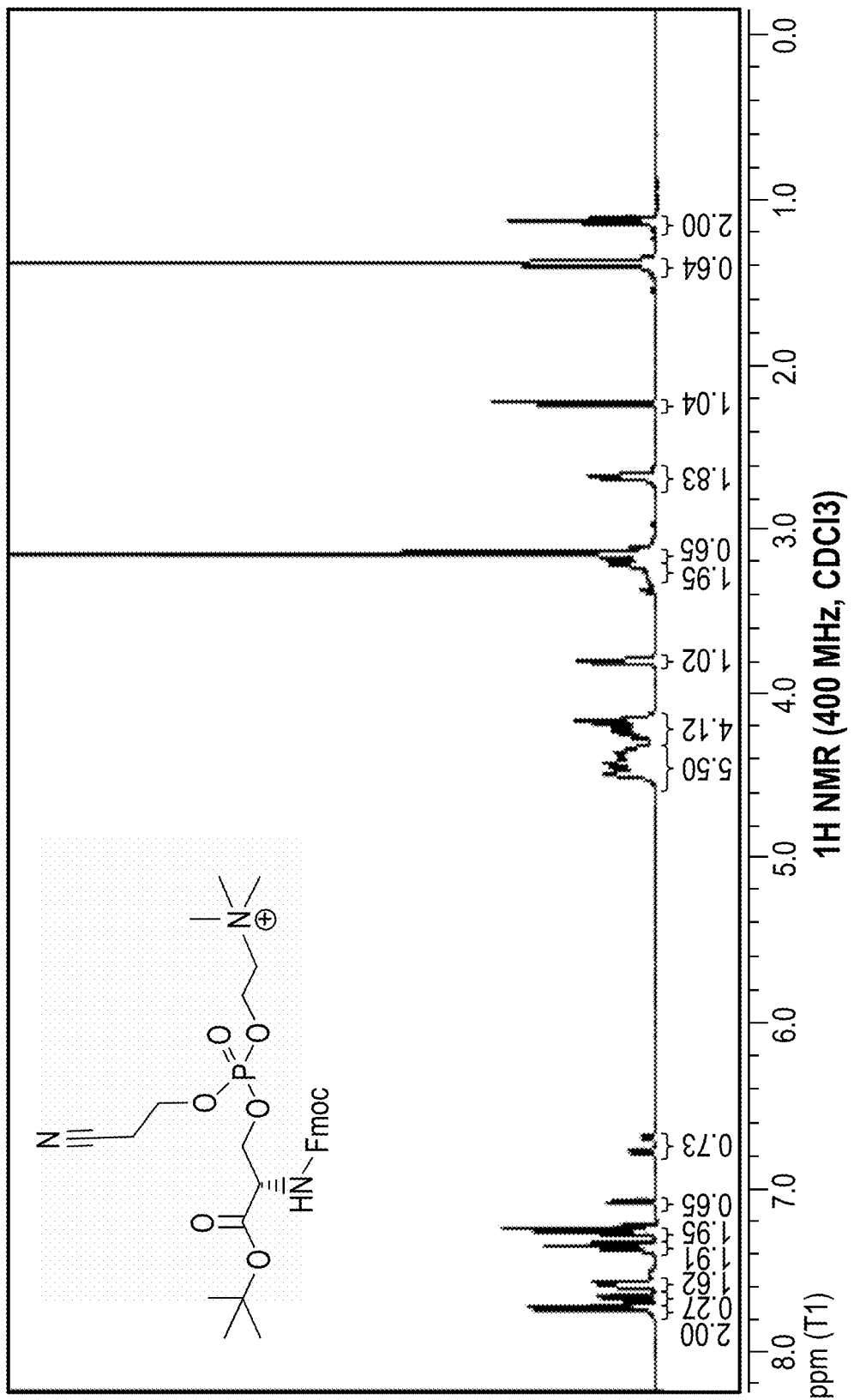
FIG. 44A-D show NMR and HRMS characterization of a synthesis intermediate shown in FIG. 36.
Figure 44B:
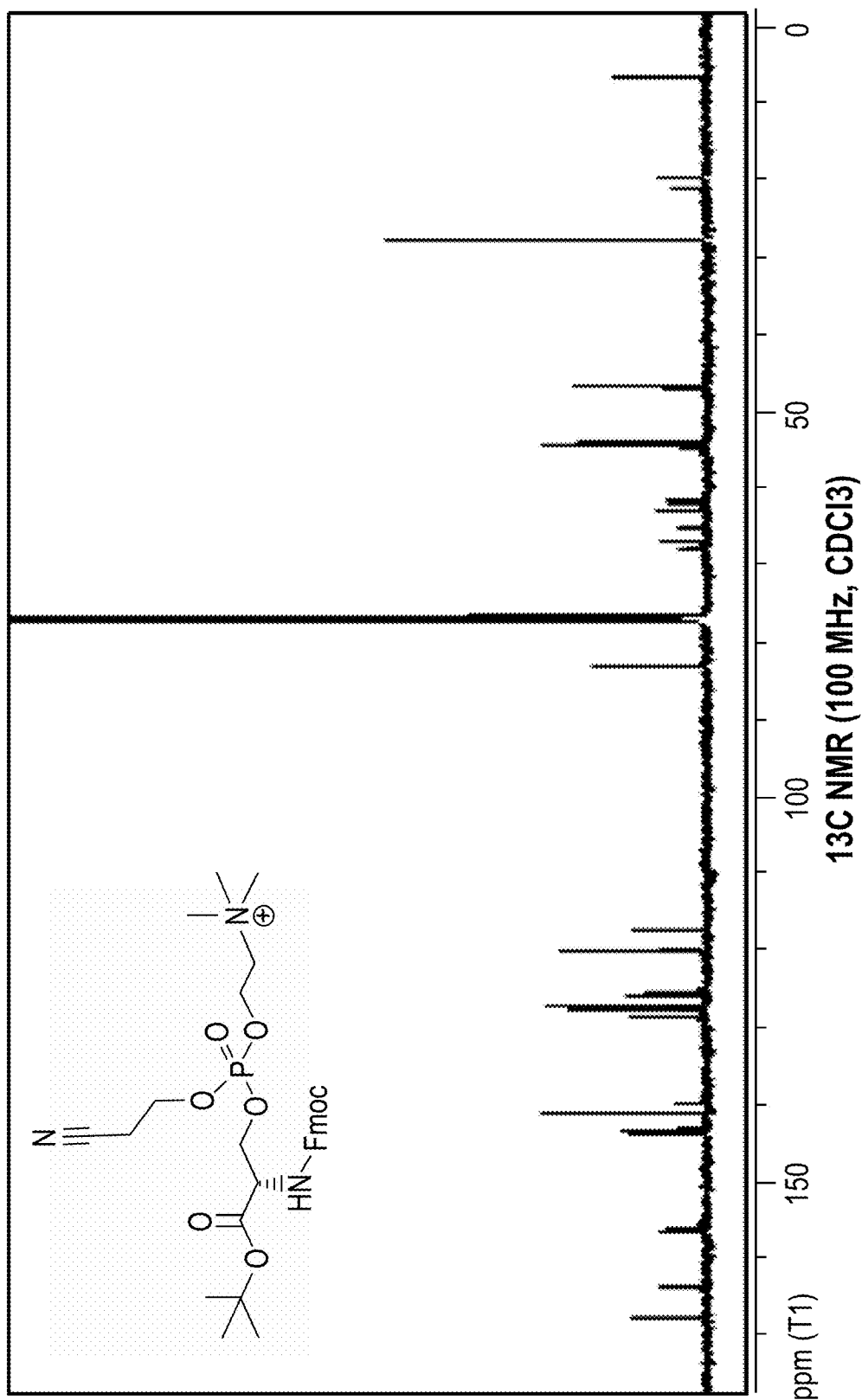
Figure 44C:
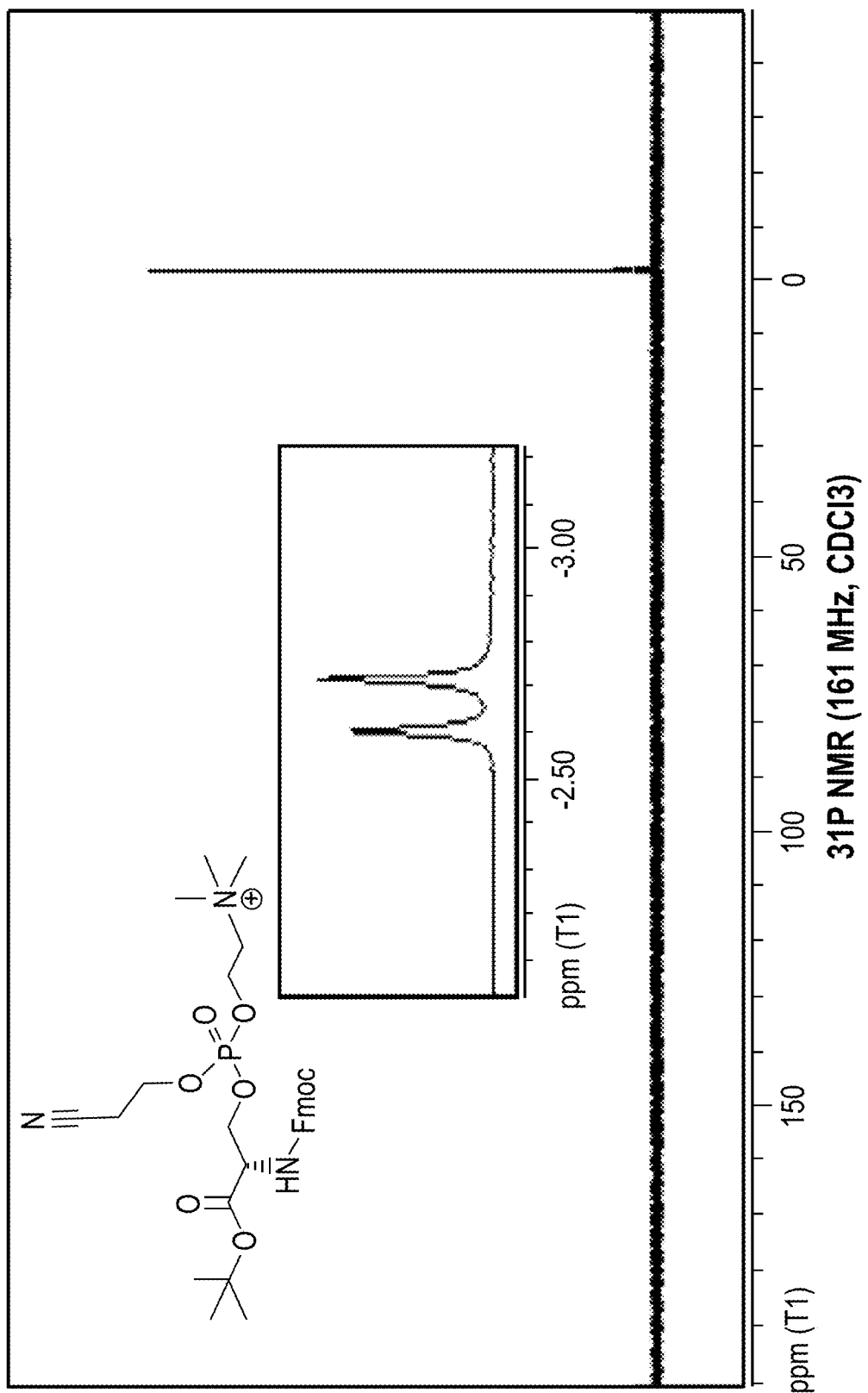
Figure 44D:
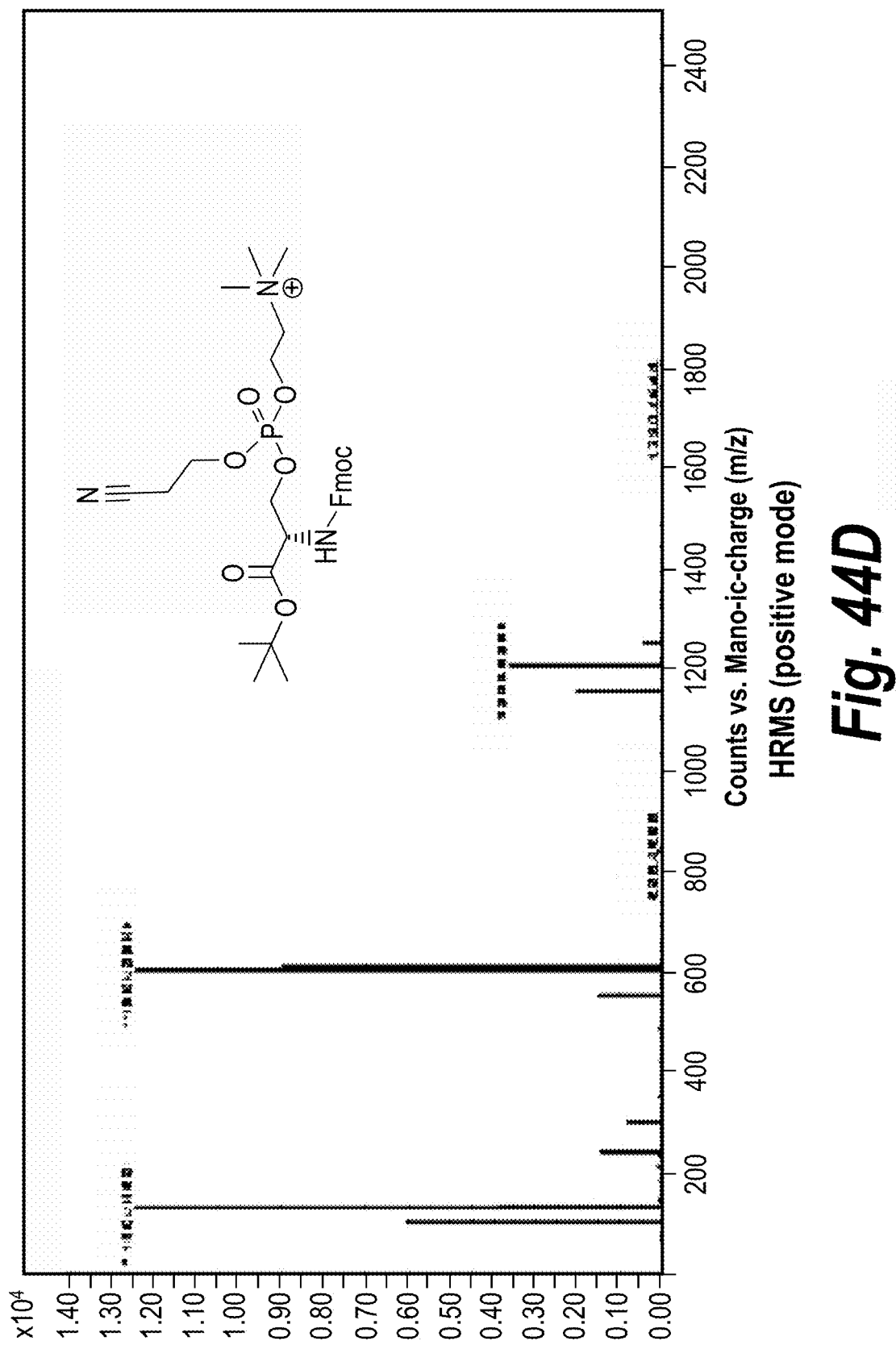
Figure 45A:
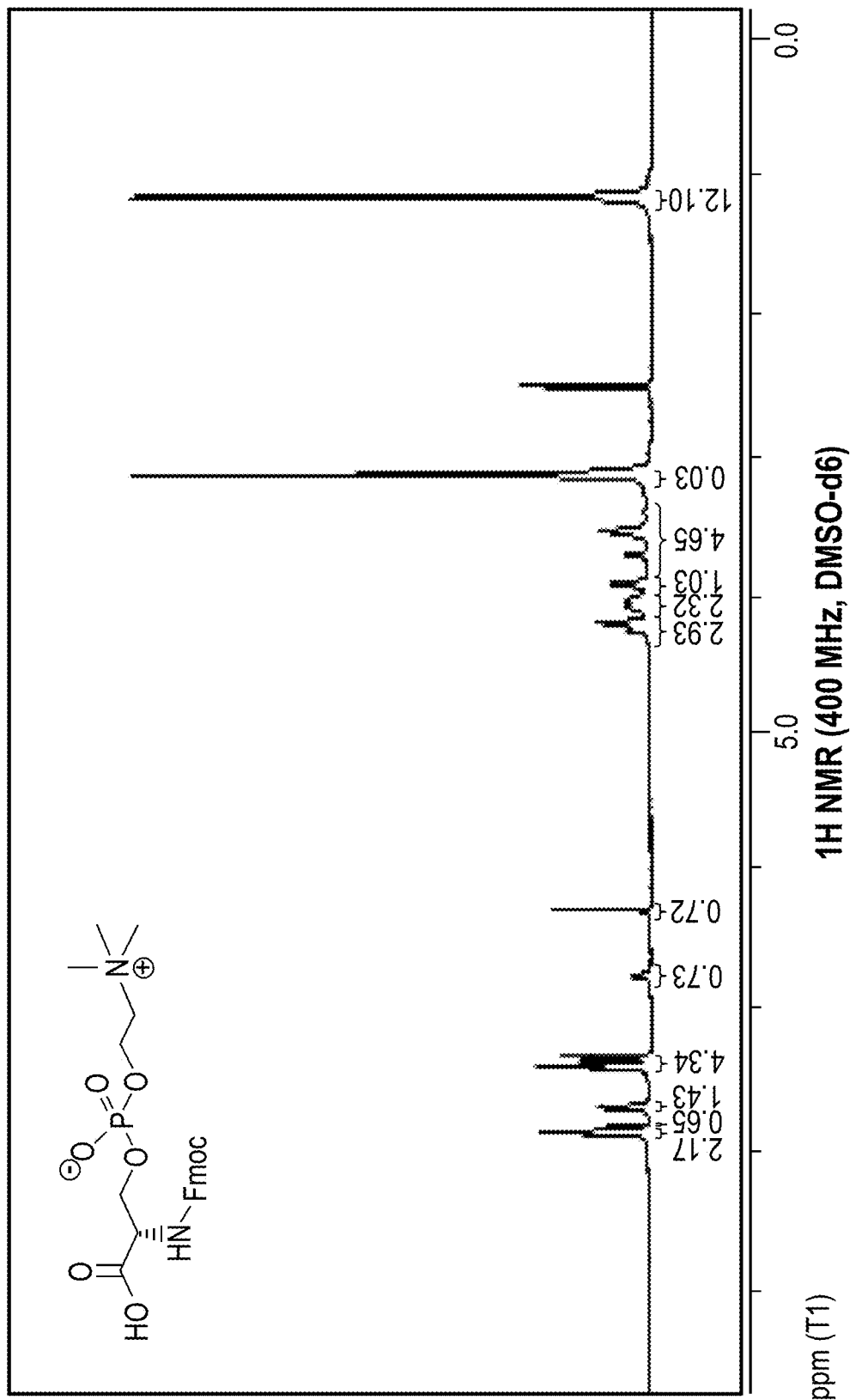
FIG. 45A-D show NMR and HRMS characterization of a synthesis intermediate shown in FIG. 36.
Figure 45B:
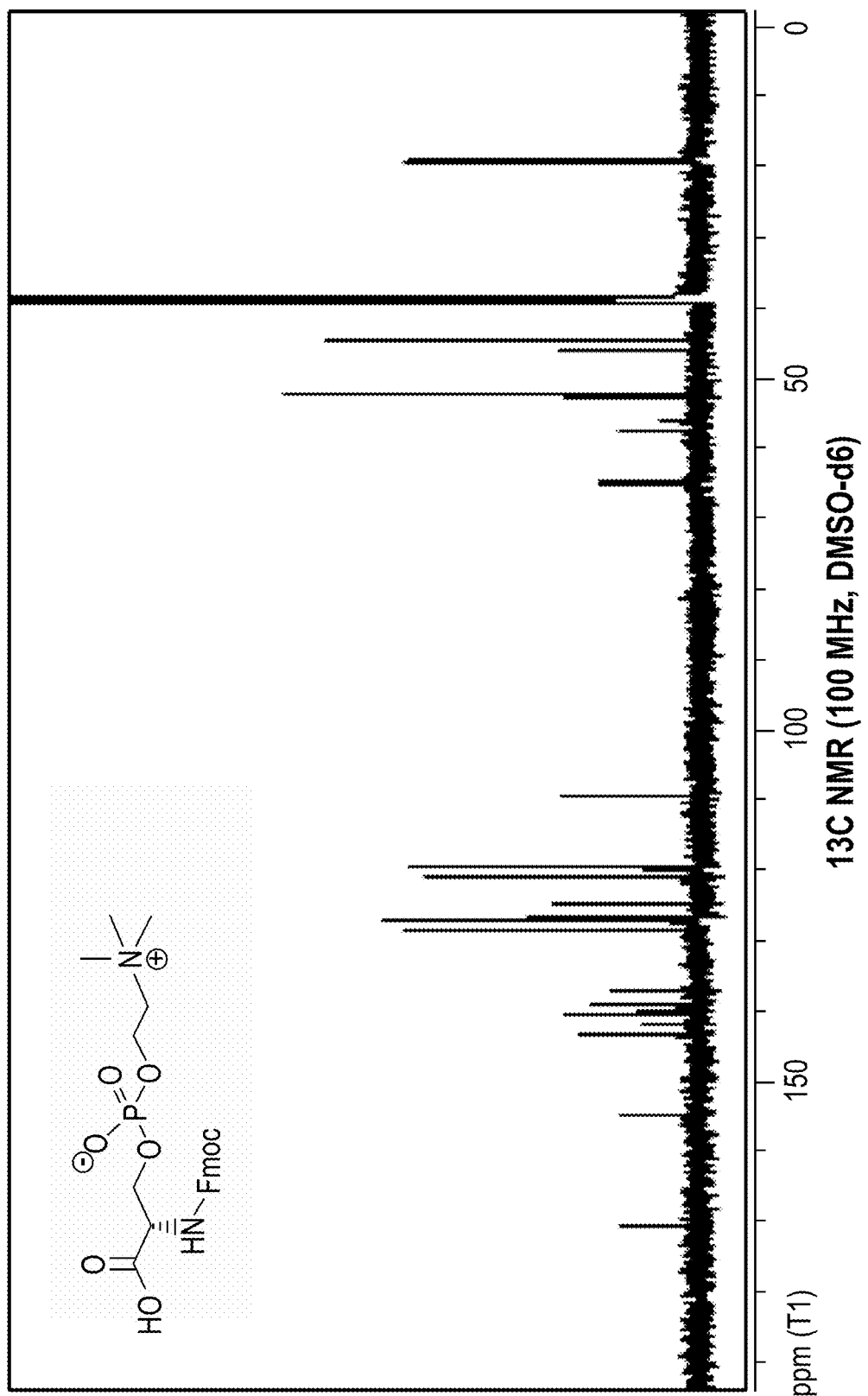
Figure 45C:
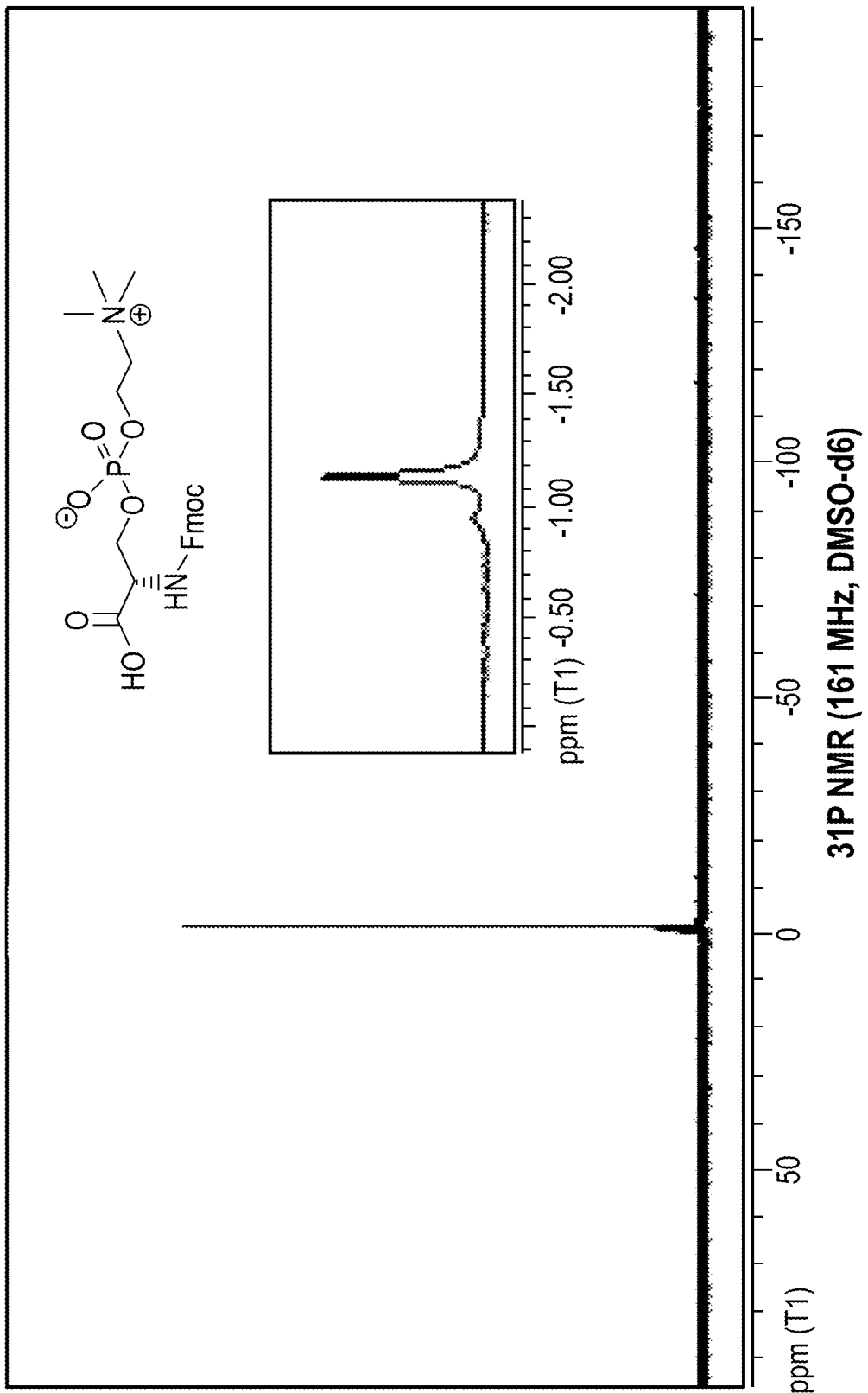
Figure 45D:
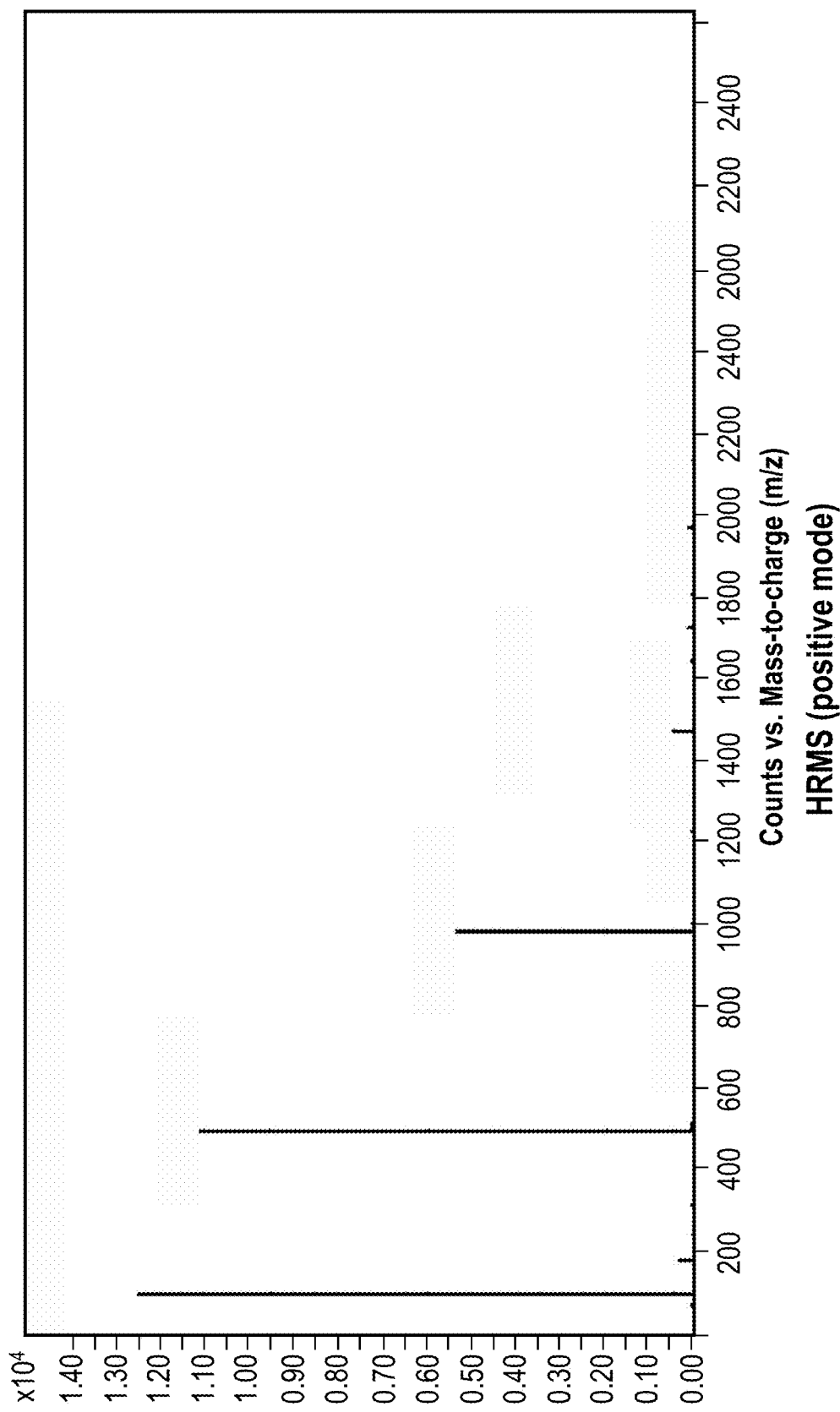

The serum lipoprotein profile of siRNA in mouse blood was analyzed. As shown in FIG. 31, Cy3-labeled siRNA conjugates were incubated ex vivo with serum isolated from wild type mice and analyzed as described previously by size exclusion chromatography. This lipoprotein binding correlates with observed PK/PD and distribution to the liver, kidney, and spleen (primarily VLDL, LDL, and IDL binding) or kidney, liver, and heart (HDL binding). Below, we demonstrate that cholesterol, DCA, and GM1 conjugates preferentially associate with IDL and LDL, while EPA, DHA, and DHAg2 conjugates preferentially associate with HDL. For polyunsaturated fatty acid-siRNA conjugates, the minimum number of double bonds necessary to achieve HDL binding and distribution to the kidney is >=3 (e.g. DHA, EPA, anandamide, alpha-linolenic acid, gamma-linolenic acid, arachidonic acid, etc.).

DHA Conjugation

Direct conjugation of DHA to a fully chemically stabilized siRNA scaffold shows significant tissue retention with wide distribution and robust efficacy in mouse brain. Notably, DHA-hsiRNA conjugates do not elicit measurable microglial activation and have no adverse effect on neuronal viability at concentrations over 20-fold higher than the efficacious dose.

DHA-hsiRNA alleviates one of the major obstacles to neurological applications of siRNA, which is achieving widespread brain distribution. Following a direct intrastriatal injection, DHA-hsiRNA distributed broadly throughout the striatum and cortex of the injected hemisphere, with no dramatic compound accumulation around the site of injection (a typical feature of Chol-hsiRNA). DHA-hsiRNA co-localizes with both neuronal (NeuN) and astrocyte (GFAP) markers. DHA-hsiRNA clearly localized to the perinuclear space in both striatal and cortical neurons (the cytoplasmic site of active RNAi).

Comparing increasing concentrations of DHA-hsiRNA and Chol-hsiRNA, it was found that Chol-hsiRNA induced significant loss of brain matter and occasionally animal morbidity at doses above 25 µg. In contrast, animals injected with 200 µg of DHA-hsiRNA appeared healthy, with normal brain morphology. 200 µg is the maximal amount that can be delivered intrastriatally, given the solubility limit of DHA-hsiRNA.

Design of siRNA Molecules

In some embodiments, an siRNA molecule of the invention is a duplex consisting of a sense strand and complementary antisense strand, the antisense strand having sufficient complementary to an htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA may be specific for a target sequence. Preferably, the first strand is substantially complementary to the target sequence, and the other strand is substantially complementary to the first strand. In an embodiment, the target sequence is outside a coding region of the target gene. Exemplary target sequences are selected from the 5' untranslated region (5'-UTR) or an intronic region of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., percent (%) homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 4, e.g., 2, nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant: wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet the criteria for evaluation.

Further general information about the design and use of siRNA may be found in "The siRNA User Guide," available at The Max-Plank-Institut fur Biophysikalishe Chemie web site.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}P$, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

Figure 14:
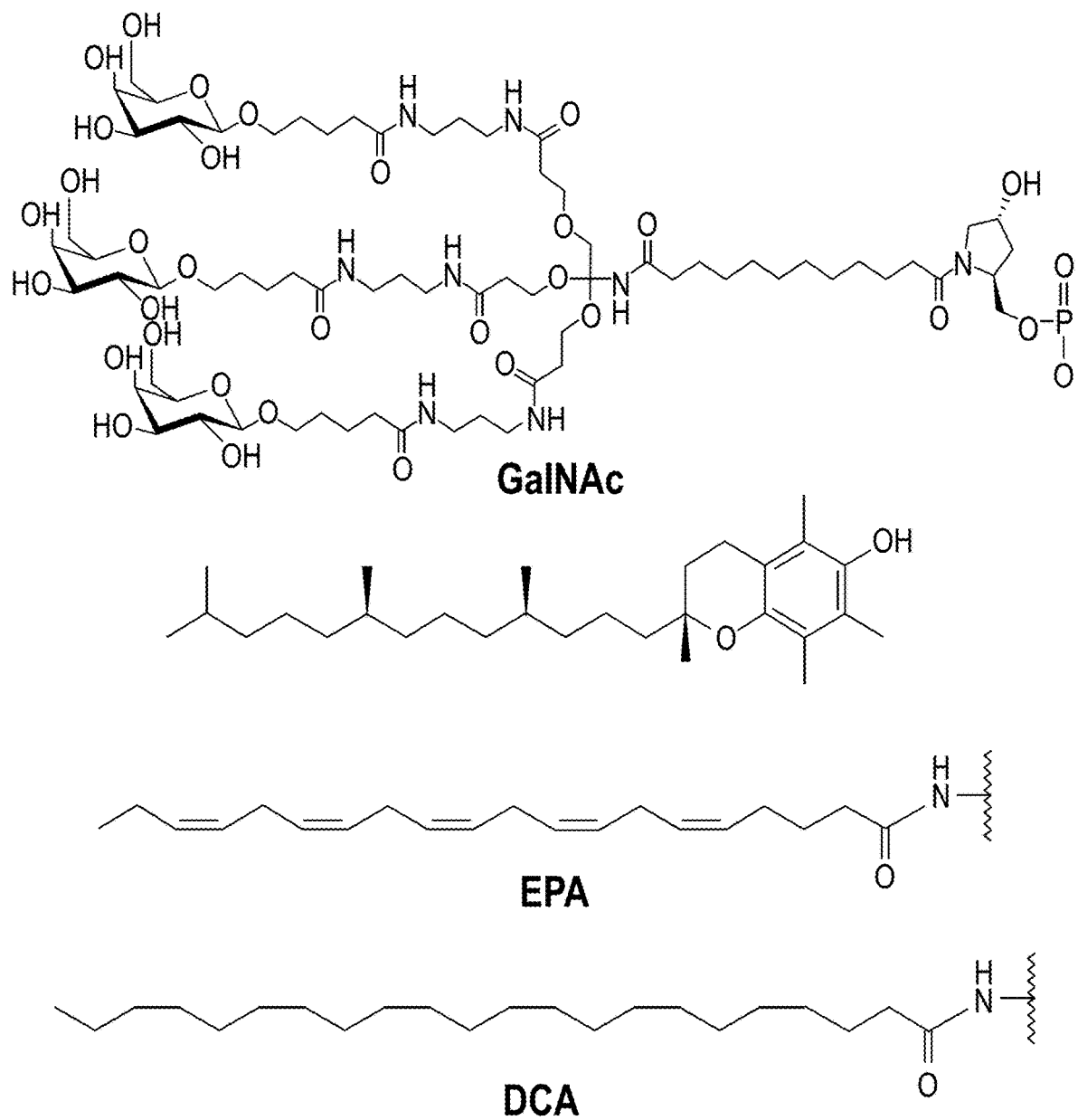
FIG. 14 depicts exemplary values of $X^c$.

In certain embodiments, the siRNA comprises a sense strand comprising a sequence set forth in FIG. 14, and an antisense strand comprising a sequence set forth in FIG. 14.

Sites of siRNA-mRNA complementation are selected which result in optimal mRNA specificity and maximal mRNA cleavage.

siRNA-Like Molecules siRNA-like molecules of the invention have a sequence (i.e., have a strand having a sequence) that is "sufficiently complementary" to a target sequence of an mRNA (e.g. htt mRNA) to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

Modified RNA Silencing Agents

In certain aspects of the invention, an RNA silencing agent (or any portion thereof) of the invention as described supra may be modified such that the activity of the agent is further improved. For example, the RNA silencing agents described in above may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g.

wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destablilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide.

2) Modifications to Enhance Efficacy and Specificity

In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S ' 5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH- group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-adenosine, 2'-amino-guanosine, 2,6-di-aminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moieties of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-O, 4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a P with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2'O Me moiety and modification of the backbone, e.g., with the replacement of a P with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e.g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

EXAMPLES

Methods

All chemical reactions were performed under argon atmosphere using anhydrous freshly distilled solvents unless otherwise stated. Dichloromethane (DCM), acetonitrile (ACN) and dimethylformamide (DMF) were dried using a PureSolv MD 5× Channel Solvent Purification System, tested with Karl Fischer titration and stored on molecular sieves. Flash chromatography was performed using Teledyne Isco CombiFlash Rf system and prepacked (silica gel) columns purchased from Bonna-Agela Technologies (Tianjin, China). Analytical thin-layer chromatography (TLC)

was performed using silica gel 60 F254 using UV light as visualizing agent. 1H, 13C and 31 P NMR spectra were recorded on a Varian 400 MHz instruments using residual solvent or 85% phosphoric acid (for 31-P NMR) as reference. High-resolution mass spectra were obtained on an Agilent 6530 accurate-mass Q-TOF LC/MS (Agilent technologies, Santa Clara, Calif.).

Example 1

Figure 1C:
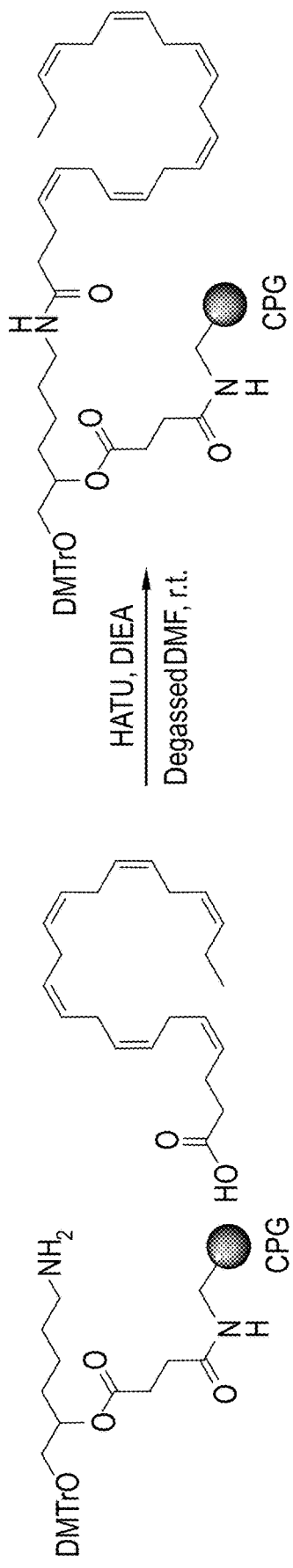
FIG. 1C shows a synthetic approach for DHA-conjugated oligonucleotides.
Figure 1D:
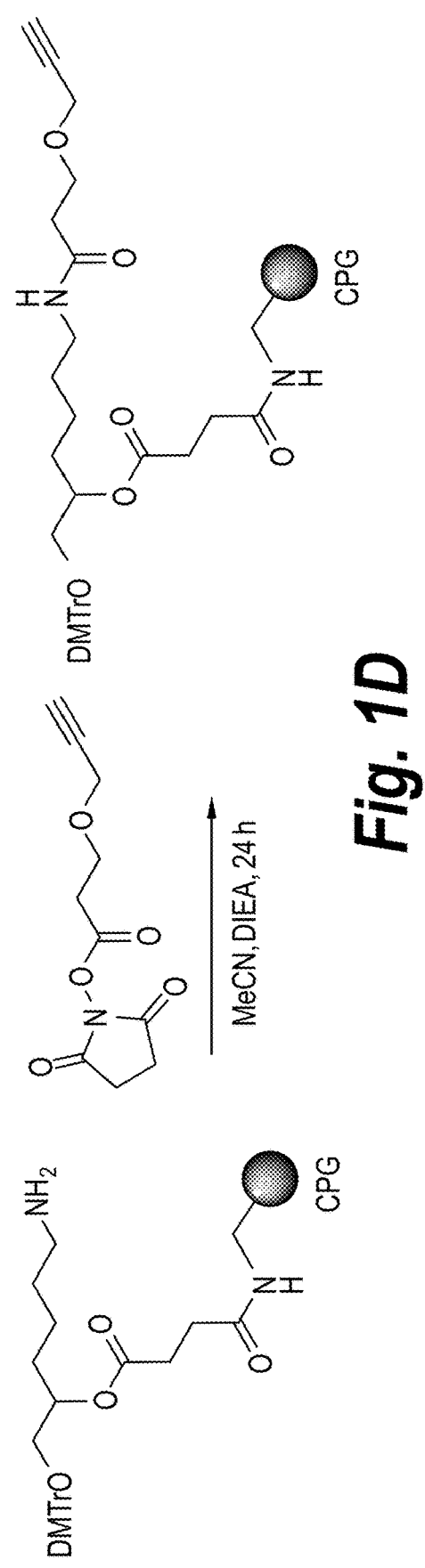
FIG. 1D shows a synthetic approach for preparation of an alkynylated-oligonucleotide for click conjugation.
Figure 1E:
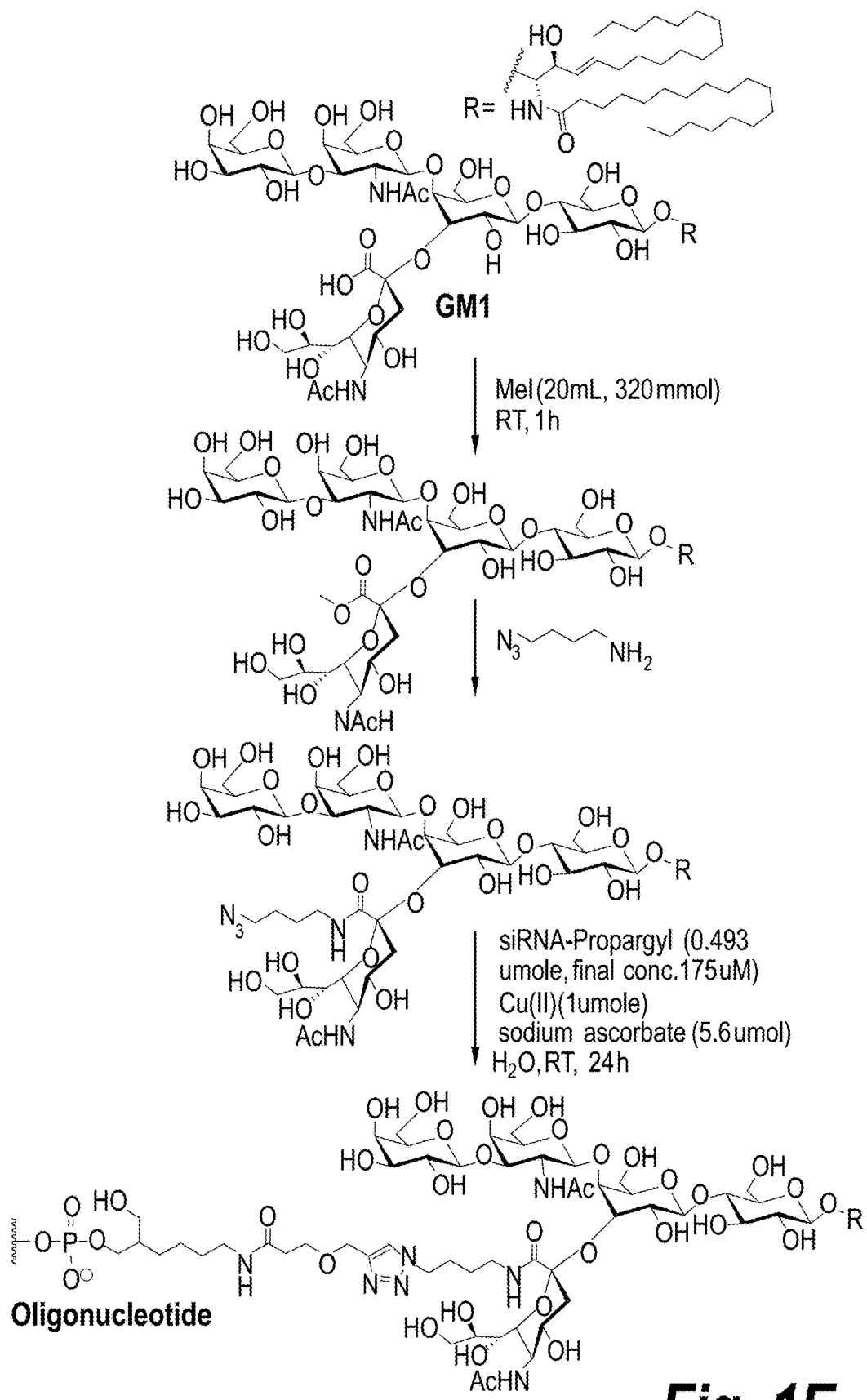
FIG. 1E shows a synthetic approach for GM1-conjugated oligonucleotides.
Figure 1G:
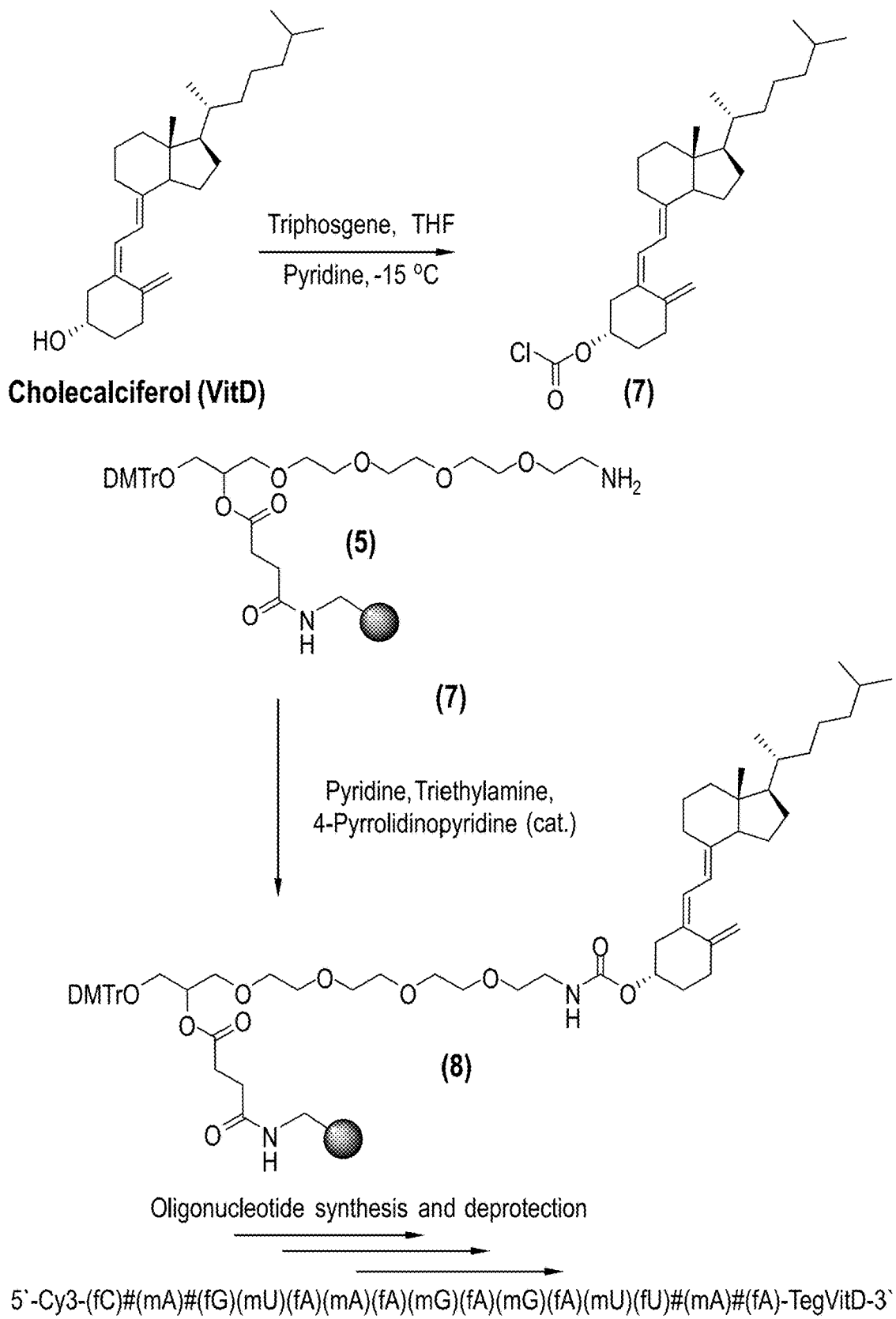
FIG. 1G shows a synthetic approach for an hsiRNA-Calciferol oligonucleotide.
Figure 1H:
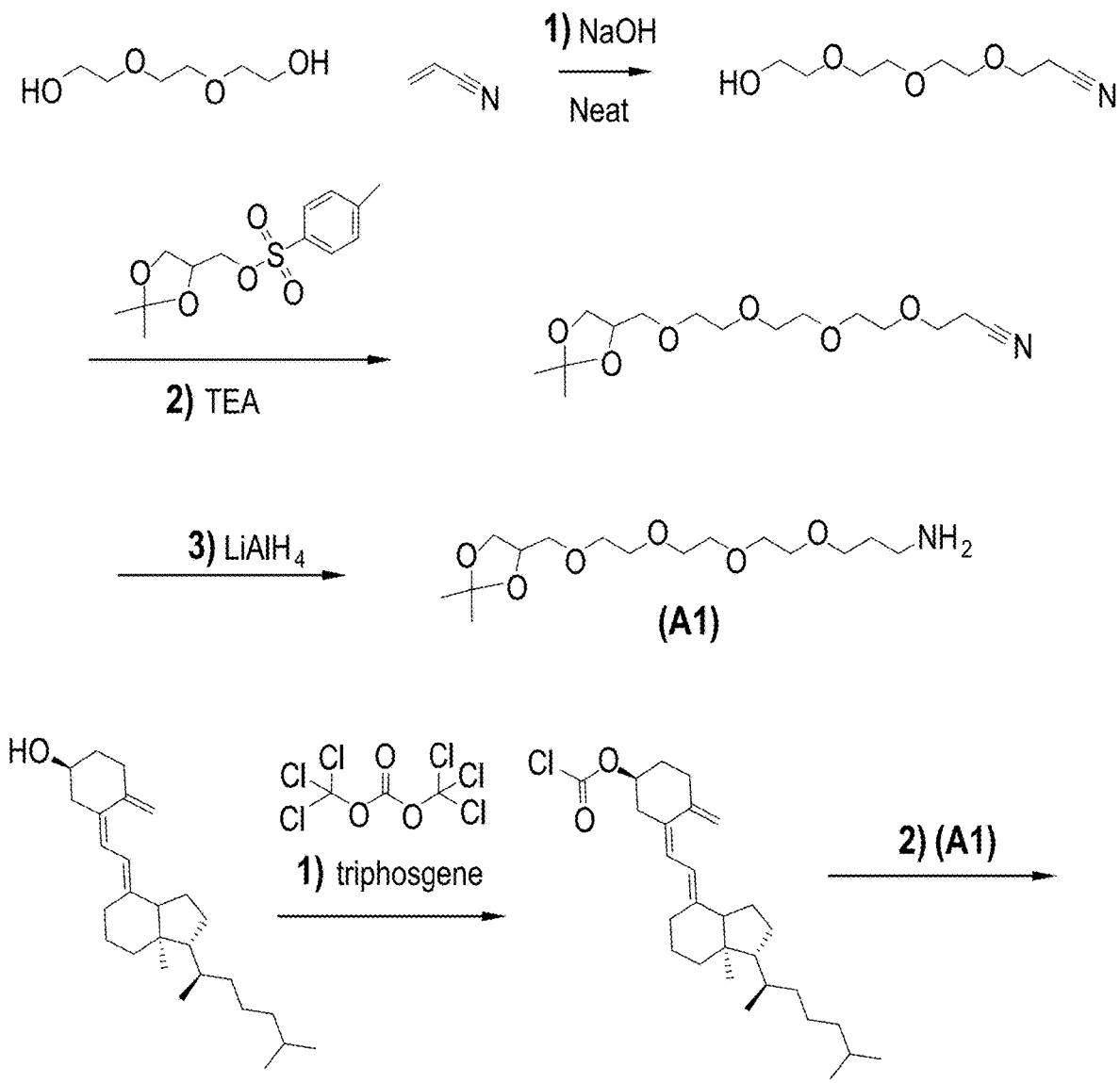
FIG. 1H shows an alternative synthetic approach for an hsiRNA-Calciferol oligonucleotide.
Figure 1H:
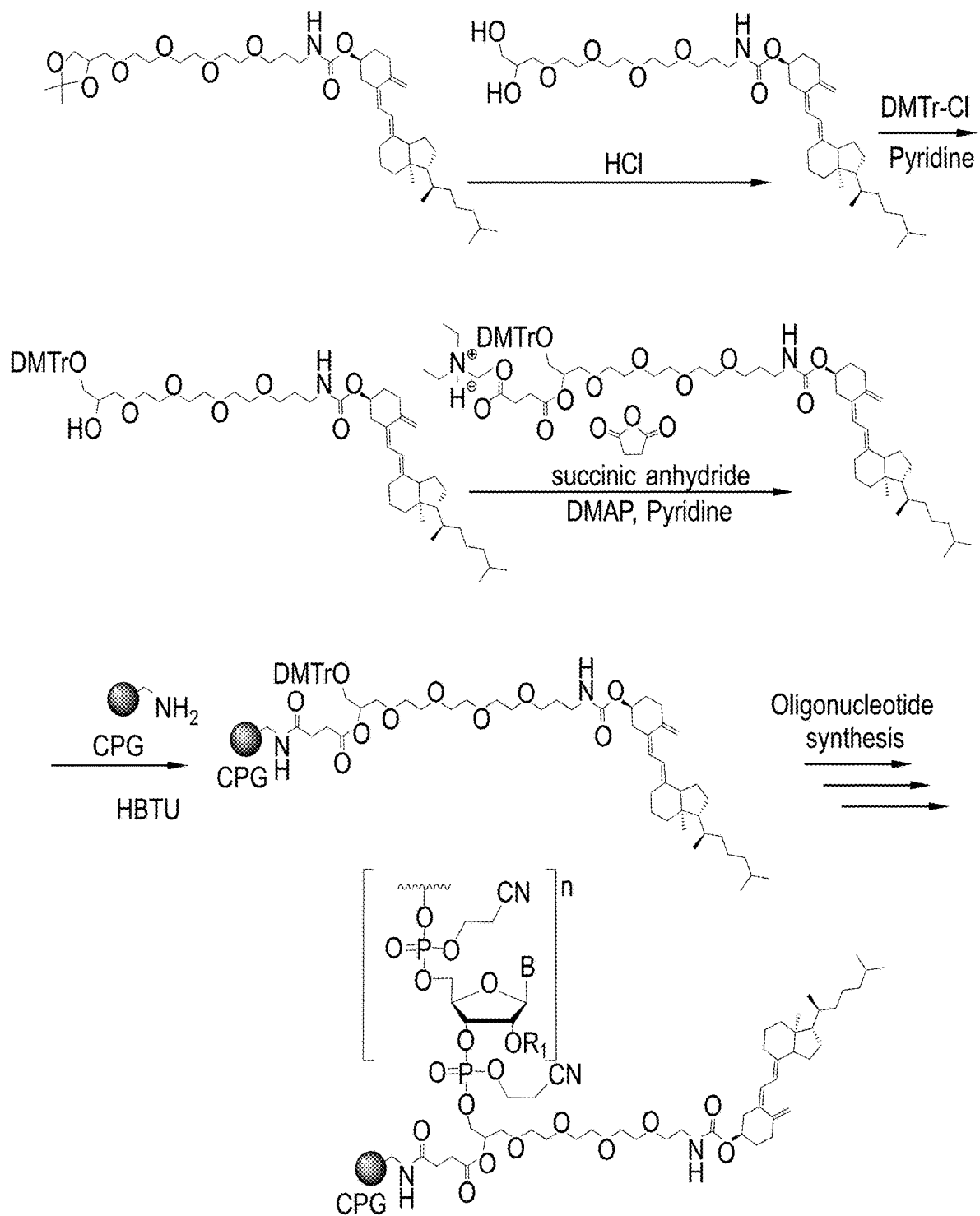

Synthetic Approaches Used for Conjugation of Hydrophobic Compounds to Oligonucleotides Using synthetic approaches outlined in FIGS. 1a-h, hsiRNAs covalently conjugated to cortisol, DHA, calciferol, cholesterol, and GM1 were synthesized. For cortisol (FIG. 1a) and calciferol (FIG. 1b), primary hydroxyls were converted to chloroformate and directly conjugated to the previously synthesized bi-functional, primary amine-containing, solid support. DHA was directly attached to the amino-modified linker using standard amide coupling conditions (FIG. 1c). GM1 was attached post-synthetically by click chemistry through the reaction of GM1-azide with alkyne modified siRNA (FIG. 1d and FIG. 1e). All compounds were HPLC-purified and characterized by mass spectrometry. The general synthesis strategies outlined in FIG. 1a-e are used to synthesize other related conjugates of FIG. 1f. Additional synthetic strategies are shown in FIG. 1g and FIG. 1h for the synthesis of calciferol conjugation, which may improve yields.

Figure 1I:
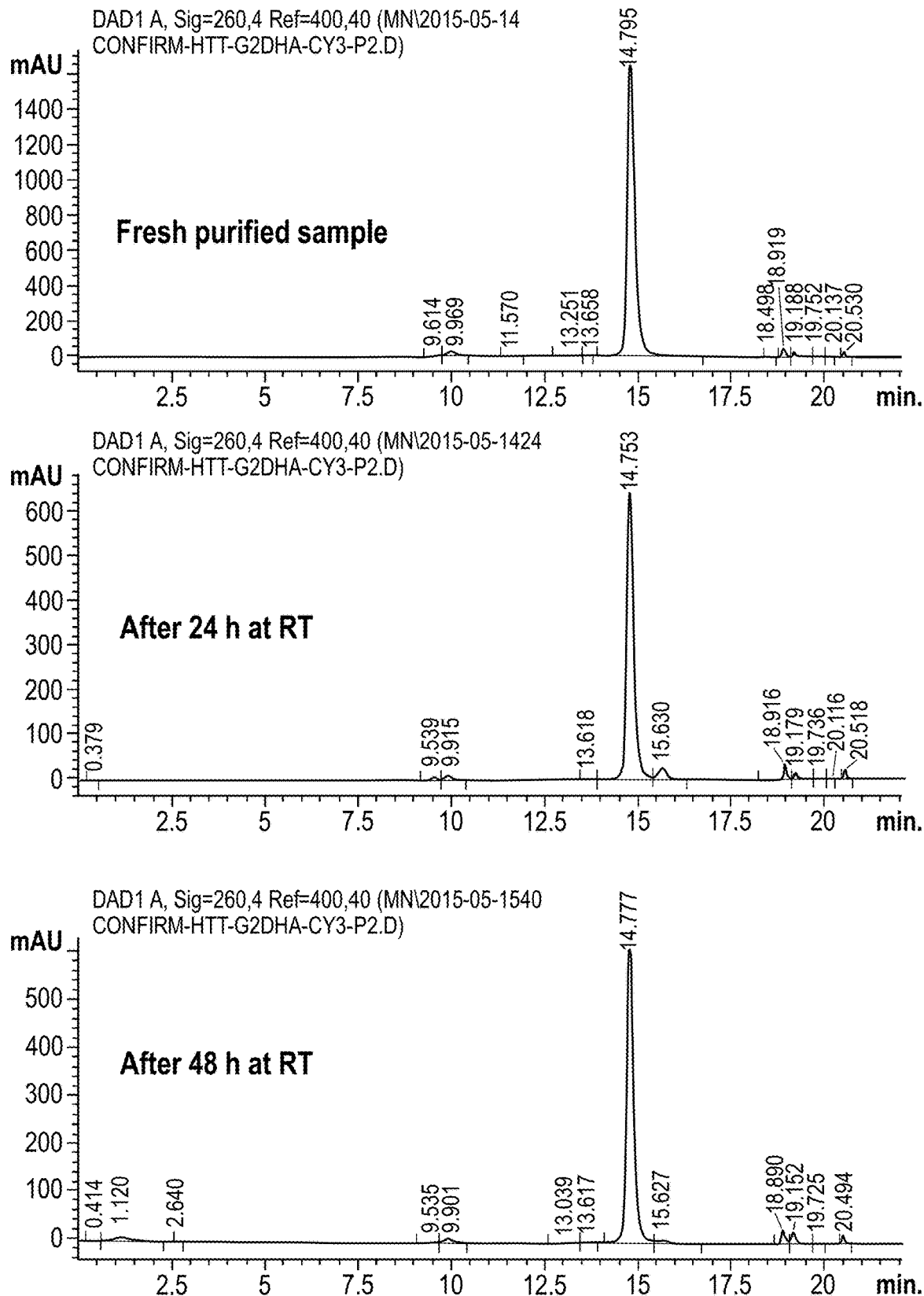
FIG. 1I shows a representative analytical HPLC trace of a synthesized hsiRNA conjugate, and its stability at room temperature immediately after purification, after 24 hours at room temperature, and after 48 hours at room temperature; sFLT-g2DHA-Cy3-P2 is shown.
Figure 1K:
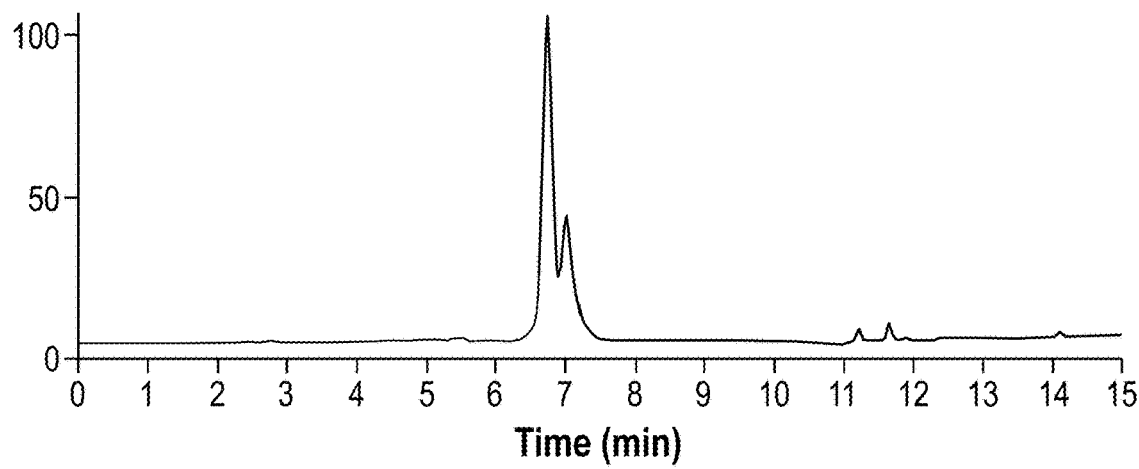
FIG. 1K shows a representative analytical HPLC trace of an hsiRNA conjugate prepared according to the synthetic approach of FIG. 1I; hsiRNA-Calciferol shown.
Figure 1L:
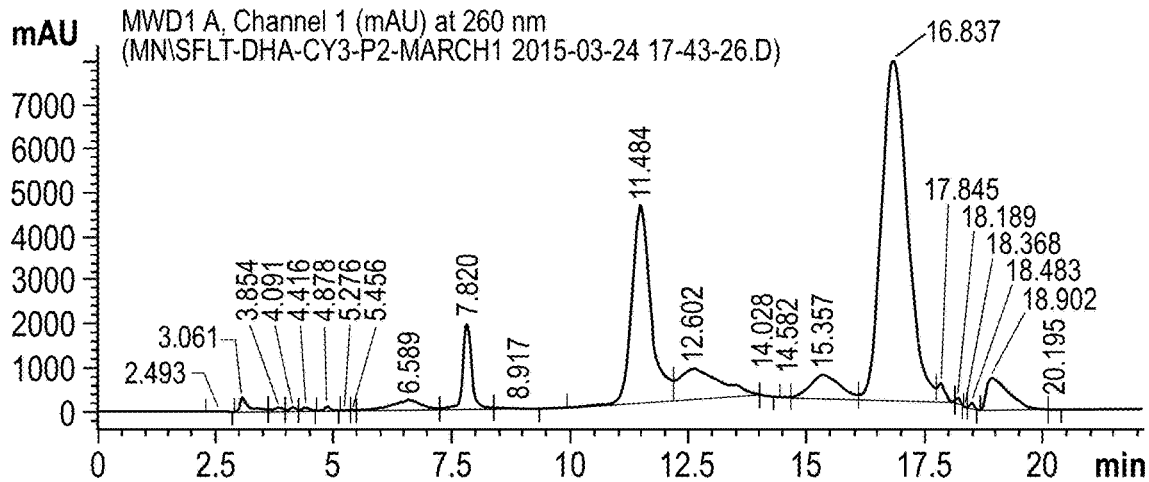
FIG. 1L shows a representative semi-prep reverse-phase-HPLC trace of a synthesized hsiRNA conjugate; Cy3-labeled sFLT-DHA conjugate (crude reaction mixture) shown.
Figure 1M:
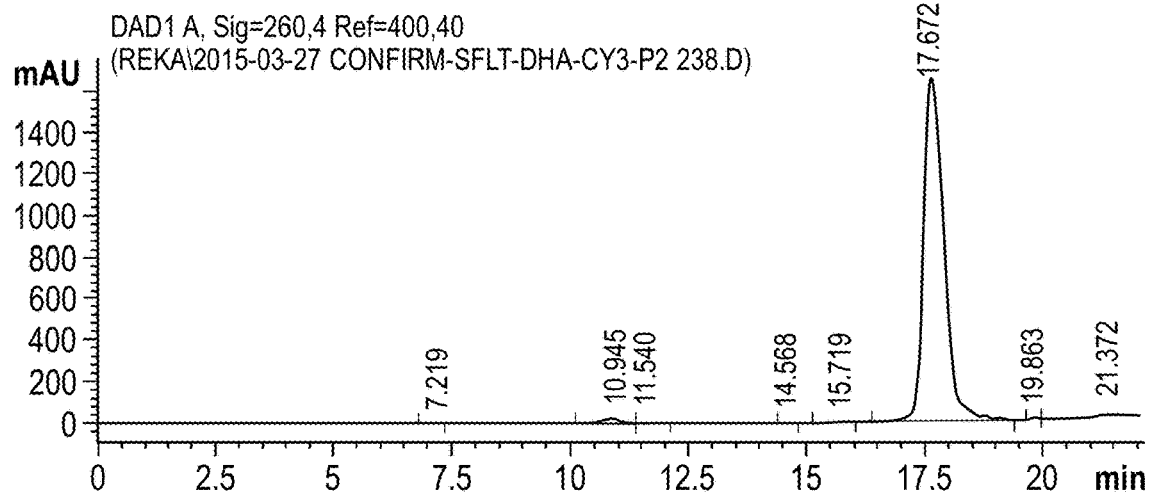
FIG. 1M shows a representative analytical reverse-phase-HPLC following purification of a synthesized hsiRNA conjugate as in FIG. 1L; Cy3-labeled sFLT-DHA conjugate (pure product) shown.

The oligonucleotide-conjugates were purified by reverse-phase HPLC, and the purity was assessed by liquid chromatography-mass spectrometry (LC-MS). Conditions: for analytical (FIG. 1i and FIG. 1j) (Anal HPLC: HTT-g2DHA-Cy3-P2, Pure product, Gradient: 10% MeCN, 90% TEAA to 90% MeCN, 10% TEAA in 30 minutes, Temp: room temperature, C8); for semi-preparative RP-HPLC (FIG. 1l) (Hamilton column, C18 HxSil 5 µm, 150×21.2 mm); for analytical RP-HPLC (FIG. 1m) (Agilent eclipse plus column, C18, 3.5 um, 4.6×100 mm): Cy3-labeled sFLT-DHA conjugate (pure product), gradient: 10% acetonitrile, 90% TEAA to 90% acetonitrile, 10% TEAA in 30 minutes, Temperature: 60° C. (Analytical) and 55° C. (Preparative), flow rate: 20 mL/min (Preparative) and 1 ml/min (Analytical); for LC-MS (FIG. 1n) (Buffer A: 15 mM Dibutylamine/ 25 mM HFIP, Buffer B: 20% A in MeOH, Column: xbidge OST C18, 2.5 µm).

Example 2

Structure and Hydrophobicity Profile of Selected Oligonucleotide Conjugates

Figure 2B:
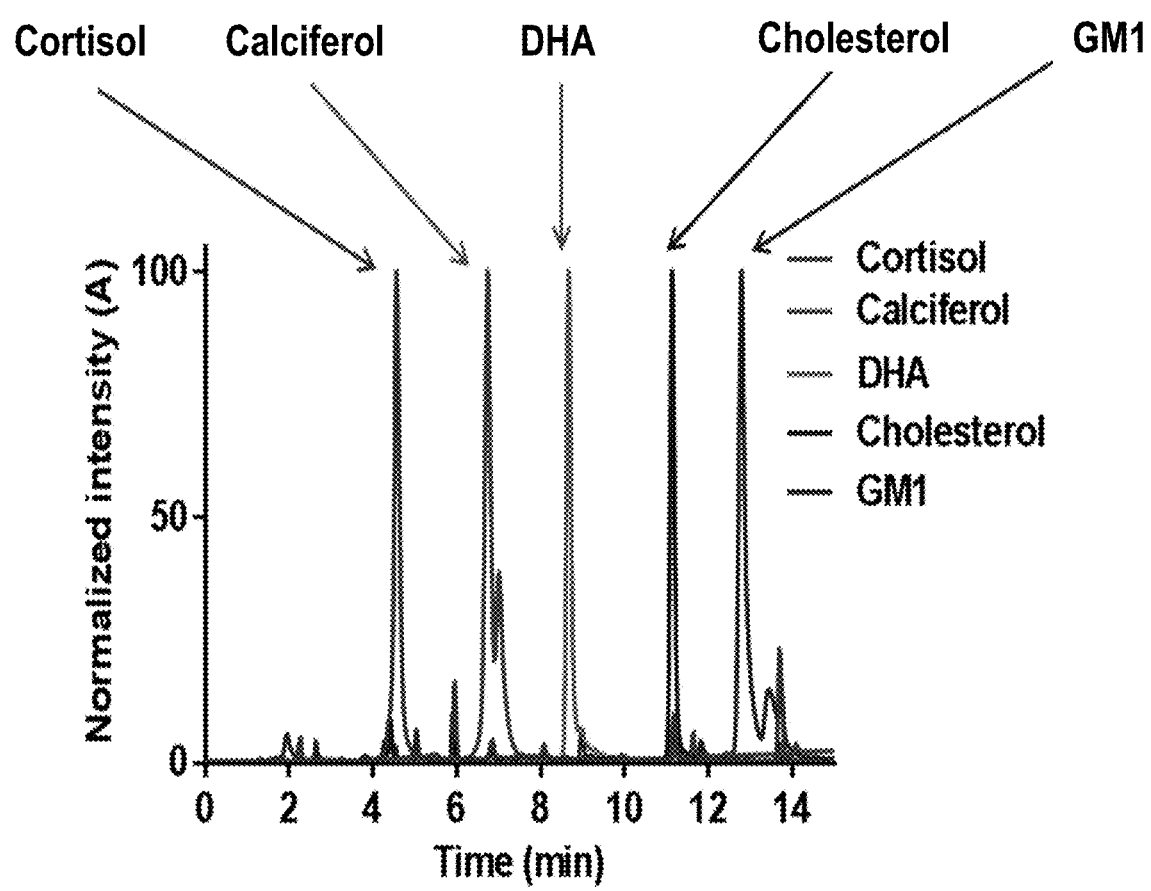
FIG. 2B shows the differences in hydrophobicity profiles of synthesized siRNA conjugates as observed by reverse-phase HPLC (C8).

To determine the relative hydrophobicity of a panel of novel conjugates, the retention time on a C8 reversed-phase HPLC column was measured. A higher hydrophobicity is correlated with longer retention times. FIG. 2b shows that the synthesized panel of conjugates encompasses a range of hydrophobicities: from cortisol (elution time of 4.5 min) to GM1 (elution time of 14 min).

All oligonucleotide conjugates were purified by reverse phase HPLC, and characterized by mass spectrometry (data for DHA-hsiRNA shown in FIG. 2c). The HPLC method was as follows: Reverse phase HPLC, C8; Buffer A: 100 mM NaAc and 5% acetonitrile, Buffer B: acetonitrile; Gradient: 5% B to 100% B over 15 minutes, 1.5 mL/min at 50° C.

Example 3

In Vivo Brain Distribution of FMS-hsiRNA is Directly Related to Hydrophobicity

Figure 3A:
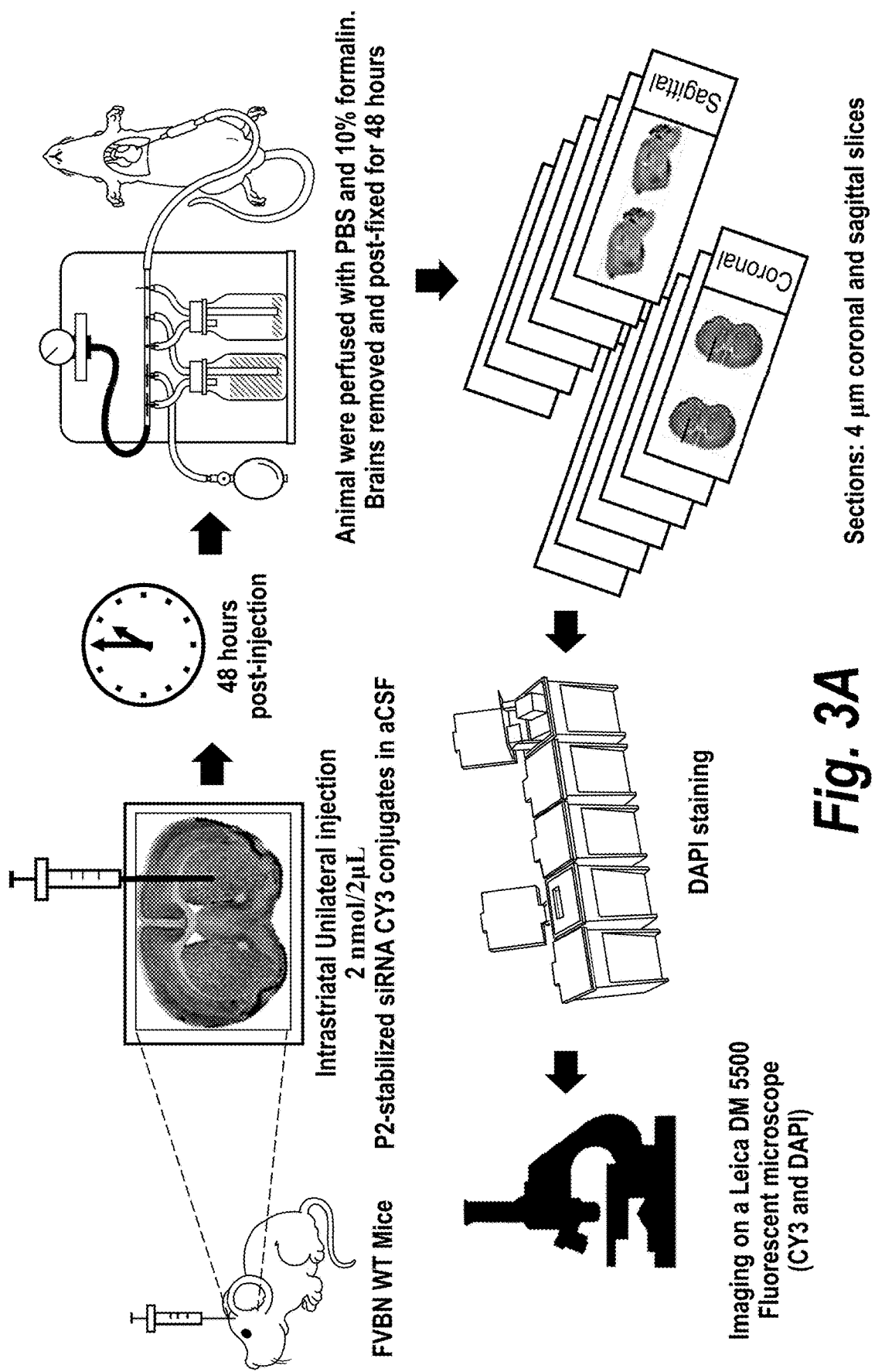
FIG. 3A shows a biodistribution study protocol.
Figure 3B:
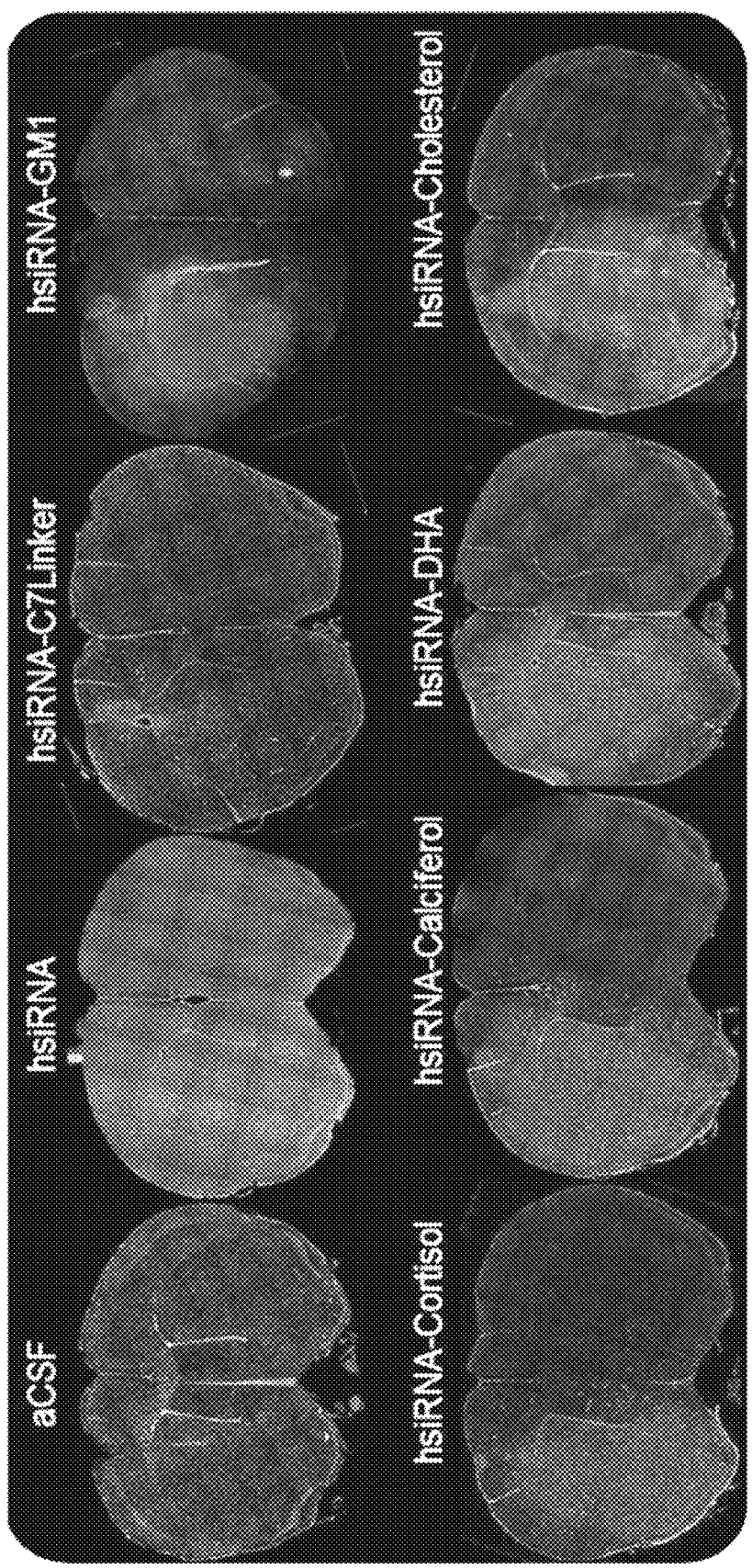
FIG. 3B shows that the in vivo brain distribution of FMS-hsiRNA is defined by conjugation modality.

The present disclosure (FIG. 3a) shows that chemically modified and fully stabilized hydrophobic siRNA (hsiRNA) conjugates are successfully internalized by neurons and glia in the brain after intrastriatal administration (FIG. 3b). Furthermore, these data show a profound effect of conjugate chemistries on the pattern of in vivo brain distribution. The distribution of highly hydrophobic hsiRNA conjugates, including cholesterol- and GM1-, seem to be somewhat limited to the site of injection with very high intensity at this site. On the other hand, less hydrophobic hsiRNA conjugates, such as C7Linker- and TEGLinker-, show a more diffuse pattern with lower overall intensities. In addition, conjugates containing Calciferol- and DHA- show a distinct pattern of distribution characterized by a good spread throughout the section, which might be explained by potential receptor-mediated mechanism of uptake. Finally, it is also important to highlight that more hydrophobic hsiRNA conjugates, such as hsiRNA-GM1, hsiRNA-Calciferol, hsiRNA-DHA, and hsiRNA-cholesterol, enabled distribution to neuronal nerve bundles in the striatum. This may potentially result in retrograde axonal transport to the cortex.

To test the impact of hydrophobicity on tissue retention and brain distribution, 25 µg Cy3-labeled novel conjugates were injected unilaterally into striatum of wild-type mice and the fluorescence distribution was examined 48 hours later in both coronal and sagittal sections of the brain (FIG. 3b). Non-conjugated or linker-only hsiRNAs showed minimal but detectable retention in brain tissue. Importantly, it was found that the degree of tissue retention and distribution strongly correlates with hydrophobicity. Cortisol-hsiRNA (lowest degree of hydrophobicity) showed diffuse distribution, but the lowest tissue retention. The most hydrophobic compounds, cholesterol, and GM1, are effectively retained but do not distribute far from the site of injection. Tissue retention of FMS-hsiRNA was similar to that of LNA-gapmers, suggesting that the 13 phosphorothioate linkages in FMS-hsiRNA confer some level of tissue association. DHA and Calciferol hsiRNAs show optimal retention and spread throughout the injected side of the brain. The distribution of the calciferol-hsiRNA was so uniform, that it was impossible to map the site of injection, which is easily observed in animals injected with cholesterol or GM1 conjugates. In summary, it has been demonstrated that tuning the hydrophobicity of conjugates can be utilized to attain optimal retention and distribution in brain tissue.

As shown in the biodistribution study protocol of FIG. 3a, FVBN WT mice (n-3 per chemistry) were injected with 25 µg of Cy3-hsiRNA variants (P2-stabilized siRNA Cy3 conjugates in aCSF) via intrastitial unilateral injection (2 nmol/2 µL). After 48 hours, animals were perfused with PBS and 10% formalin. Brains were removed and post-fixed for 48 hours. 4 µm slices of coronal and sagittal sections were obtained, followed by DAPI staining. The samples were imaged (10x) on a Leica DM 5500 fluorescent microscope (Cy3 and DAPI); hsiRNA-FMS conjugates (Cy3-red), nuclei (DAPI-blue).

Example 4

Systemic Delivery

Different hsiRNA variants were synthesized as described above and injected systemically (iv/sc) at 20 mg/kg. The level of accumulation of oligonucleotide in various tissues was determined by PNA Assay. The PNA (Peptide Nucleic Acid) hybridization assay directly measures an amount of intact guide strand in tissue lysates. This assay allows direct assessment of the rate of oligonucleotide clearance from CSF or blood as well as the degree of tissue distribution and accumulation (e.g., in different brain regions). This assay can detect both labeled and unlabeled compounds. Tissue accumulation of oligonucleotides above 10 ng/mg was sufficient to induce silencing.

Figure 4:
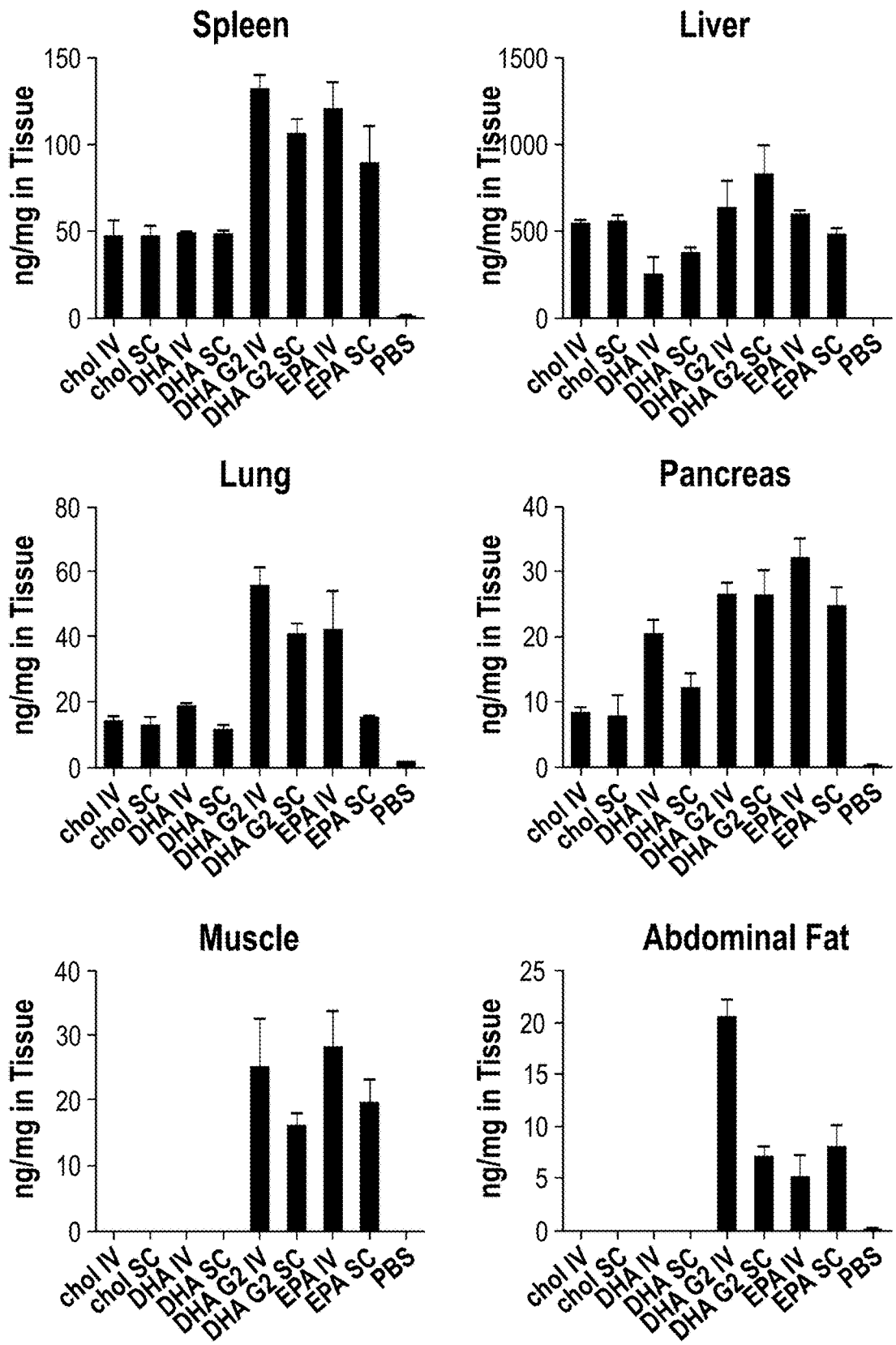
FIG. 4 shows accumulation in various tissues upon systemic administration of hsiRNA-conjugates. hsiRNA-conjugate structures and modifications are found in FIG. 5A-F. All compounds have the sequence of PPIB, as shown in FIG. 7.
Figure 4:
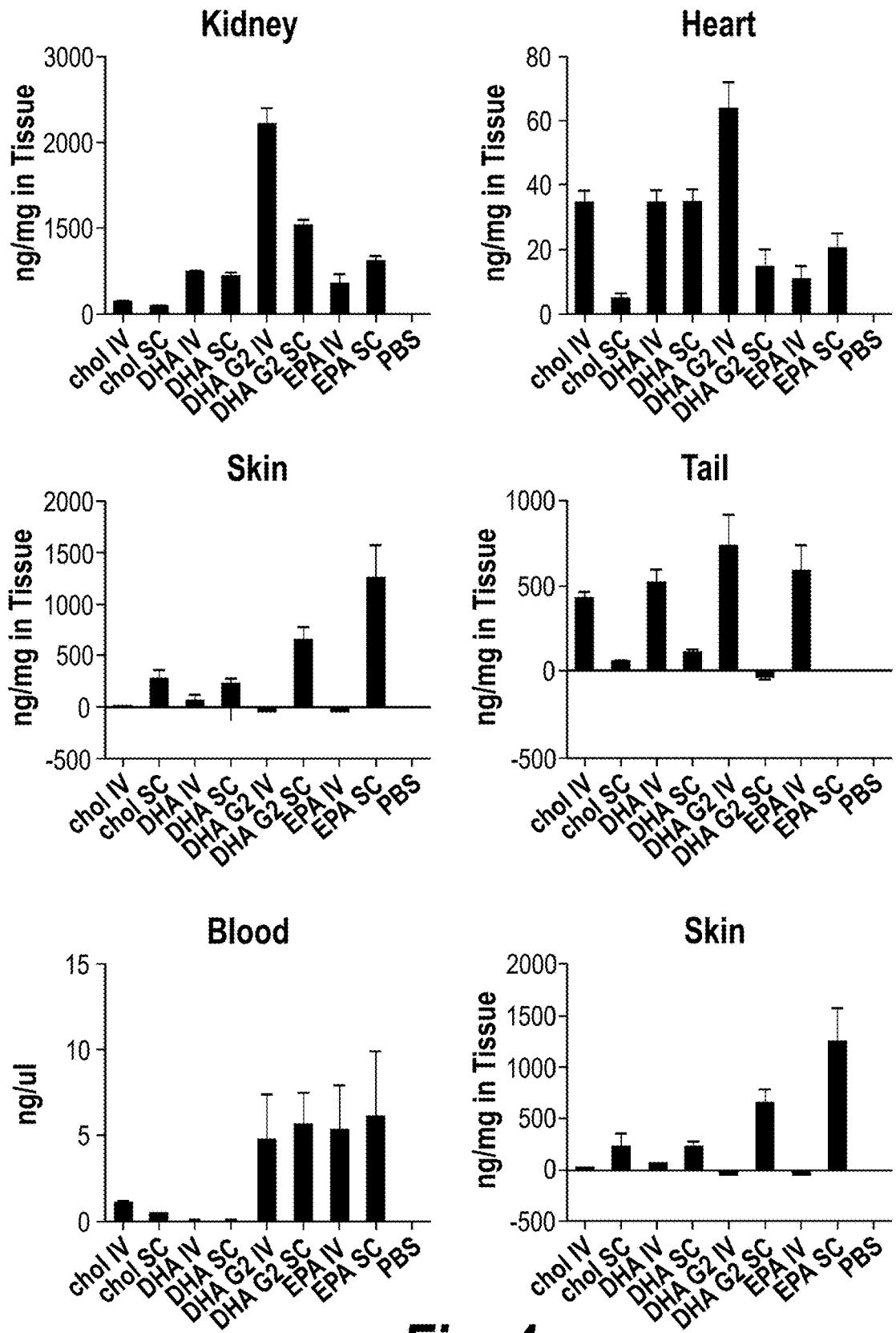
Figure 4:
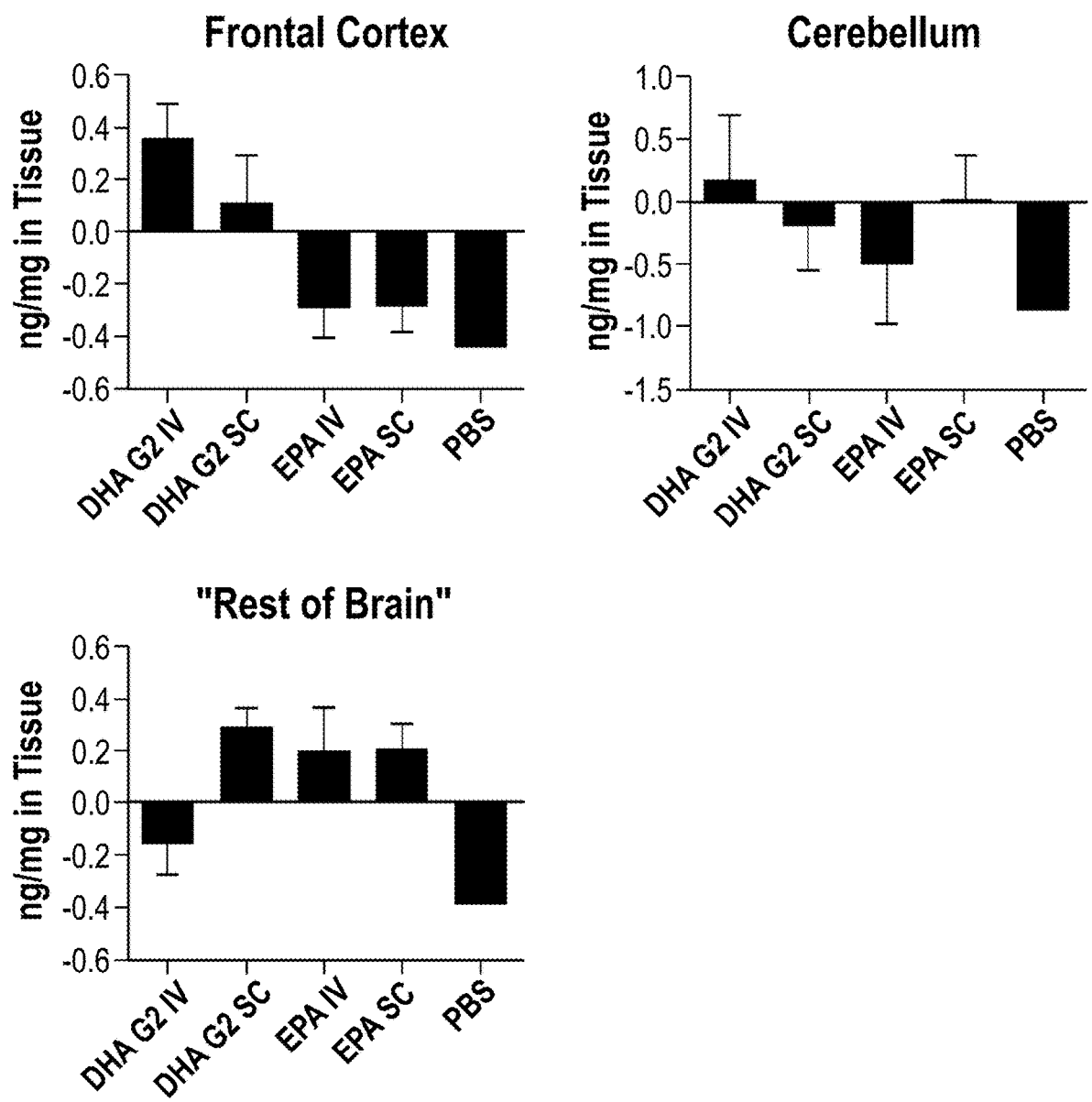
Figure 5A:
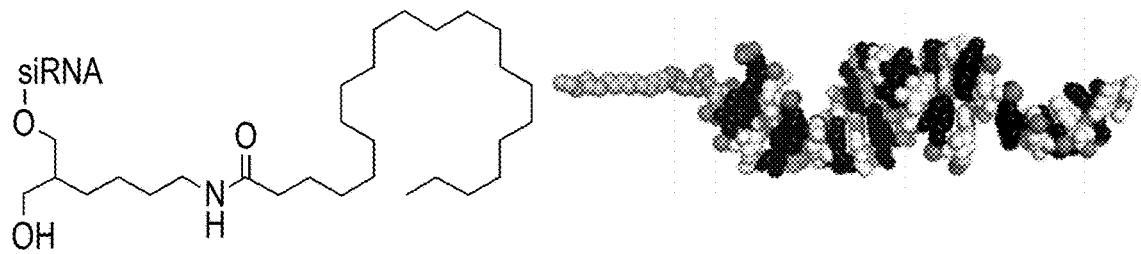
FIG. 5A-F show chemical structures of conjugated hsiRNAs. (A) Docosanoic (DCA)-conjugated hsiRNA. (B) Docosahexaenoic acid (DHA)-conjugated hsiRNA, 22:6 (n-3). (C) Phosphatidylcholine-DHA-conjugated hsiRNA (g2DHA-hsiRNA or DHAPCL-hsiRNA) (D) Eicosapentanoic acid (EPA)-conjugated hsiRNA, 20:5(n-3). (E) Cholesterol (Chol)-conjugated hsiRNA. (F) Cholesterol (Chol)-conjugated hsiRNA. hsiRNA conjugates represented to scale using PyMOL.
Figure 5B:
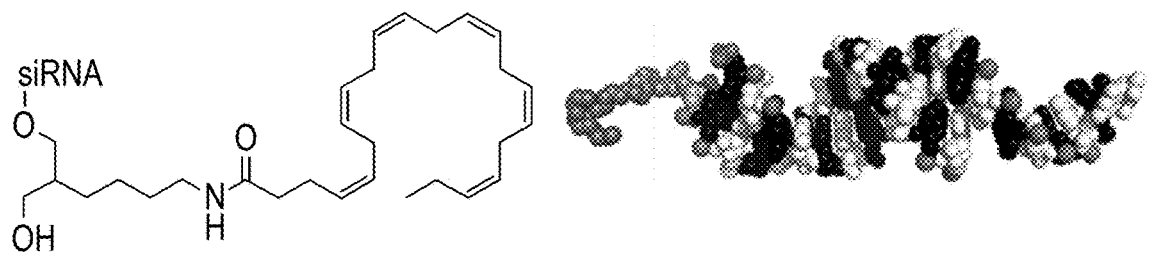
Figure 5C:
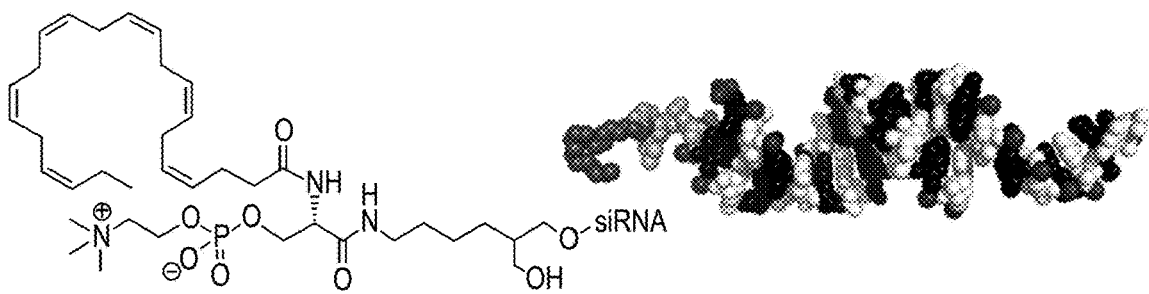
Figure 5D:
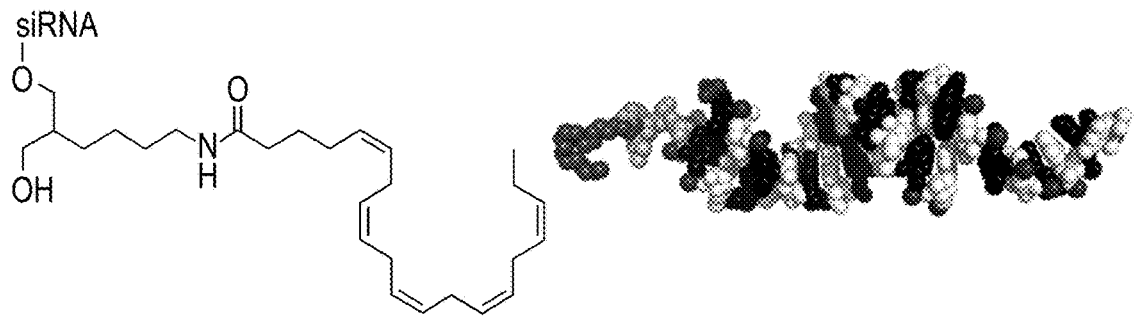
Figure 5E:
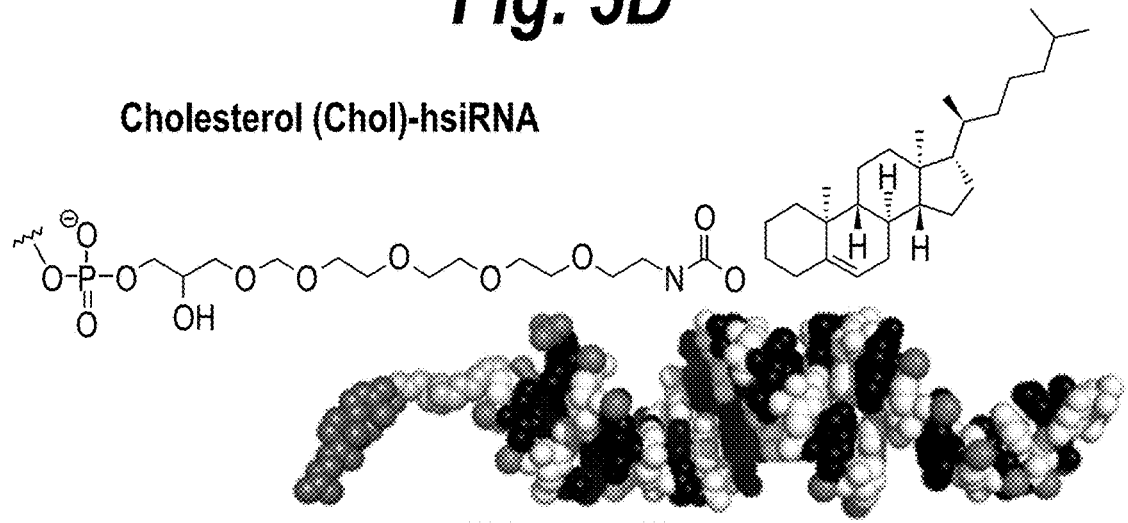
Figure 5F:
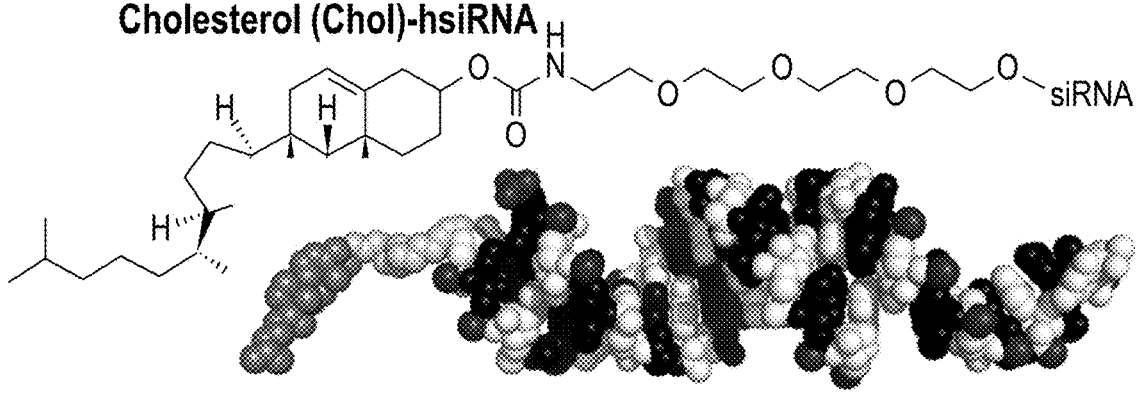
Figure 6A:
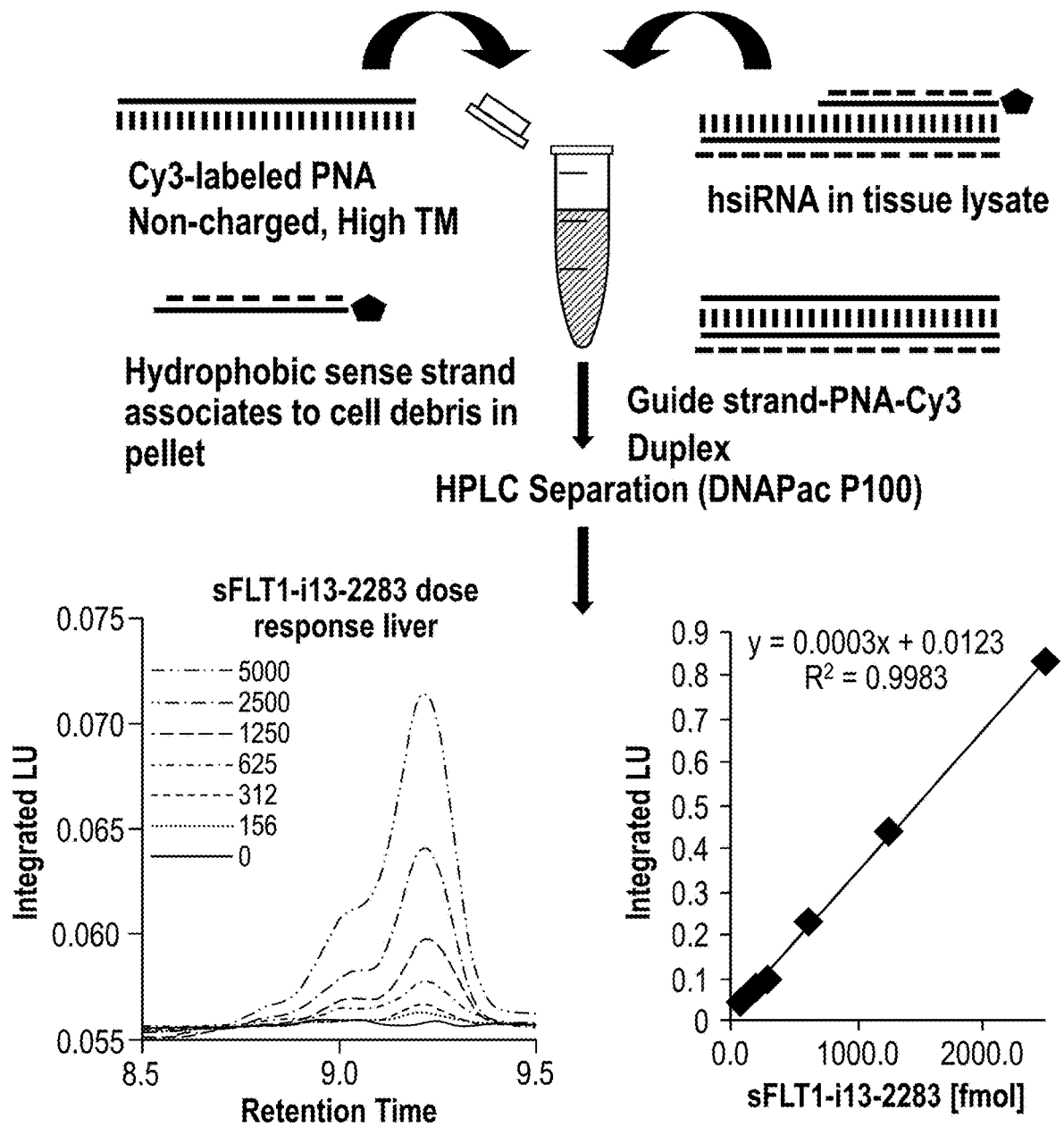
FIG. 6A-B show PNA (Peptide Nucleic Acid) based assay for detection of hsiRNA guide strand in mouse tissues. (A) Tissues were lysed, debris separated by precipitation, PNA-guide strand duplex purified by HPLC (DNAPac P100, 50% water 50% acetonitrile, salt gradient 0-1M NaClO4). (B) Liver and kidney from mice injected with 40 mg/kg of either cholesterol, DCA, EPA, or DHA were used to quantify the guide strand after 48 hours, showing differential distribution of fatty acid conjugates.
Figure 6B:
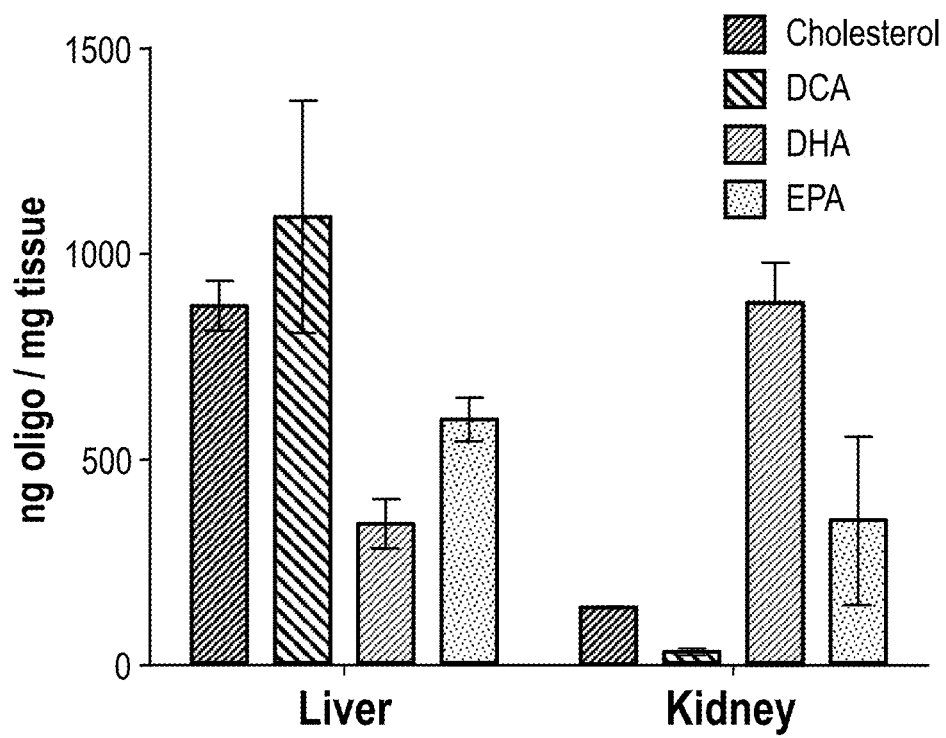
Figure 8:
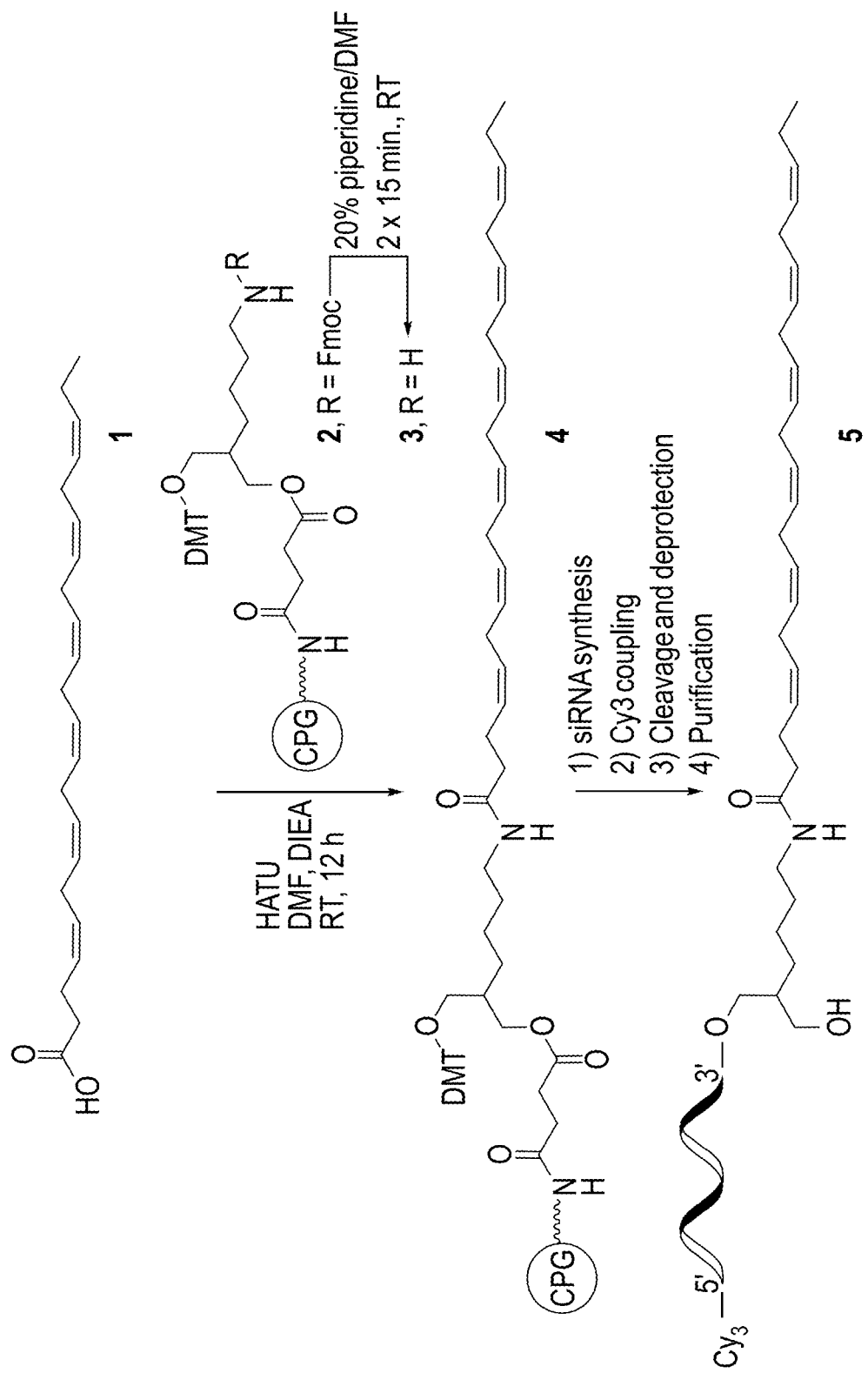
FIG. 8 shows the solid-phase synthesis of DHA-conjugated hsiRNA.
Figure 11A:
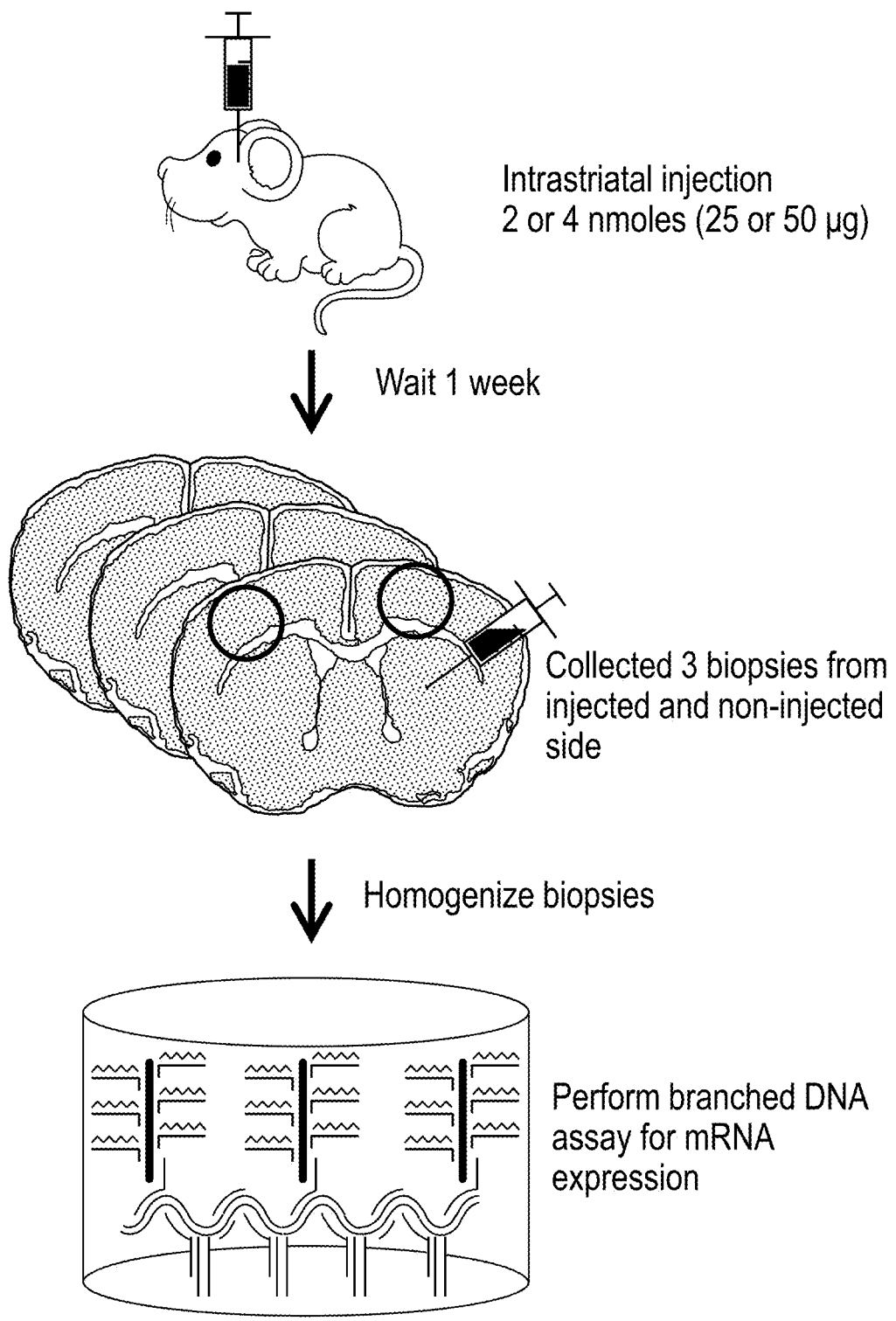
FIG. 11A-C show the effects upon single IS injection of g2DHA-hsiRNA: (A) experimental procedure; (B) approximately 80% silencing in mouse striatum; (C) approximately 80% silencing in mouse cortex. There was no indication of toxicity and silencing was limited to injected side of the brain. hsiRNA-conjugate structures and modifications are shown in FIG. 5A-F.
Figure 11B:
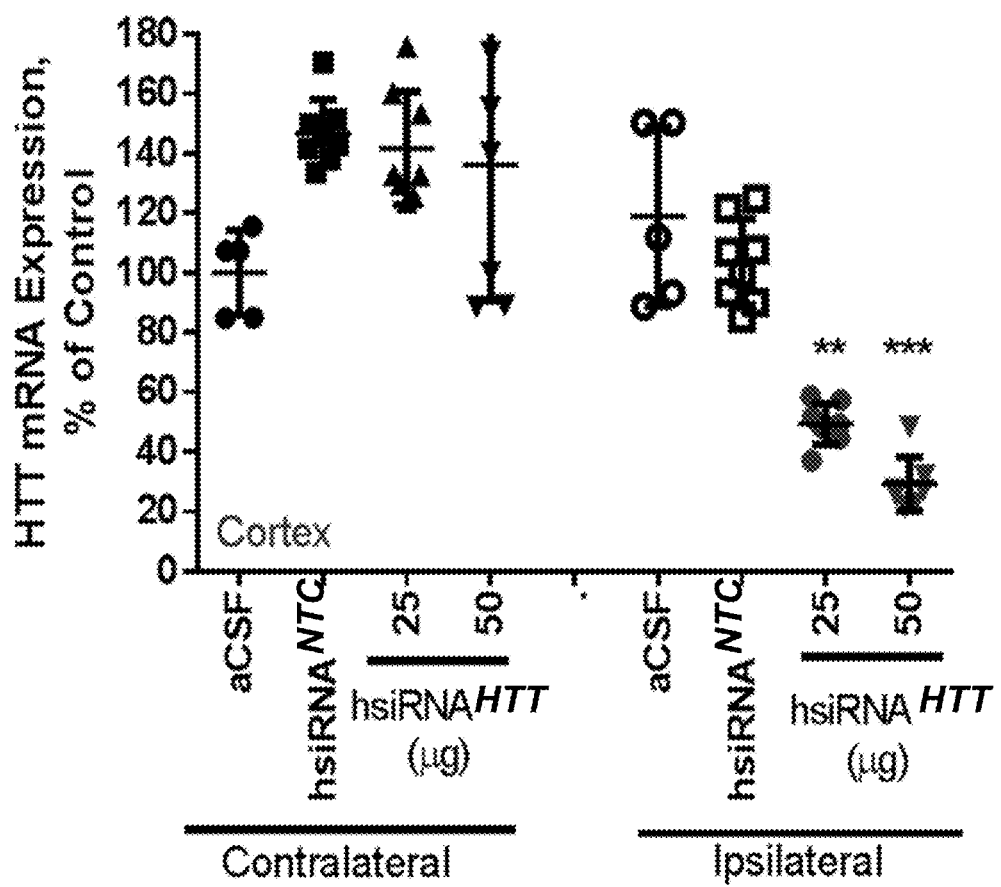
Figure 11C:
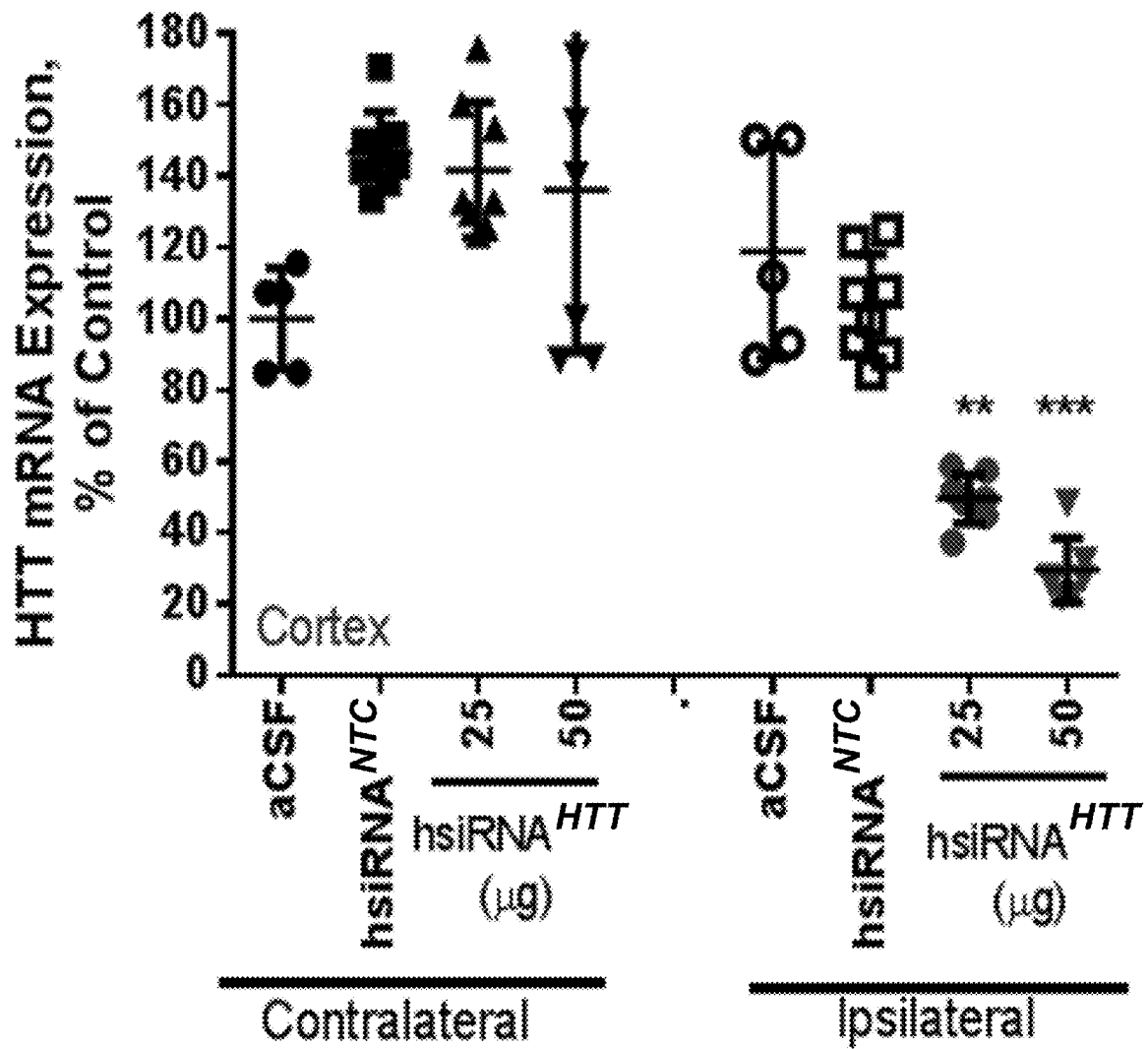
Figure 12:
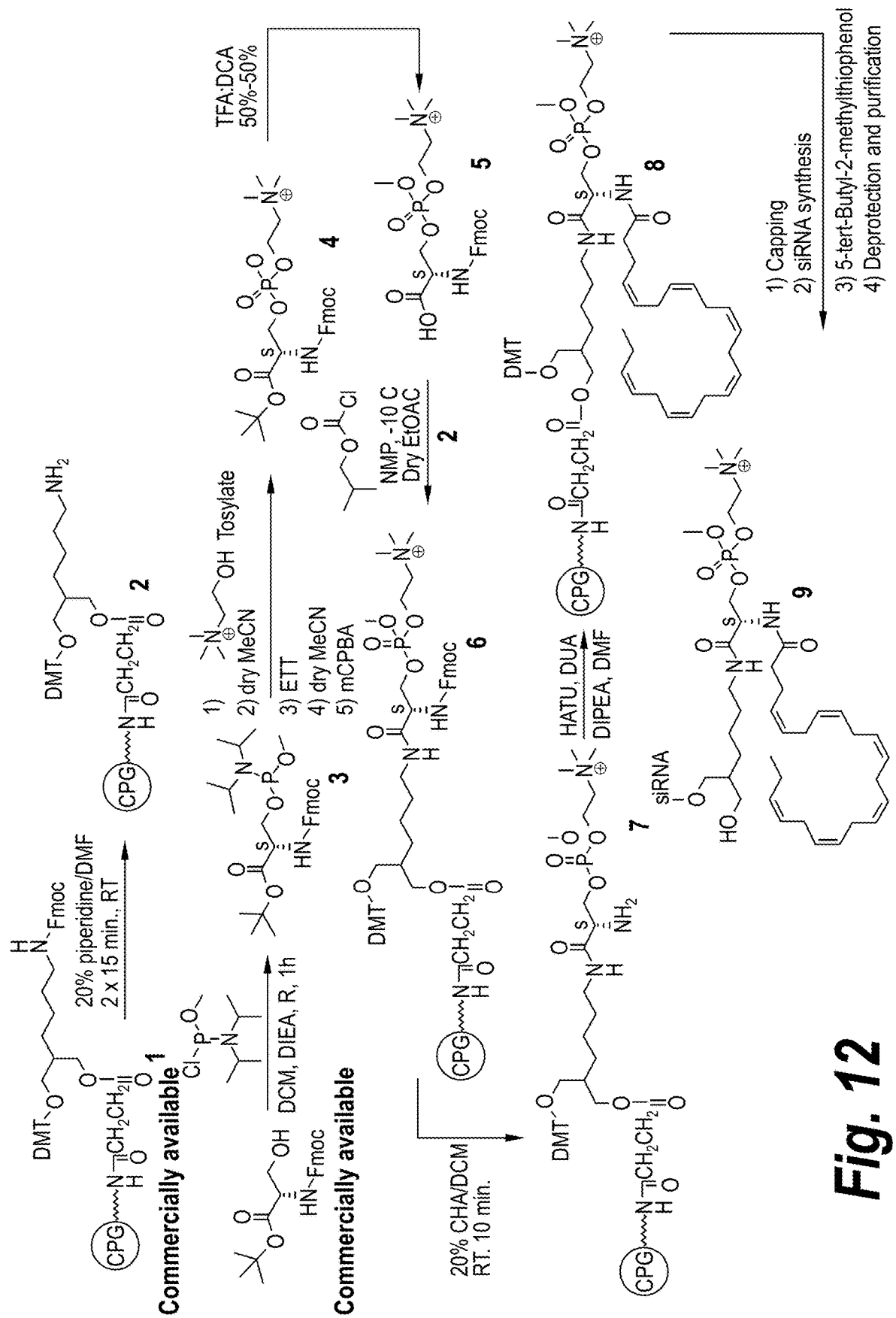
FIG. 12 shows g2DHA support synthesis I.

Surprisingly, different chemistries show preferential distribution to different tissues (FIG. 4). For example, PC-DHA shows accumulation in kidneys at above 2000 ng/mg levels and more compounds goes to kidney than to lung. Calciferol shows unprecedented distribution and preferential delivery to neurons in the brain. EPA shows the best skin distribution, relative to the compounds tested herein, where local injection delivers to a very wide area near the injection side.

Example 5 g2DHA Support Synthesis II

Figure 13:
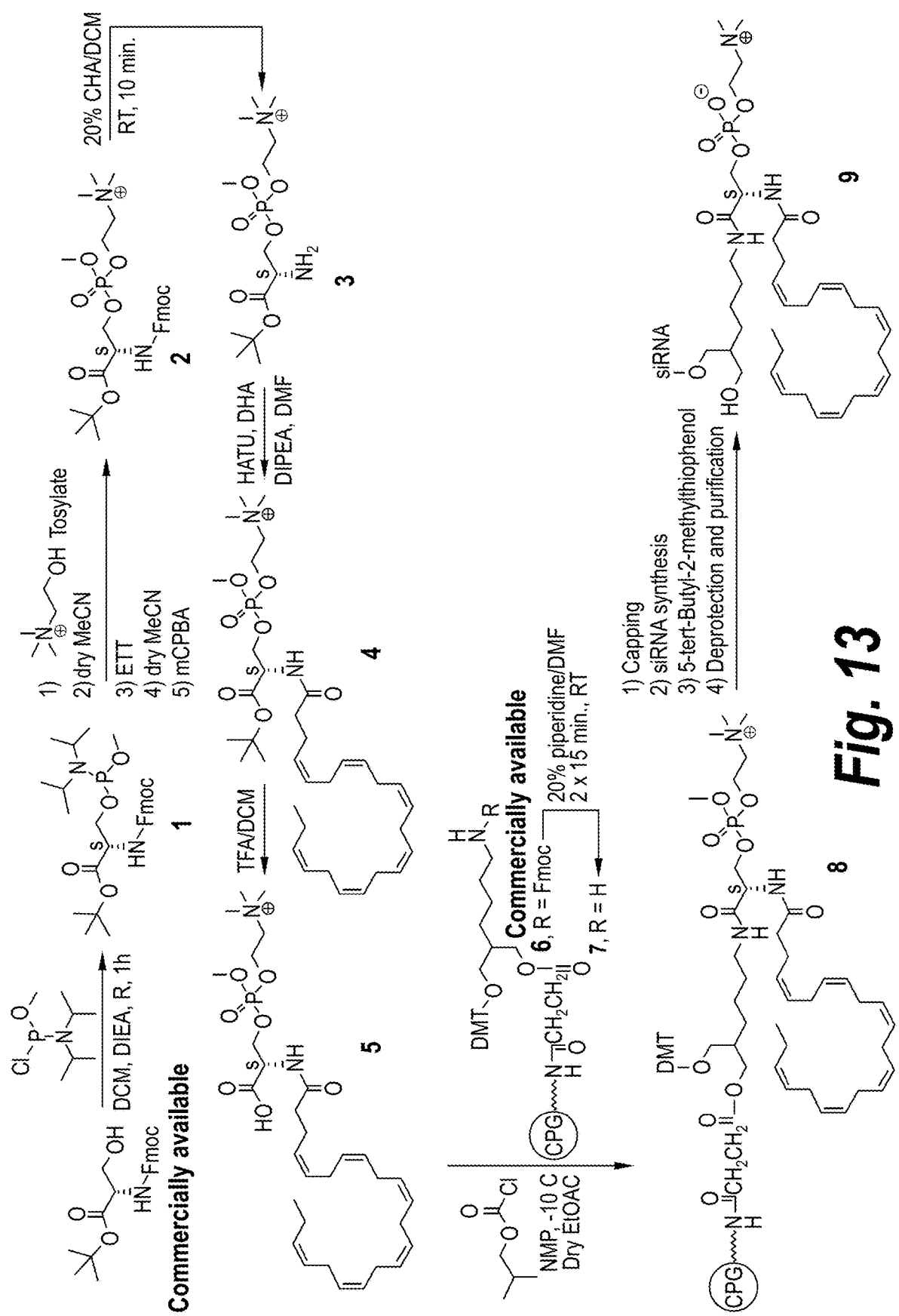
FIG. 13 shows g2DHA support synthesis II (see Example 5).

As shown in FIG. 13, commercially available Fmoc-Ser (tBu)-OH is reacted with N,N-diisopropylamino methoxy phosphonamidic chloride to afford (1). (1) is then reacted with choline tosylate followed by oxidation with mCPBA to afford (2). Next, the Fmoc group on (2) is removed with 20% cyclohexylamine in DCM and the free amine is coupled to docosahexaenoic acid to afford (3) and (4) respectively. Following this, the tBu ester group on (4) is deprotected under acidic condition to yield (5). In a parallel line, the Fmoc group on a commercially available 1-O-DMT-6-N-Fmoc-2-hydroxymethylhexane support (6) is removed using a solution of 20% piperidine in dimethylformamide to produce (7). Finally, (5) and (7) are coupled in the presence of isobutyl chloroformate to yield the functionalized support (8).

CPG 8 (6.00 g, 330 μmol, 1 equiv.) was first treated with 20% piperidine in dry DMF for 15 minutes. This procedure was repeated twice to ensure complete deprotection of the Fmoc group. The amine-bearing CPG 9 was filtered off and washed successively with DCM, ACN and ether and dried under vacuum. Then the CPG 9 was mixed with a mixture of DHA (0.65 g, 1.98 mmol, 6 equiv.), HATU (0.25 g, 0.66 mmol, 2 equiv.) and DIEA (449 μL, 2.64 mmol, 8 equiv.) in dry DMF (42 mL). The suspension was mixed on a rotary mixer for 24 h. The CPG was then filtered off and washed with DCM, ACN and ether and dried under vacuum. The CPG was capped with 16% N-methylimidazole in THF (CAP A) and acetic anhydride:pyridine:THF (1:2:2, v/v/v) (CAP B) (1:1, v/v) during 15 min and was washed with DCM, ACN and ether and dried under vacuum.

Example 6

Synthesis of DHAg2-hsiRNA From Functionalized Solid Support

Preparation of Amine-Bearing CPG 3

Figure 19:
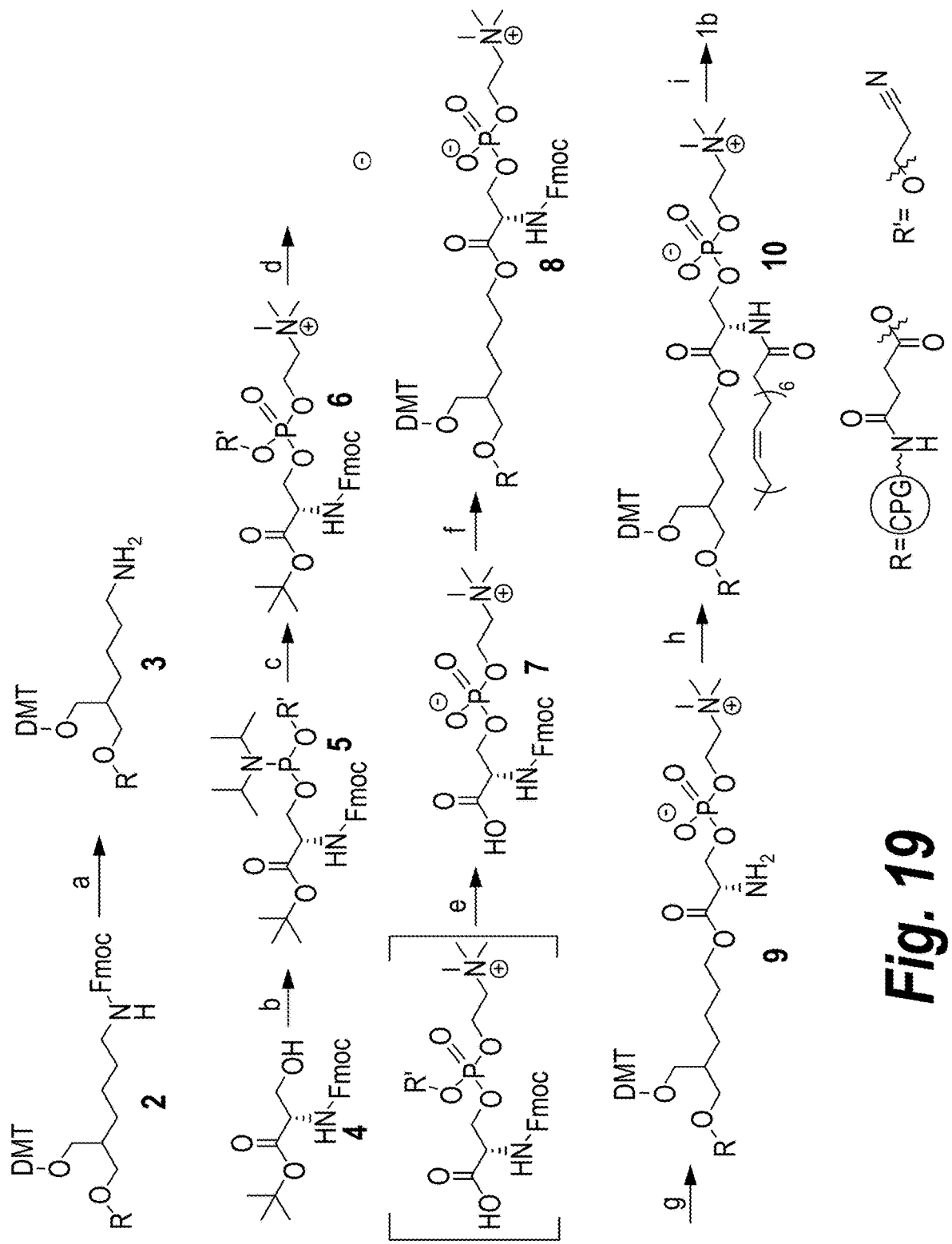
FIG. 19 shows the optimized solution phase synthetic route to g2DHA-hsiRNA (1b). Reagents and conditions: (a) 20% piperidine in DMF (2×15 min); (b) 2-cyanoethyl N,N-diisopropylchlorophosphoramidite, DIEA, DCM, 2 h, rt, 95%; (c) choline tosylate, ETT, MeCN, 2 h, rt, followed by mCPBA, 10 min, rt, 69%; (d) TFA in dry DCM (1:1), triisopropylsilane, 2 h, rt then 10% diisopropylethylamine in MeCN, 1.5 h, rt 74% (f) 3, BOP, HOBt, DMF, 2,4,6-collidine, rt, 12 h; (g) 20% piperidine in DMF (2×15 min), rt; (h) DHA, HATU, DMF, rt, 12 h; (i) RNA synthesis, cleaving, deprotection, purification and ion-exchange. See also Example 6.

As shown in FIG. 19, a functionalized CPG (3, Scheme 2) was prepared and used for the solid-phase conjugation of DHA. First, the LCAA-CPG support (particle size 125-177 μm, pore diameter 500 Å and primary amino loading 145 μmol/g) was activated and dried overnight according to published protocols.[1] Then, the commercially available 1-O-DMT-6-N-Fmoc-2-hydroxymethylhexane was converted to succinate and loaded on CPG following a reported procedure to afford 2.[2] The linker loading was determined by DMT assay to be around 55 μmol/g. Subsequently, the Fmoc goup was removed from 2 using a solution of 20% piperidine in DMF for 15 minutes. This procedure was repeated twice to ensure complete deprotection of the Fmoc group. The amine-bearing CPG 3 was filtered off and washed successively with DCM, ACN and ether and dried under vacuum.

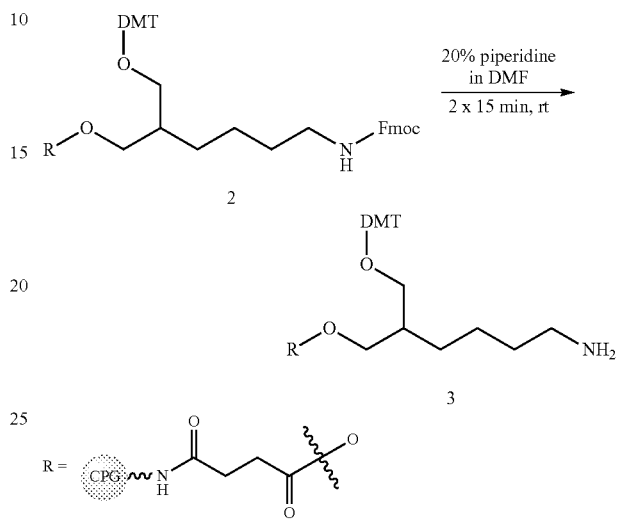

Scheme S1: Synthesis route of compound 3

[1] M. J. Damha, P. A. Giannaris, S. V. Zabarylo, An improved procedure dor derivatization of controlled-pore glass beads for solid-phase oligonucleotide synthesis. *Nucleic acids research* 1990, 18, 3813-3821.

[2] P. S. Nelson, M. Kent, S. Muthini, Oligonucleotide labeling methods 3. Direct labeling of oligonucleotides employing a novel, non-nucleosidic, 2-aminobutyl-1,3-propanediol backbone. *Nucleic acids research* 1992, 20, 6253-6259.

Synthesis of 5

Compound 4 (2.0 g, 5.21 mmol, 1 equiv.) was first dried by co-evaporation with toluene. Dry DCM (15 mL) and DIPEA (1.54 mL, 8.86 mmol, 1.7 equiv.) were added under argon and 2'-cyanoethyl-N,N-diisopropylchlorophosphoramidite (1.6 g, 6.78 mmol, 1.3 equiv.) was added slowly via a syringe. The reaction mixture was stirred 2 h at room temperature. After reaching completion, the reaction mixture was quenched with methanol and was washed with a solution of sodium bicarbonate and brine. The aqueous phase was extracted with DCM. The organic phase was dried on magnesium sulfate, filtrated and evaporated under vacuum. The crude was then purified by column chromatography on silica gel using a mixture of EtOAc/Hexane (8/2) with 1% pyridine as eluent, to afford 5 as a white solid (2.9 g, 4.97 mmol, yield 95%).

Scheme S2: Synthesis route of compound 5

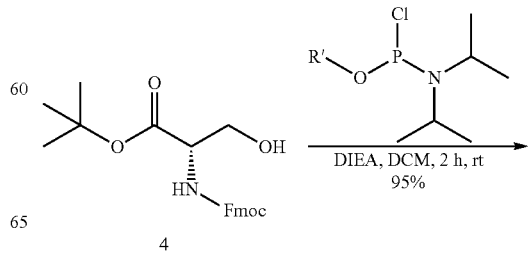

65
-continued

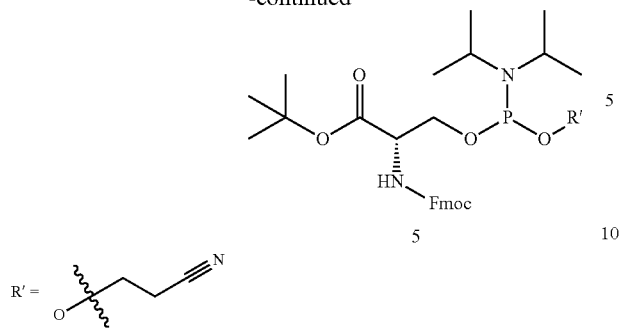

5

$^1$HMNR (400 MHz, CDCl$_3$) δ$_H$ (ppm) 7.76 (d, J=7.6 Hz, 2H, Ar Fmoc); 7.62 (t, J=6.8 Hz, 2H, Ar Fmoc); 7.41 (t, J=7.6 Hz, 2H, Ar Fmoc); 7.32 (m, 2H, Ar Fmoc); 5.79-5.68 (dd, J=36.4 Hz, J=8.0 Hz, 1H, NH); 4.43-4.22 (m, 4H, CH$_2$ Fmoc+CH$_2$); 4.11-3.73 (m, 4H, 2*CH+CH$_2$ CE); 3.59 (m, 2H, 2*CH); 2.63-2.53 (m, 2H, CH$_2$ CE); 1.50, 1.49 (s, s, 9H, CH$_3$ tBu); 1.18 (m, 12H, CH$_3$). $^{13}$C NMR (100 MHz, CDCl$_3$) δ$_C$ (ppm) 168.95 (C=O); 155.75 (C=O); 143.85, 143.70, 141.20, 141.18 (Cq Fmoc); 127.62, 126.99, 125.15, 125.09, 125.05, 125.03, 119.93, 119.80 (CH Ar Fmoc); 117.53 (Cq CE); 82.40 (Cq tBu); 67.08 (CH$_2$ Fmoc); 64.35 (CH$_2$); 63.93 (CH); 58.36 (CH$_2$ CE); 55.39 (CH); 47.07 (CH); 43.10 (CH Fmoc); 27.94 (CH$_3$ tBu); 24.56, 24.49 (CH$_3$); 20.30 (CH$_2$ CE). $^{31}$P NMR (161 MHz, CDCl$_3$) δ$_P$ (ppm) 149.77, 149.74. HRMS (ESI$^-$) m/z calculated for C$_{31}$H$_{42}$N$_3$O$_6$P (M+Na) 605.2708; Found 605.2306.

Synthesis of 6

Compound 5 (2.9 g, 5.39 mmol, 1 equiv.) was dried with dry toluene and dry ACN. Choline p-toluenesulfonate (1.63 g, 5.93 mmol, 1.1 equiv.) was dried with toluene and dissolved in dry ACN (46 mL). This mixture was added to compound 5 through a cannula. ETT (0.25 M in ACN) (21.6 mL, 5.39 mmol, 1 equiv.) was added slowly with a syringe. The mixture was stirred 2 h at room temperature. After reaching completion, the reaction mixture was quenched with methanol. Meta-chloroperoxybenzoic acid (mCPBA) (1.86 g, 10.78 mmol, 2 equiv.) was added by portion to the mixture. After 30 min of stirring, the mixture was reduced under vacuum. The crude was then purified by column chromatography on silica gel using a gradient of MeOH in DCM (0-30%) as eluent, to afford 6 as a mixture of tetrazolium (major counter anion) and tosylate (less than 5%) salts (2.7 g, 3.69 mmol, yield 69%).

Scheme S3: Synthesis route of compoud 6

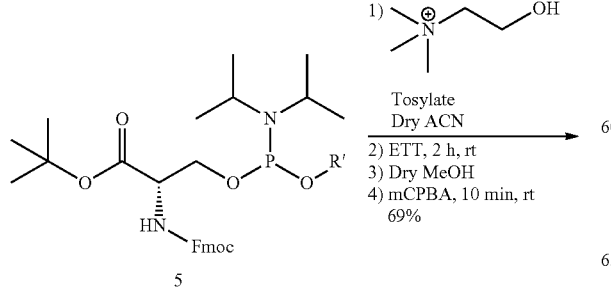

66
-continued

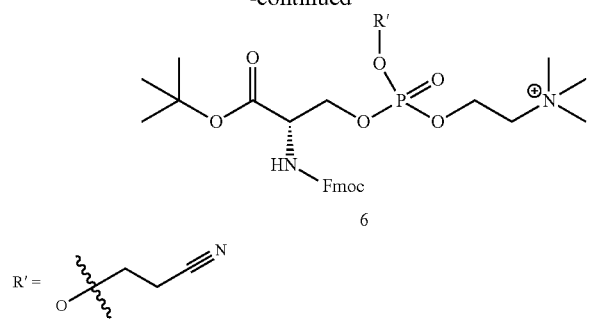

6

$^1$H NMR (400 MHz, CDCl$_3$) δ$_H$ (ppm) 7.72 (d, J=7.6 Hz, 2H, Ar Fmoc); 7.66 (d, J=8.0 Hz, 2H, Ar tosylate); 7.59 (d, J=7.2 Hz, 2H, Ar Fmoc); 7.36 (t, J=7.2 Hz, 2H, Ar Fmoc); 7.27 (t, J=8.0 Hz, 2H, Ar Fmoc); 7.09 (d, J=8.0 Hz, 2H, Ar tosylate); 6.80-6.70 (dd, J=33.2 Hz, J=7.2 Hz, 1H, NH); 4.51-4.36 (m, 6H, CH$_2$ Fmoc+2*CH$_2$); 4.29-4.15 (m, 4H, CH$_2$ CE+2*CH); 3.83 (m, 2H, CH$_2$); 3.25 (q, J=7.2 Hz, 2H, CH$_2$ tetrazolium); 3.19 (s, 9H, CH$_3$); 2.72 (m, 2H, CH$_2$ CE); 2.27 (s, 3H, CH$_3$ tosylate); 1.44 (s, 9H, CH$_3$ tBu); 1.18 (t, J=7.2 Hz, 3H, CH$_3$ tetrazolium). $^{13}$C NMR (100 MHz, CDCl$_3$) δ$_C$ (ppm) 167.77 (C=O); 163.89 (Cq tetrazolium); 156.16 (C=O); 143.69, 143.63, 141.11 (Cq Fmoc); 128.81, 125.63 (CH tosylate); 127.69, 127.07, 125.24, 125.17, 119.91, (CH Ar Fmoc); 143.15, 139.73 (Cq tosylate); 117.18 (Cq CE); 83.22 (Cq tBu); 67.96 (CH$_2$); 67.14 (CH$_2$ Fmoc); 65.25 (CH$_2$); 62.91 (CH$_2$ CE); 61.88 (CH); 54.85 (CH$_2$); 54.10 (CH$_3$); 46.88 (CH Fmoc); 27.86 (CH$_3$ tBu); 21.18 (CH$_3$ tosylate); 19.58 (CH$_2$ tetrazolium); 19.51 (CH$_2$ CE); 6.80 (CH$_3$ tetrazolium). $^{31}$P NMR (161 MHz, CDCl$_3$) δ$_P$ (ppm) −2.60, −2.71. HRMS (ESI$^+$) m/z for calculated C$_{30}$H$_{41}$, N$_3$O$_8$P (M+H) 603.2799; Found 603.2853.

Note: The order of addition of reactants during the synthesis of 6 is important. If compound 5 and ETT are mixed prior to the addition of choline p-toluenesulfonate a side reaction will occur according to the Scheme S4.

Scheme S4: Side reaction between 5 and ETT, which forms a cyclic byproduct

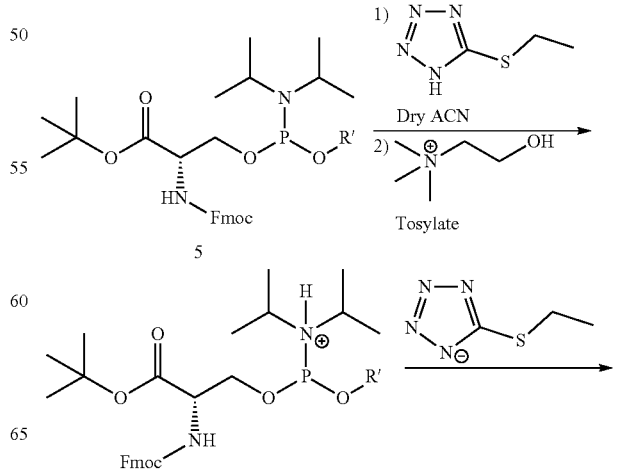

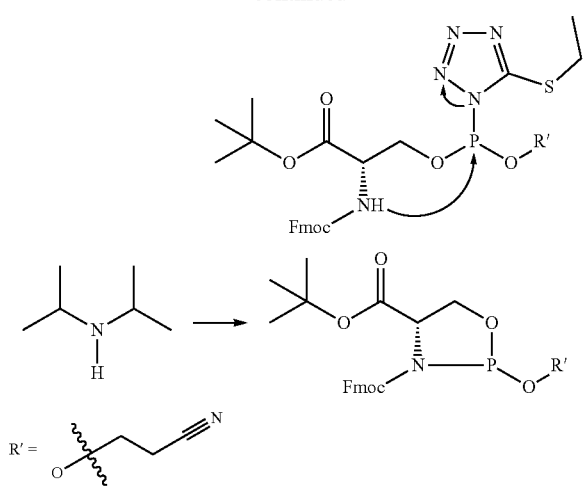

Synthesis of 7

Compound 6 (2.30 g, 3.15 mmol, 1 equiv.) was dissolved in 60 mL of (1:1) solution of TFA:dry DCM. Triisopropylsilane (2.39 mL, 11.66 mmol, 3.7 equiv.) was added and the mixture was stirred at room temperature for 2 h. The solvent and TFA were evaporated and the residue was purified by reverse phase HPLC ($C_{18}$, Buffer A=Water, Buffer B=ACN, Gradient=5-65% of B in 12 min, T=45° C.). The ACN was removed under vacuum and the aqueous solution was freeze-dried. The lyophilized powder was dissolved in 10% diisopropylethylamine (14 mL) in ACN (140 mL) and the mixture was stirred at room temperature for 2 h. The solvent was evaporated under vacuum and the crude was purified by reverse phase HPLC ($C_{18}$, Buffer A=Water, Buffer B=ACN, Gradient=5-65% of B in 12 min, T=45° C.). The ACN was removed under vacuum and the aqueous solution was freeze-dried to afford 7 as diisopropylammonium salt (1.38 g, 2.32 mmol, yield 74% over two steps).

Scheme S5: Synthesis route of compound 7

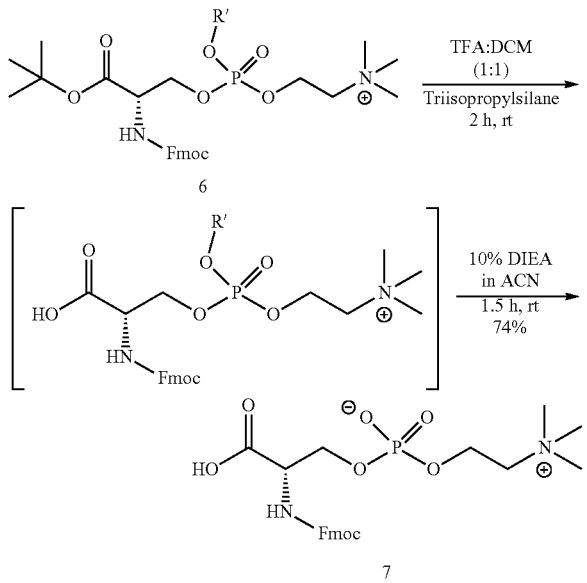

$^1$H NMR (400 MHz, DMSO-d6) $\delta_H$ (ppm) 7.88 (d, J=7.5 Hz, 2H, Ar Fmoc); 7.85-7.70 (m, 2H, Ar Fmoc); 7.41 (t, J=7.0 Hz, 2H, Ar Fmoc); 7.34 (t, J=7.0 Hz, 2H, Ar Fmoc); 6.75 (s, 1H NH); 7.28 (s, 1H NH); 4.26-4.04 (m, 5H, $CH_2$+CH Fmoc+$CH_2$ Fmoc); 3.92 (s, 2H, $CH_2$); 3.78-3.38 (m, 5H, CH+$CH_2$+2*CH DIPEA); 3.13 (s, 9H, $CH_3$); 1.14, 1.12 (s,s, 12H, $CH_3$ DIPEA). $^{13}$C NMR (100 MHz, DMSO-$d_6$) $\delta_C$ (ppm) 170.94 (C=O); 155.13 (C=O); 143.90, 142.46, 140.57, 139.31 (Cq Fmoc); 137.32, 128.81, 127.48, 127.18, 125.11, 121.27, 119.92, 109.64 (CH Ar Fmoc); 65.39 ($CH_2$); 65.24 ($CH_2$ Fmoc); 65.15 (CH); 58.21 ($CH_2$); 56.78 ($CH_2$); 52.89 ($CH_3$); 46.61 (CH Fmoc); 45.12 (CH DIPEA); 19.78 ($CH_3$ DIPEA). $^{31}$P NMR (161 MHz, $CDCl_3$) $\delta_P$ (ppm) −1.15 HRMS (ESI$^+$) m/z for calculated $C_{23}H_{29}N_2O_8P$ (M+H) 493.1788; Found 493.1783.

Solid-Phase Synthesis of 8

Compound 7 (1.00 g, 1.69 mmol, 4.75 equiv.) was dissolved in dry DMF (100 mL). (Benzotriazol-1-yloxy)tris(dimethylamino)phosphonium hexafluorophosphate (BOP) (0.59 g, 1.34 mmol, 3.76 equiv.) and hydroxybenzotriazol (HOBt) (0.21 g, 1.34 mmol, 3.76 equiv.) were added and stirred until the solution went clear. 2,4,6-collidine (560 µL, 4.32 mmol, 12.42 equiv.) was added followed by 3 (6.55 g, loading of 55 µmol/g, 360 µmol, 1 equiv.) and the suspension was mixed overnight on a rotary mixer. The CPG was filtered off and washed with DCM, ACN and ether and dried under vacuum. The CPG was capped with 16% N-methylimidazole in THF (CAP A) and acetic anhydride:pyridine: THF (1:2:2, v/v/v) (CAP B) (1:1, v/v) for 1 h and was washed with DCM, ACN and ether and dried under vacuum.

Scheme S6: Synthesis route of compounds 8

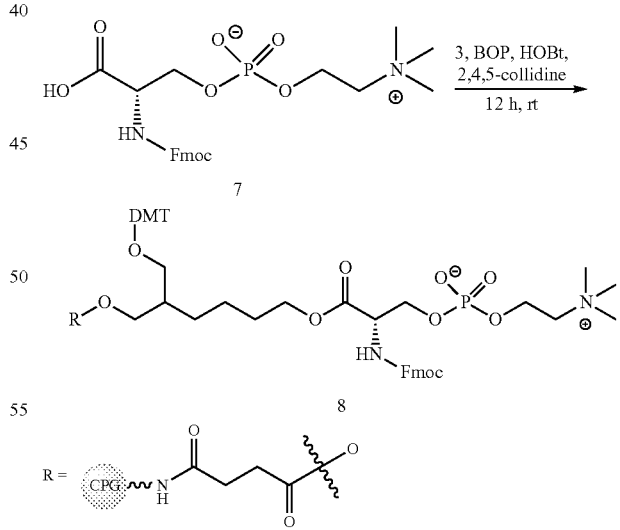

Solid-Phase Synthesis of 9 and 10

CPG 8 (6.00 g, 330 µmol, 1 equiv.) was first treated with 20% piperidine in dry DMF for 15 minutes. This procedure was repeated twice to ensure complete deprotection of the Fmoc group. The amine-bearing CPG 9 was filtered off and washed successively with DCM, ACN and ether and dried under vacuum. Then the CPG 9 was mixed with a mixture of DHA (0.65 g, 1.98 mmol, 6 equiv.), HATU (0.25 g, 0.66 mmol, 2 equiv.) and DIEA (449 μL, 2.64 mmol, 8 equiv.) in dry DMF (42 mL). The suspension was mixed on a rotary mixer for 24 h. The CPG was then filtered off and washed with DCM, ACN and ether and dried under vacuum. The CPG was capped with 16% N-methylimidazole in THF (CAP A) and acetic anhydride:pyridine:THF (1:2:2, v/v/v) (CAP B) (1:1, v/v) during 15 min and was washed with DCM, ACN and ether and dried under vacuum.

DDTT in ACN for 3 minutes. Oxidation was performed using 0.02 M iodine in THF:pyridine:water (70:20:10, v/v/v) for 80 s. Phosphoramidite coupling times were 250 s for all amidites.

Deprotection and Purification of Oligonucleotides

Both sense and antisense strands were cleaved and deprotected using 1 mL of 40% aq. methylamine at 65° C. for 10 minutes. The oligonucleotide solutions were then cooled in a freezer for a few minutes and dried under vacuum in a Speedvac. The resulting pellets were suspended in 10 mL of triethylammonium acetate (TEAA) buffer (0.1 M, pH 7) and

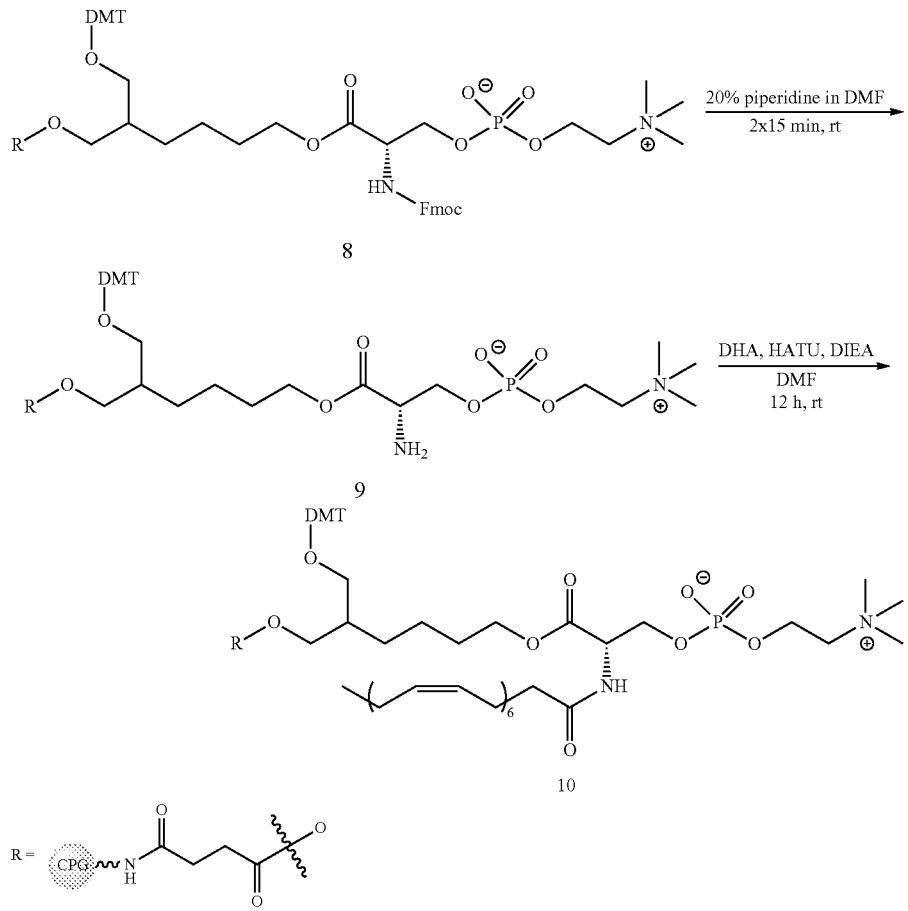

Standard Solid-Phase Oligonucleotide Synthesis

Oligonucleotides were synthesized on an Expedite ABI DNA/RNA Synthesizer following standard protocols. Each synthesis was done at a 1-μmole scale using DHA-conjugated CPG 10 for the sense strand and a Unylinker® terminus (ChemGenes, Wilmington, Mass.) for the antisense strand. Phosphoramidites were prepared as 0.15 M solutions for 2'-O-methyl (ChemGenes, Wilmington, Mass.) and Cy3 (Gene Pharma, Shanghai, China) and 0.13 M for 2'-fluoro (BioAutomation, Irving, Tex.) in ACN. 5-(Benzylthio)-1H-tetrazole (BTT) 0.25 M in ACN was used as coupling activator. Detritylations were performed using 3% dichloroacetic acid (DCA) in DCM for 80 s and capping was done with a 16% N-methylimidazole in THF (CAP A) and THF: acetic anhydride:2,6-lutidine, (80:10:10, v/v/v) (CAP B) for 15 s. Sulfurizations were carried out with 0.1 M solution of filtered through a 0.2 μm filter. The final purification of oligonucleotides was performed on an Agilent Prostar System (Agilent, Santa Clara, Calif.) equipped with a Hamilton HxSil C8 column (150×21.2) using the following conditions: buffer A: (0.1 M, TEAA, PH 7), B: (ACN), gradient: 90% A, 10% B to 10% A, 90% B in 30 minutes, temperature: 55° C., flow rate: 20 ml/min. The pure oligonucleotides were collected and cation-exchanged on a HiTrap 5 ml SP HP column (GE Healthcare Life Sciences, Marlborough, Mass.) and lyophilized.

Example 7

Solid Phase Synthesis of DHAg2-hsiRNA

Figure 20:
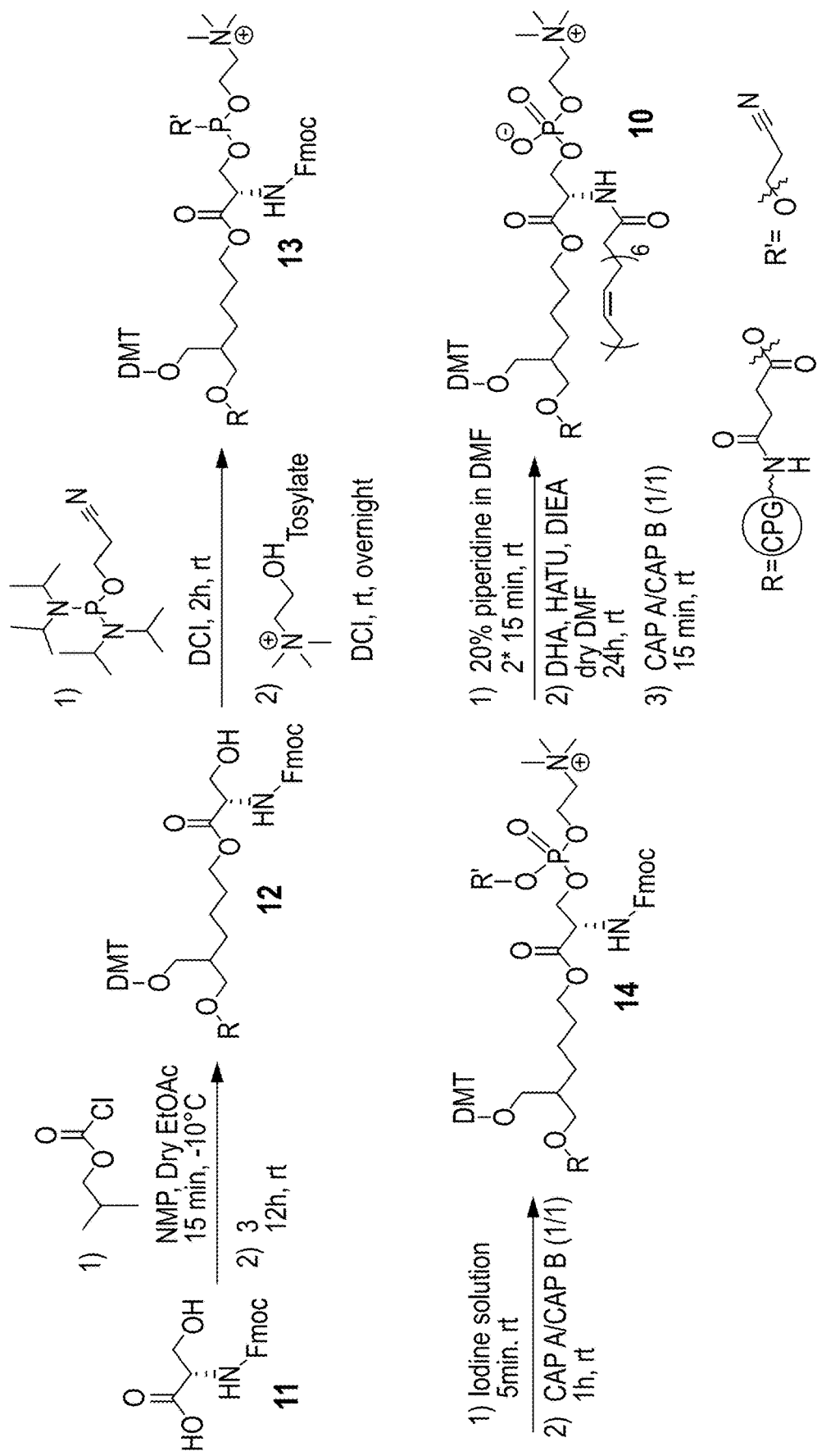
FIG. 20 shows the optimized solid-phase synthetic route to g2DHA-hsiRNA (1b). See also Example 7.

As shown in FIG. 20, the commercially available N-Fmoc-L-serine 11 (0.38 g, 1.14 mmol) was placed in a round bottom flask and dried by co-evaporation with toluene. Anhydrous ethyl acetate (3 mL) was delivered to the flask and the solution was cooled down to −10° C. Isobutyl chloroformate (0.15 mL, 0.16 g, 1.16 mmol) and N-methyl-2-pyrrolidone (NMP) (0.26 mL, 2.65 mmol) were added to this solution and the mixture was stirred for 15 minutes. Linker 3 (0.08 mmol) was added under argon and the suspension was mixed on a rotary mixer for 12 h. The CPG was filtered off and washed with DCM, ACN and ether and dried under vacuum to afford 12. 12 was placed in a small peptide synthesis flask and rinsed twice with dry ACN and kept under argon. 2-cyanoethyl-N,N,N'N'-tetraisopropylphosphorodiamidite (0.61 mL, 1.91 mmol) and 4,5-dicyanoimmidazole (DCI) (7.65 mL of a 0.25 M solution in ACN, 1.91 mmol) were added and the suspension was mixed on a rotary mixer for 2 h. The solution was decanted and the CPG was kept under argon. Choline p-toluenesulfonate (0.53 g, 1.91 mmol) that was previously dried by co-evaporation with toluene was mixed with 4,5-dicyanoimmidazole (DCI) (7.65 mL of a 0.25 M solution in ACN, 1.91 mmol) and delivered to the flask via a syringe. The suspension was mixed on a rotary mixer overnight. The solution was decanted and the CPG was washed with dry acetonitrile to afford CPG 13. Subsequently, the phosphotriester group was oxidized with iodine solution (7.6 mL of a 0.02 M iodine in THF:pyridine:water 70:20:10, v/v/v, 0.15 mmol) for 5 minutes and capped with a mixture (1/1, v/v) of 16% N-methylimidazole in THF (CAP A) and THF:acetic anhydride:2,6-lutidine, (80:10:10, v/v/v) (CAP B) for 1 h. The CPG was washed with DCM, ACN and ether and dried under vacuum to yield 14. The Fmoc group of 14 was then removed by treating the CPG with 20% piperidine in DMF (2×15 minutes). Piperidine simultaneously removes the β-cyanoethyl protecting group generating a phosphodiester specie. The CPG was washed and dried again as previously described. The amine-bearing CPG was then added to a mixture of DHA (0.19 g, 0.20 mL, 0.568 mmol), HATU (0.07 g, 0.18 mmol, and DIEA (0.39 mL, 2.24 mL) in dry DMF and stirred overnight. The solution was decanted and the CPG was capped with 16% N-methylimidazole in THF (CAP A) and acetic anhydride:pyridine:THF (1:2:2, v/v/v) (CAP B) (1:1, v/v) for 30 minutes. Finally, the CPG was washed with DCM, ACN and ether and dried under vacuum to afford 10.

Example 8

In Vivo Assays of Various Conjugates Microscopy

Wild-type (FVBN/J) mice (female, 6-7-week-old, n=3 per conjugate) were injected subcutaneous with Cy3-HTT hsiRNA duplexes (20 mg/kg). After 48 h, the mice were euthanized, perfused with 1×PBS and the organs were collected and let in 10% formalin overnight at 4C. The tissues were post-fixed, paraffin-embedded, and sliced into 4 μm sections. Each tissue section was mounted on a glass slide and stained with DAPI to visualize nuclei prior to image collection on a Leica DMi8 inverted microscope with 5× objective. The cy3 channel of all organs are represented.

DHA g1 was observed by microscopy (5×) in the thymus, bladder, intestine, skin, bone marrow, placenta, adipose, spleen, liver and kidney. DHA g2 was observed by microscopy (5×) in the thymus, bladder, intestine, skin, bone marrow, placenta, adipose, muscle, spleen, pancreas, liver and kidney.

DCA g1 was observed by microscopy (5×) in the skin, bone marrow, placenta, adipose, spleen, lung, adrenal gland, heart, kidney and liver. DCA g2 was observed by microscopy (5×) in the thymus, skin, bone marrow, placenta, adipose, muscle, spleen, pancreas, lung, fallopian tube, adrenal gland, heart, kidney and liver.

EPA g1 was observed by microscopy (5×) in the bladder, intestine, skin, bone marrow, adipose, muscle, spleen, pancreas, lung, heart, kidney and liver. EPA g2 was observed by microscopy (5×) in the intestine, skin, bone marrow, muscle, spleen, lung, fallopian tube, heart, kidney and liver.

Cholesterol g1 was observed by microscopy (5×) in the placenta, spleen, adrenal gland, heart, kidney and liver. Cholesterol g2 was observed by microscopy (5×) in the bone marrow, spleen, adrenal gland, heart, kidney and liver.

LA g1 was observed by microscopy (5×) in the bladder, skin, bone marrow, adipose, spleen, pancreas, adrenal gland, kidney and liver. LA g2 was observed by microscopy (5×) in the bladder, intestine, skin, bone marrow, adipose, spleen, fallopian tube, adrenal gland and kidney.

RA g1 was observed by microscopy (5×) in the thymus, intestine, skin, bone marrow, adipose, muscle, spleen, lung, fallopian tube, adrenal gland, kidney and liver. RA g2 was observed by microscopy (5×) in the thymus, skin, bone marrow, spleen, pancreas, lung, adrenal gland, kidney and liver.

TOCO g1 was observed by microscopy (5×) in the bone marrow, muscle, spleen, fallopian tube kidney and liver. TOCO g2 was observed by microscopy (5×) in the spleen and liver.

Choline was observed by microscopy (5×) in the placenta, kidney and bone marrow.

PNA Hybridization Assay

Levels of hsiRNA guide (antisense) strand accumulation in tissues were quantified using a PNA hybridization assay. Tissue punches were homogenized in MasterPure Tissue Lysis Solution (EpiCentre) with added proteinase K (2 mg/mL, Invitrogen) and homogenized using a TissueLyser II (Qiagen), using 100 μL of lysis solution per 10 mg tissue. Following lysis, sodium dodecyl sulfate was precipitated with KCl (3 mol/l) and cleared supernatant was hybridized to a Cy3-labeled PNA oligonucleotide fully complementary to the guide strand (PNABio). This mixture was analyzed by high-performance liquid chromatography. Cy3-labeled peaks were integrated and plotted on an internal calibration curve. Mobile phase for HPLC was 50% water, 50% acetonitrile, 25 mmol/l Tris-HCl (pH 8.5) and 1 mmol/l ethylenediamine-tetraacetate. The salt gradient was 0-800 mmol/lNaClO$_4$.

Figure 47A:
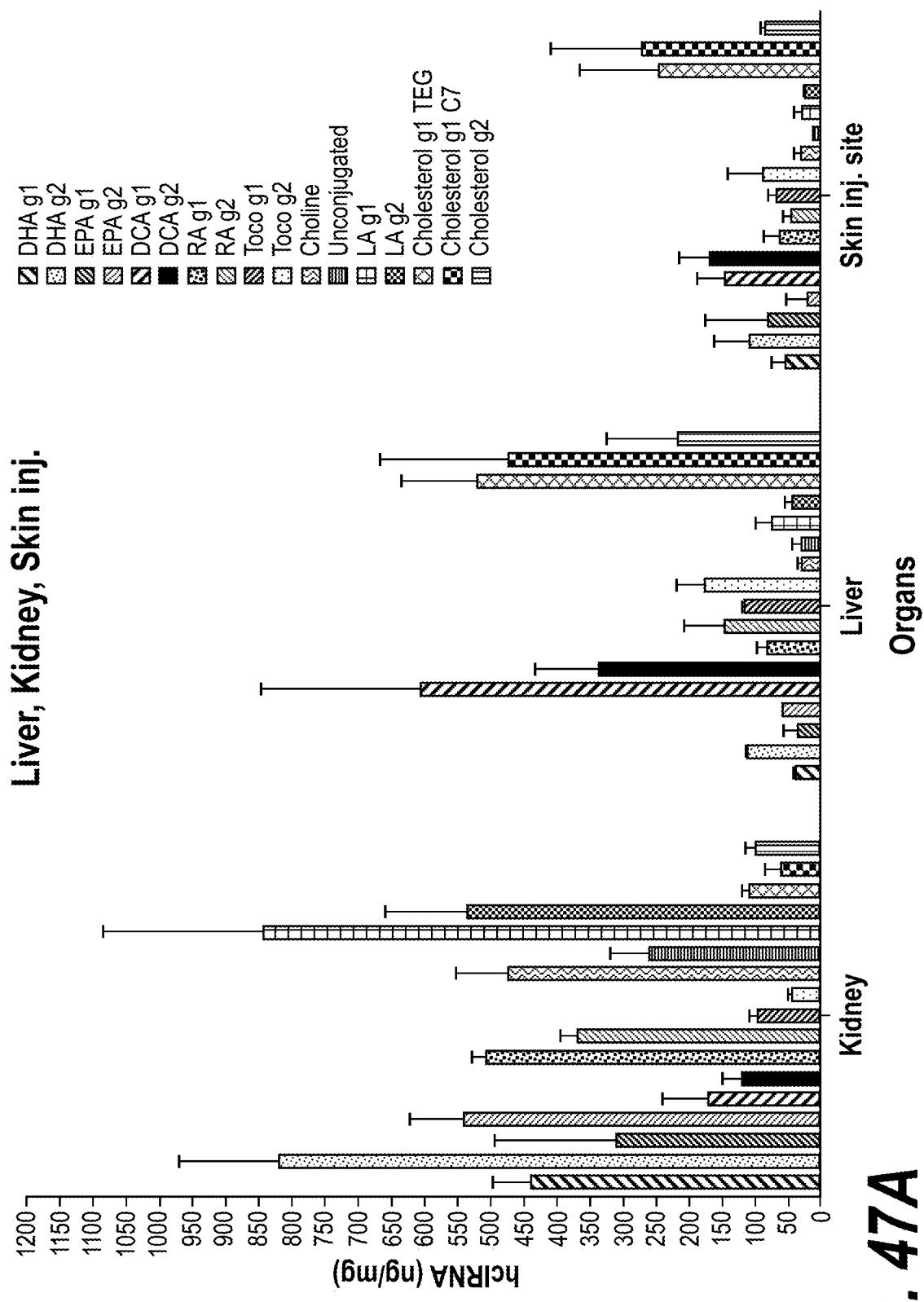
FIG. 47A-B show PNA assays depicting the effects of conjugate modality on hsiRNA tissue distribution 48 hours after a 20 mg/kg subcutaneous injection using g1 and g2 conjugates for DHA, EPA, DCA, RA, TOCO (α-tocopherol succinate), choline, LA (lithocholic acid) and cholesterol, or using unconjugated hsiRNA. (n=3.)
Figure 47B:
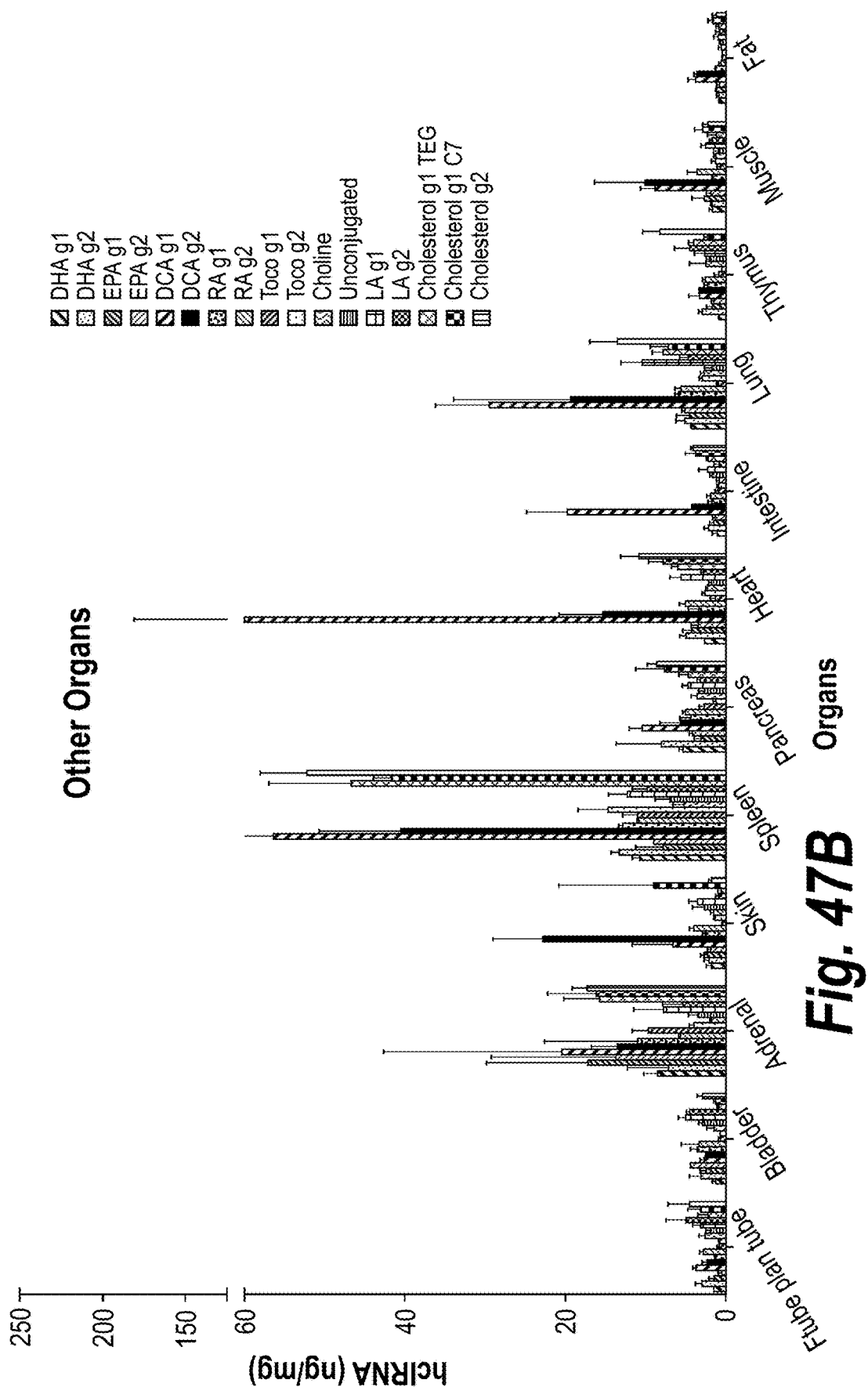

Results of the PNA assays are shown in FIGS. 47A-B, which depict delivery of each of DHA g1, DHA g2, EPA g1, EPA g2, DCA g1, DCA g2, RA g1, RA g2, TOCO g1, TOCO g2, choline, LA g1, LA g2, cholesterol g1, cholesterol C7 g1 and cholesterol g2 in the kidney, liver, skin at the injection site, skin distal to the injection site, fallopian tube, bladder, adrenal gland, spleen, pancreas, intestine, lung, thymus, muscle and adipose tissue.

Efficacy Studies

Wild-type (FVBN/J) mice (female, 6-7 week-old, n=8 per conjugate) were injected subcutaneous with Cy3-HTT hsiRNA or Cy3-PPIB hsiRNA duplexes (20 mg/kg). After 1 week, the mice were euthanized, perfused with 1×PBS and the organs were placed in RNA later overnight at 4 C and at −80 C. Punches were processed and mRNA levels were measured using QuantiGene® 2.0 DNA Assay, normalized to housekeeping gene (HPRT) and presented as % of PBS control (+/−SD). Data were analyzed using GraphPad Prism 6 software using one-way ANOVA comparison.

The results of such efficacy studies are set forth in FIGS. 48-60.

Figure 48:
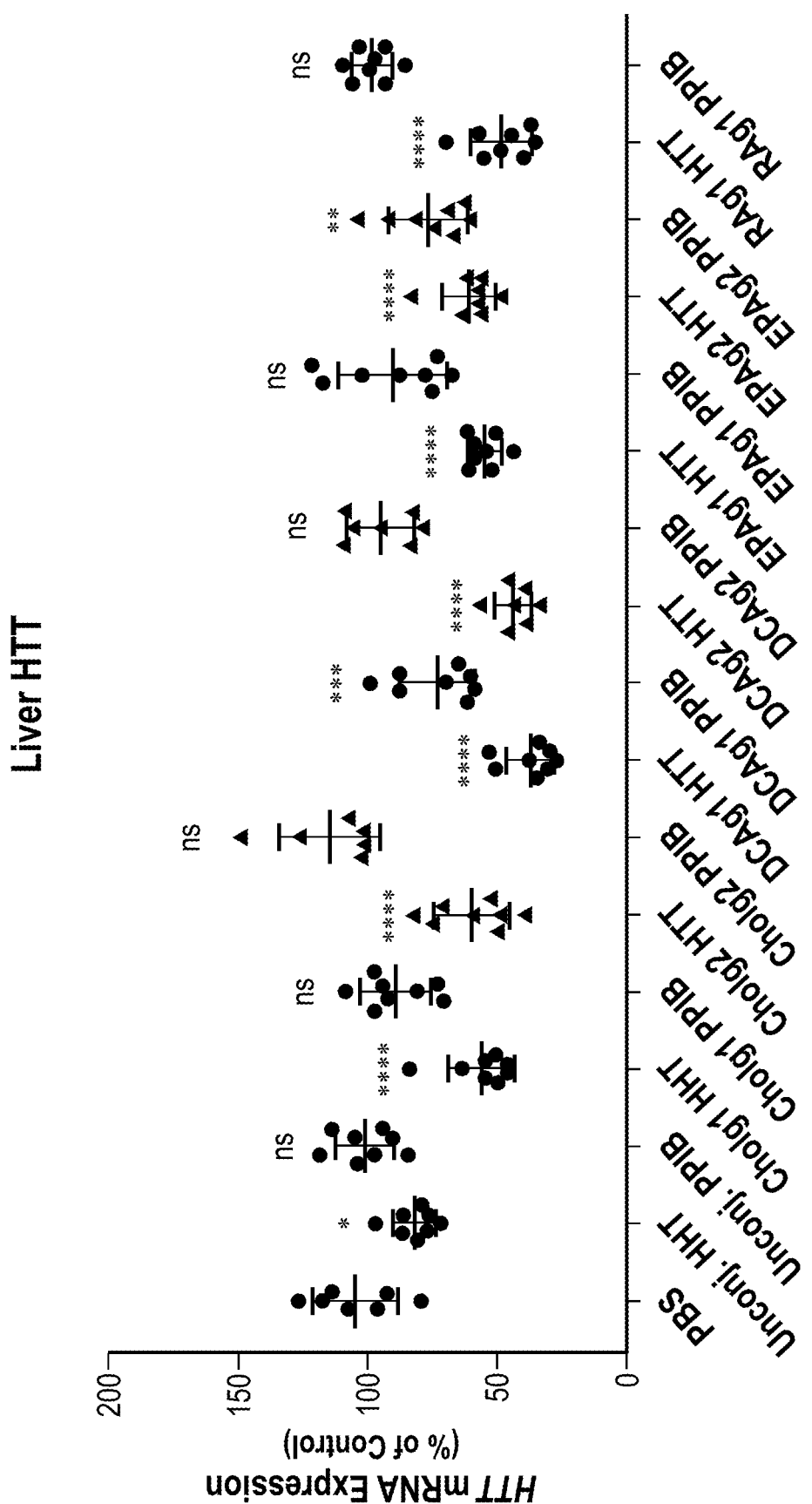
FIG. 48 depicts efficacy of HTT mRNA silencing in liver using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 49:
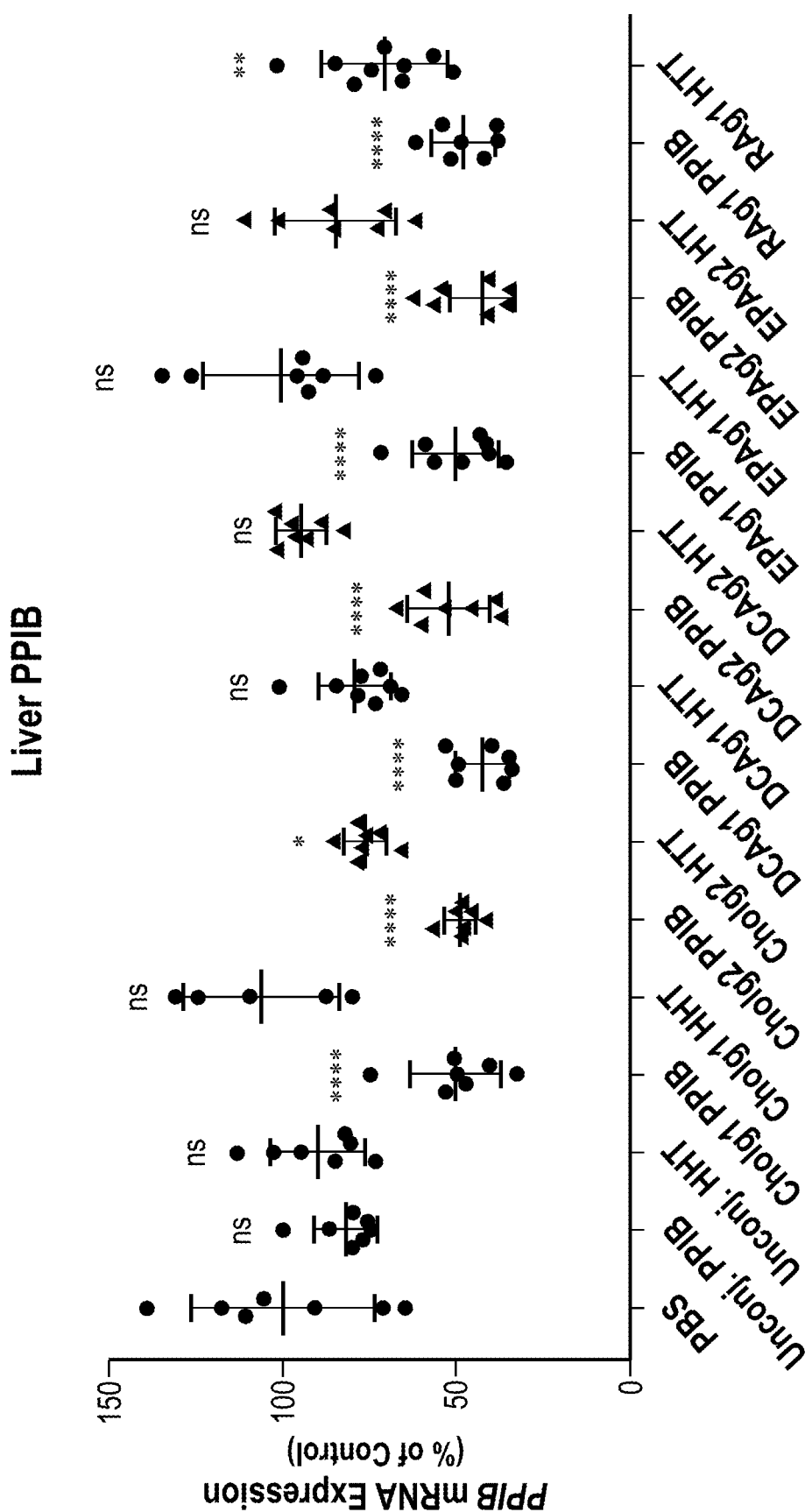
FIG. 49 depicts efficacy of PPIB mRNA silencing in liver using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 48 depicts efficacy of unconjugated htt hsiRNA, cholesterol g1-congugated htt hsiRNA, cholesterol g2-conjugated htt hsiRNA, DCA g1-conjugated htt hsiRNA, DCA g2-conjugated htt hsiRNA, EPA g1-conjugated htt hsiRNA, EPA g2-conjugated htt hsiRNA and RA g1-conjugated htt hsiRNA for silencing htt mRNA in the liver. FIG. 49 depicts efficacy of cholesterol g1-congugated PPIB hsiRNA, cholesterol g2-conjugated PPIB hsiRNA, DCA g1-conjugated PPIB hsiRNA, DCA g2-conjugated PPIB hsiRNA, EPA g1-conjugated PPIB hsiRNA, EPA g2-conjugated PPIB hsiRNA and RA g1-conjugated PPIB hsiRNA for silencing PPIB mRNA in the liver.

Figure 50:
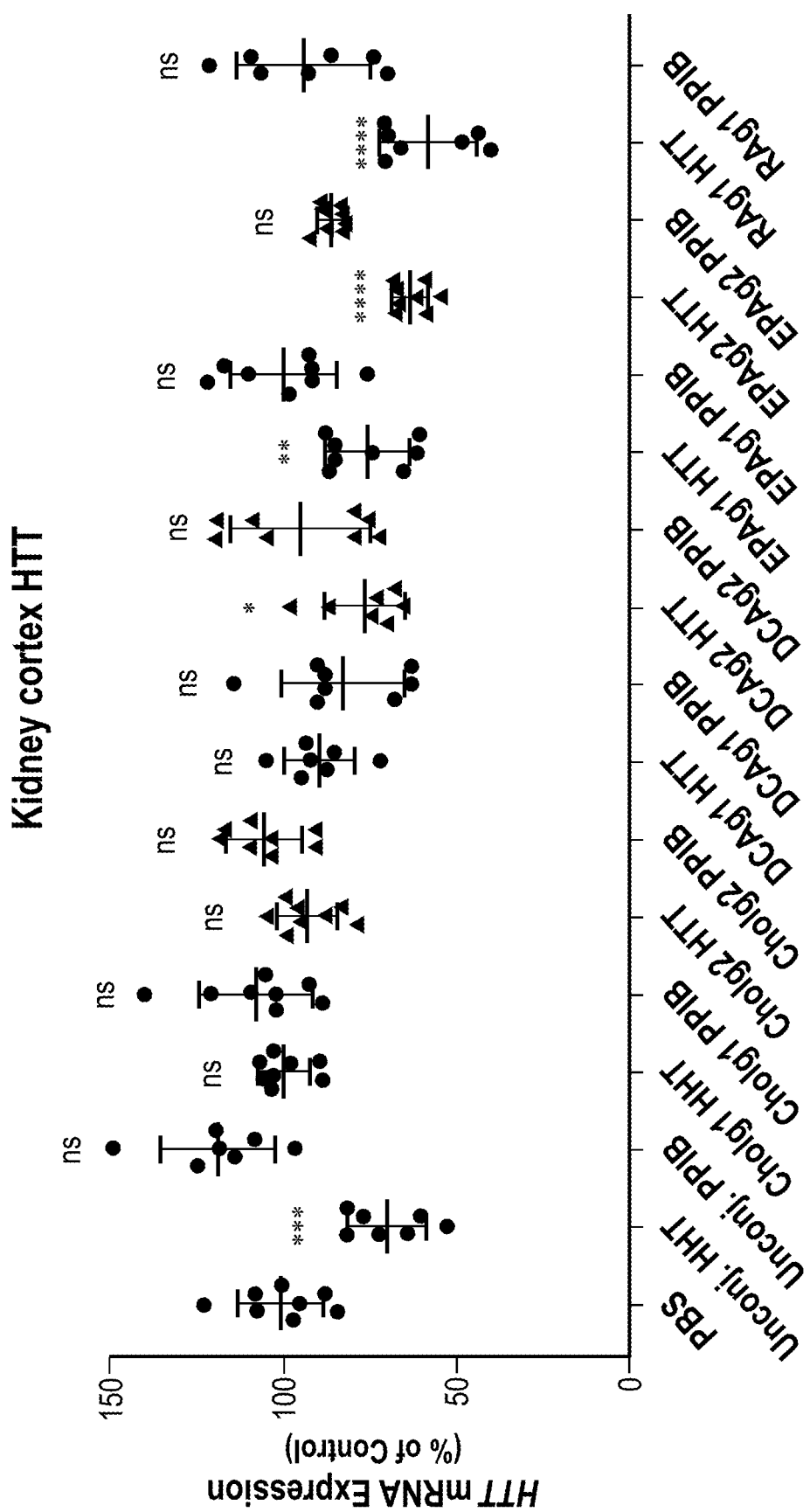
FIG. 50 depicts efficacy of HTT mRNA silencing in kidney cortex using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 51:
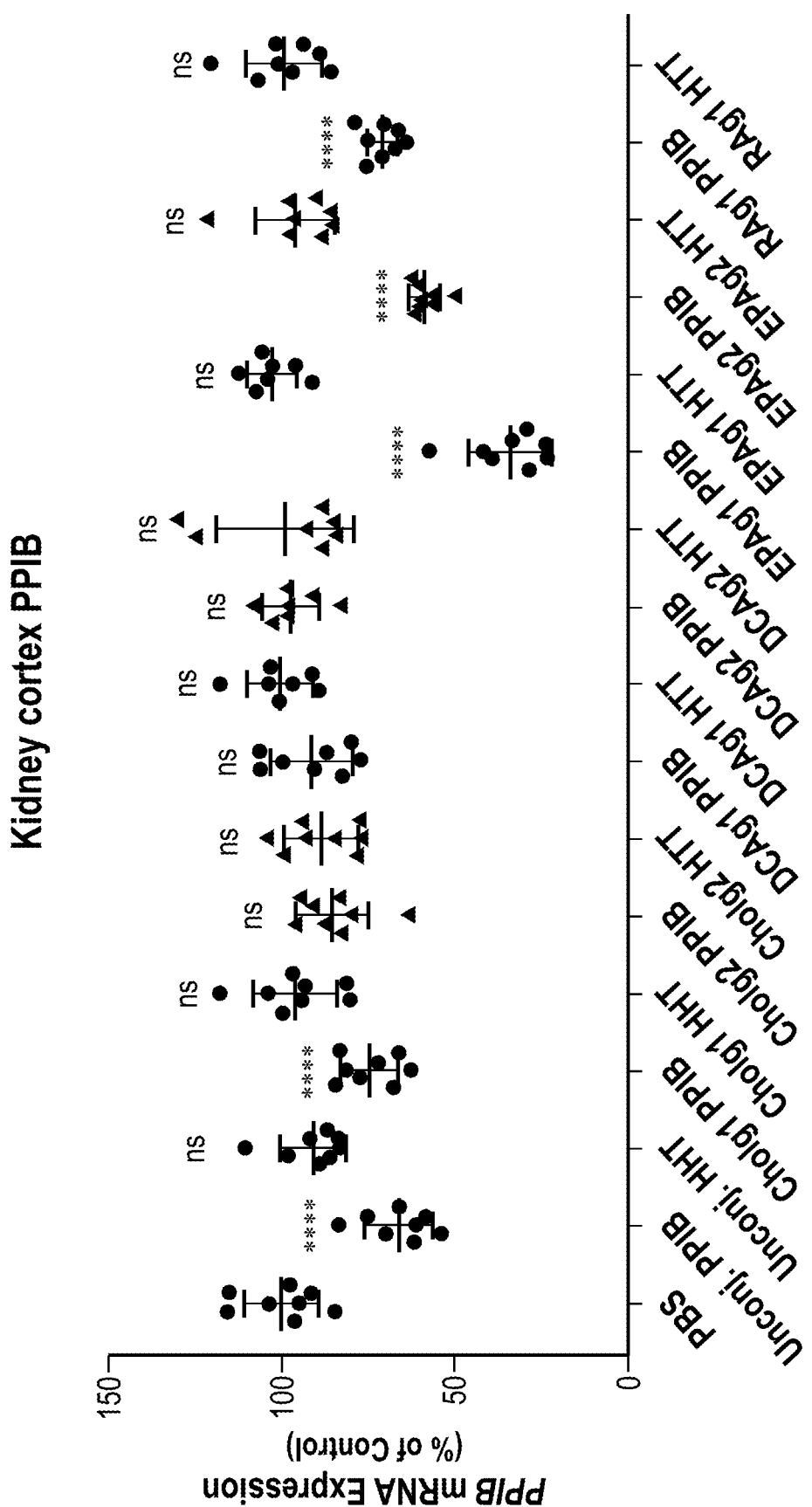
FIG. 51 depicts efficacy of PPIB mRNA silencing in kidney cortex using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 50 depicts efficacy of unconjugated htt hsiRNA, DCA g2-conjugated htt hsiRNA, EPA g1-conjugated htt hsiRNA, EPA g2-conjugated htt hsiRNA and RA g1-conjugated htt hsiRNA for silencing htt mRNA in kidney cortex. FIG. 51 depicts efficacy of unconjugated PPIB hsiRNA, cholesterol g1-conjugated PPIB hsiRNA, EPA g1-conjugated PPIB hsiRNA, EPA g2-conjugated PPIB hsiRNA and RA g1-conjugated PPIB hsiRNA for silencing PPIB mRNA in kidney cortex.

Figure 52:
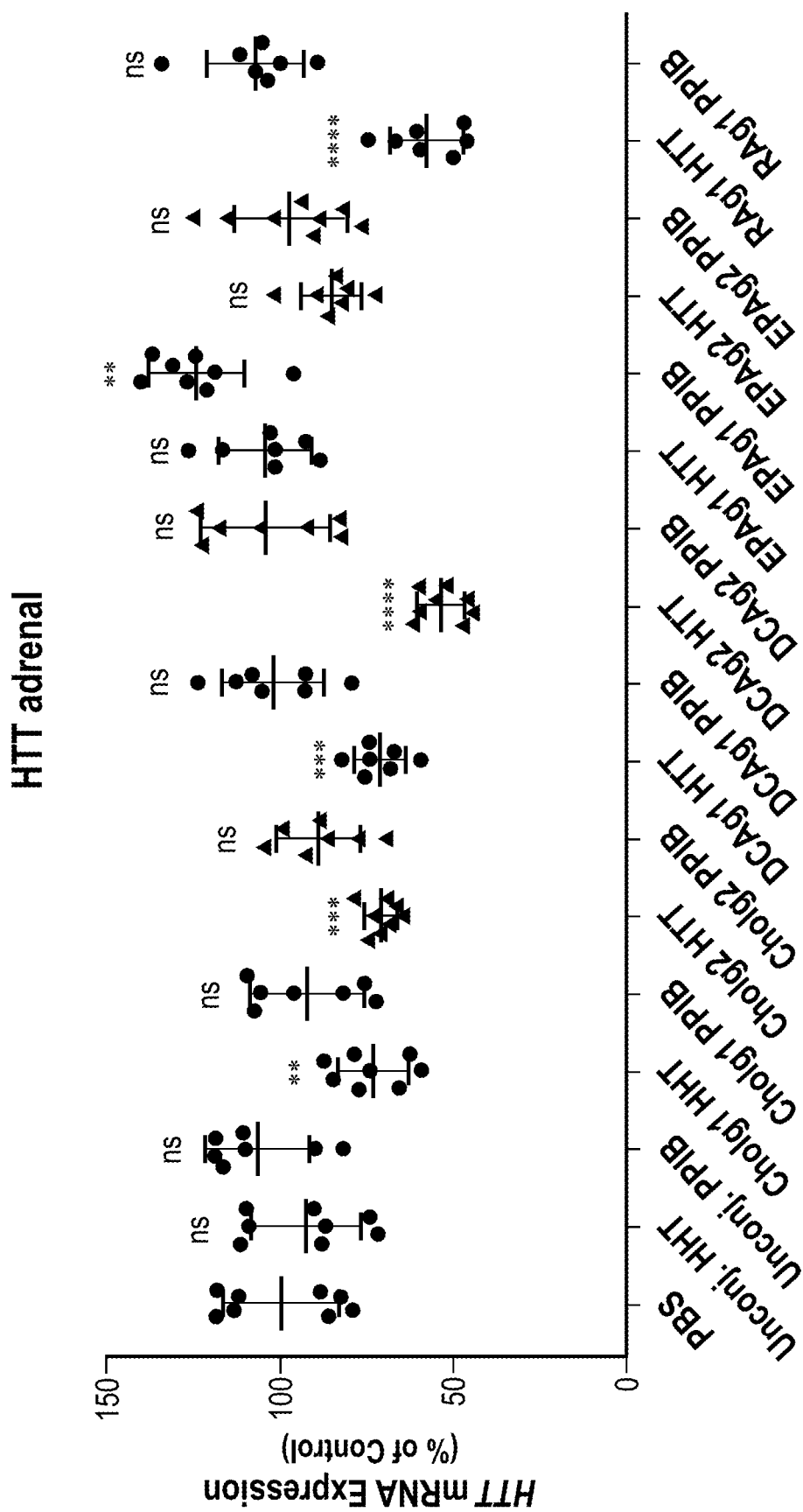
FIG. 52 depicts efficacy of HTT mRNA silencing in adrenal gland using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 53:
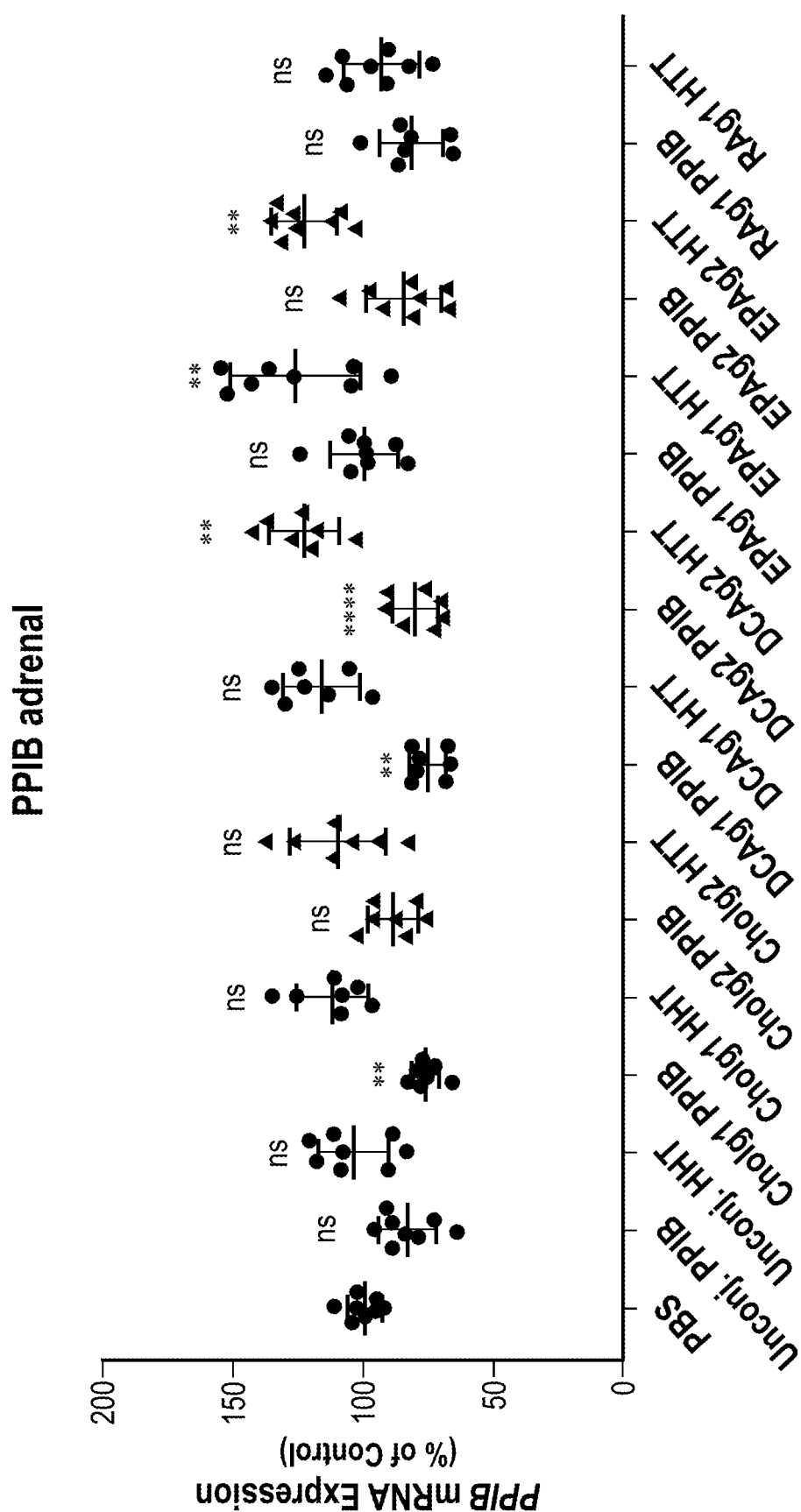
FIG. 53 depicts efficacy of PPIB mRNA silencing in adrenal gland using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 52 depicts efficacy of cholesterol g1-conjugated htt hsiRNA, cholesterol g2-conjugated htt hsiRNA, DCA g1-conjugated htt hsiRNA, DCA g2-conjugated htt hsiRNA and RA g1-conjugated htt hsiRNA for silencing htt mRNA in the adrenal gland. FIG. 53 depicts efficacy of cholesterol g1-conjugated PPIB hsiRNA, DCA g1-conjugated PPIB hsiRNA and DCA g2-conjugated PPIB hsiRNA for silencing PPIB mRNA in the adrenal gland.

Figure 54:
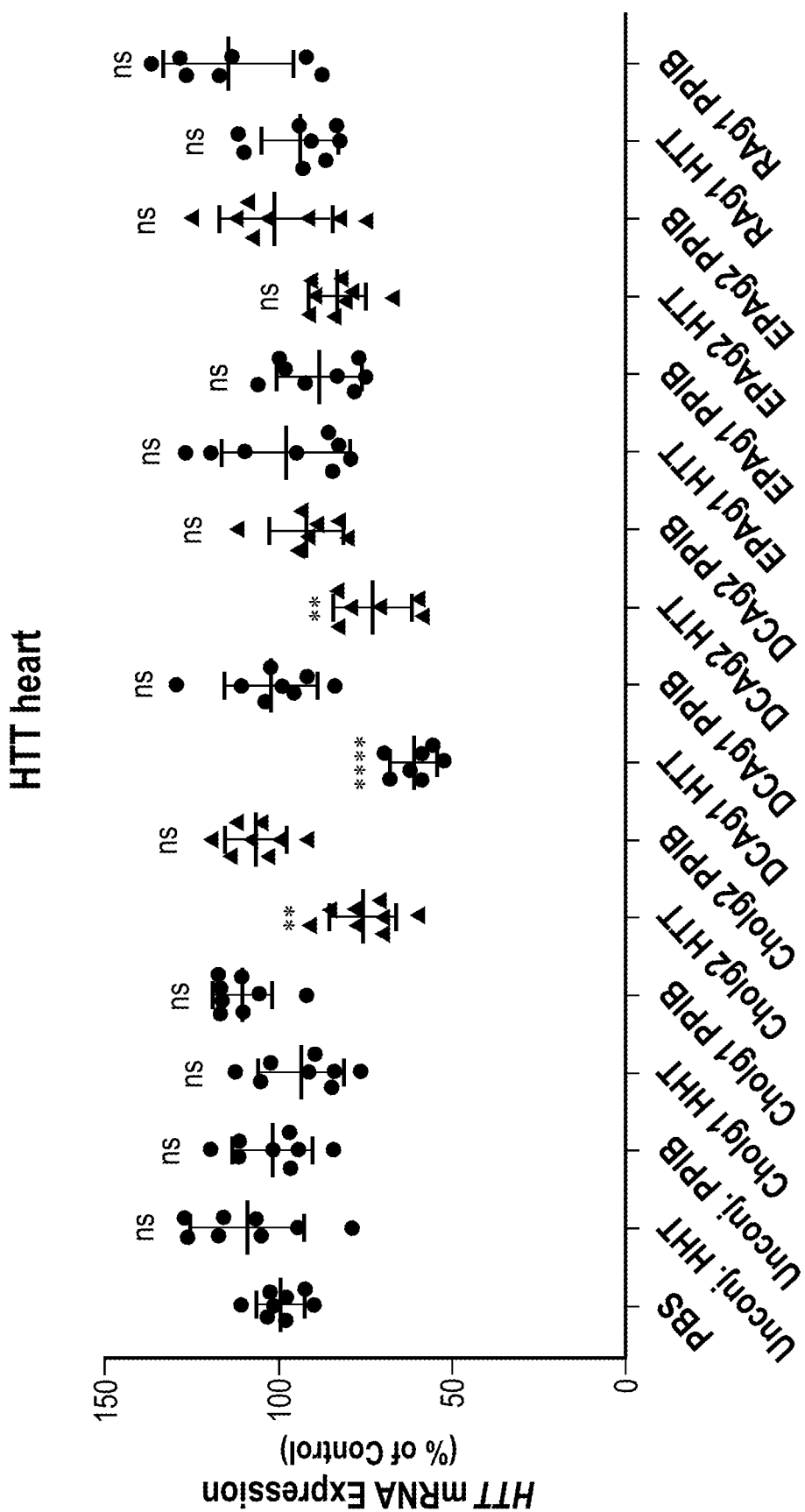
FIG. 54 depicts efficacy of HTT mRNA silencing in heart using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 55:
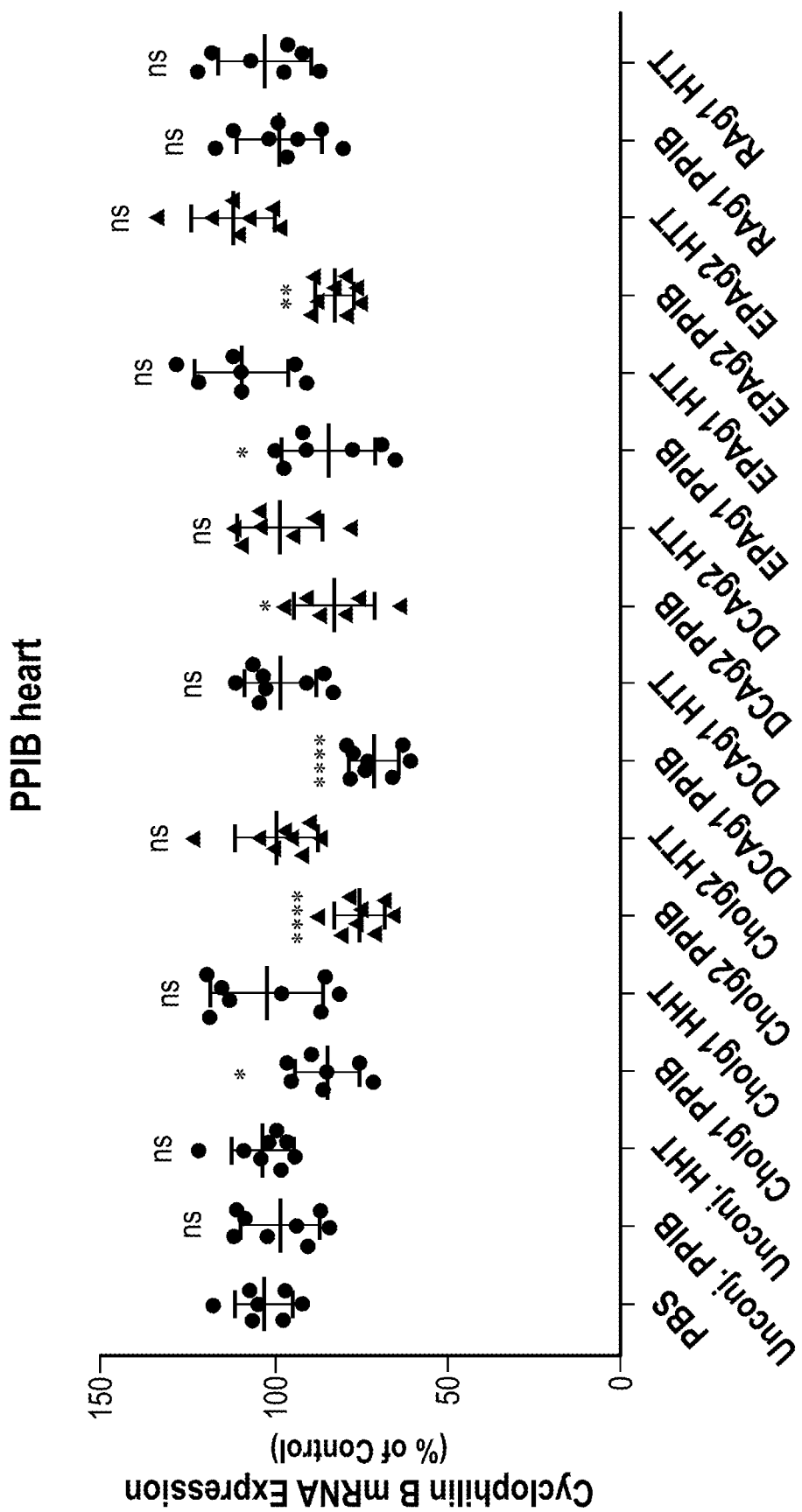
FIG. 55 depicts efficacy of PPIB mRNA silencing in heart using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 54 depicts efficacy of cholesterol g2-conjugated htt hsiRNA, DCA g1-conjugated htt hsiRNA and DCA g2-conjugated htt hsiRNA for silencing htt mRNA in the heart. FIG. 55 depicts efficacy of cholesterol g1-conjugated PPIB hsiRNA, cholesterol g2-conjugated PPIB hsiRNA, DCA g1-conjugated PPIB hsiRNA, DCA g2-conjugated PPIB hsiRNA, EPA g1-conjugated PPIB hsiRNA and EPA g2-conjugated PPIB hsiRNA for silencing PPIB mRNA in the heart.

Figure 56:
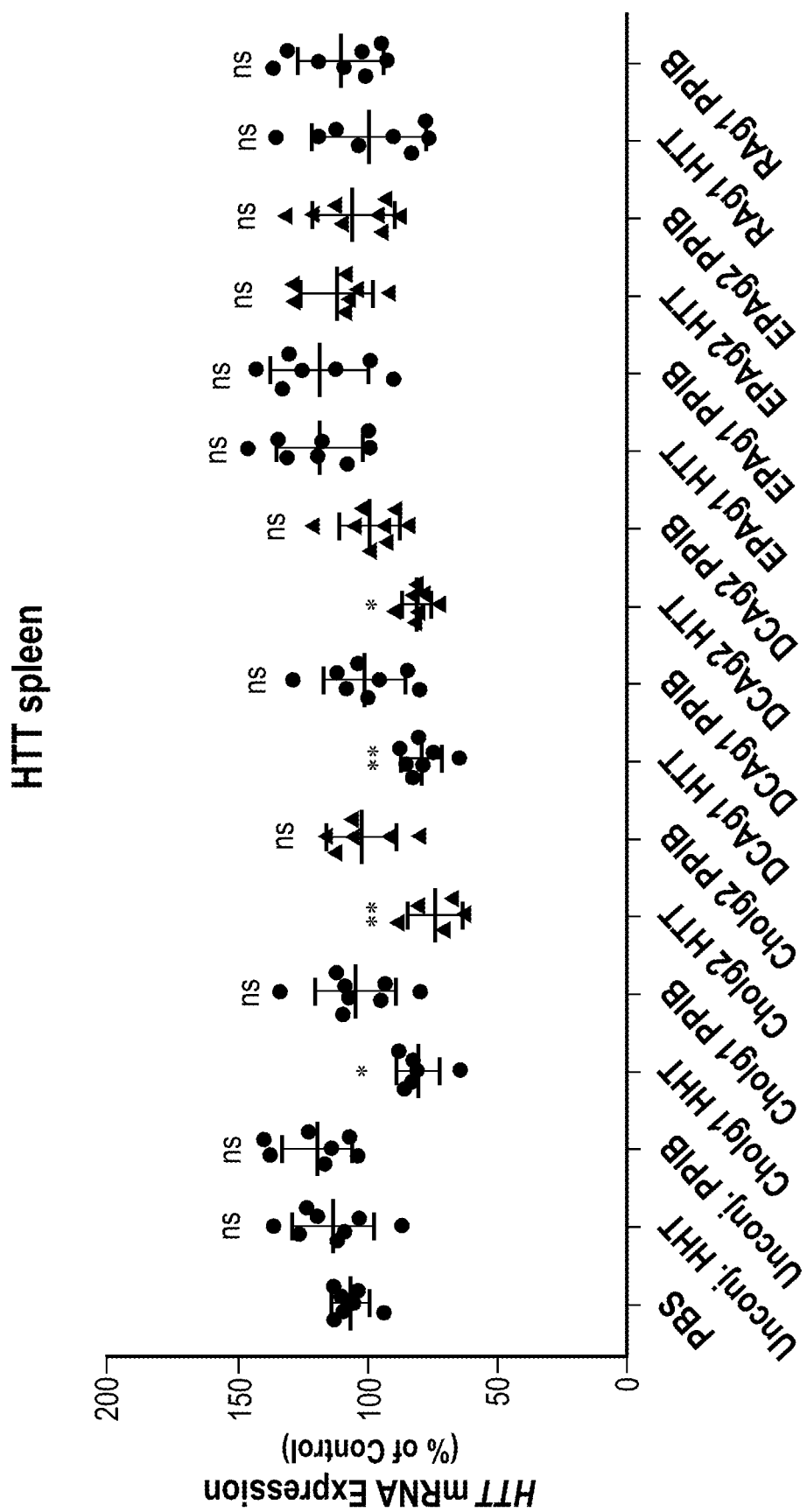
FIG. 56 depicts efficacy of HTT mRNA silencing in spleen using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 57:
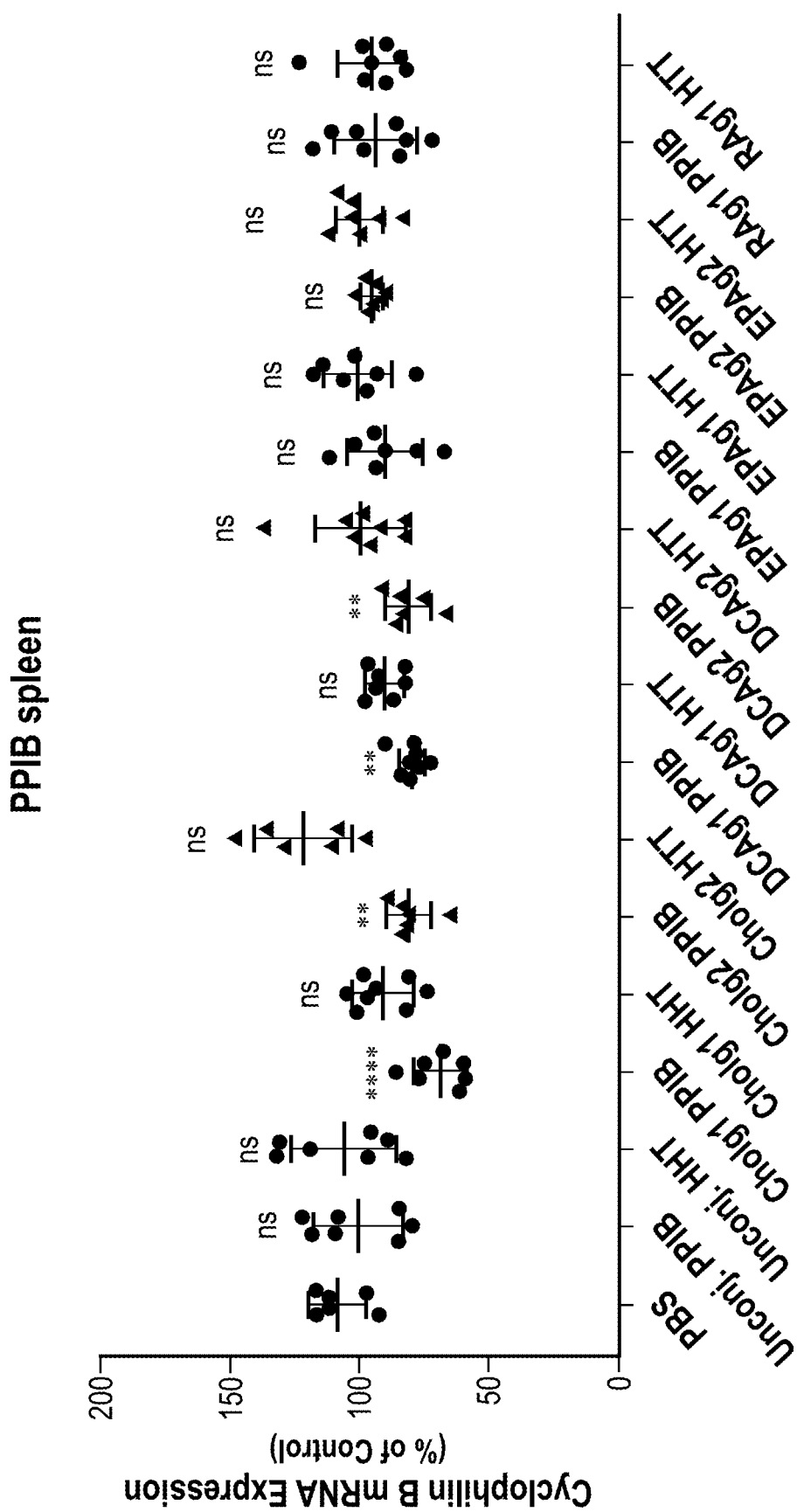
FIG. 57 depicts efficacy of PPIB mRNA silencing in spleen using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 56 depicts efficacy of cholesterol g1-conjugated htt hsiRNA, cholesterol g2-conjugated htt hsiRNA, DCA g1-conjugated htt hsiRNA and DCA g2-conjugated htt hsiRNA for silencing htt mRNA in the spleen. FIG. 57 depicts efficacy of cholesterol g1-conjugated PPIB hsiRNA, cholesterol g2-conjugated PPIB hsiRNA, DCA g1-conjugated PPIB hsiRNA and DCA g2-conjugated PPIB hsiRNA for silencing PPIB mRNA in the spleen.

Figure 58:
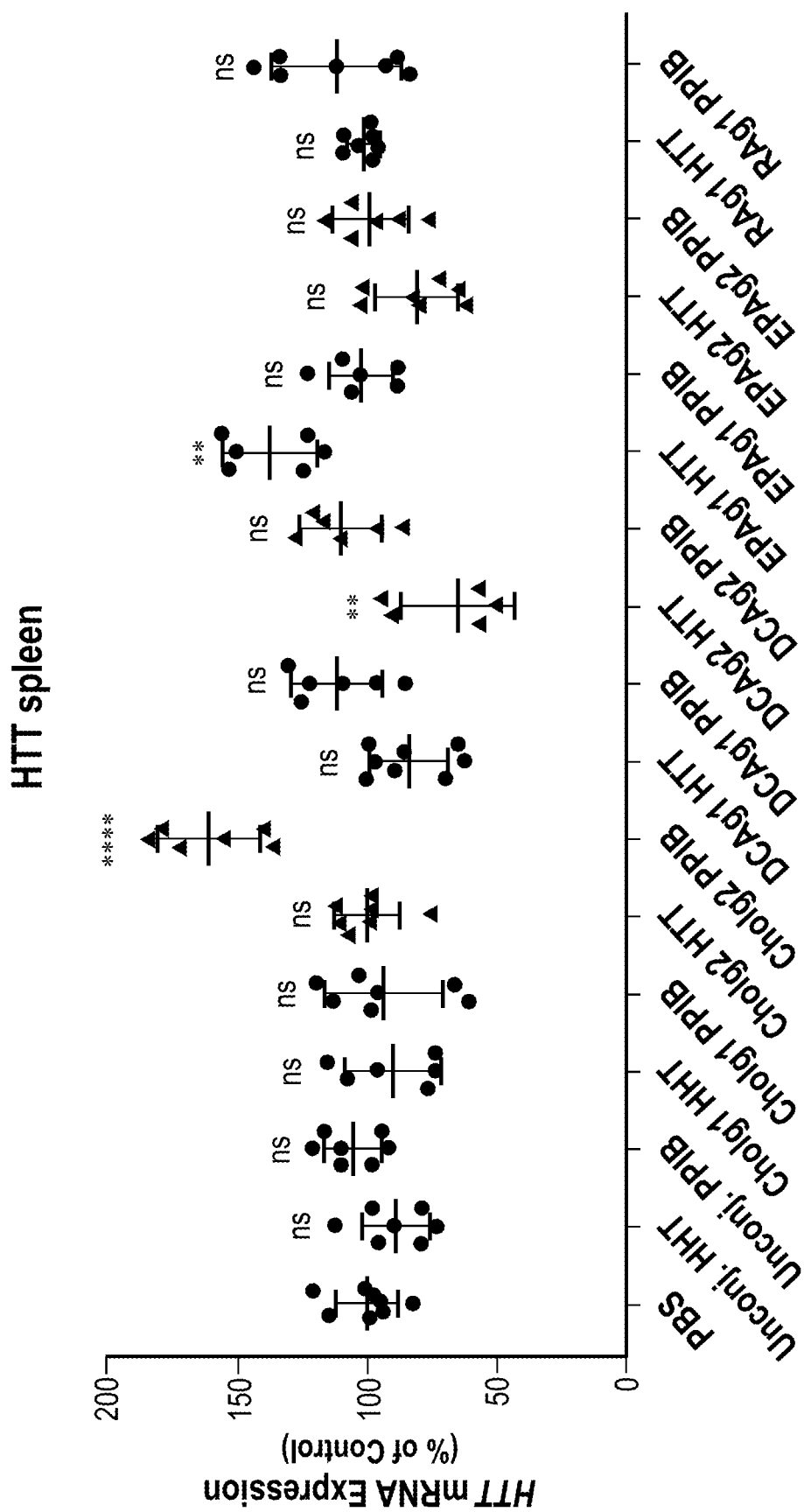
FIG. 58 depicts efficacy of HTT mRNA silencing in lung using various lipid conjugated hsiRNAs. Samples were analyzed 1 week post-subcutaneous injection of 20 mg/kg. (PPIB mRNA is non-targeting control; n=8 mice; normalization to PBS; one-way ANOVA comparison.)
Figure 59:
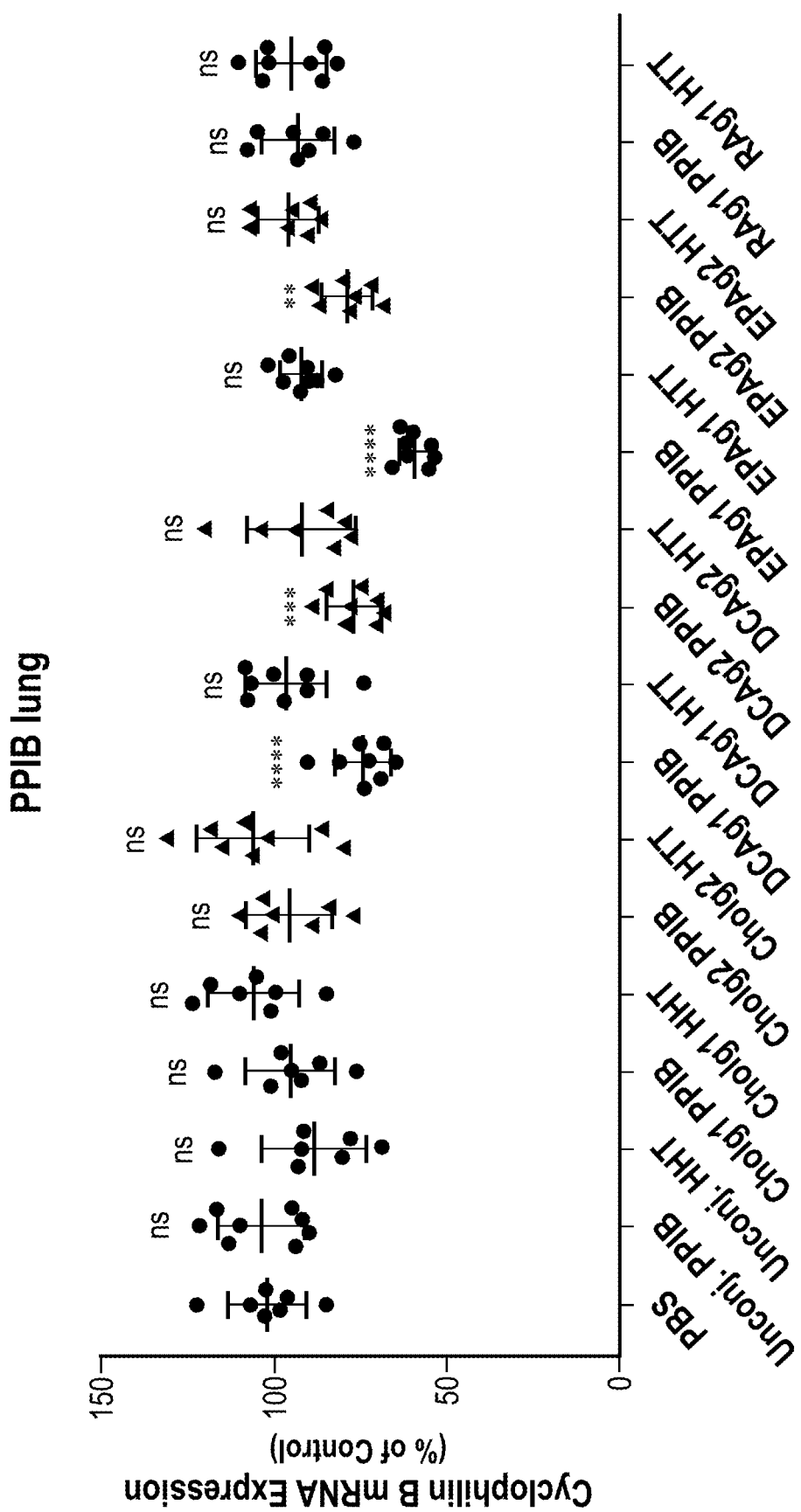
FIG. 59 depicts efficacy of PPIB mRNA silencing in lung using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 58 depicts efficacy of DCA g2-conjugated htt hsiRNA and EPA g1-conjugated htt hsiRNA for silencing htt mRNA in the lung. FIG. 59 depicts efficacy of DCA g1-conjugated PPIB hsiRNA, DCA g2-conjugated PPIB hsiRNA, EPA g1-conjugated PPIB hsiRNA and EPA g2-conjugated PPIB hsiRNA for silencing PPIB mRNA in the lung.

Figure 60:
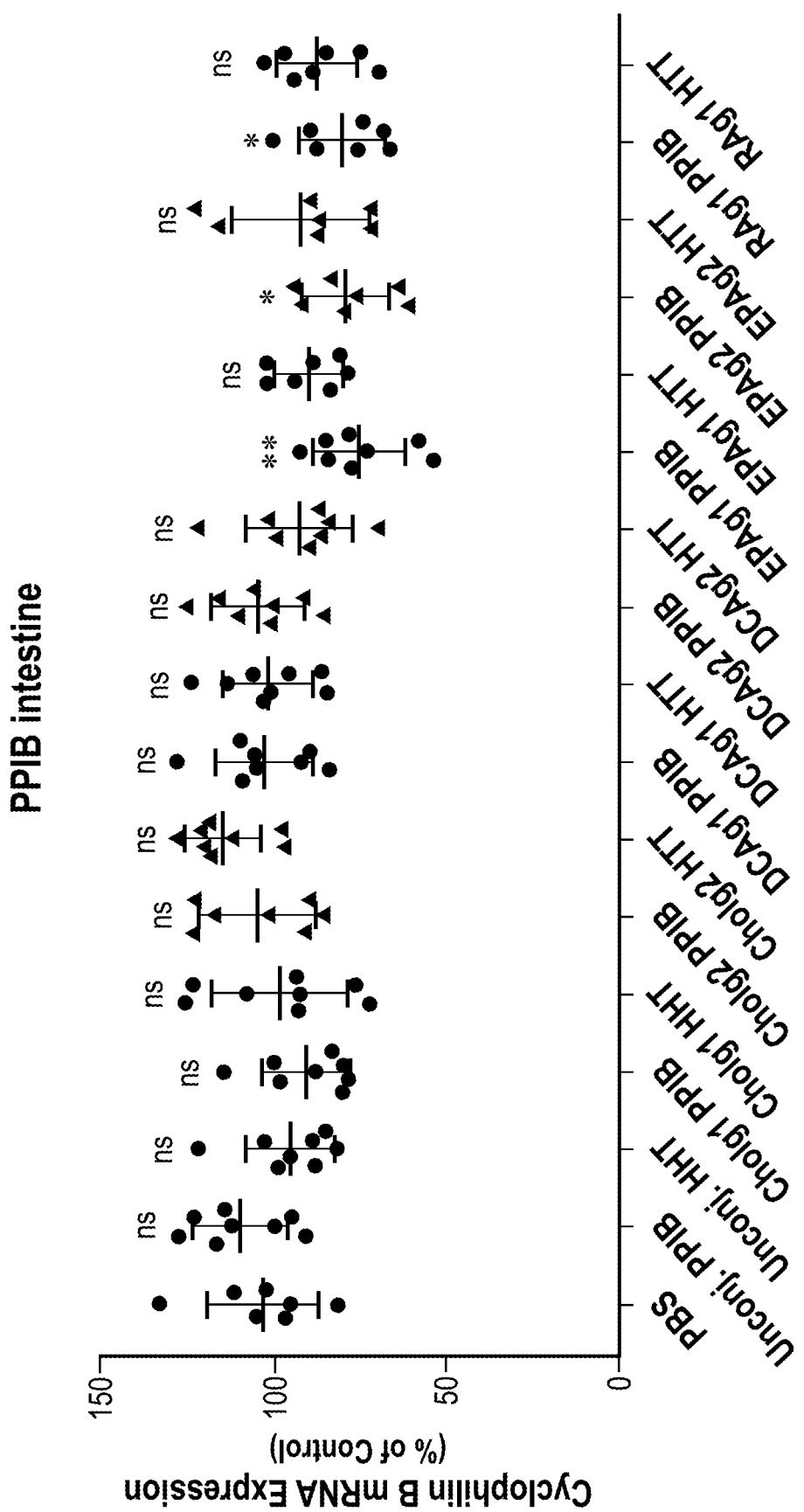
FIG. 60 depicts efficacy of PPIB mRNA silencing in spleen using various lipid conjugated hsiRNAs. Samples were analyzed 1 week post-subcutaneous injection of 20 mg/kg. (HTT mRNA is non-targeting control; n=8 mice; normalization to PBS; one-way ANOVA comparison.)

FIG. 60 depicts efficacy of EPA g1-conjugated htt hsiRNA, EPA g2-conjugated htt hsiRNA and RA g1-conjugated htt hsiRNA for silencing htt mRNA in the intestine.

Cy3-HTT hsiRNA sequences:

```
Sense strand    Cy3-
5'-3'           (fC)#(mA)#(fG)(mU)(fA)(mA)(fA)(mG)(fA)(mG)(fA)(mU)(fU)#(mA)#(fA)-
                conjugate (SEQ ID NO: 1)

Antisense       VP(mU)#(fU)#(mA)(fA)(mU)(fC)(mU)(fC)(mU)(fU)(mU)(fA)(mC)#(fU)#(mG)
strand 5'-3'    #(fA)#(mU)#(fA)#(mU)#(fA)  (SEQ ID NO: 2)
```

VP = vinyl phosphonate; mU, mA, mC, mG = 2'-OMe; fU, fA, fC, fG = 2'-F; # = phosphorothioate linkage.

Cy3-PPIB hsiRNA sequences:

```
Sense strand    Cy3-
5'-3'           (fC)#(mA)#(fA)(mA)(fU)(mU)(fC)(mC)(fA)(mU)(fC)(mG)(fU)#(mG)#(fA)-
                conjugate (SEQ ID NO: 3)

Antisense       VP(mU)#(fC)#(mA)(fC)(mG)(fA)(mU)(fG)(mG)(fA)(mA)(fU)(mU)#(fU)#(mG)
strand 5'-3'    #(fC)#(mU)#(fG)#(mU)#(fU)  (SEQ ID NO: 4)
```

VP = vinyl phosphonate; mU, mA, mC, mG = 2'-OMe; fU, fA, fC, fG = 2'-F; # = phosphorothioate linkage.

The invention claimed is:

1. A compound of formula (I):

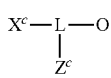

wherein:

O is an oligonucleotide;

L is a linker selected from:

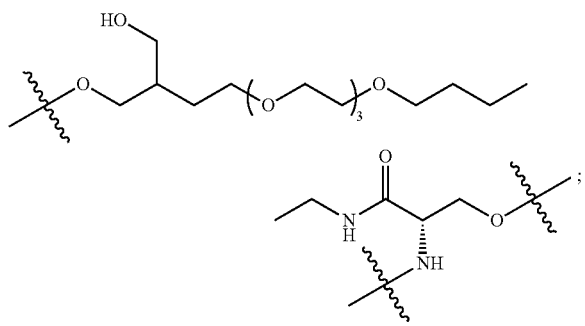

or

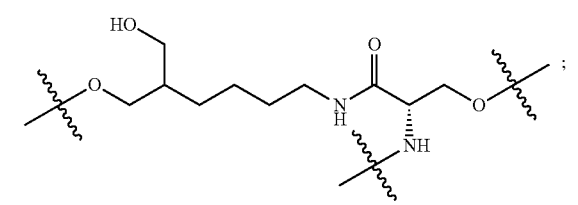

$X^c$ is a cholesterol, Lithocholic acid, Retinoic acid or α-tocopheryl succinate; and $Z^c$ is a phosphodiester or phosphodiester derivative selected from

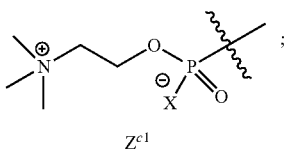

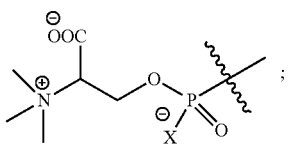

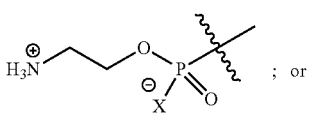

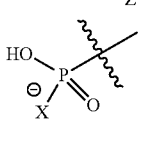

wherein X is O, S or $BH_3$.

2. The compound of claim 1, wherein O is a double-stranded nucleic acid comprising a first oligonucleotide and a second oligonucleotide, wherein:

(1) the first oligonucleotide comprises at least 16 contiguous nucleotides, a 5' end, a 3' end and has complementarity to a target;

(2) the second oligonucleotide comprises at least 15 contiguous nucleotides, a 5' end, a 3' end, and has homology with a target; and (3) a portion of the first oligonucleotide is complementary to a portion of the second oligonucleotide.

3. The compound of claim 2, wherein the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides.

4. The compound of claim 2, wherein the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides.

5. The compound of claim 2, wherein the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages.

6. The compound of claim 2, wherein the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

7. The compound of claim 2, wherein the first oligonucleotide comprises a moiety X at the 5' end, wherein X is selected from the group consisting of:

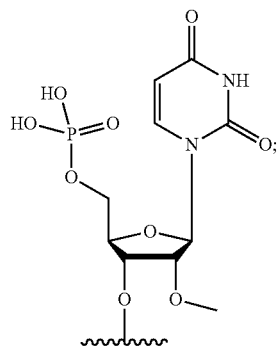

X1

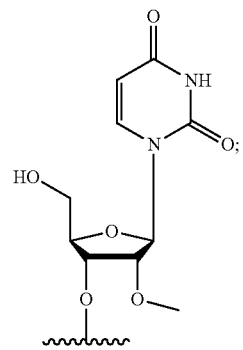

X2

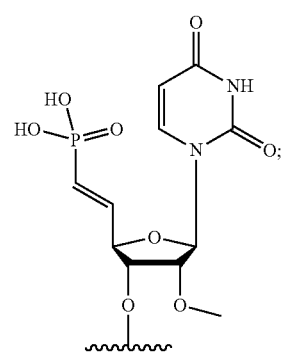

X3

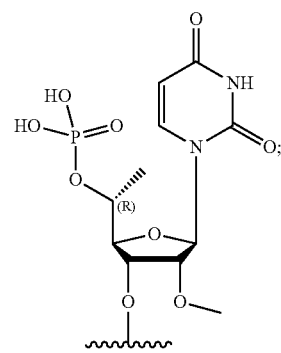

X4

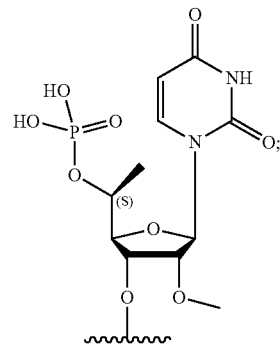

X5

X6
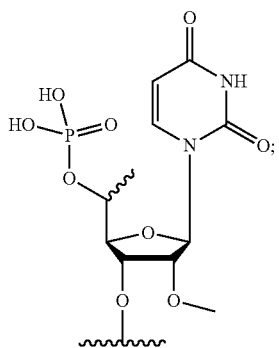
X7
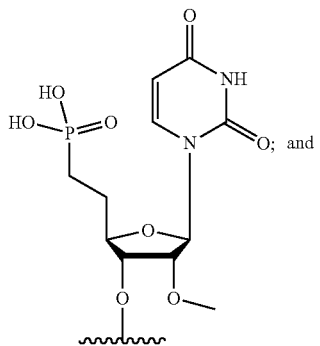; and
X8
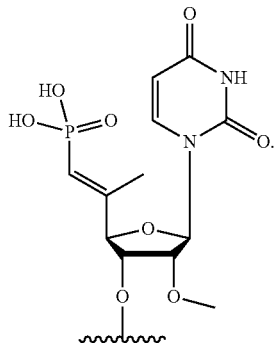.
8. The compound of claim 2, wherein the first oligonucleotide has the structure of formula (Ia):
X(—K—B—K-A)$_j$(—S—B—S-A)$_r$(—S—B)$_t$—OR  (Ia)
wherein:
X is selected from the group consisting of:
X1
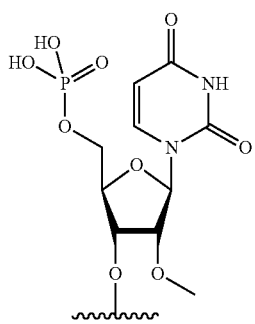
X2
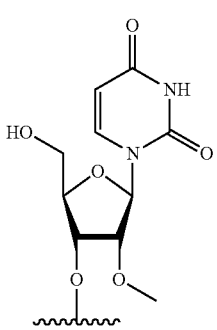
X3
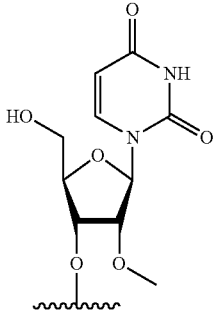
X4
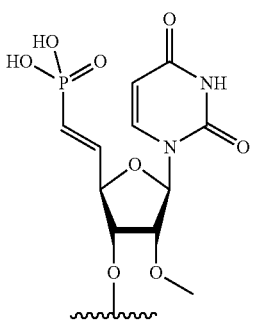
X5
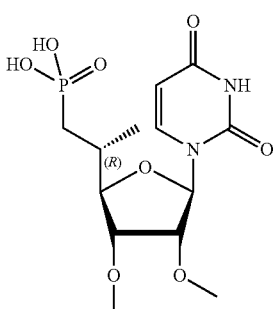
X6
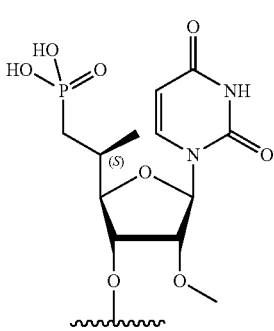

-continued

X7 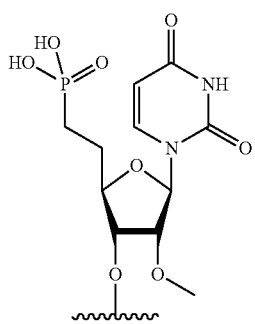

X8 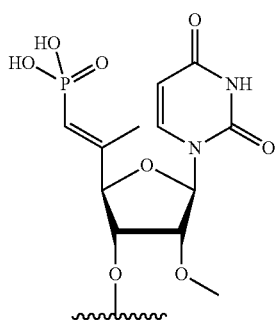

A, for each occurrence, independently is a 2'-methoxy-ribonucleotide;
B, for each occurrence, independently is a 2'-fluoro-ribonucleotide;
K, for each occurrence independently is a phosphodiester or phosphorothioate linker;

S is a phosphorothioate linker;
R is hydrogen, phosphate, vinylphosphonate, or a capping group;
j is 4, 5, 6 or 7;
r is 2 or 3; and
t is 0 or 1.

9. The compound of claim 2, wherein the first oligonucleotide has the structure of formula (IIa):

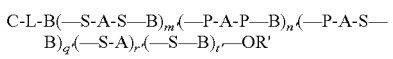 (IIa)

wherein:
C-L is:

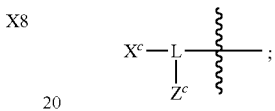

A, for each occurrence, independently is a 2'-methoxy-ribonucleotide;
B, for each occurrence, independently is a 2'-fluoro-ribonucleotide;
S is a phosphorothioate linker;
P is a phosphodiester linker;
R' is hydrogen, phosphate, vinylphosphonate, or a capping group;
m' is 0 or 1;
n' is 4, 5 or 6;
q' is 0 or 1;
r' is 0 or 1; and
t' is 0 or 1.

10. A compound comprising a structure selected from:

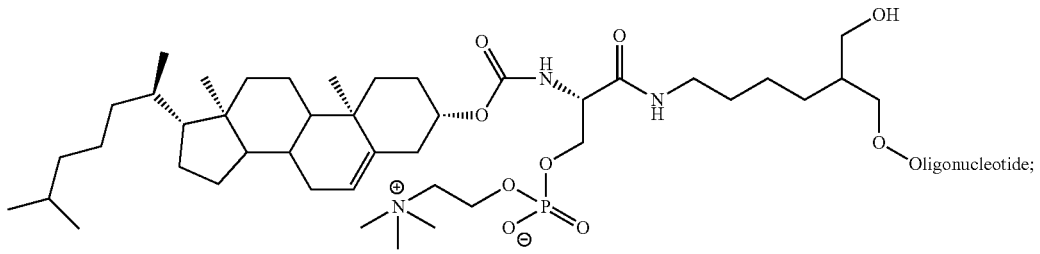

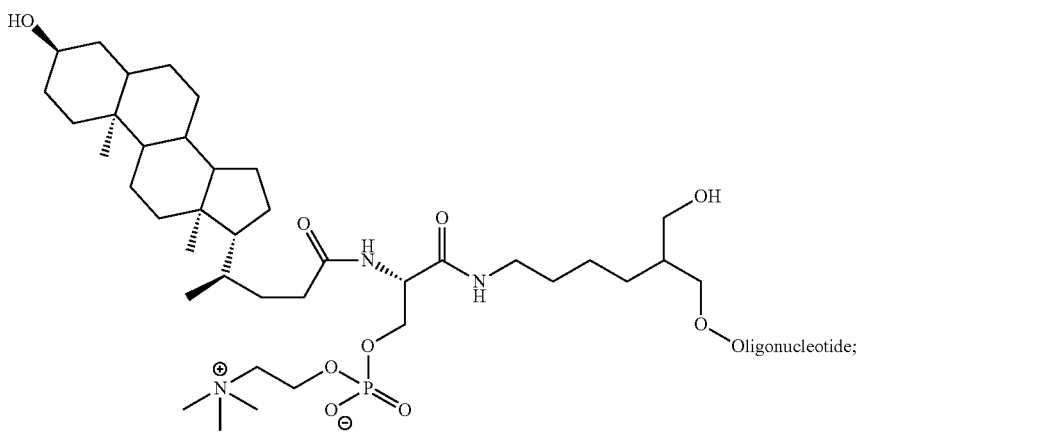

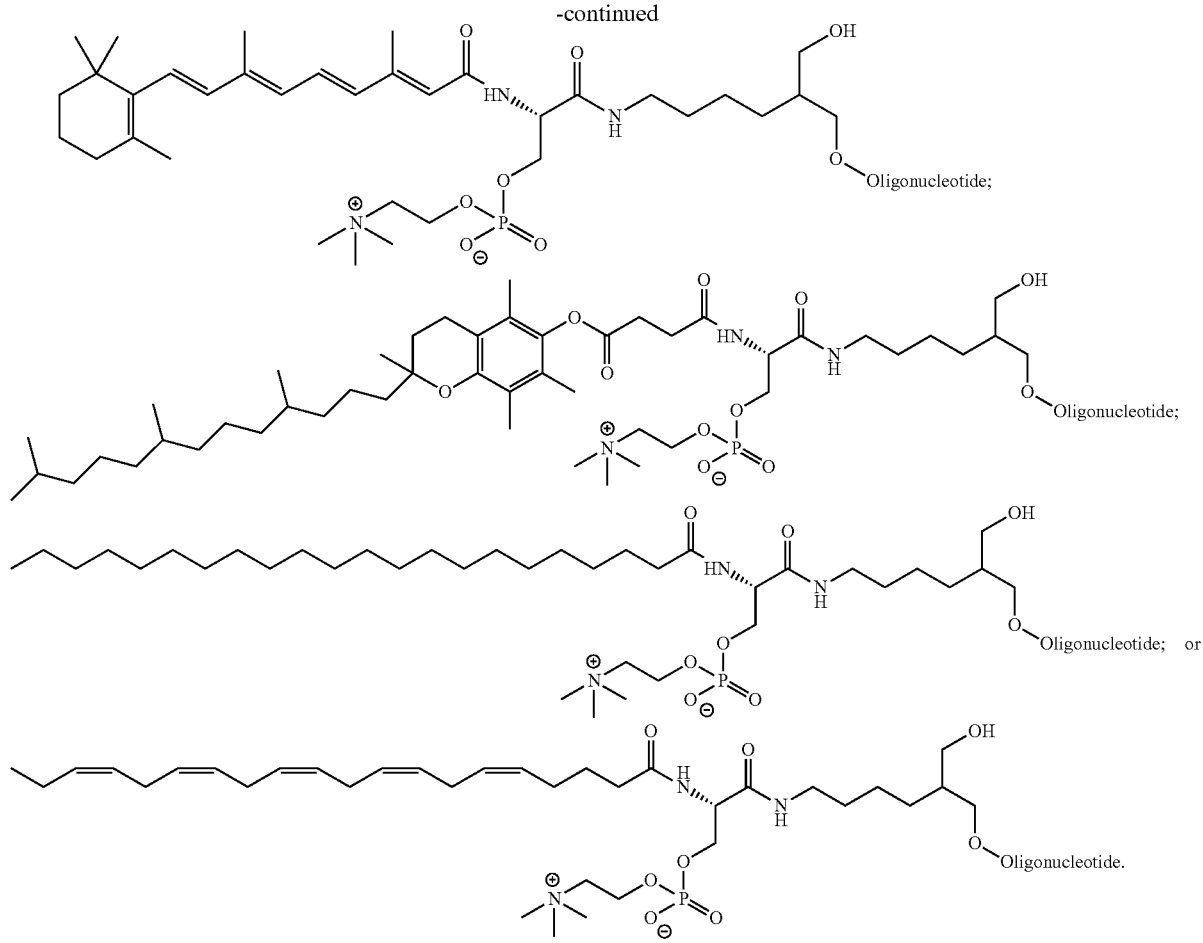

11. The compound of claim 10, wherein oligonucleotide is a double-stranded nucleic acid comprising a first oligonucleotide and a second oligonucleotide, wherein:
(1) the first oligonucleotide comprises at least 16 contiguous nucleotides, a 5' end, a 3' end and has complementarity to a target;
(2) the second oligonucleotide comprises at least 15 contiguous nucleotides, a 5' end, a 3' end, and has homology with a target; and
(3) a portion of the first oligonucleotide is complementary to a portion of the second oligonucleotide.

12. The compound of claim 11, wherein the first oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the first oligonucleotide are not 2'-methoxy-ribonucleotides.

13. The compound of claim 11, wherein the second oligonucleotide comprises alternating 2'-methoxy-ribonucleotides and 2'-fluoro-ribonucleotides, wherein each nucleotide is a 2'-methoxy-ribonucleotide or a 2'-fluoro-ribonucleotide; and the nucleotides at positions 2 and 14 from the 5' end of the second oligonucleotide are 2'-methoxy-ribonucleotides.

14. The compound of claim 11, wherein the nucleotides of the first oligonucleotide are connected to adjacent nucleotides via phosphodiester or phosphorothioate linkages, wherein the nucleotides at positions 1-6 from the 3' end, or positions 1-7 from the 3' end are connected to adjacent nucleotides via phosphorothioate linkages.

15. The compound of claim 11, wherein the nucleotides of the second oligonucleotide are connected to adjacent nucleotides via phosphodiester or phosphorothioate linkages, wherein the nucleotides at positions 1 and 2 from the 3' end are connected to adjacent nucleotides via phosphorothioate linkages.

16. The compound of claim 11, wherein the first oligonucleotide comprises a moiety X at the 5' end, wherein X is selected from the group consisting of:

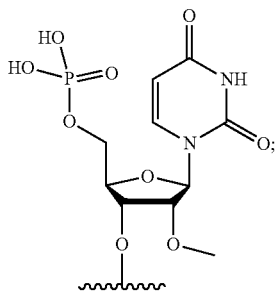

X1

17. The compound of claim 11, wherein the first oligonucleotide has the structure of formula (Ia):

$$X(-K-B-K-A)_j(-S-B-S-A)_r(-S-B)_t-OR \quad \text{(Ia)}$$

wherein:

X is selected from the group consisting of:

-continued

X3 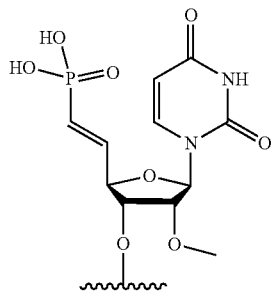

X4 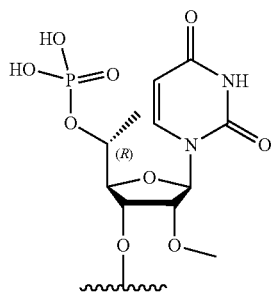

X5 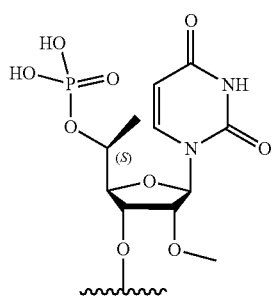

X6 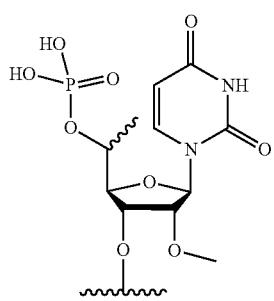

X7 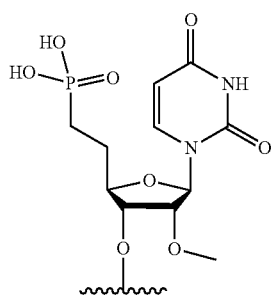

-continued

X8 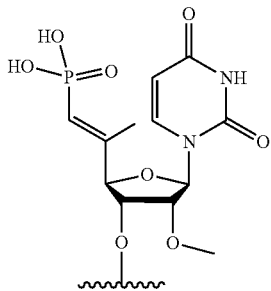

A, for each occurrence, independently is a 2'-methoxy-ribonucleotide;

B, for each occurrence, independently is a 2'-fluoro-ribonucleotide;

K, for each occurrence independently is a phosphodiester or phosphorothioate linker;

S is a phosphorothioate linker;

R is hydrogen, phosphate, vinylphosphonate, or a capping group;

j is 4, 5, 6 or 7;

r is 2 or 3; and t is 0 or 1.

18. The compound of claim 11, wherein the first oligonucleotide has the structure of formula (IIa):

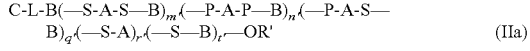   (IIa)

wherein:

C-L is:

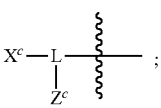 ;

A, for each occurrence, independently is a 2'-methoxy-ribonucleotide;

B, for each occurrence, independently is a 2'-fluoro-ribonucleotide;

S is a phosphorothioate linker;

P is a phosphodiester linker;

R' is hydrogen, phosphate, vinylphosphonate, or a capping group;

m' is 0 or 1;

n' is 4, 5 or 6;

q' is 0 or 1;

r' is 0 or 1; and t' is 0 or 1.

* * * * *

SEQUENCE LISTING

<160> NUMBER OF SEQ ID NOS: 10

<210> SEQ ID NO 1
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
caguaaagag auuaa                                                    15

```
<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuaaucucuu uacugauaua                                                    20

<210> SEQ ID NO 3
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
caaauuccau cguga                                                         15

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucacgaugga auuugcuguu                                                    20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuaaucucuu uacugauaua                                                    20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucacgaugga auuugcuguu                                                    20

<210> SEQ ID NO 7
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gcacauuaaa cagaa                                                         15
```

```
<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uucuguuuaa ugugcauaaa                                              20

<210> SEQ ID NO 9
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugacaaauac gauua                                                   15

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uaaucguauu ugucaaucau                                              20
```